US012612650B2

(12) United States Patent
Liang et al.

(10) Patent No.: US 12,612,650 B2
(45) Date of Patent: Apr. 28, 2026

(54) METHODS FOR IMPROVED HOMOLOGOUS RECOMBINATION AND COMPOSITIONS THEREOF

(71) Applicant: LIFE TECHNOLOGIES CORPORATION, Carlsbad, CA (US)

(72) Inventors: Xiquan Liang, San Diego, CA (US); Robert Jason Potter, San Marcos, CA (US); Lansha Peng, Poway, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 18/374,673

(22) Filed: Sep. 29, 2023

(65) Prior Publication Data

US 2024/0247286 A1 Jul. 25, 2024

Related U.S. Application Data

(62) Division of application No. 16/124,931, filed on Sep. 7, 2018, now abandoned.

(60) Provisional application No. 62/717,403, filed on Aug. 10, 2018, provisional application No. 62/626,792, filed on Feb. 6, 2018, provisional application No. 62/574,936, filed on Oct. 20, 2017, provisional application No. 62/568,661, filed on Oct. 5, 2017, provisional application No. 62/555,862, filed on Sep. 8, 2017.

(51) Int. Cl.
| | |
|---|---|
| *C12N 15/63* | (2006.01) |
| *C07K 14/195* | (2006.01) |
| *C12N 9/22* | (2006.01) |
| *C12N 15/90* | (2006.01) |

(52) U.S. Cl.
CPC .......... *C12N 15/907* (2013.01); *C07K 14/195* (2013.01); *C12N 9/22* (2013.01); *C12N 15/63* (2013.01); *C12N 2800/80* (2013.01); *C12N 2800/95* (2013.01); *C12N 2810/40* (2013.01)

(58) Field of Classification Search
None
See application file for complete search history.

(56) References Cited

U.S. PATENT DOCUMENTS

| | | | |
|---|---|---|---|
| 9,005,973 | B2 | 4/2015 | Cost et al. |
| 2014/0068797 | A1 | 3/2014 | Doudna et al. |
| 2014/0304847 | A1 | 10/2014 | Kühn et al. |
| 2015/0140664 | A1* | 5/2015 | Byrne .................. C12N 15/102 |
| | | | 435/468 |
| 2016/0177278 | A1* | 6/2016 | Wolfe ..................... C12N 9/22 |
| | | | 435/199 |
| 2016/0257973 | A1* | 9/2016 | Cameron .............. C12N 15/111 |
| 2016/0298096 | A1 | 10/2016 | Charpentier et al. |
| 2017/0137801 | A1 | 5/2017 | Liras et al. |
| 2017/0253888 | A1 | 9/2017 | Gebeyehu et al. |
| 2017/0306306 | A1 | 10/2017 | Potter et al. |
| 2018/0023075 | A1 | 1/2018 | Liang et al. |
| 2019/0032091 | A1 | 1/2019 | Dever et al. |
| 2019/0225991 | A1 | 7/2019 | Izpisua Belmonte et al. |
| 2020/0308581 | A1* | 10/2020 | Clarke ................. C12N 15/113 |

FOREIGN PATENT DOCUMENTS

| | | |
|---|---|---|
| CN | 106795521 A | 5/2017 |
| JP | 2016505256 A | 2/2016 |
| JP | 2016509063 A | 3/2016 |
| JP | 2016519652 A | 7/2016 |
| JP | 2017501149 A | 1/2017 |
| WO | WO-03012036 A2 | 2/2003 |
| WO | WO-2009131632 A1 | 10/2009 |
| WO | WO-2011100058 A1 | 8/2011 |
| WO | WO-2012120176 A2 | 9/2012 |
| WO | WO-2012168307 A2 | 12/2012 |
| WO | WO-2014099744 A1 | 6/2014 |
| WO | WO-2014102688 A1 | 7/2014 |
| WO | WO-2014150624 A1 | 9/2014 |
| WO | WO-2014173955 A1 | 10/2014 |
| WO | WO-2014189628 A1 | 11/2014 |
| WO | WO-2016054326 A1 | 4/2016 |
| WO | WO-2016057951 A2 | 4/2016 |
| WO | WO-2016065364 A1 | 4/2016 |
| WO | WO-2016073990 A2 | 5/2016 |
| WO | WO-2017040335 A2 | 3/2017 |

(Continued)

OTHER PUBLICATIONS

Hilton et al., Epigenome editing by a CRISPR-Cas9-based acetyltransferase activates genes from promoters and enhancers. Nature Biotechnology (2015), 33: 510-517 and Online Methods (Year: 2015).*
Chen et al., Probing the impact of chromatin conformation on genome editing tools. Nucleic Acids Research (2016), 44(13): 6482-6492 (Year: 2016).*
Liu et al., Neuronal cell-type engineering by transcriptional activation. Front. Genome Ed. (2021), 3:715697 (Year: 2021).*
Milbradt et al., Structure of the VP16 transactivator target in the Mediator. Nature Structural & Molecular Biology (2011), 18: 410-416 (Year: 2011).*
Aird E.J et al., "Increasing Cas9-Mediated Homology-Directed Repair Efficiency Through Covalent Tethering of DNA Repair Template", Communications Biology, 2018, p. 6, DOI: 10.1038/s42003-018-0054-2.
Ansai S., et al., Targeted Mutagenesis using CRISPR/Cas System in Medaka, Biology Open, 2014, vol. 3, pp. 362-371.

(Continued)

*Primary Examiner* — Catherine Konopka

(57) ABSTRACT
The present disclosure relates to methods, kits, and compositions for improving the efficiency of homologous recombination. In particular, the disclosure relates to methods for cloning DNA molecules directly into a genome with the combined use of promoter trapping and short homology arms, nuclear localization signal, and/or binding one or more DNA binding agents (TAL effector domain or truncated guide RNA bound by Cas9) to specific sites thereby displacing or restructuring chromatin at the target locus, and/or it increasing the accessibility of the target locus to further enzymatic modifications. The methods and compositions provided herein are, inter alia, useful for genome editing and enhancing enzymatic processes involved therein.

12 Claims, 46 Drawing Sheets

Specification includes a Sequence Listing.

(56) References Cited

FOREIGN PATENT DOCUMENTS

WO      WO-2017096041 A1      6/2017
WO      WO-2017205650 A1      11/2017
WO      WO-2019051237 A1      3/2019

OTHER PUBLICATIONS

Arras S.D.M et al: "Chemical Inhibitors of Non-Homologous End Joining Increase Targeted Construct Integration in Cryptococcus Neoformans", PLOS ONE, Public Library of Science, US, vol. 11, No. 9, Jan. 1, 2016 (Jan. 1, 2016), p. 14, DOI:10.1371/journal.pone. 0163049, XP002786040, ISSB: 1932-6203.

Bi et al. High-efficiency targeted editing of large viral genomes by RNA-guided nucleases. PLOS Pathogens, vol. 10, No. 5, e1 004090, May 1, 2014, printed as pp. 1/11, 11/11. (Year: 2014).

Boettcher, et al., "Choosing the Right Tool for the Job: RNAi, TALEN, or CRISPR", Molecular Cell, vol. 58, No. 4, May 21, 2015, 575-585.

Brown, D. et al., "Effect of Phosphorothioate Modification of Oligodeoxynucleotides on Specific Protein Binding", The Journal of Biological Chemistry, vol. 269, No. 43, Oct. 28, 1994, 26801-26805.

Burger A., et al., "Maximizing Mutagenesis with Solubilized CRISPR-Cas9 Ribonucleoprotein Complexes", Development, vol. 143, No. 11,Apr. 29, 2016 (Apr. 29, 2016), pp. 2025-2037, XP055636227, GB, ISSN: 0950-1991, DOI: 10.1242/dev. 134809.

Burkard C., et al., "Precision Engineering for PRRSV Resistance in Pigs: Macrophages from Genome Edited Pigs Lacking CD163 SRCR5 Domain are fully Resistant to both PRRSV Genotypes while Maintaining Biological Function," PLOS Pathogens, 2017, vol. 13, No. 2, e1006206, pp. 1-28.

Chu V.T et al., "Increasing the Efficiency of Homology-Directed Repair for CRISPR-Cas9-Induced Precise Gene Editing in Mammalian Cells", Nature Biotechnology, 2015, 33(5), pp. 543-548, DOI:10.1038/nbt.3198.

Eyquem J et al., "Targeting a CAR to the TRAC locus with CRISPR/Cas9 Enhances Tumour Rejection", Nature, 2017, 543:113-117, p. 19, DOI:10.1038/nature21405.

Gaj, et al., "ZFN, TALEN, and CRISPR/Cas-based methods for genome engineering", Trends in Biotechnoloav. vol. 31, No. 7, Jul. 3, 2013, 397-405.

GENEART® Genomic Cleavage Detection kit (Thermo Fisher Scientific, cat. No. A24372), 16 pages.

Guilinger J.P., et al., "Fusion of catalytically Inactive Cas9 to FokI Nuclease Improves the Specificity of Genome Modification," Nature Biotechnology, 2014, vol. 32, 15 pages.

Guoling Li et al: "Small Molecules Enhance CRISPR/Cas9-Mediated Homology-Directed Genome Editing in Primary Cells", Scientific Reports, vol. 7, No. 1, Aug. 21, 2017 (Aug. 21, 2017), 11 pages, XP055525717.

Hisano Y., et al., Precise In-Frame Integration of Exogenous DNA Mediated by CRISPR/Cas9 System in Zebrafish, Scientific Reports, 2015, vol. 5, No. 8841, pp. 1-7.

Hodel M.R et al., "Dissection of a Nuclear Localization Signal", Journal of Biological Chemistry, 2001, 276(2), pp. 1317-1325, DOI:10.1074/jbc.m008522200.

Hsu, et al., "Development and Applications of CRISPR-Cas9 for Genome Editing", Cell. vol. 157, No. 6, Jun. 5, 2014, 1262-1278.

Hsu et al. DNA targeting specificity of RNA-guided Cas9 nucleases. Nature Biotechnology, vol. 31, No. 9, pp. 827-832, Jul. 21, 2013, including pp. 1/2-2/2 of Online Methods, and pp. 1/27, 27/27 of Supplementary Information. (Year: 2013).

Igoucheva, 0. et al., "Targeted gene correction by small single-stranded oligonucleotides in mammalian cells", Gene Therapy. vol. 8, No. 5, Mar. 2001, 391-399.

International Search Report and Written Opinion for Application No. PCT/US2017/34520, mailed Nov. 6, 2017, 23 pages.

International Search Report and Written Opinion for Application No. PCT/US2018/050088, mailed Nov. 30, 2018, 14 pages.

International Search Report PCT/EP2014/079473, mailed Jun. 17, 2015, 5 pages.

Jackson et al. "Fitting CRISPR-associated Cas3 into the helicase family tree", Current Opinion in Structural Biology, vol. 24, pp. 106-114, Jan. 28, 2014.

Kan, Y. et al., "The Mechanism of Gene Targeting in Human Somatic Cells", PLOS Genetics. vol. 10, No. 4, Apr. 2014, e1 004251.

Kleinstiver B.P., et al., "High-fidelity CRISPR-Cas9 Nucleases with No Detectable Genome-wide Off-tarqet Effects", Molecular Therapy, May 2016, vol. 24, No. 1, pp. S288.

Liang, X. et al., "Enhanced CRISPR/Cas9-mediated precise genome editing by improved design and delivery of gRNA, Cas9 nuclease, and donor DNA", Journal of Biotechnology, vol. 241, Nov. 11, 2016, 136-146.

Li-Ma A., et al., "Establishment of CRISPR/Cas9-edited FGF5 Cell Strains in Cashmere Goat," China Biotechnology, 2016, vol. 36, No. 7, pp. 41-47.

Lin, S. et al., "Enhanced homology-directed human genome engineering by controlled timing of CRISPR/Cas9 delivery", eLIFE, vol. 3, Dec. 15, 2014, e04766.

Makarova et al. Unification of Cas protein families and a simple scenario for the origin and evolution of CRISPR-Cas systems. Biology Direct, vol. 6, No. 38, pp. 1/27, 27/27, 2011. (Year: 2011).

Morbitzer, et al., "Assembly of custom TALE-type DNA binding domains by modular cloning", Nucleic Acids Research vol. 39, No. 13, Jul. 2011, 5790-5799.

International Search Report and Written Opinion for Application No. PCT/US2018/049966, mailed Dec. 7, 2018, 14 pages.

PCT/US2015/057401, "International Search Report and Written Opinion mailed", Mar. 9, 2016, 1-11.

PCT/US2017/034520, "International Search Report mailed", Nov. 6, 2017, 11 Pages.

Ran, et al., "Double Nicking by RNA-Guided CRISPR Cas9 for Enhanced Genome Editing Specificity", Cell vol. 154, Sep. 12, 2013, 1380-1389.

Ran et al. Genome engineering using the CRISPR-Cas9 system. Nature Protocols, vol. 8, No. 11, pp. 2281-2308, Oct. 24, 2013. (Year: 2013).

Renaud et al. Improved genome editing efficiency and flexibility using modified oligonucleotides with TALEN and CRISPR-Cas9 nucleases. Cell Reports, vol. 14, pp. 2263-2272, Mar. 8, 2016, including pp. 1/21, 21/21 of Supplemental Information. (Year:2016).

Richardson, C et al., "Enhancing homology-directed genome editing by catalytically active and inactive CRISPR-Cas9 using asymmetric donor DNA", Nature Biotechnology, vol. 34, No. 3, Mar. 2016, 339-344.

Richardson, C et al., "Supplemental Material to "Enhancing homology-directed genome editing by catalytically active and inactive CRISPR-Cas9 using asymmetric donor DNA"", Nature Biotechnology, vol. 34, No. 3, Mar. 2016, 1-108.

Rong, Z. et al., "Homologous recombination in human embryonic stem cells using CRISPR/CAS9 nickase and a long DNA donor template", Protein & Cell, vol. 5, No. 4, Mar. 14, 2014, 258-260.

Ruff et al. Aptamer-guided gene targeting in yeast and human cells. Nucleic Acids Research, vol. 42, No. 7, e61, Feb. 5, 2014, printed as pp. 1/16, 16/16. (Year: 2014).

Saito S et al., "Dual Loss Of Human POLQ and LIG4 Abolishes Random Integration", Nature Communications, 2017, 8:16112, p. 10, DOI:10.1038/ncomms16112.

Savic N et al., "Covalent Linkage of the DNA Repair Template to the CRISPR-Cas9 Nuclease Enhances Homology-Directed Repair", eLife, 2018, 7:e33761, p. 18, DOI:10.7554/elife.33761.

Shao et al. Recognition and cleavage of a nonstructured CRISPR RNA by its processing endoribonuclease Case, Structure, vol. 21, pp. 385-393, Mar. 5, 2013.

Slaymaker, et al., "Rationally engineered Cas9 nucleases with improved specificity", Science vol. 351, Issue 6268, Dec. 1, 2015, 84-88.

(56) References Cited

OTHER PUBLICATIONS

Song, F. et al., "Optimizing the DNA Donor TEmplate for Homology-Directed Repair of Double-Strand Breaks", Molecular Therapy-Nucleic Acids vol. 7, Jun. 2017, 53-60.

Sorrell, et al., "Targeted modification of mammalian genomes", Biotechnology Advances, vol. 23, No. 7-8, Nov. 2005, 431-469.

Staahl B.T., et al., Efficient Genome Editing in the Mouse Brain by Local Delivery of Engineered Cas9 Ribonucleoprotein Complexes, Nature Biotechnology, 2017, vol. 35, No. 5, pp. 431-434.

Su Y., et al., "Construction of a CRISPR-Cas9 System for Pig Genome Targeting, " Animal Biotechnology, Jul. 9, 2015, vol. 26, pp. 279-288.

TriLink Biotechnologies: "Clean Cap Cas9 mRNA," 2022, 1 page, retrieved from the Internet URL: https://www.trilinkbiotech.com/media/folio3/productattachments/product_insert/L7606_Insert.pdf.

Tsai, et al., "Dimeric CRISPR RNA-guided FokI nucleases for highly specific genome editing", Nature Biotechnology, vol. 32, 2014, 569-576.

Uemura T et al., "Fluorescent Protein Tagging of Endogenous Protein in Brain Neurons Using CRISPR/Cas9-Mediated Knock-in And in Utero Electroporation Techniques", Scientific Reports, 2016, 6:35861, DOI:10.1038/srep35861.

Wang B et al: "Highly Efficient CRISPR/HDR-Mediated Knock-in for Mouse Embryonic Stem Cells and Zygotes", Biotechniques Rapid Dispatches, vol. 59, No. 4, Oct. 1, 2015 (Oct. 1, 2015), XP055393775, US, pp. 201-208, ISSN: 0736-6205, DOI: 10.2144/000114339.

Wang J., et al., Homology-Driven Genome Editing in Hematopoietic Stem and Progenitor Cells using ZFN mRNA and AAV6 donors, Nature Biotechnology, 2015, vol. 33, No. 12, pp. 1256-1263.

Wang Y., et al., A 'suicide' CRISPR-Cas9 System to Promote Gene Deletion and Restoration by Electroporation in Cryptococcus Neoformans, Scientific Reports, 2016, vol. 6, No. 31145, pp. 1-13.

Written Opinion of the International Searching Authority PCT2014/079473, mailed Jun. 17, 2015, 9 pages.

Xiquan L et al: "Rapid And Highly Efficient Mammalian Cell Engineering Via Cas9 Protein Transfection", Journal of Biotechnology, vol. 208, May 21, 2015 (May 21, 2015), pp. 44-53, XP055196365, Amsterdam, NL, ISSN: 0168-1656, DOI: 10.1016/j.jbiotec.2015.04.024.

Yang H., et al., "One-Step Generation of Mice Carrying Reporter and Conditional Alleles by CRISPR/Cas-Mediated Genome Engineering," Cell, 2013, vol. 154, pp. 1370-1379.

Zanta, et al., "Gene Delivery: A Single NLS Peptide is Sufficient to Carry DNA to the Cell Nucleus", PNAS, 96,(1999),91-96.

Tinland B., et al., "The T-DNA-linked VirD2 Protein Contains Two Distinct Functional Nuclear Localization Signals," Proceedings of the National Academy of Sciences of the United States of America (PNAS), Aug. 1992, vol. 89, pp. 7442-7446.

Chen F., et al., "Targeted Activation of Diverse CRISPR-Cas Systems for Mammalian Genome Editing via Proximal CRISPR Targeting," Nature Communications, Apr. 7, 2017, vol. 8, No. 14958, 12 pages.

Kubo T., et al., "Controlled Intracellular Localization and Enhanced Antisense Effect of Oligonucleotides by Chemical Conjugation," Organic & Biomolecular Chemistry, 2005, vol. 3, No. 18, pp. 3257-3259.

Leung S.W., et al., "Dissection of the Karyopherin Nuclear Localization Signal (NLS)—Binding Groove: Functional Requirements for NLS Binding," Journal of Biological Chemistry,2003, vol. 278, No. 43, pp. 41947-41953.

* cited by examiner

Effect of dose on HDR

Effect of homology arm length on HDR

Effect of donor format on HDR

C-terminal Junction analysis of 86 clonal cells (precise HDR: 86/86)

C-terminal Junction

N-terminal Junction analysis of clonal cells (precise HDR: 19/19)

Homology arm                                    EGFR C-ter    EmGFP

GAATACCTAAGGGTCGCGCCACAAAGCAGTGAATTTATTGGAGCATGGGTGAGCAAGGG

Junction

C-terminal Junction analysis of clonal cells (precise HDR: 19/19)

Puro    EGFR                    stop    Homology arm

GAAAGCCTGGCGCCTACCACGGAGGATAGTATGAGCCCTAAAAATCCAGACTCTTTCG

Junction

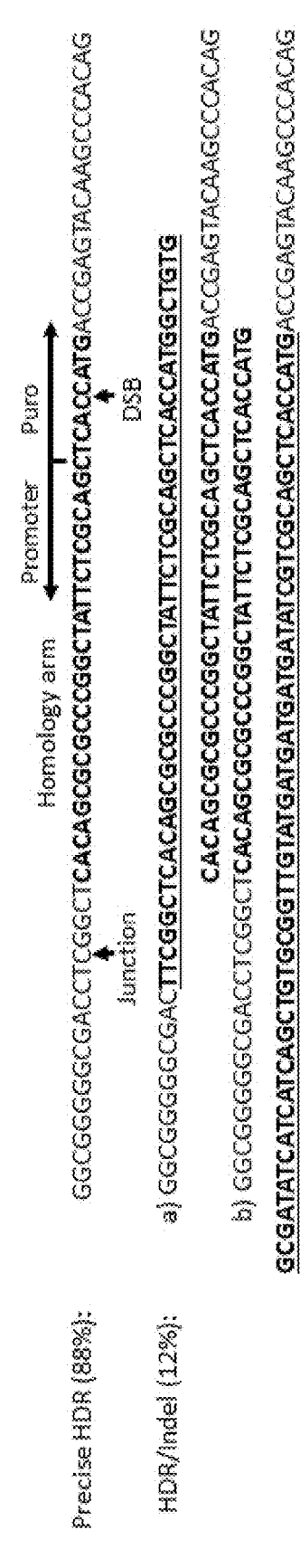

N-terminal Junction

Precise HDR (88%):
GGCGGGGGGGCGACCTGGCTCACAGCGCGCCGGCTATTCTCGCAGCTCACCATGACCGAGTACAAGCCCACAG
(Junction) (Homology arm) (Promoter) (Puro) (DSB)

HDR/indel (12%):
a) GGCGGGGGGGCGACTTCGGCTCACAGCGCGCCGGCTATTCTCGCAGCTCACCATGGCTGTG
b) GGCGGGGGGGCGACCTCGGCTCACAGCGCGCCGGCTATTCTCGCAGCTCACCATG
GCGGATATCATCAGCTGTGCGGTTGTATGATGATGATCGTGCAGCTCACCATG CACAGCGCGCCGGCTATTCTCGCAGCTCACCATG
GCGGATATCATCAGCTGTGCGGTTGTATGATGATCGTGCAGCTCACCATGACCGAGTACAAGCCCACAG

FIG. 8B

C-terminal Junction

Precise HDR (41%):
...GAGTGTTGA...   CCTCCCCGCCTGG   G   ATGATGATATCGCCGGCTCGTCGTGCGCTGCGACAACGGGCTCCGGCATGTGCAAG
(LC IgG) (stop) (WPRE) (Beta) (Homology) (Junction)

HDR/indel (59%):
a) ...GAGTGTTGA...   CCTCCCCGCCTGT   G   ATGATGATATCGCCGGCTCGTCGTGCGCTGCGACAACGGCTCCGGCATGTGCAAG
b) ...GAGTGTTGA...   CCTCCCCGCCGCT   G   ATGATGATATCGCCGGCTCGTCGTGCGCTGCGACAACGGCTCCGGCATGTGCAAG
c) ...GAGTGTTGA...   CCTCCCCGCCTGGG   A   ATGATGATATCGCCGGCTCGTCGTGCGCTGCGACAACGGCTCCGGCATGTGCAAG
d) ...GAGTGTTGA...   CCTCCCCGCCTGGG   G   ATGATGATATCGCCGGCTCGTCGTGCGCTGCGACAACGGCTCCGGCATGTGCAAG
e) ...GAGTGTTGA...   CCTCCCCGCCTGGGGCTGATGATGATATCGCCGGCTCGTCGTGCGCTGCGACAACGGCTCCGGCATGTGCAAG

FIG. 8C

Functional Assays

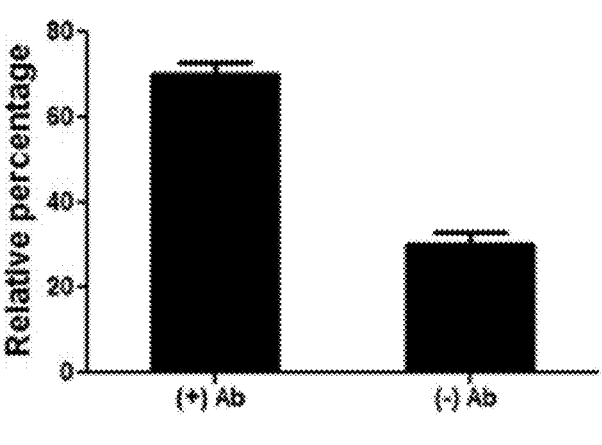

FIG. 8D

| Item Name | Description |
|---|---|
| 1 - BFP | N-terminal of peptide-KRTADGSEFESPKKKRKVEGG-Linker-5'-GCTGCCCGTGCCCTGGCCCACCCTCGTGACCACCCTGACCTACGGCGTGCAGTGCTTCAGCCGCTACCCCGACCACATGA 3'<br><br>"Cys-SMCC-C6" linker: 0.5-1 OD (19-38 µg), with >85% HPLC purity |
| 2 – 6 base | N-terminal of peptide-KRTADGSEFESPKKKRKVEGG-Linker-5'-CGGGGTAGCGGGCGAAGCACTGCACGCCGTAGGTGAAGGTGGTCACGAGGGTGGGCCAGGGCACGGGCAGCTTGCCGGTG GTGCAGATGAACTTCAG 3'<br><br>"Click chemistry linker": 0.5-1 OD (20-38 µg), with >85% HPLC purity |

FIG. 9

| Phosphorothioate-modified donor (pmoles per reaction) | | | | | | | | NLS-modified donor (pmoles per reaction) | | | | |
| --- | --- | --- | --- | --- | --- | --- | --- | --- | --- | --- | --- | --- |
| | Neg | 0.03 | 0.1 | 0.3 | 1 | 3 | 10 | 0.01 | 0.03 | 0.1 | 0.3 | |
| Avg | 0 | 3.24 | 9.58 | 18.81 | 31.50 | 35.80 | 36.00 | 29.10 | 46.10 | 51.90 | 56.25 | |
| Std | 0 | 0.37 | 0.59 | 0.44 | 0.71 | 1.13 | 1.13 | 2.26 | 1.56 | 0.14 | 1.20 | |

FIG. 11

| | Neg | unmodified donor (pmoles per reaction) | | | | | | NLS-modified donor (pmoles per reaction) | | | | |
|---|---|---|---|---|---|---|---|---|---|---|---|---|---|
| | | 0.03 | 0.1 | 0.3 | 1 | 3 | 10 | 0.01 | 0.03 | 0.1 | 0.3 |
| Avg | 0 | 6.15 | 8.3 | 15.1 | 33 | 52.05 | 58.5 | 21.15 | 33.1 | 49.35 | 75.85 |
| Std | 0 | 0.21 | 0.28 | 0.57 | 2.83 | 0.78 | 0.42 | 0.21 | 4.38 | 1.20 | 0.78 |

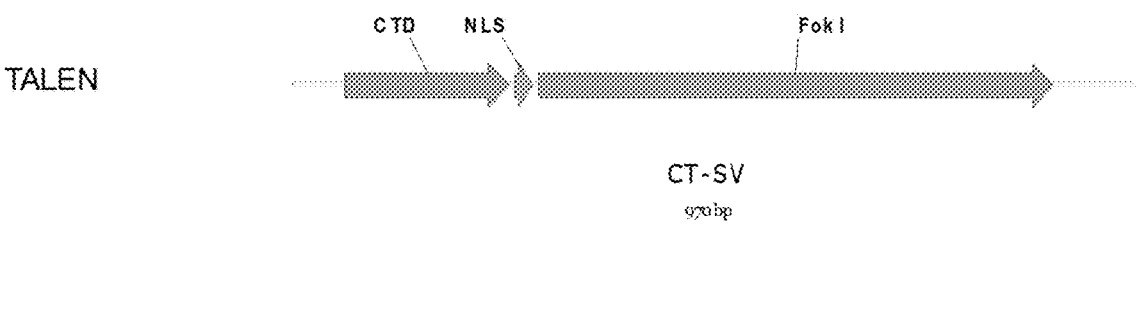
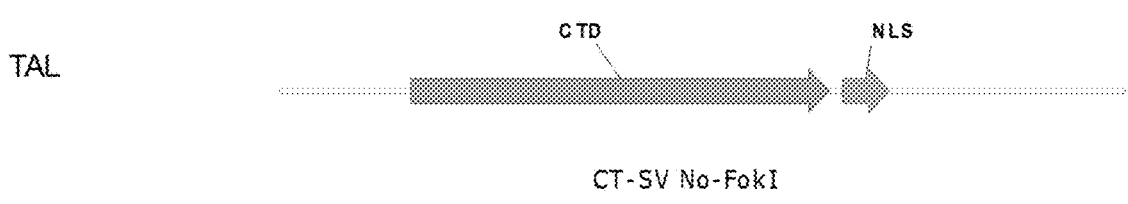
FIG. 22
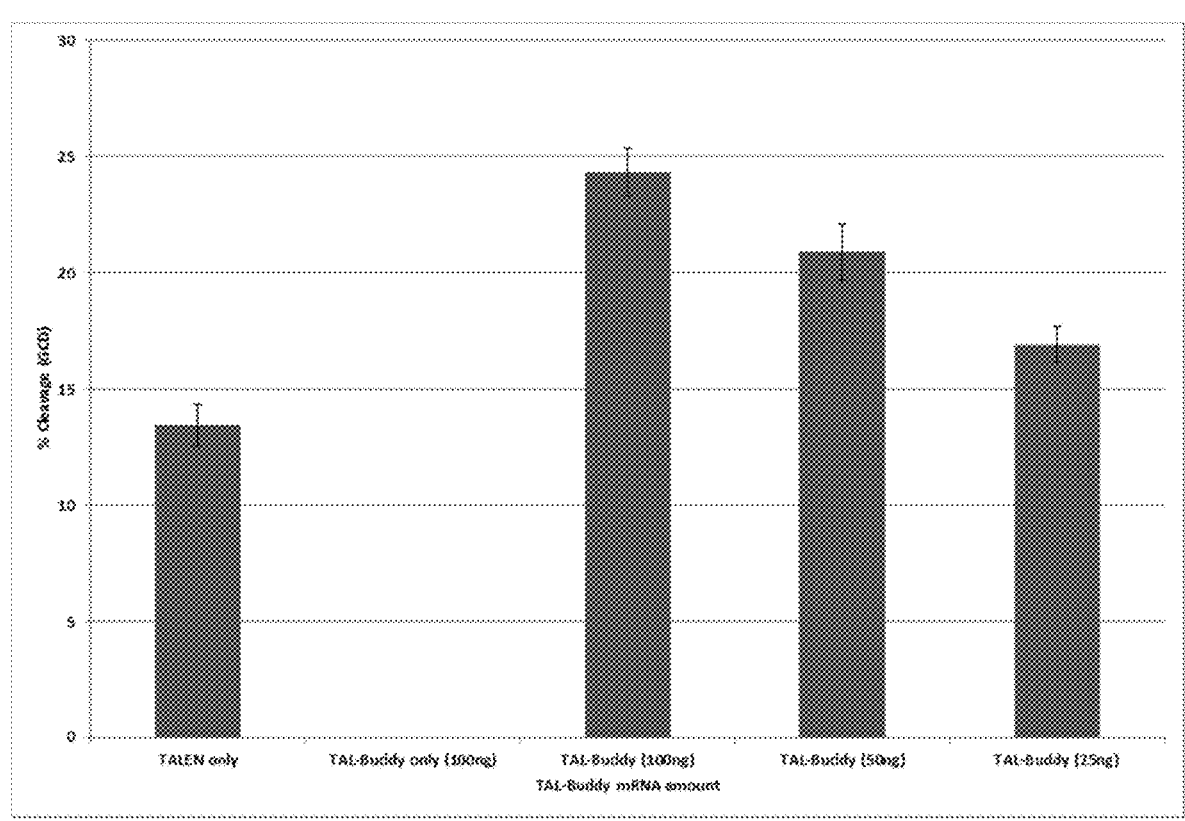
FIG. 23

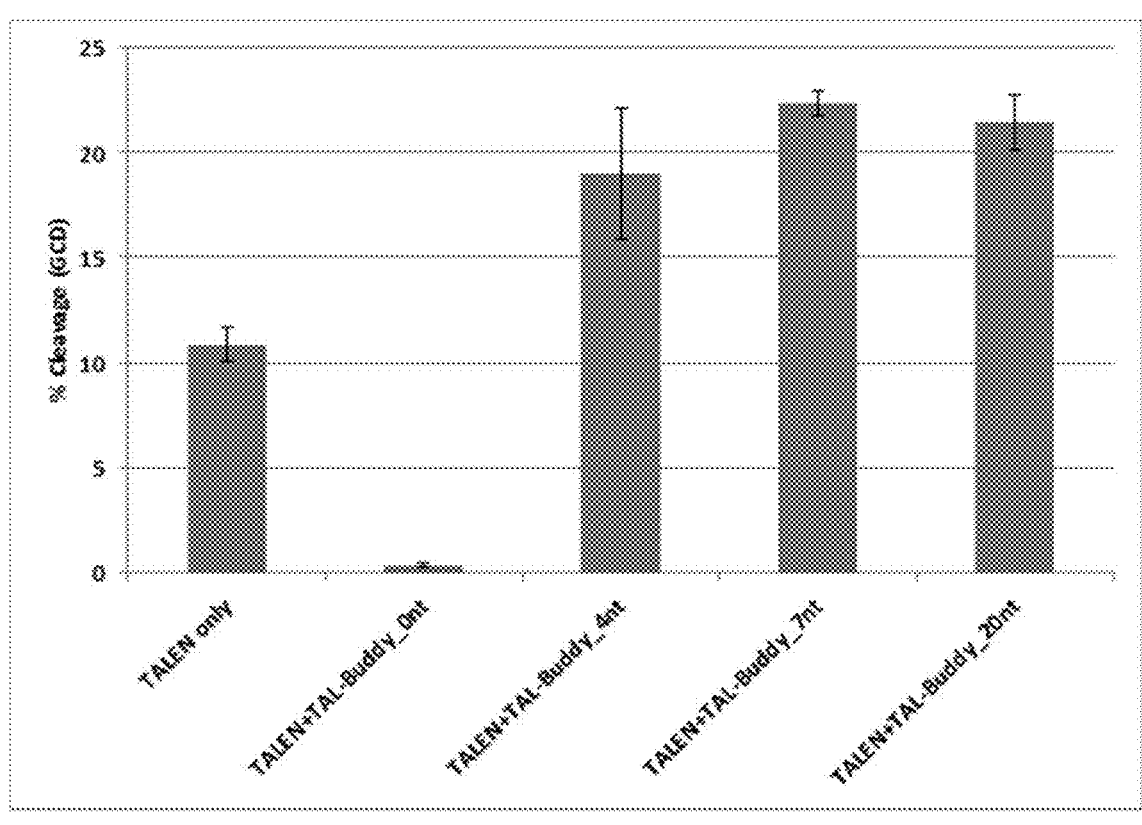
FIG. 24
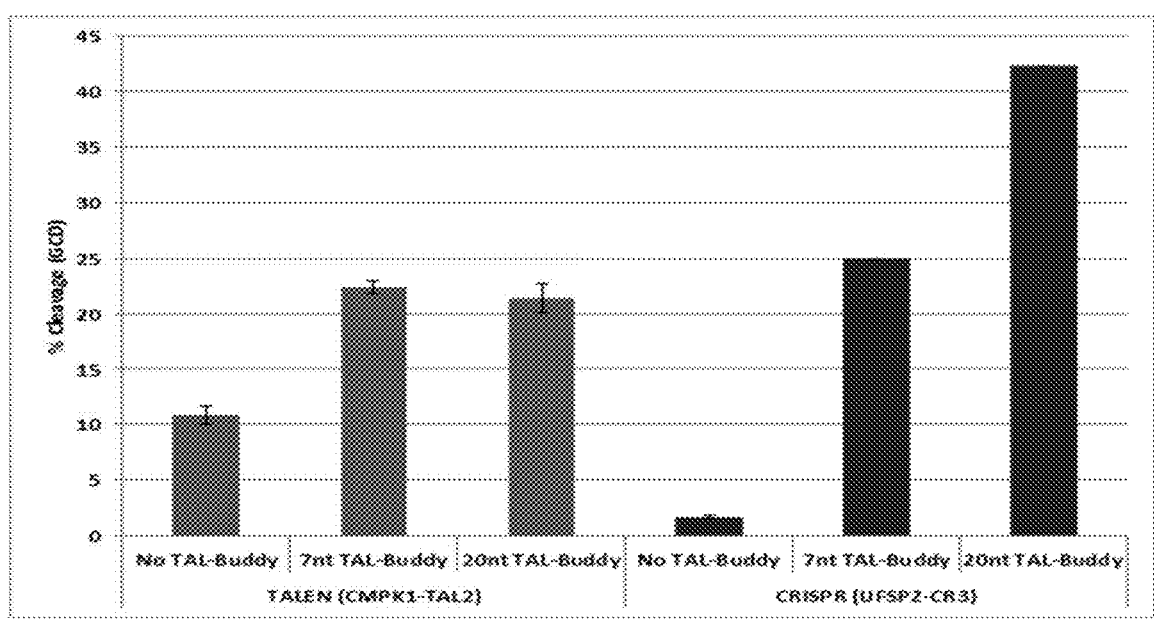
FIG. 25

```
MDKKYSIGLD IGTNSVGWAV ITDEYKVPSK KFKVLGNTDR HSIKKNLIGA LLFDSGETAE ATRLKRTARR
RYTRRKNRIC YLQEIFSNEM AKVDDSFFHR LEESFLVEED NIVDEVAYHE KYPTIYHLRK
KLVDSTDKAD MIKFRGHFLI EGDLNPDNSD VDKLFIQLVQ TYNQLFEENP INASGVDAKA
ILSARLSKSR RLENLIAQLP GEKKNGLFGN LIALSLGLTP NFKSNFDLAE YDDDLDNLLA
QIGDQYADLF LAAKNLSDAI LLSDILRVNT EITKAPLSAS MIKRYDEHHQ DLTLLKALVR QQLPEKYKEI
FFDQSKNGYA GYIDGGASQE EFYKFIKPIL EKMDGTEELL VKLNREDLLR KQRTFDNGSI PHQIHLGELH
AILRRQEDFY PFLKDNREKI EKILTFRIPY YVGPLARGNS RFAWMTRKSE ETITPWNFEE VVDKGASAQS
FIERMTNFDK NLPNEKVLPK HSLLYEYFTV YNELTKVKYV TEGMRKPAFL SGEQKKAIVD LLFKTNRKVT
VKQLKEDYFK KIECFDSVEI SGVEDRFNAS LGTYHDLLKI IKDKDFLDNE ENEDILEDIV LTLTLFEDRE
MIEERLKTYA HLFDDKVMKQ LKRRRYTGWG RLSRKLINGI RDKQSGKTIL DELKSDGFAN RNFMQLIHDD
SLTFKEDIQK AQVSGQGDSL HEHIANLAGS PAIKKGILQT VKVVDELVKV MGRHKPENIV IEMARENQTT
QKGQKNSRER MKRIEEGIKE LGSQILKEHP VENTQLQNEK LYLYYLQNGR DMYVDQELDI NRLSDYDVDH
IVPQSFLKDD SIDNKVLTRS DKNRGKSDNV PSEEVVKKMK NYWRQLLNAK LITQRKFDNL TKAERGGLSE
LDKAGFIKRQ LVETRQITKH VAQILDSRMN TKYDENDKLI REVKVITLKS QFYKVREINN
YHHAHDAYLN AVVGTALIKK YPKLESEFVY GDYKVYDVRK MIAKSEQEIG NIMNFFKTEI
TLANGEIRKR PLIETNGETG EIVWDKGRDF ATVRKVLSMP QVNIVKKTEV LPKRNSDKLI
ARKKDWDPKK YGGFDSPTVA YSVLVVAKVE KGKSKKLKSV KELLGITIME RSSFEKNPID FLEAKGYKEV
KKDLIIKLPK YSLFELENGR KRMLASAGEL QKGNELALPS KYVNFLYLAS HYEKLKGSPE DNEQKQLFVE
QHKHYLDEII EQISEFSKRV ILADANLDKV LSAYNKHRDK PIREQAENII HLFTLTNLGA PAAFKYFDTT
IDRKRYTSTK EVLDATLIHQ SITGLYETRI DLSQLGGDRS RAD PKKKRKV DPKKKRKV DP KKKRKV GSTG
SRGSGSA HHH HHH
```

His Tag    NLS2    NLS3    NLS4

FIG. 41

NLS1

```
   1  MKRTADGSEF ESPKKKRKVE DKKYSIGLDI GTNSVGWAVI TDEYKVPSKK FKVLGNTDRH SIKKNLIGAL
  71  LFDSGETAEA TRLKRTARRR YTRRKNRICY LQEIFSNEMA KVDDSFFHRL EESFLVEEDK KHERHPIFGN
 141  IVDEVAYHEK YPTIYHLRKK LVDSTDKADL RLIYLALAHM IKFRGHFLIE GDLNPDNSDV DKLFIQLVQT
 211  YNQLFEENPI NASGVDAKAI LSARLSKSRR LENLIAQLPG EKKNGLFGNL IALSLGLTPN FKSNFDLAED
 281  AKLQLSKDTY DDDLDNLLAQ IGDQYADLFL AAKNLSDAIL LSDILRVNTE ITKAPLSASM IKRYDEHHQD
 351  LTLLKALVRQ QLPEKYKEIF FDQSKNGYAG YIDGGASQEE FYKFIKPILE KMDGTEELLV KLNREDLLRK
 421  QRTFDNGSIP HQIHLGELHA ILRRQEDFYP FLKDNREKIE KILTFRIPYY VGPLARGNSR FAWMTRKSEE
 491  TITPWNFEEV VDKGASAQSF IERMTNFDKN LPNEKVLPKH SLLYEYFTVY NELTKVKYVT EGMRKPAFLS
 561  GEQKKAIVDL LFKTNRKVTV KQLKEDYFKK IECFDSVEIS GVEDRFNASL GTYHDLLKII KDKDFLDNEE
 631  NEDILEDIVL TLTLFEDREM IEERLKTYAH LFDDKVMKQL KRRRYTGWGR LSRKLINGIR DKQSGKTILD
 701  FLKSDGFANR NFMQLIHDDS LTFKEDIQKA QVSGQGDSLH EHIANLAGSP AIKKGILQTV KVVDELVKVM
 771  GRHKPENIVI EMARENQTTQ KGQKNSRERM KRIEEGIKEL GSQILKEHPV ENTQLQNEKL YLYYLQNGRD
 841  MYVDQELDIN RLSDYDVDHI VPQSFLKDDS IDNKVLTRSD KNRGKSDNVP SEEVVKKMKN YWRQLLNAKL
 911  ITQRKFDNLT KAERGGLSEL DKAGFIKRQL VETRQITKHV AQILDSRMNT KYDENDKLIR EVKVITLKSK
 981  LVSDFRKDFQ FYKVREINNY HHAHDAYLNA VVGTALIKKY PKLESEFVYG DYKVYDVRKM IAKSEQEIGK
1051  ATAKYFFYSN IMNFFKTEIT LANGEIRKRP LIETNGETGE IVWDKGRDFA TVRKVLSMPQ VNIVKKTEVQ
1121  TGGFSKESIL PKRNSDKLIA RKKDWDPKKY GGFDSPTVAY SVLVVAKVEK GKSKKLKSVK ELLGITIMER
1191  SSFEKNPIDF LEAKGYKEVK KDLIIKLPKY SLFELENGRK RMLASAGELQ KGNELALPSK YVNFLYLASH
1261  YEKLKGSPED NEQKQLFVEQ HKHYLDEIIE QISEFSKRVI LADANLDKVL SAYNKHRDKP IREQAENIIH
1331  LFTLTNLGAP AAFKYFDTTI DRKRYTSTKE VLDATLIHQS ITGLYETRID LSQLGGDKRP AATKKAGQAK
1401  KKK
```

NLS2

```
                                    V5                                              R-3
   1   MGKPIPNPLL GLDST GGVDL  RTLG SQQQ  EKIKPKVRST  VAQHHEALVG
                                                                      R-1
  51   HG FTHAHIVA  LSQHPAALGT  VAVKYQDMIA  ALPEA THEAI  VGVGK RGAGA
                                                         R0
 101   RALEALLTVA  GELRGPPLQL  DTGQLLKIAK  RGGVTAVEAV  HAWRNALTGA
                 R-2
 151   PLN LTPEQVV  AIASHDGGKQ  ALETVQRLLP  VLCQAHGLTP  EQVVAIASNI
 201   GGKQALETVQ  RLLPVLCQAH  GLTPEQVVAI  ASNIGGKQAL  ETVQRLLPVL
 251   CQAHGLTPEQ  VVAIASNIGG  KQALETVQRL  LPVLCQAHGL  TPEQVVAIAS
 301   NGGGKQALET  VQRLLPVLCQ  AHGLTPEQVV  AIASNGGGKQ  ALETVQRLLP
 351   VLCQAHGLTP  EQVVAIASNG  GGKQALETVQ  RLLPVLCQAH  GLTPEQVVAI
 401   ASNGGGKQAL  ETVQRLLPVL  CQAHGLTPEQ  VVAIASNNGG  KQALETVQRL
 451   LPVLCQAHGL  TPEQVVAIAS  NNGGKQALET  VQRLLPVLCQ  AHGLTPEQVV
 501   AIASHDGGKQ  ALETVQRLLP  VLCQAHGLTP  EQVVAIASNG  GKQALETVQ
 551   RLLPVLCQAH  GLTPEQVVAI  ASNGGKQAL  ETVQRLLPVL  CQAHGLTPEQ
 601   VVAIASNIGG  KQALETVQRL  LPVLCQAHGL  TPEQVVAIAS  NNGGKQALET
 651   VQRLLPVLCQ  AHGLTPEQVV  AIASNNGGKQ  ALETVQRLLP  VLCQAHGLTP
                                                         R1/2
 701   EQVVAIASNI  GGKQALETVQ  RLLPVLCQAH  GLTPQQVVAI  ASNIGGRPAL
 751   ESIVAQLSRP  DPALAALTND  HLVALACLGG  RPALDAVKKG  LPHAPALIKR
                                  NLS1
 801   TNRRIPERTS  HRVA GSPKK  RKVG DLVKS  ELEEKKSELR  HKLKYVPHEY
                         FokI
 851   IELIEIARNS  TQDRILEMKV  MEFFMKVYGY  RGKHLGGSRK  PDGAIYTVGS
 901   PIDYGVIVDT  KAYSGGYNLP  IGQADEMQRY  VEENQTRNKH  INPNEWWKVY
 951   PSSVTEFKFL  FVSGHFKGNY  KAQLTRLNHI  TNCNGAVLSV  EELLIGGEMI
                                   NLS2
1001   KAGTLTLEEV  RRKFNNGEIN  F GS PKKKRKV
```

Repeat Region

FIG. 46

```
      V5                    NLS1
  1 MGKPIPNPLL GLDSTGGMAP KKKRKVGGV DLRTLGYSQQ QQEKIKPKVR

51 STVAQHHEAL VGHGFTHAHI VALSQHPAAL GTVAVKYQDM IAALPEATHE

101 AIVGVGKRGA GARALEALLT VAGELRGPPL QLDTGQLLKI AKRGGVTAVE

151 AVHAWRNALT GAPLN · · ·                              R1/2
                                                    LTPQQVV
                        ┌──────────────┐    · · ·
                        │ Repeat Region │
744                     └──────────────┘
                                                 NLS2
751 AIASNIGGRP ALESIVAQLS RPDPALAALT NDHLVALACL GGRPALDAVK 801 KGLPHAPALI KRTNRRIPER TSHRVAGSEK KKRKVGSQLV KSELEEKKSE
                                            FokI
851 LRHKLKYVPH EYIELIEIAR NSTQDRILEM KVMEFFMKVY GYRGKHLGGS 901 RKPDGAIYTV GSPIDYGVIV DTKAYSGGYN LPIGQADEMQ RYVEENQTRN
                                                 NLS3
951 KHINPNEWWK VYPSSVTEFK FLFVSGHFKG NYKAQLTRLN HITNCNGAVL

1001 SVEELLIGGE MIKAGTLTLE EVRRKFNNGE INFGSPKKKR KV
```

FIG. 47

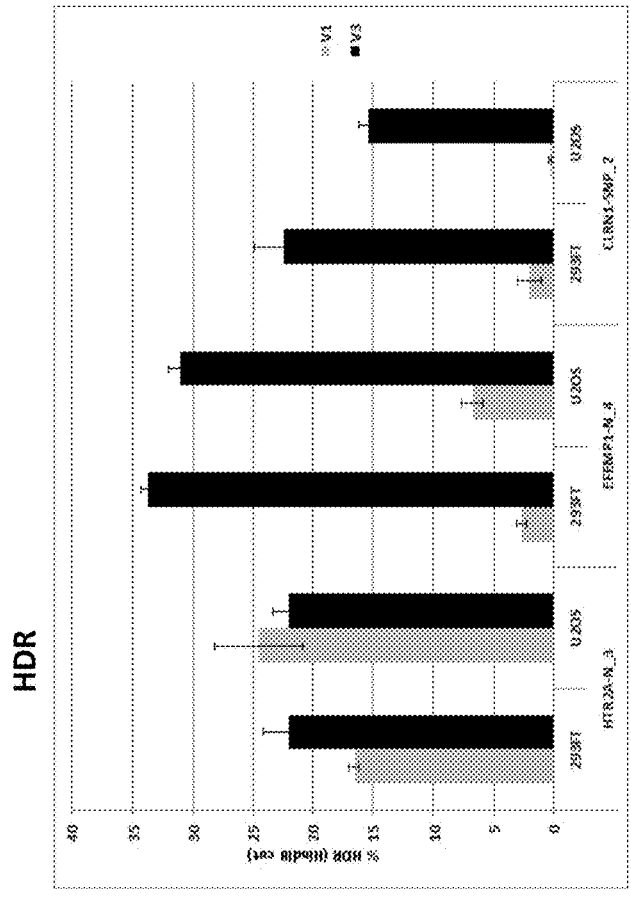
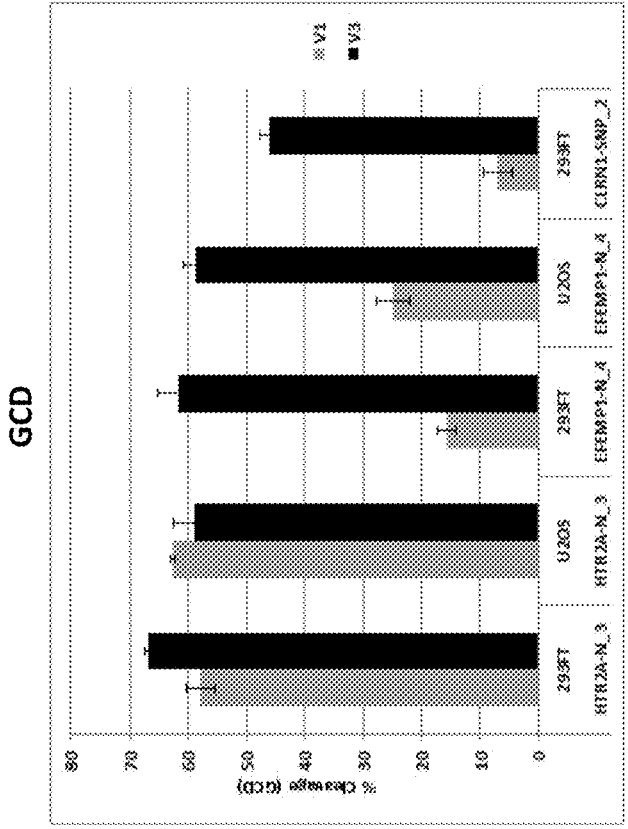
FIG. 49

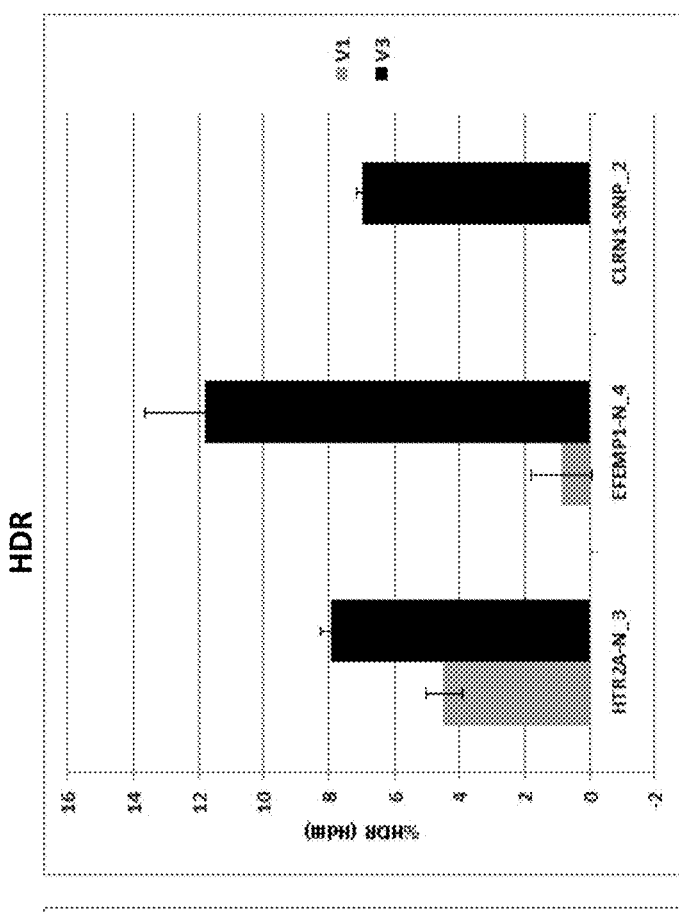
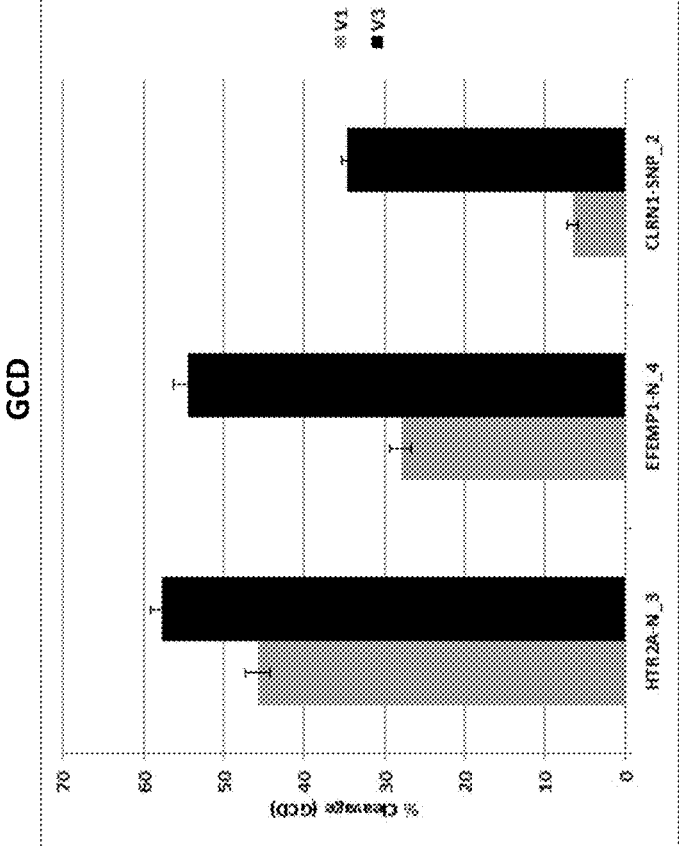
FIG. 50

```
1-50      MGKPIPNPLL  GLDSTGGVDL  RTLGYSQQQQ  EKIKPKVRST  VAQHHEALVG
51-100    HGFTHAHIVA  LSQHPAALGT  VAVKYQDMIA  ALPEATHEAI  VGVGKRGAGA
101-150   RALEALLTVA  GELRGPPLQL  DTGQLLKIAK  RGGVTAVEAV  HAWRNALTGA
151-200   PLNLTPEQVV  AIASHDGGKQ  ALETVQRLLP  VLCQAHGLTP  EQVVAIASNI
201-250   GGKQALETVQ  RLLPVLCQAH  GLTPEQVVAI  ASNIGGKQAL  ETVQRLLPVL
251-300   CQAHGLTPEQ  VVAIASNIGG  KQALETVQRL  LPVLCQAHGL  TPEQVVAIAS
301-350   NIGGKQALET  VQRLLPVLCQ  AHGLTPEQVV  AIASNIGGKQ  ALETVQRLLP
351-400   VLCQAHGLTP  EQVVAIASHD  GGKQALETVQ  RLLPVLCQAH  GLTPEQVVAI
401-450   ASHDGGKQAL  ETVQRLLPVL  CQAHGLTPEQ  VVAIASNGGG  KQALETVQRL
451-500   LPVLCQAHGL  TPEQVVAIAS  NNGGKQALET  VQRLLPVLCQ  AHGLTPEQVV
501-550   AIASNGGGKQ  ALETVQRLLP  VLCQAHGLTP  EQVVAIASNI  GGKQALETVQ
551-600   RLLPVLCQAH  GLTPEQVVAI  ASNIGGKQAL  ETVQRLLPVL  CQAHGLTPEQ
601-650   VVAIASNIGG  KQALETVQRL  LPVLCQAHGL  TPEQVVAIAS  NNGGKQALET
651-700   VQRLLPVLCQ  AHGLTPEQVV  AIASNGGGKQ  ALETVQRLLP  VLCQAHGLTP
701-750   EQVVAIASNI  GGKQALETVQ  RLLPVLCQAH  GLTPQQVVAI  ASNIGGRPAL
751-800   ESIVAQLSRP  DPALAALTND  HLVALACLGG  RPALDAVKKG  LPHAPALIKR
801-825   TNRRIPERTS  HRVAGSPKKK  RKVGS
```

FIG. 52

METHODS FOR IMPROVED HOMOLOGOUS RECOMBINATION AND COMPOSITIONS THEREOF

RELATED APPLICATIONS

This application is a divisional of U.S. application Ser. No. 16/124,931, filed Sep. 7, 2018, which claims priority to U.S. Provisional Application Nos.: 62/568,661, filed on Oct. 5, 2017; 62/574,936, filed on Oct. 20, 2017; 62/626,792, filed on Feb. 6, 2018; and 62/717,403, filed on Aug. 10, 2018. The content of each of the foregoing patent applications is incorporated by reference in their entirety.

SEQUENCE LISTING

This application contains a Sequence Listing which has been submitted electronically in XML format and is hereby incorporated by reference in its entirety. Said XML copy, created on Apr. 3, 2024, is named TP106002USDIV1.xml and is 214,994 bytes in size.

FIELD OF THE INVENTION

The present disclosure relates to methods, kits, and compositions for improving the efficiency of homologous recombination. In particular, the disclosure relates to methods for cloning DNA molecules directly into a genome with the combined use of promoter trapping and short homology arms, nuclear localization signal, and/or binding one or more DNA binding agents (TAL effector domain or truncated guide RNA bound by Cas9) to specific sites thereby displacing or restructuring chromatin at the target locus, and/or it increasing the accessibility of the target locus to further enzymatic modifications. The methods and compositions provided herein are, inter alia, useful for genome editing and enhancing enzymatic processes involved therein.

BACKGROUND

The recent advances in TALENs or CRISPR-mediated genome editing tools enable researchers to introduce double-strand breaks (DSBs) in mammalian genome efficiently. The DSBs are then mostly repaired by either the non-homologous end joining (NHEJ) pathway or the homology-directed repair (HDR) pathway. In mammalian cells, the NHEJ pathway is predominant and error-prone. However, the HDR pathway allows for precise genome editing via the use of sister chromatids or exogenous DNA molecules. Many attempts have been made to improve the HDR efficiency, but the efficiency remains relatively low. For example, the simultaneous knock-down of both KU70 and DNA ligase IV with siRNAs improved the HDR efficiency by 4 to 5 fold. See Chu, et al., *Nat. Biotechnol.* 33:543-548 (2015). The use of a Cas9 nickase and a long DNA donor template resulted in 5% HDR efficiency in human embryonic stem cells (hESCs). Sec Rong, et al., *"Homologous recombination in human embryonic stem cells using CRISPR/Cas9 nickase and a long DNA donor template"*, Protein Cell 5:258-260 (2014). A recent report showed that the combined use of CRISPR system and in utero electroporation technique resulted in approximately 2% EGFP integration efficiency to β-actin gene in neurons in the brain. Sec Uemura, et al., *"Fluorescent protein tagging of endogenous protein in brain neurons using CRISPR/Cas9-mediated knock-in and in utero electroporation techniques"*, Sci Rep. 6:35861 (2016). The dual loss of human POLQ and LIG4 was shown to eliminate random integration. However, a large number of undefined insertions were also observed. See Saito, et al., *"Dual loss of human POLQ and LIG4 abolishes random integration"*, Nat. Commun. 8:16112 (2017). The use of adeno-associated virus (AAV) system at a multiplicity of infection of 106 allowed integration of a chimeric antigen receptor (CAR) into TRAC locus with approximately 40% efficiency. See Eyquem, et al., *"Targeting a CAR to the TRAC locus with CRISPR/Cas9 enhances tumour rejection"*, Nature 543:113-117 (2017). Although recombinant AAV system is considered to be safe to treat serious human diseases, the production of GMP grade AAV requires establishment of rigorous quality control systems.

Traditionally, long homology arms (500 bp to 2 kb) are used to integrate relatively large DNA fragments into the mammalian genome, which requires constructing of targeting vectors and screening of a large number of single cell colonies due to low efficiency and random integration. Thus, this process is usually slow (about 4 to 6 months) and tedious, which hampers the use of mammalian cells for expression of recombinant proteins. To accelerate the protein production process, transient gene expression is often used to eliminate the colony screening step. Although transient expression results in high level of protein production, the transgenes are only expressed for a limited period of time. Therefore, it becomes expensive to produce recombinant proteins using mammalian systems. To meet the future market demands of recombinant proteins for biopharmaceutical use, cost effective methods for rapid and efficient selection of highly productive clones are needed.

The present disclosure relates, in part, to compositions and methods for editing of nucleic acid molecules. There exists a substantial need for efficient systems and techniques for modifying genomes. This need is addressed herein, as well as related advantages. In particular, some embodiments provide a method for cloning of relatively large DNA molecules into mammalian genome directly via the combined use of promoter trapping and short homology arms. Because of the high efficiency and specificity, one could bypass the clonal cell isolation step to produce recombinant protein using the stable cell pool.

SUMMARY

Compositions and methods set out here are directed to improvements in gene editing. As set out elsewhere herein, a number of compositions and methods have been identified that allow for increased gene editing efficiency.

Described herein are methods for homologous recombination in an initial nucleic acid molecule comprising generating a double-stranded break in the initial nucleic acid molecule to produce a cleaved nucleic acid molecule, and contacting the cleaved nucleic acid molecule with a donor nucleic acid molecule, wherein the initial nucleic acid molecule comprises a promoter and a gene, wherein the donor nucleic acid molecule comprises: (i) matched termini on the 5' and 3' ends of 12 bp to 250 bp in length, (ii) a promoterless selection marker, (iii) a reporter gene, (iv) a self-cleaving peptide linking the promoterless selection marker and the reporter gene or LoxP on either side of the promoterless selection marker, and (iv) optionally a linker between the promoterless selection marker and the reporter gene.

In some embodiments, the double-stranded break in the nucleic acid molecule is: (i) less than or equal to 250 bp from the ATG start codon for N-terminal tagging of the cleaved nucleic acid molecule; or (ii) less than or equal to 250 bp from the stop codon for C-terminal tagging of the cleaved nucleic acid molecule.

In some embodiments, the double-stranded break is induced by at least one nucleic acid cutting entity or electroporation. In some embodiments, the at least one nucleic acid cutting entity comprises a nuclease comprising at least one or one or more zinc finger protein, one or more transcription activator-like effectors (TALEs), one or more CRISPR complex, one or more argonaute-nucleic acid complex, or one or more macronuclease. In some embodiments, the at least one nucleic acid cutting entity is administered using an expression vector, a plasmid, ribonucleoprotein complex (RNC), or mRNA.

In some embodiments, the promoterless selection marker comprises a protein, antibiotic resistance selection marker, cell surface marker, cell surface protein, metabolite, or active fragment thereof. In some embodiments, the promoterless selection marker is a protein. In some embodiments, the protein is focal adhesion kinase (FAK), angiopoietin-related growth factor (AGF) receptor, or epidermal growth factor receptor (EGFR).

In some embodiments, the promoterless selection marker is an antibiotic resistance selection marker. In some embodiments, the antibiotic resistance selection marker is a recombinant antibody. In some embodiments, the antibiotic resistance selection marker is a human IgG antibody.

In some embodiments, the reporter gene comprises a fluorescent protein reporter. In some embodiments, the fluorescent protein reporter is emerald green fluorescent protein (EmGFP) reporter or orange fluorescent protein (OFP) reporter.

In some embodiments, the promoterless selection marker is: (i) linked to the 5' end of a reporter gene for N-terminal tagging of the cleaved nucleic acid molecule; or (ii) linked to the 3' end of the reporter gene for C-terminal tagging of the cleaved nucleic acid molecule.

In some embodiments, the donor nucleic acid molecule comprises the linker between the promoterless selection marker and the reporter gene. In some embodiments, the distance between the promoterless selection marker and the reporter gene is less than or equal to 300 nt, 240 nt, 180 nt, 150 nt, 120 nt, 90 nt, 60 nt, 30 nt, 15 nt, 12 nt, or 9 nt. In some embodiments, the distance is 6 nucleotides. In some embodiments, the linker is a polyglycine linker (e.g., from about 2 to about 5 glycine residues).

In some embodiments, the self-cleaving peptide is a self-cleaving 2A peptide.

In some embodiments, the matched termini are added to the 5' and 3' ends of the donor nucleic acid molecule by PCR amplification.

In some embodiments, the matched termini share a sequence identity greater than or equal to 95%.

In some embodiments, the matched termini comprise single-stranded DNA or double-stranded DNA.

In some embodiments, the matched termini on the 5' and 3' ends of the donor nucleic acid molecule have a length of 12 bp to 200 bp, 12 bp to 150 bp, 12 bp to 100 bp, 12 bp to 50 bp, or 12 bp to 40 bp. In some embodiments, the matched termini have a length of 35 base pairs (bp).

In some embodiments, the initial nucleic acid molecule is in a cell or a plasmid.

In some embodiments, the donor nucleic acid molecule comprises a length of less than or equal to 1 kb, 2 kb, 3 kb, 5 kb, 10 kb, 15 kb, 20 kb, 25 kb, or 30 kb.

In some embodiments, the donor nucleic acid molecule is integrated into the cleaved nucleic acid molecule by homology directed repair (HDR). In some embodiments, wherein the HDR is greater than or equal to 10%, 25%, 50%, 75%, 90%, 95%, 98%, 99%, or 100%. In some embodiments, the HDR is 100%.

In some embodiments, integration efficiency of the donor nucleic acid molecule is greater than or equal to 50%, 75%, 90%, 95%, 98%, 99%, or 100%. In some embodiments, integration efficiency of the donor nucleic acid molecule is 100%.

In some embodiments, the method further comprises modifying the donor nucleic acid molecule at the 5' end, the 3' end, or the 5' and 3' ends. In some embodiments, the donor nucleic acid molecule is modified at the 5' and 3' ends. In some embodiments, the donor nucleic acid molecule is modified with one or more nuclease resistant groups in at least one strand of at least one terminus. In some embodiments, the one or more nuclease resistant groups comprises one or more phosphorothioate groups, one or more amine groups, 2'-O-methyl nucleotides, 2'-deoxy-2'-fluoro nucleotides, 2'-deoxy nucleotides, 5-C-methyl nucleotides, or a combination thereof.

In some embodiments, the method further comprises treating the donor nucleic acid molecule with at least one non-homologous end joining (NHEJ) inhibitor. In some embodiments, the at least one NHEJ inhibitor is a DNA-dependent protein kinase (DNA-PK), a DNA ligase IV, DNA polymerase 1 or 2 (PARP-1 or PARP-2), or combination thereof. In some embodiments, the DNA-PK inhibitor is Nu7206 (2-(4-Morpholinyl)-4H-naphthol[1,2-b]pyran-4-one), Nu7441 (8-(4-Dibenzothienyl)-2-(4-morpholinyl)-4H-1-benzopyran-4-one), Ku-0060648 (4-Ethyl-N-[4-[2-(4-morpholinyl)-4-oxo-4H-1-benzopyran-8-yl]-1-dibenzothienyl]-1-piperazineacetamide), Compound 401 (2-(4-Morpholinyl)-4H-pyrimido[2,1-a]isoquinolin-4-one), DMNB (4,5-Dimethoxy-2-nitrobenzaldehyde), ETP 45658 (3-[1-Methyl-4-(4-morpholinyl)-1H-pyrazolo[3,4-d]pyrimidin-6-ylphenol), LTURM 34 (8-(4-Dibenzothienyll)-2-(4-morpholinyl)-4H-1,3-benzoxazin-4-one), or Pl 103 hydrochloride (3-[4-(4-Morpholinylpyrido[3',2':4,5]furo[3,2-d] pyrimidin-2-yl]phenol hydrochloride).

In some embodiments, the mammal is a human, a mammalian laboratory animal, a mammalian farm animal, a mammalian sport animal, or a mammalian pet. In some embodiments, the mammal is a human.

In some embodiments, a cell or plasmid is made by any of the methods for homologous recombination described herein. In some embodiments, the cell is a eukaryotic cell. In some embodiments, the eukaryotic cell is a mammalian cell.

Also described herein is a method of cell therapy, comprising administering an effective amount of any of the cells described herein to a subject in need thereof.

In some embodiments, the cell is a T-cell and the promoterless selection marker is a chimeric antigen receptor (CAR).

Also described herein is a method for producing a promoterless selection marker, comprising activating the promoter of a cell or plasmid made by any of the methods of homologous recombination described herein to produce the promoterless selection marker.

Also described herein is a composition comprising a promoterless selection marker produced by any of the methods for producing a promotorless selection marker described herein.

Also described herein is a method for therapeutic treatment of a subject in need thereof, comprising administering an effective amount of the promoterless selection marker produced by any of the methods for producing a promotorless selection marker described herein.

Also described herein is a drug screening assay comprising the promoterless selection marker produced by any of the methods for producing a promotorless selection marker described herein.

Also described herein is a kit for producing a promoterless selection marker, comprising a promoterless selection marker linked to a reporter gene by a self-cleaving peptide or LoxP on either side of the selection marker. In some embodiments, the reporter gene is GFP or OFP. In some embodiments, the kit further comprises at least one nucleic acid cutting entity. In some embodiments, the kit further comprises at least one NHEJ inhibitor. In some embodiments, the kit further comprises one or more nuclease resistant groups.

Also described herein is a recombinant antibody expression cassette comprising: matched termini on the 5' and 3' ends of the cassette, wherein the matched termini are of less than or equal to 250 bp in length; a promoterless selection marker; a reporter gene; a self-cleaving peptide linking the promoterless selection marker and the reporter gene; and optionally, a linker between the promoterless selection marker and the reporter gene, wherein the promoterless selection marker is linked at the 5' end of the reporter gene for N-terminal tagging of a cleaved nucleic acid molecule, or at the 3' end of the reporter gene for C-terminal tagging of a cleaved nucleic acid molecule.

Also described herein are compositions and methods for altering an endogenous nucleic acid molecule present within a cell, the method comprising introducing a donor nucleic acid molecule (e.g., a donor DNA molecule) into the cell, wherein the donor nucleic acid molecule is operably linked to one or more intracellular targeting moiety capable of localizing the donor nucleic acid molecule to a location in the cell where the endogenous nucleic acid molecule is located.

In some embodiments, the location in the cell where the endogenous nucleic acid molecule is located is in the nucleus, mitochondria, or chloroplasts.

In some aspects, gene editing proteins, as well as associated methods, are provided that allow for the efficient site specific cleavage of intracellular nucleic acid molecule even when introduced into cells in small amounts. Thus, compositions and methods are provided that allow for high levels of site specific cleavage even when present in low concentrations. A number of factors may affect the amount of intracellular nucleic acid cleavage that occurs. Such factors include (1) the amount of active gene editing reagent that contact the genetic locus intended for cleavage, (2) the level of cleavage activity exhibited by the gene editing reagent, and (3) the amount of donor nucleic acid that is in close proximity to the cleavage site. Put a more general way, the amount editing that occurs at a specific intracellular genetic locus in a cell population is determined by the percent of cells where, with respect to diploid cells, at least one locus is cleaved.

In some embodiments, the one or more intracellular targeting moiety is a nuclear localization signal. In some embodiments, the nuclear localization signal is operable linked to the 5' end of the donor nucleic acid molecule.

In some embodiments, the donor nucleic acid molecule is operable linked to at least one nucleic acid cutting entity. In some embodiments, the at least one nucleic acid cutting entity comprises a nuclease comprising one or more zinc finger protein, one or more transcription activator-like effectors (TALEs), one or more CRISPR complex, one or more argonaute-nucleic acid complex, one or more macronuclease, or one or more meganuclease.

In some embodiments, the donor DNA molecule is not linked to a nucleic acid cutting entity.

In some embodiments, the donor nucleic acid molecule (e.g., a donor DNA molecule) is from about 25 to about 8,000 nucleotides (e.g., from about 25 to about 8,000 nucleotides, from about 25 to about 5,000 nucleotides, from about 25 to about 3,000 nucleotides, from about 25 to about 2,000 nucleotides, from about 25 to about 1,500 nucleotides, from about 30 to about 100 nucleotides, from about 30 to about 200 nucleotides, from about 50 to about 500 nucleotides, from about 50 to about 2,000 nucleotides, from about 50 to about 8,000 nucleotides, from about 75 to about 2,000 nucleotides, from about 250 to about 5,000 nucleotides, etc.) in length. One example of where a short donor nucleic acid molecule may be desirable is for SNP insertion or correction. As an example, in such an instance, the donor nucleic acid molecule may have two homology arms of 15 nucleotides each and a single nucleotide for altering the target locus.

Further, the donor nucleic acid molecule may be single-stranded, double-stranded, linear or circular.

Additionally, the donor nucleic acid molecule may have one or more nuclease resistant groups within 50 nucleotides of at least one terminus. These the nuclease resistant groups may be phosphorothioate groups. Further, two phosphorothioate groups may be located within 50 nucleotides of at least one terminus.

In some embodiments, the donor nucleic acid molecule contains a positive selectable marker and/or a negative selectable marker. Further, the negative selectable marker may be Herpes simplex virus thymidine kinase.

In certain embodiments, the donor nucleic acid molecule has two regions of sequence complementarity with a target locus present in the cell. Further, the positive selectable marker, when present, may be located between the two regions of sequence complementarity of the donor nucleic acid molecule. Additionally, the negative selectable marker, when present may not located between the two regions of sequence complementarity of the donor nucleic acid molecule. In other words, the negative selectable marker may be located outside of the two regions of sequence complementarity.

In some embodiments, donor nucleic acid molecules operably linked to one or more intracellular targeting moiety capable of localizing the donor DNA molecule to a location in the cell where the endogenous nucleic acid molecule is located may be used in conjunction with other compositions and methods set out herein. Thus, further provided herein are methods where the cell is additionally contacted with one or more of the following: (1) one or more nucleic acid cutting entity, (2) one or more nucleic acid molecule encoding at least one component of a nucleic acid cutting entity, (3) one or more DNA-binding modulation-enhancing agent, (4) one or more nucleic acid molecule encoding at least one component of a DNA-binding modulation-enhancing agent, or (5) one or more non-homologous end joining (NHEJ) inhibitor.

As set out elsewhere herein, the use of non-homologous end joining (NHEJ) inhibitor has been found to enhance the efficiency of homologous recombination. Thus, further provided herein are methods where the cells are contacted with and, in particular, where the one or more non-homologous end joining (NHEJ) inhibitor is a DNA-dependent protein kinase inhibitor. Additional, non-homologous end joining (NHEJ) inhibitors that may be used include one or more compound selected from the groups consisting of: (1)

Nu7206, (2) Nu7441, (3) Ku-0060648, (4) DMNB, (5) ETP 45658, (6) LTURM 34, and (7) Pl 103 hydrochloride.

Further, donor nucleic acid molecules operably linked to one or more intracellular targeting moiety may be introduced into cells in conjunction with the use of gene editing reagents designed to cut intracellular DNA at the target locus. Thus, the at least one of the one or more nucleic acid cutting entities may be selected from the group consisting of: (1) a zinc finger nuclease, (2) a TAL effector nuclease, and (3) a CRISPR complex. Similarly, the invention includes the use of at least one of the one or more DNA-binding modulation-enhancing agent selected from the group consisting of: (1) a zinc finger nuclease, (2) a TAL effector nuclease, and (3) a CRISPR complex. Further, the at least one of the one or more DNA-binding modulation-enhancing agents, when used, may be designed to bind within 50 nucleotides of the target locus.

The invention further includes, in part, methods for performing homologous recombination in eukaryotic cells, these method comprising contacting the cells with: (1) a donor nucleic acid molecule (e.g., a donor DNA molecule) and (2) (i) a nucleic acid cutting entity, (ii) nucleic acid encoding a nucleic acid cutting entity, or (iii) at least one component of a nucleic acid cutting entity and nucleic acid encoding at least one components of a nucleic acid cutting entity, wherein the donor nucleic acid molecule is bound to an intracellular targeting moiety capable of localizing the donor nucleic acid molecule to a location in the cells where the endogenous nucleic acid molecule is located.

Such methods further include contacting the cells with one or more of the following: (1) one or more non-homologous end joining (NHEJ) inhibitor, (2) one or more DNA-binding modulation-enhancing agent, (3) one or more nucleic acid encoding a DNA-binding modulation-enhancing agent, and (4) at least one component of one or more a DNA-binding modulation-enhancing agent and nucleic acid encoding at least one components of one or more a DNA-binding modulation-enhancing agent.

The invention also includes, in part, compositions comprising nucleic acid molecules (e.g., DNA molecules), wherein the nucleic acid molecules are covalently linked to one or more intracellular targeting moiety and wherein the nucleic acid molecule is from about 25 nucleotides to about 8,000 nucleotides (e.g., from about 25 to about 8,000 nucleotides, from about 25 to about 5,000 nucleotides, from about 25 to about 3,000 nucleotides, from about 25 to about 2,000 nucleotides, from about 25 to about 1,500 nucleotides, from about 30 to about 100 nucleotides, from about 30 to about 200 nucleotides, from about 50 to about 500 nucleotides, from about 50 to about 2,000 nucleotides, from about 50 to about 8,000 nucleotides, from about 75 to about 2,000 nucleotides, from about 250 to about 5,000 nucleotides, etc.) in length. In some instances, the nucleic acid molecules are donor nucleic acid molecules (e.g., donor DNA molecules). In some instances, the one or more intracellular targeting moiety is a nuclear localization signal. In additional instances, two or more intracellular targeting moieties (e.g., nuclear localization signals, a chloroplast targeting signals, a mitochondrial targeting signals, etc.) are covalently linked to nucleic acid molecules.

In one aspect, a method of increasing accessibility of a target locus in a cell is provided. The method includes (1) introducing into a cell including a nucleic acid encoding a target locus a first DNA-binding modulation-enhancing agent, wherein the first DNA-binding modulation-enhancing agent is not endogenous to the cell; and (2) allowing the first DNA-binding modulation-enhancing agent to bind a first enhancer binding sequence of the target locus, thereby increasing accessibility of the target locus relative to the absence of the first DNA-binding modulation-enhancing agent.

In one aspect, a method of displacing chromatin of a target locus in a cell is provided. The method includes (1) introducing into a cell including a nucleic acid encoding a target locus a first DNA-binding modulation-enhancing agent, wherein the first DNA-binding modulation-enhancing agent is not endogenous to the cell; and (2) allowing the first DNA-binding modulation-enhancing agent to bind a first enhancer binding sequence of the target locus, thereby displacing chromatin of the target locus.

In one aspect, a method of restructuring chromatin of a target locus in a cell is provided. The method includes (1) introducing into a cell including a nucleic acid encoding a target locus a first DNA-binding modulation-enhancing agent, wherein the first DNA-binding modulation-enhancing agent is not endogenous to the cell; and (2) allowing the first DNA-binding modulation-enhancing agent to bind a first enhancer binding sequence of the target locus, thereby restructuring chromatin of the target locus.

In one aspect, a method of increasing accessibility of a target locus in a cell is provided. The method includes (1) introducing into a cell including a nucleic acid encoding a target locus (i) a first DNA-binding modulation-enhancing agent, wherein the first DNA-binding modulation-enhancing agent is not endogenous to the cell; and (ii) a second DNA-binding modulation-enhancing agent, wherein the second DNA-binding modulation-enhancing agent is not endogenous to the cell. (2) The first DNA-binding modulation-enhancing agent is allowed to bind a first enhancer binding sequence of the target locus; and (3) the second DNA-binding modulation-enhancing agent is allowed to bind a second enhancer binding sequence of the target locus, thereby increasing accessibility of the target locus relative to the absence of the first DNA-binding modulation-enhancing agent or the second DNA-binding modulation-enhancing agent.

In one aspect, a method of displacing chromatin of a target locus in a cell is provided. The method includes (1) introducing into a cell including a nucleic acid encoding a target locus: (i) a first DNA-binding modulation-enhancing agent, wherein the first DNA-binding modulation-enhancing agent is not endogenous to the cell; and (ii) a second DNA-binding modulation-enhancing agent, wherein the second DNA-binding modulation-enhancing agent is not endogenous to the cell. (2) The first DNA-binding modulation-enhancing agent is allowed to bind a first enhancer binding sequence of the target locus; and (3) the second DNA-binding modulation-enhancing agent is allowed to bind a second enhancer binding sequence of the target locus, thereby displacing chromatin of the target locus.

In one aspect, a method of restructuring chromatin of a target locus in a cell is provided. The method includes (1) introducing into a cell including a nucleic acid encoding a target locus: (i) a first DNA-binding modulation-enhancing agent, wherein the first DNA-binding modulation-enhancing agent is not endogenous to the cell; and (ii) a second DNA-binding modulation-enhancing agent, wherein the second DNA-binding modulation-enhancing agent is not endogenous to the cell. (2) The first DNA-binding modulation-enhancing agent is allowed to bind a first enhancer binding sequence of the target locus; and (3) the second DNA-binding modulation-enhancing agent is allowed to bind a second enhancer binding sequence of the target locus, thereby restructuring chromatin of the target locus.

In one aspect, a method of enhancing activity of a modulating protein or a modulating complex at a target locus in a cell is provided. The method includes (1) introducing into a cell including a nucleic acid encoding a target locus: (i) a first modulating protein or a first modulating complex capable of binding a modulator binding sequence of the target locus, wherein the modulator binding sequence includes a modulation site; and (ii) a first DNA-binding modulation-enhancing agent capable of binding a first enhancer binding sequence of the target locus. And (2) allowing the first DNA-binding modulation-enhancing agent to bind the first enhancer binding sequence, thereby enhancing activity of the first modulating protein or the first modulating complex at a target locus in a cell.

In one aspect, a method of modulating a target locus in a cell is provided. The method includes (1) introducing into a cell including a nucleic acid encoding a target locus: (i) a first modulating protein or a first modulating complex capable of binding a modulator binding sequence of the target locus, wherein the modulator binding sequence includes a modulation site; and (ii) a first DNA-binding modulation-enhancing agent capable of binding a first enhancer binding sequence of the target locus. And (2) allowing the first modulating protein or the first modulating complex to modulate the modulation site, thereby modulating the target locus in a cell.

In embodiments, the method includes introducing a second DNA-binding modulation-enhancing agent capable of binding a second enhancer binding sequence of the target locus.

In embodiments, the first modulating protein or the first modulating complex is not endogenous to the cell.

In embodiments, the rate of homologous recombination at the target locus is increased relative to the absence of the first DNA-binding modulation-enhancing agent.

In embodiments, the second enhancer binding sequence is linked to the first enhancer binding sequence by the modulator binding sequence.

In embodiments, the method further includes introducing a second modulating protein or a second modulating complex capable of binding the modulator binding sequence.

In embodiments, the first modulating protein or the second modulating protein includes a DNA binding protein or a DNA modulating enzyme. In embodiments, the DNA binding protein is a transcriptional repressor or a transcriptional activator. In embodiments, the DNA modulating enzyme is a nuclease, a deaminase, a methylase or a demethylase.

In embodiments, the first modulating protein or the second modulating protein includes a histone modulating enzyme. In embodiments, the histone modulating enzyme is a deacetylase or an acetylase.

In embodiments, the first modulating protein is a first DNA binding nuclease conjugate. In embodiments, the second modulating protein is a second DNA binding nuclease conjugate. In embodiments, the first DNA binding nuclease conjugate includes a first nuclease and the second DNA binding nuclease conjugate includes a second nuclease. In embodiments, the first nuclease and the second nuclease form a dimer. In embodiments, the first nuclease and the second nuclease are independently a transcription activator-like effector nuclease (TALEN).

In embodiments, the first DNA binding nuclease conjugate includes a first transcription activator-like (TAL) effector domain operably linked to a first nuclease (TALEN). In embodiments, the first DNA binding nuclease conjugate includes a first TAL effector domain operably linked to a first FokI nuclease. In embodiments, the second DNA binding nuclease conjugate includes a second TAL effector domain operably linked to a second nuclease (TALEN). In embodiments, the second DNA binding nuclease conjugate includes a second TAL effector domain operably linked to a second FokI nuclease. In embodiments, the first DNA binding nuclease conjugate includes a first Zinc finger nuclease. In embodiments, the second DNA binding nuclease conjugate includes a first Zinc finger nuclease.

In embodiments, the first modulating complex is a first ribonucleoprotein complex. In embodiments, the second modulating complex is a second ribonucleoprotein complex. In embodiments, the first ribonucleoprotein complex includes a CRISPR associated protein 9 (Cas9) domain bound to a gRNA or an Argonaute protein domain bound to a guide DNA (gDNA). In embodiments, the second ribonucleoprotein complex includes a CRISPR associated protein 9 (Cas9) domain bound to a gRNA or an Argonaute protein domain bound to a guide DNA (gDNA).

In embodiments, the first modulating protein, the first modulating complex, the second modulating protein or the second modulating complex is not endogenous to the cell. In embodiments, the first modulating protein and the second modulating protein are not endogenous to the cell. In embodiments, the first modulating complex and the second modulating complex are not endogenous to the cell. In embodiments, the first DNA-binding modulation-enhancing agent or the second DNA-binding modulation-enhancing agent is not endogenous to the cell. In embodiments, the first DNA-binding modulation-enhancing agent and the second DNA-binding modulation-enhancing agent are not endogenous to the cell.

In embodiments, the first DNA-binding modulation-enhancing agent is a first DNA binding protein or a first DNA binding nucleic acid. In embodiments, the first DNA-binding modulation-enhancing agent is a first transcription activator-like (TAL) effector protein or a first truncated guide RNA (gRNA).

In embodiments, the second DNA-binding modulation-enhancing agent is a second DNA binding protein or a second DNA binding nucleic acid. In embodiments, the second DNA-binding modulation-enhancing agent is a TAL effector protein or a truncated gRNA.

In embodiments, the first DNA-binding modulation-enhancing agent is a first TAL effector protein and the second DNA-binding modulation-enhancing agent is a second TAL effector protein. In embodiments, the first DNA-binding modulation-enhancing agent is a TAL effector protein and the second DNA-binding modulation-enhancing agent is a truncated gRNA. In embodiments, the first DNA-binding modulation-enhancing agent is a first truncated gRNA and the second DNA-binding modulation-enhancing agent is a second truncated gRNA. In embodiments, the first DNA-binding modulation-enhancing agent is a truncated gRNA and the second DNA-binding modulation-enhancing agent is a TAL effector protein.

In embodiments, the first modulating protein is a first DNA binding nuclease conjugate and the second modulating protein is a second DNA binding nuclease conjugate. In embodiments, the first modulating protein is a DNA binding nuclease conjugate and the second modulating complex is a ribonucleoprotein complex. In embodiments, the first modulating complex is a first ribonucleoprotein complex and the second modulating complex is a second ribonucleoprotein complex. In embodiments, the first modulating complex is a ribonucleoprotein complex and the second modulating protein is a DNA binding nuclease conjugate.

In embodiments, the first enhancer binding sequence and/or second enhancer binding sequence are independently separated from the modulator binding sequence by less than 200 nucleotides (e.g., from about 5 to about 180, from about 10 to about 180, from about 20 to about 180, from about 5 to about 90, from about 5 to about 70, from about 5 to about 60, from about 5 to about 50, from about 5 to about 40, from about 5 to about 30, from about 15 to about 80, from about 15 to about 60, from about 15 to about 50, from about 15 to about 40, from about 20 to about 40, from about 20 to about 40, etc. nucleotides). In embodiments, the first enhancer binding sequences are independently separated from the modulator binding sequence by less than 150 nucleotides. In embodiments, the first enhancer binding sequence and/or second enhancer binding sequence is separated from the modulator binding sequence by less than 100 nucleotides. In embodiments, the first enhancer binding sequence and/or second enhancer binding sequence are independently separated from the modulator binding sequence by less than 50 nucleotides. In embodiments, the first enhancer binding sequence and/or second enhancer binding sequence are independently separated from the modulator binding sequence by 4 to 30 nucleotides. In embodiments, the first enhancer binding sequence and/or second enhancer binding sequence are independently separated from the modulator binding sequence by 7 to 30 nucleotides. In embodiments, the first enhancer binding sequence and/or second enhancer binding sequence is separated from the modulator binding sequence by 4 nucleotides, by 7 nucleotides, by 12 nucleotides, by 20 nucleotides or by 30 nucleotides.

In embodiments, the first enhancer binding sequence and/or the second enhancer binding sequence are independently separated from the modulation site by 10 to 40 nucleotides. In embodiments, the first enhancer binding sequence and/or the second enhancer binding sequence are independently separated from the modulation site by 33 nucleotides.

In embodiments, the first enhancer binding sequence has the sequence of SEQ ID NO:26, SEQ ID NO:28, SEQ ID NO:30, SEQ ID NO:32, SEQ ID NO:34, SEQ ID NO:36, SEQ ID NO:38, or SEQ ID NO:40. In embodiments, the second enhancer binding sequence has the sequence of SEQ ID NO:27, SEQ ID NO:29, SEQ ID NO:31, SEQ ID NO:33, SEQ ID NO:35, SEQ ID NO:37, SEQ ID NO:39, or SEQ ID NO:41.

In embodiments, the first DNA-binding modulation-enhancing agent or the second DNA-binding modulation-enhancing agent enhance activity of the first modulating protein, the first modulating complex, the second modulating protein or the second modulating complex at the modulation site.

In one aspect, a cell including a nucleic acid encoding a target locus modulating complex is provided. The complex includes, (i) a target locus including a first enhancer binding sequence and a modulator binding sequence including a modulation site; (ii) a first modulating protein or a first modulating complex bound to the modulator binding sequence; and (iii) a first DNA-binding modulation-enhancing agent bound to the first enhancer binding sequence.

In embodiments, the target locus further includes a second enhancer binding sequence linked to the first enhancer binding sequence by the modulator binding sequence.

In embodiments, the cell includes a second DNA-binding modulation-enhancing agent bound to the second enhancer binding sequence.

In one aspect, a cell including a nucleic acid encoding a target locus complex is provided. The complex includes (i)

a target locus including a first enhancer binding sequence; and (ii) a first DNA-binding modulation-enhancing agent bound to the first enhancer binding sequence, wherein the first DNA-binding modulation-enhancing agent is not endogenous to the cell and wherein the first DNA-binding modulation-enhancing agent is capable of increasing accessibility of the target locus relative to the absence of the first DNA-binding modulation-enhancing agent.

In one aspect, a cell including a nucleic acid encoding a target locus complex is provided. The complex includes (1) a target locus including: (i) a first enhancer binding sequence; and (ii) a second enhancer binding sequence. (2) A first DNA-binding modulation-enhancing agent bound to the first enhancer binding sequence of the target locus, wherein the first DNA-binding modulation-enhancing agent is not endogenous to the cell; and (3) a second DNA-binding modulation-enhancing agent bound to the second enhancer binding sequence of the target locus, wherein the second DNA-binding modulation-enhancing agent is not endogenous to the cell, wherein the first DNA-binding modulation-enhancing agent and the second DNA-binding modulation-enhancing agent are capable of increasing accessibility of the target locus relative to the absence of the first DNA-binding modulation-enhancing agent and the second DNA-binding modulation-enhancing agent.

In some aspects, kits are provided. Kits provided herein may include one or more of the following (i) a first modulating protein a first modulating complex; (ii) a first DNA-binding modulation-enhancing agent, (iii) one or more nucleic acid molecule, (iv) one or more intracellular targeting moiety, and (v) one or more non-homologous end joining inhibitor.

Also provided herein are gene editing reagents, such as Cas9 protein, and nucleic acids that encode such reagents comprising two or more (e.g., from about two to about twelve, from about three to about twelve, from about four to about twelve, from about five to about twelve, from about two to about seven, from about three to about seven, etc.) nuclear localization signals (NLS) (e.g., non-classical, monopartite and/or bipartite NLSs). Exemplary Cas9 proteins are those comprising two or more bipartite nuclear localization signals (NLS). Further, all or some of the two or more bipartite nuclear localization signals may be located within twenty amino acids of at least one terminus, such as the N-terminus and/or the C-terminus of the Cas9 protein. Location here refers to the portion of the NLS closest to the terminus. Thus, if the C-terminal amino acid of the NLS is followed by ten additional amino acids with the last amino acid being the C-terminus of the protein, then the NLS is located eleven amino acids from the C-terminus. In other word, the location count is determined by the last amino acid of the NLS.

Further, gene editing reagents (e.g., Cas9 proteins) may comprise NLSs that differ in amino acid sequence or have the same amino acid sequences. Also, gene editing reagents (e.g., Cas9 proteins) may comprise one or more (e.g., from about one to about five, from about one to about four, etc.) affinity tag. NLSs used in conjunction with gene editing reagent may comprise one or more of the following amino acid sequences: (A) KRTAD GSEFE SPKKK RKVE (SEQ ID NO: 48), (B) KRTAD GSEFE SPKKA RKVE (SEQ ID NO: 49), (C) KRTAD GSEFE SPKKK AKVE (SEQ ID NO: 50), (D) KRPAA TKKAG QAKKK K (SEQ ID NO: 51), and (E) KRTAD GSEFEP AAKRV KLDE (SEQ ID NO: 52). NLSs used in conjunction with gene editing reagent may comprise one or more amino acid sequence that fall within the scope of one or more of the following formulas:

(A) $KRX_{5-15}KKN_1N_2KV$ (SEQ ID NO: 53), (B) $KRX_{(5-15)}$ $K(K/R)(K/R)_{1-2}$ (SEQ ID NO: 54), (C) $KRX_{(5-15)}K(K/R)X$ $(K/R)_{1-2}$ (SEQ ID NO: 55), wherein X is an amino acid sequence from 5 to 15 amino acids in length and wherein $N_1$ is L or A, and wherein $N_2$ is L, A, or R. Further, specific Cas9 proteins of claim that may be used in compositions and methods setout herein comprise the amino acid sequence shown in FIG. 41 and FIG. 42.

Also, provided herein are TALE proteins comprising one or more (e.g., from about two to about six, from about two to about five, from about two to about four, from about two to about three, from about three to about five, etc.) heterologous nuclear localization signals (e.g., monopartite NLSs, bipartite NLSs, etc.). In some aspects, provided herein are TALE proteins comprising amino acids amino acids 811-830 of FIG. 46, wherein the amino acids at positions 815-816 and 824-825 are Gly-Ser or Gly-Gly, as well as TALE proteins comprising amino acids amino acids 810-1029 of FIG. 46, wherein the amino acids at positions 1022-1023 are Gly-Ser or Gly-Gly. Further, TALE protein provided herein may comprise amino acids amino acids 752-1021 of FIG. 46.

In some aspects, provided herein are TALE protein comprising amino acids amino acids 20-165 of FIG. 47, wherein the amino acids at positions 28-29 is Gly-Ser or Gly-Gly and wherein the amino acids at positions 108-110 and 823-824 are Arg-Gly-Ala or Gln-Trp-Ser. Further, TALE proteins provided herein may comprise amino acids amino acids 821-840 of FIG. 47, wherein the amino acids at positions 827-828 are Gly-Ser or Gly-Gly. TALE proteins may also comprise amino acids corresponding to FIG. 46.

TAL proteins in various aspects provided herein may comprising a repeat region comprising from 4 to 25 (e.g., from about 5 to about 22, from about 6 to about 22, from about 8 to about 22, from about 10 to about 22, from about 12 to about 22, from about 12 to about 26, from about 13 to about 20, etc.) repeat units.

Also provided herein are methods for engineering intracellular nucleic acid in cells, the methods comprising introducing into the cells one or more TALE protein (e.g., one or more TALE protein referred to above) or nucleic acid encoding the one or more TALE protein, wherein the one or more TALE protein is designed to bind to a target locus within the cells. In some aspects such methods further comprise introducing one or more donor nucleic acid molecule into the cells, wherein the one or more donor nucleic acid molecule has one or more region of sequence homology to nucleic acid within 50 (e.g., from about 0 to about 50, from about 0 to about 40, from about 0 to about 30, from about 0 to about 20, from about 6 to about 40, etc.) nucleotides of the target locus.

Further provided herein are methods for performing homologous recombination of intracellular nucleic acid molecules at cleavage sites within populations of cells, the method comprising: (a) generating one or more double-stranded breaks in the intracellular nucleic acid molecules at the cleavage site to produce cleaved nucleic acid molecules, and (b) contacting the cleaved nucleic acid molecules with one or more donor nucleic acid molecules, wherein the one or more donor nucleic acid molecules have at least ten (e.g., from about 10 to about 500, from about ten to about 500, from about 10 to about 400, from about 10 to about 300, from about 10 to about 250, from about 20 to about 300, from about 25 to about 300, from about 30 to about 350, etc.) nucleotides or base pairs of homology to nucleic acid located within 100 base pairs of each side of the cleavage sites, wherein at least 95% (e.g., from about 95% to about 100%, from about 95% to about 99%, from about 96% to about 99%, from about 95% to about 98%, from about 96% to about 99%, etc.) of the cells within the populations of cells undergo homology directed repair with at least one of the one or more donor nucleic acid molecules at the cleavage sites. In some aspects, the one or more donor nucleic acid molecules contains one or more selection marker or one or more reporter gene that is operably linked to a promoter present in the intracellular nucleic acid molecule after homology directed repair. Further, the one or more donor nucleic acid molecules may be linked to one or more nuclear localization signal that allow for the one or more donor nucleic acid molecules the donor nucleic acid molecule to localize to the nucleus of cells of the population of cells.

In some aspects, the populations of cells may be contacted with one or more of the following: (1) one or more nucleic acid cutting entity, (2) one or more nucleic acid molecule encoding at least one component of a nucleic acid cutting entity, (3) one or more DNA-binding modulation-enhancing agent, (4) one or more nucleic acid molecule encoding at least one component of a DNA-binding modulation-enhancing agent, and/or (5) one or more non-homologous end joining (NHEJ) inhibitor. Further, one or more of the one or more donor nucleic acid molecule may be single-stranded.

In additional aspects, the populations of cells may be contacted with one or more nucleic acid cutting entity or one of more nucleic acid molecule encoding one or more nucleic acid cutting entity and then the population of cells may be contacted with one or more donor nucleic acid molecule. Further, the population of cells may be contacted with one or more donor nucleic acid molecule, then the populations of cells may be contacted with one or more nucleic acid cutting entity or one of more nucleic acid molecule encoding one or more nucleic acid cutting entity. Further, the population of cells may be contacted with one or more donor nucleic acid molecule from 1 to 60 minutes after the population of cells is contacted with the one or more nucleic acid cutting entity or one of more nucleic acid molecule encoding one or more nucleic acid cutting entity. Conversely, the population of cells may be contacted with the one or more nucleic acid cutting entity or one of more nucleic acid molecule encoding one or more nucleic acid cutting entity from 1 to 60 minutes after the population of cells may be contacted with one or more donor nucleic acid molecule. In some instances, the population of cells may be contacted with the one or more nucleic acid cutting entity or one of more nucleic acid molecule encoding one or more nucleic acid cutting entity and one or more donor nucleic acid molecule simultaneously.

In additional aspects related to the above, one or more nucleic acid cutting entity or one of more nucleic acid molecule encoding one or more nucleic acid cutting entity and one or more donor nucleic acid molecule may be introduced into cells together or separately by electroporation. Further, one or more nucleic acid cutting entity or one of more nucleic acid molecule encoding one or more nucleic acid cutting entity may be introduced into cells first, followed by electroporation of one or more donor nucleic acid molecule OR one or more donor nucleic acid molecule may be introduced into cells first, followed by electroporation of one or more nucleic acid cutting entity or one of more nucleic acid molecule encoding one or more nucleic acid cutting entity.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate several embodiments and together with the description, serve to explain the principles described herein.

BRIEF DESCRIPTION OF THE DRAWINGS

For a more complete understanding of the principles disclosed herein, and the advantages thereof, reference is made to the following descriptions taken in conjunction with the accompanying drawings, in which:

FIG. 1A shows N-terminal tagging. The promoterless selection marker, puromycin, is linked to emerald green fluorescent protein (EmGFP) reporter or orange fluorescent protein (OFP) reporter gene via a self-cleaving 2A peptide, followed by addition of 35 nt homology arms at both 5' and 3' ends by PCR. The endogenous promoter drives the expression of puromycin, reporter gene, and endogenous gene. Double-stranded breaks (DSBs) are induced by either TALEN or CRISPR close to the translational start site. FIG. 1B shows C-terminal tagging. The EmGFP or OFP reporter gene is linked to a promoterless selection marker, puromycin, via a self-cleaving 2A peptide, followed by addition of 35 nt homology arms at both 5' and 3' ends. The endogenous promoter drives the expression of endogenous gene, reporter gene, and puromycin. DSBs are induced by either TALEN or CRISPR close to the translational stop site. The stop codon is eliminated between the endogenous gene and the reporter gene. In FIGS. 1A and 1B, the donor DNA is inserted into the genome through homologous recombination. Junctions at the 5' and 3' ends are analyzed by PCR with F1/R1 and F2/R2 primer sets, respectively.

In FIG. 2A, Cas9 RNP and various amounts of donor DNA with 35 nt homology arms were delivered into 293FT cells via electroporation. Samples in the absence of gRNA served as control. At 48 hours post transfection, the cells were analyzed by flow cytometry to determine the percentages of OFP-positive cells without puromycin selection (−). Alternatively, the cells were treated with puromycin for 7 days prior to flow cytometric analysis (+). In FIG. 2B, various homology arm lengths were added to the insertion cassette by PCR amplification and then co-transfected with Cas9 RNP into 293FT cells. The cells were analyzed by flow cytometry as described for FIG. 2A. In FIGS. 2C and 2D, Cas9 RNP and a donor plasmid with approximately 500 nt homology arms, or single-stranded (ss) or double-stranded (ds) DNA donor with 35 nt homology arms were transfected into either 293FT or human primary T cells via electroporation. At 48 hours post transfection, the cells were subjected to flow cytometric analysis.

FIGS. 3A and 3B show N-terminal and C-terminal junctions, respectively, with precise HDR (1) or HDR with Indel (2). The precise HDR (1) arrows in FIGS. 3A and 3B indicate the junction between genomic DNA and donor DNA or the Cas9 cleavage site. The sequences in bold in FIGS. 3A and 3B indicate the 35 nt homology arm. The Italic ATG indicates the start codon for beta actin. HDR with Indel (2) in FIGS. 3A and 3B show examples of Indel formation around the junction. FIG. 3A discloses SEQ ID NOS 130-134, respectively, in order of appearance. FIG. 3B discloses SEQ ID NOS 135-139, respectively, in order of appearance. FIG. 3C shows characterization of zygosity in clonal cells. Allele 1 had approximately 68% precise HDR at both junctions and 32% HDR with Indel occurred at either C or N terminus or both termini. Allele 2 had an "A" insertion in approximately 80% of the clones (∇1ntA), more than 2 nt deletion (Δ>2 nt) in 18% of the clones, and 2% wild type (wt). FIGS. 3D and 3E show N-terminal tagging of beta-actin with OFP via TALE nuclease. TALEN mRNA alone or TALEN mRNA with donor DNA were transfected into HEK293FT cells via NEON® electroporation (Thermo Fisher Scientific, cat. no. MPK5000). FIG. 3D shows genome editing efficiency (% Indel) and FIG. 3E shows the analysis by flow cytometry of the percentages of OFP-positive cells (−) and percentage OFP-positive puromycin treated cells (+).

FIG. 4A discloses SEQ ID NO: 140. FIG. 4B discloses SEQ ID NO: 141. Alternatively, a pair of outer primers was used to analyze the genome modification of two alleles (FIG. 4C). The resulting PCR products were analyzed by sequencing. Sequences in Bold in FIGS. 4A and 4B indicate the homology arms. Bottom arrows indicate the Cas9 cleavage site or junctions between genome DNA and donor DNA. Δ7nt_noHDR in FIG. 4C indicate no HDR occurred but with 7 nt deletion.

FIG. 6A shows the N-terminal junction analysis (SEQ ID NO: 70)
and FIG. 6B shows C-terminal junction analysis (SEQ ID NO: 71).
FIG. 6C shows genome modification on each allele. ∇1ntA_noHDR in FIG.
6C refers to one "A" insertion without insert.

In FIG. 7A end-modified
DNA primers were synthesized chemically and used for
preparation of donor DNA via PCR amplification. The Cas9
RNP and donor DNA were transfected into primary T cells
via electroporation. At 48 hours post transfection, the inser-
tion efficiency of puromycin-P2A-OFP DNA fragment into
beta-actin locus was monitored by flow cytometric assays.
In FIG. 7B NHEJ inhibitor was added to the culture medium
immediately after electroporation. "F" refers to forward
primer; "R" refers to reverse primer; "PS" refers to phos-
phorothioate; "NH2" refers to amine modification, and
"ssDNA" refers to single-stranded DNA.

FIGS. 8A, 8B, 8C, and 8D show cloning and expression
of recombinant antibody in mammalian genome. FIG. 8A
shows an antibody expression cassette that contains a pro-
moterless puromycin selection marker, followed by a self-
cleaving 2A peptide (SEQ ID NO:5). The expression of IgG
heavy chain (HC) and light chain (LC) was driven by a
CMV promoter. 35 nt homology arms were added by PCR.
FIG. 8B (SEQ ID NO: 72-76) and FIG. 8C (SEQ ID NO:
77-82) show N-terminal and C-terminal junction analysis,
respectively. Double-stranded breaks (DSBs) and junctions
between genomic DNA and donor DNA were indicated by
the arrows. The 35 nt homology arms and some extra
sequences were also highlighted in bold. The WPRE (Wood-
chuck Hepatitis Virus Posttranscriptional Regulatory Ele-
ment) and stop codon were shown in FIG. 8C. FIG. 8D
shows the relative percentage of clonal cells that produced
antibody (+) or did not produce antibody (–), which were
determined by ELISA assay.

FIG. 9. Nuclear localization signal (NLS)-donor DNA
designs (SEQ ID NOs: 83 & 127 and 84 & 128). Conjuga-
tion chemistries used to connect the NLS peptide were
succinimidyl 4-(N-maleimidomethyl) cyclohexane-1-car-
boxylate (SMCC) or CLICK-IT®.

FIG. 11. Dose response of a phosphorothioate (PS) oligo
donor DNA compared to an NLS modified donor DNA in
adding a 6 base sequence to restore GFP activity. Dose
response of PS oligo donor DNA compared to CLICK-IT®
linked NLS modified donor DNA.

FIG. 22. The figure shows the making of No-FokI C-term
fragment for "TAL-Buddy".

FIG. 23. The figure shows test "Buddy TAL" (293FT).
Target: CMPK1-C (SEQ ID NO:19); TALEN mRNA: 100
ng/each; TAL-Buddy: 7 nt spacing (SEQ ID NO:18);
NEON®: 1300/20/2. Repeat.

FIG. 24. The figure shows test spacing of Buddy TAL on
TALEN. Target: CMPK1; Cell: 293FT; NEON®: 1300/20/2.
Spacing matters, TAL cannot be directly next to TALEN.
Spacing (0, 4, 7, 20 nt) indicates the space between the 18
base recognition sequences of the TAL and the nearest
TALEN pair.

FIG. 25. The figure shows test Buddy TAL on enhancing
TALEN and CRISPR efficiency. Spacing can influence
cutting efficiency. TAL (grey hexagons) no difference
between 7 nt away from TALEN (dark grey arrows) and 20
nt away. With TAL and a CRISPR target (black circle
fragment), TAL 20 nt away is better.

FIG. 41 shows the amino acid sequence of Cas9 V1 (SEQ ID NO: 93). NLSs and His tag are labeled as such.

FIG. 42 shows the amino acid sequence of Cas9 V2 (SEQ ID NO: 94). NLSs are labeled as such.

FIG. 43 shows the format of a series of Cas9-NLS fusion proteins. "NP" refers to nucleoplasmin NLS. FIG. 43 discloses "6his" as SEQ ID NO: 129.

FIG. 46 shows the amino acid sequence of a TALEN protein (SEQ ID NO: 95). The format of this TALEN is referred to herein as "TALEN V3". The N-terminal region contains a V5 epitope and a "G-G" linker followed by a 136 amino acid region before the Repeat Region. The 136 amino acid region contains (1) a series of repeating units (labeled "R-3", "R-2", R-1", and "R0") with some sequence homology to the individual repeats of the Repeat Region and (2) a "T-Less Box", the amino acid sequence "RGA", which can be altered to alleviate the 5′ T requirement of the nucleic acid to which the TALEN binds to. The Repeat Region contains sixteen repeats of thirty-four amino acids. A half-repeat (labeled "R½") is immediately to the C-terminal end of the Repeat Region. Two nuclear localization signals (labeled "NLS") are located further towards the C-terminal end of the protein before and after the FokI nuclease domain.

FIG. 47 shows the amino acid sequence of a TALEN protein (SEQ ID NOs: 96 and 97) but the amino acid sequence of the Repeat Region has been removed to simplify the figure. Also, the protein represented in this figure has three NLSs.

FIG. 49 shows genomic cleavage detection and homology directed repair data, generated as set out below in Example 8, for three different genomic loci in two different cell types.

FIG. 50 shows genomic cleavage detection data, generated as set out below in Example 8, for three different genomic loci in A549 cells.

FIG. 52 show the amino acid sequence of a Buddy-TAL (SEQ ID NO: 143), which is the expression product of the nucleotide sequence set out in SEQ ID NO: 18. This Buddy-TAL has two NLSs (boxed), one each located at the N-terminus and the C-terminus of the protein. Further, the transcriptional activation domain normally present near the C-terminus has been deleted. The underlined central region of the protein is the repeat region. Two linkers (GS and GG) are also shown in boxes.

DETAILED DESCRIPTION

Overview

Figures 1A, 1B:
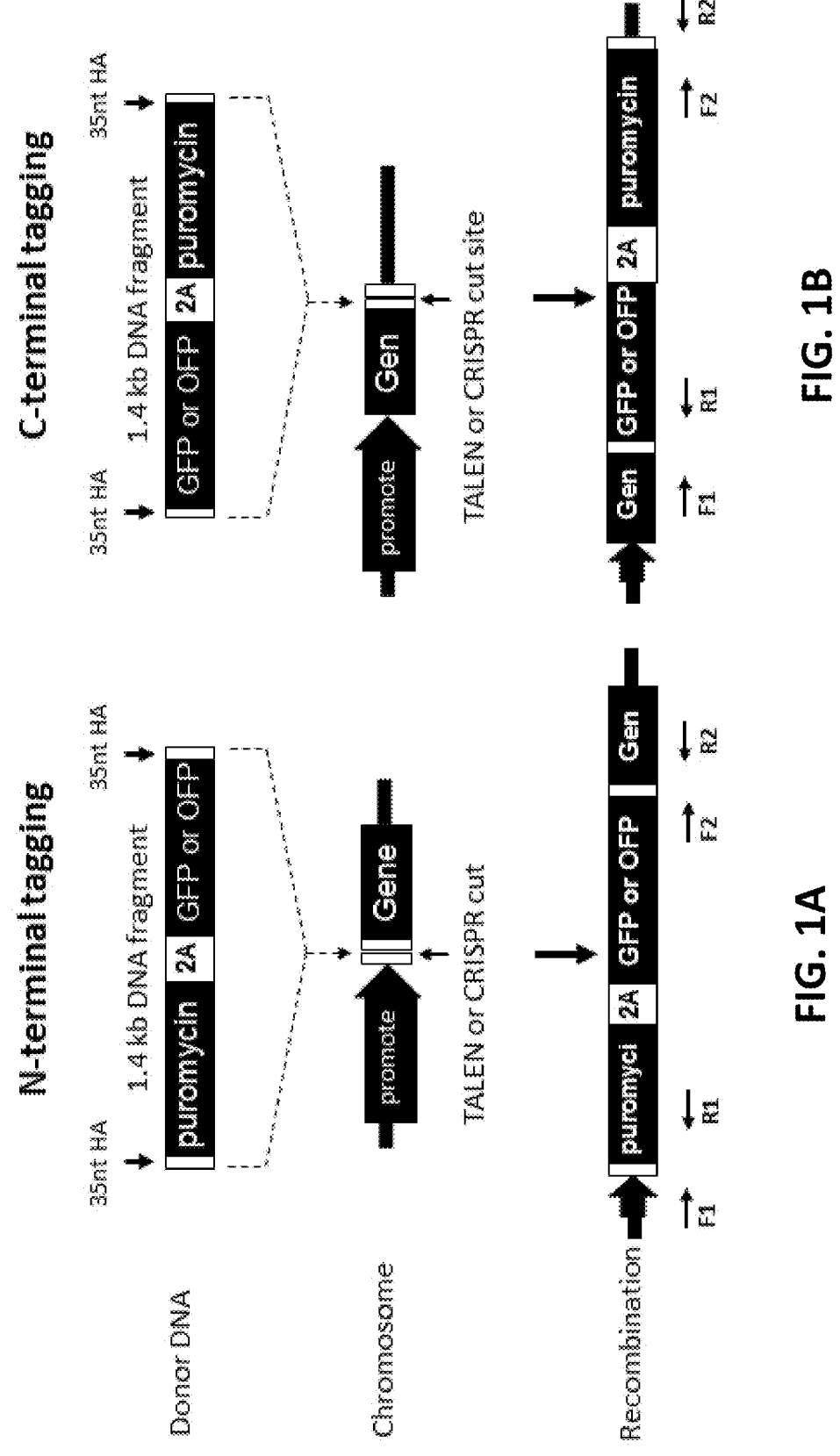
FIGS. 1A and 1B show protein tagging by promoter trapping and short homology arms.

Compositions and methods set out here are directed to improvements in gene editing. As examples, these improvements include the following:

i. The insertion of nucleic acid molecules (e.g., donor DNA molecules) into intracellular nucleic acid molecules, wherein the inserted nucleic acid molecules are operably linked to promoters present in the intracellular nucleic acid molecules.

ii. The use of non-homologous end-joining inhibitors to facilitate gene editing.

iii. The use of DNA binding molecules (e.g., DNA binging proteins, DNA binding protein/nucleic acid complexes) that bind at or near intracellular target loci, wherein the DNA binding proteins facilitate increased accessibility at target loci to other DNA binding molecules.

iv. The intracellular delivery of donor DNA to gene editing loci, as well as other DNA molecules to various locations within cells (e.g., linear DNA molecules containing open reading frames operably linked to promoter with delivery to mitochondria).

The above improvements may be used individually or in conjunction with other methods listed above, as well as additional methods.

In part, this disclosure concerns the discovery that the combined use of promoter trapping for the selection marker and short homology arms for recombination allows for near 100% integration efficiency with up to 100% precise HDR.

Unlike the traditional method using a targeting vector with 0.5 kb to 2 kb homology arms, the use of short homology arms appears to minimize the occurrence of random integration of foreign DNA of interest into the genome. On top of that, the use of promoter trapping of a selection marker allows selection of the correctly-integrated species because the promoterless selection marker expresses only when the DNA molecule is inserted into the genomic locus precisely. In some embodiments, end modification of donor DNA with, for example, phosphorothioate or amine groups, and/or treatment with NHEJ inhibitors, further improved the efficiency of HDR. The precision of integration of donor DNA is sequence-dependent. At some loci, 100% integration efficiency with 100% precise HDR can be achieved.

The disclosure also relates, in part, to compositions and methods for increasing the accessibility of intracellular nucleic acid regions to molecules or molecular complexes that interaction with the intracellular nucleic acid in these regions.

The disclosure further relates, in part, to compositions and methods for intracellular localization of nucleic acid molecules. In some instances, the nucleic acid molecules will be donor DNA molecules.

The disclosure also relates to various combinations of the above for facilitating processes such as gene editing, gene activation, gene repression, DNA methylation, etc.

The invention is directed, in part, to compositions and methods for enhanced gene editing. A number of variables factor into the efficiency of gene editing. With respect to homology directed repair (HDR), these factors include:

(1) the amount of (i) donor DNA and (ii) site-specific nuclease localized in the cell nucleus, as well as the amount of site-specific nuclease activity in the nucleus, (2) the degree of accessibility of the target locus to site-specific nucleases, (3) timing aspects related to the presence of donor and nuclease in cell nucleus, (4) target locus cleavage efficiency, (5) HDR efficiency (including the HDR:NHEJ ratio), and (6) donor DNA structure and composition.

It is expected that, in some instances, gene editing efficiencies of close to 100% can be achieved, especially with respect to HDR.

Localization of Gene Editing Reagents to the Nucleus: Since it is believed that many of the factors that affect gene editing efficiency are based upon concentration dependent mechanisms, the higher the amount of site-specific nuclease activity (a combination of the activity level of the nuclease and the amount of nuclease present) and the higher the concentration of donor DNA in the nucleus, the more HDR is expected to dominate over NHEJ.

While nucleic acid molecules and proteins may be produced in cells (e.g., vector based systems), in many instances, components of gene editing systems (e.g., donor DNAs, site specific nucleases, DNA-binding modulation-enhancing agents, etc.) will be introduced into cells. Such cellular introduction may be accomplished by methods such as transfection and electroporation.

Once gene editing system components have been introduce into cells, efficient localization to the nucleus is typically desirable. This is so because it is believed that efficient localization of gene editing system components to the nuclease is at least partly tied to cytoplasmic degradation (a combination of (i) degradation activity and (ii) the amount of time spent in the cytoplasm). Further, a number of factors can affect the efficiency of nuclear localization, including (1) association of gene editing system components with one or more NLS, (2) the choice NLS(s) used, and (3) chemical modification of one or more of the gene editing system components (e.g., donor DNA).

Figure 7A:
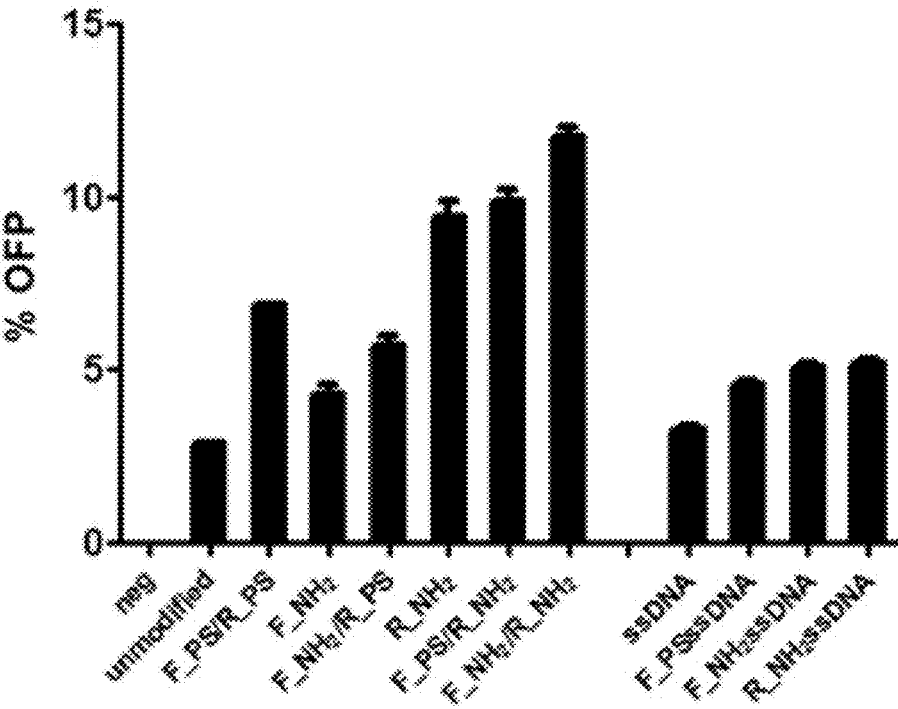
FIG. 7A shows the effect of end modification of DNA
donor on HDR efficiency and FIG. 7B shows the effect of
NHEJ inhibitor on HDR efficiency.

In many instances, nucleic acid molecules used in methods set out herein may be chemically modified. Chemical modifications include nuclease resistant groups such phosphorothioate groups, amine groups, 2'-O-methyl nucleotides, 2'-deoxy-2'-fluoro nucleotides, 2'-deoxy nucleotides, 5-C-methyl nucleotides, and combinations thereof. By way of example, the three nucleotides at the 5' and 3' termini gRNA molecules may contain phosphorothioate linkages and/or may be 2'-O-methyl nucleotides. It has also been found that amine terminal modifications of donor DNA enhances HDR (see, e.g., FIGS. 7A and 7B). This is believed in both instances to at least partly result from stabilization of donor DNA molecules in the cytoplasm. gRNA is also believed to be stabilized by association with Cas9 protein. It is thus believed that the cytoplasmic half-life of gRNA is increased when the gRNA is bound to Cas9 protein.

Data indicates and it is believed that gene editing efficiency is increased when gene editing system component are stabilized with respect to cytoplasmic degradation and are "shuttled" rapidly through the cytoplasm into the nucleus. Rapid movement of gene editing system component through the cytoplasm has another effect that will be beneficial in many instances. This allows for transient high nuclear concentration of gene editing system component activity in conjunction with a low cytoplasmic gene editing system component pool. Thus, once depletion of the high nuclear concentration of gene editing system component activity occurs, there is little or no cytoplasmic reservoir for additional gene editing activity.

Site Specific Target Locus Cleavage Activity: Target locus cleavage efficiency is determined by a number of factors, some of which are set out above. These factors include: (1) gene editing system cleavage activity, (2) the amount of cleavage mediating gene editing system components present at or near the target locus, and (3) the accessibility of the target locus to gene editing system cleavage activity, as set out herein.

The accessibility of a target locus to gene editing system cleavage activity can vary with natural effects in that it may be accessible or inaccessible in the genome or a particular cell type, or somewhere in between. Induction of transcriptional activation of the target locus prior to cleavage of that target locus may render the locus more accessible to cleavage activity. Another way to increase the accessibility of particular target loci is through the use of DNA-binding modulation-enhancing agents.

One consideration with respect to site specific target locus cleavage activity is "off-target" effects. Off-target effects can be minimized through the separate or combined use of DNA-binding modulation-enhancing agents, gRNA high target locus specificity, and high fidelity gene editing reagents (e.g., high fidelity Cas9).

Target Locus Alteration: There are two main types of gene editing that are commonly performed. These are where nucleic acid molecules are inserted into target loci and where no nucleic acid molecules are inserted into target loci but the nucleotide sequences at the target loci are altered. Further, there are three possibilities when a target locus is cleaved and "repaired". The target locus may be (1) unaltered as compared to the pre-cleavage nucleotide sequence, (2) modified by the deletion or additional of one or more bases without donor nucleic acid insertion, or (3) donor DNA insertion may be introduced at or near the cleavage site. The first two of these possibilities often result from NHEJ based repair mechanisms. The third of these possibilities is typically based upon HDR based mechanisms. In many instances, especially where it is desirable to insert donor DNA at the target locus, the third possibility is preferred. Thus, provided herein are compositions and methods for enhancing the efficiency of HDR and/or favoring HDR over NHEJ.

A number of factors have been found that result in efficient HDR with the insertion of donor nucleic acid molecules at cleavage sites. Some of these factors relate to features of the donor nucleic acid molecule. One of these factors is the length of donor DNA homology arms. In many instances, donor DNA molecules will have two homology arms that independently range in length from about 20 to about 2,000 nucleotides or base pairs, depending on whether the donor DNA is single-stranded or double-stranded. Further, double-stranded donor DNA may have 3' overhangs on one or both termini and these overhangs (as well as 5' overhangs) may range in length from about 10 to about 40 nucleotides. Also, one or both strands of one or both of homology arms of donor DNA molecules may contain one or more nuclease resistant groups (as discussed elsewhere herein) located at the termini or other locations within the arms.

A number of methods are available for favoring HDR over NHEJ repair. One method is by treating cells about to undergo gene editing with one or more inhibitors of NHEJ (see FIG. 7B). Another is by "knockdown" of intracellular NHEJ activity. This can be achieved by the use of, for example, antisense, microRNA and/or RNAi reagents designed to inhibit expression of one or more NHEJ repair pathway (e.g., DNA-dependent protein kinase, catalytic subunit; Ku70; and/or Ku80).

Definitions

As utilized in accordance with the present disclosure, the following terms, unless otherwise indicated, shall be understood to have the following meanings:

"Nucleic acid" refers to deoxyribonucleotides or ribonucleotides and polymers thereof in either single-, double-or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism. An "inhibitory nucleic acid" is a nucleic acid (e.g. DNA, RNA, polymer of nucleotide analogs) that is capable of binding to a target nucleic acid (e.g. an mRNA translatable into a protein) and reducing transcription of the target nucleic acid (e.g. mRNA from DNA) or reducing the translation of the target nucleic acid (e.g. mRNA) or altering transcript splicing (e.g. single stranded morpholino oligo).

As used herein the term "nucleic acid molecule" refers to a covalently linked sequence of nucleotides or bases (e.g., ribonucleotides for RNA and deoxyribonucleotides for DNA but also include DNA/RNA hybrids where the DNA is in separate strands or in the same strands) in which the 3' position of the pentose of one nucleotide is joined by a phosphodiester linkage to the 5' position of the pentose of the next nucleotide. A nucleic acid molecule may be singleor double-stranded or partially double-stranded. A nucleic acid molecule may appear in linear or circularized form in a supercoiled or relaxed formation with blunt or sticky ends and may contain "nicks". Nucleic acid molecules may be composed of completely complementary single strands or of partially complementary single strands forming at least one mismatch of bases. Nucleic acid molecules may further comprise two self-complementary sequences that may form a double-stranded stem region, optionally separated at one end by a loop sequence. The two regions of nucleic acid molecules which comprise the double-stranded stem region are substantially complementary to each other, resulting in self-hybridization. However, the stem can include one or more mismatches, insertions or deletions. As described above, nucleic acid molecules may include chemically, enzymatically, or metabolically modified forms of nucleic acid molecules or combinations thereof. Chemically synthesized nucleic acid molecules may refer to nucleic acids typically less than or equal to 150 nucleotides long (e.g., between 5 and 150, between 10 and 100, between 15 and 50 nucleotides in length) whereas enzymatically synthesized nucleic acid molecules may encompass smaller as well as larger nucleic acid molecules as described elsewhere in the application. Enzymatic synthesis of nucleic acid molecules may include stepwise processes using enzymes such as polymerases, ligases, exonucleases, endonucleases or the like or a combination thereof. The terms "genome editing" or "gene editing" as provided herein refer to stepwise processes involving enzymes such as polymerases, ligases, exonucleases, endonucleases or the like or a combinations thereof. For example, gene editing may include processes where a nucleic acid molecule is cleaved, nucleotides at the cleavage site or in close vicinity thereto are excised, new nucleotides are newly synthesized and the cleaved strands are ligated.

The term nucleic acid molecule also refers to short nucleic acid molecules, often referred to as, for example, "primers" or "probes." Primers are often referred to as single stranded starter nucleic acid molecules for enzymatic assembly reactions whereas probes may be typically used to detect at least partially complementary nucleic acid molecules. A nucleic acid molecule has a "5 '-terminus" and a "3'-terminus" because nucleic acid molecule phosphodiester linkages occur between the 5' carbon and 3' carbon of the pentose ring of the substituent mononucleotides. The end of a nucleic acid molecule at which a new linkage would be to a 5' carbon is its 5' terminal nucleotide. The end of a nucleic acid molecule at which a new linkage would be to a 3' carbon is its 3' terminal nucleotide. A terminal nucleotide or base, as used herein, is the nucleotide at the end position of the 3'- or 5'-terminus. A nucleic acid molecule sequence, even if internal to a larger nucleic acid molecule (e.g., a sequence region within a nucleic acid molecule), also can be said to have 5'- and 3'-ends.

A "vector" as used herein is a nucleic acid molecule that can be used as a vehicle to transfer genetic material into a cell. A vector can be a plasmid, a virus or bacteriophage, a cosmid or an artificial chromosome such as, e.g., yeast artificial chromosomes (YACs), bacterial artificial chromosomes (BAC) or other sequences which are able to replicate or be replicated in vitro or in a host cell, or to convey a desired nucleic acid segment to a desired location within a host cell. In embodiments a vector refers to a DNA molecule harboring at least one origin of replication, a multiple cloning site (MCS) and one or more selection markers. A vector is typically composed of a backbone region and at least one insert or transgene region or a region designed for insertion of a DNA fragment or transgene such as a MCS. The backbone region often contains an origin of replication for propagation in at least one host and one or more selection markers. A vector can have one or more restriction endonuclease recognition sites (e.g., two, three, four, five, seven, ten, etc.) at which the sequences can be cut in a determinable fashion without loss of an essential biological function of the vector, and into which a nucleic acid fragment can be spliced in order to bring about its replication and cloning. Vectors can further provide primer sites (e.g., for PCR), transcriptional and/or translational initiation and/or regulation sites, recombinational signals, replicons, selectable markers, etc. Clearly, methods of inserting a desired nucleic acid fragment which do not require the use of recombination, transpositions or restriction enzymes (such as, but not limited to, uracil N glycosylase (UDG) cloning of PCR fragments (U.S. Pat. Nos. 5,334,575 and 5,888,795, both of which are entirely incorporated herein by reference), T:A cloning, and the like) can also be applied to clone a fragment into a cloning vector to be used according to the present invention. In embodiments, a vector contains additional features. Such additional features may include natural or synthetic promoters, genetic markers, antibiotic resistance cassettes or selection markers (e.g., toxins such as ccdB or tse2), epitopes or tags for detection, manipulation or purification (e.g., V5 epitope, c-myc, hemagglutinin (HA), FLAG™, polyhistidine (His), glutathione-S-transferase (GST), maltose binding protein (MBP)), scaffold attachment regions (SARs) or reporter genes (e.g., green fluorescent protein (GFP), red fluorescence protein (RFP), luciferase, β-galactosidase etc.). In embodiments, vectors are used to isolate, multiply or express inserted DNA fragments in a target host. A vector can for example be a cloning vector, an expression vector, a functional vector, a capture vector, a co-expression vector (for expression of more than one open reading frame), a viral vector or an episome (i.e., a nucleic acid capable of extrachromosomal replication) etc.

A "cloning vector" as used herein includes any vector that can be used to delete, insert, replace or assemble one or more nucleic acid molecules. In embodiments a cloning vector may contain a counter selectable marker gene (such as, e.g., ccdB or tse2) that can be removed or replaced by another transgene or DNA fragment. In embodiments a cloning vector may be referred to as donor vector, entry vector, shuttle vector, destination vector, target vector, functional vector or capture vector. Cloning vectors typically contain a series of unique restriction enzyme cleavage sites (e.g., type II or type IIS) for removal, insertion or replacement of DNA fragments. Alternatively, DNA fragments can be replaced or inserted by TOPO® Cloning or recombination as, e.g., employed in the GATEWAY® Cloning System offered by Invitrogen/Life Technologies (Carlsbad, CA) and described in more detail elsewhere herein. A cloning vector that can be used for expression of a transgene in a target host may also be referred to as expression vector. In embodiments a cloning vector is engineered to obtain a TAL effector conjugate.

An "expression vector" is designed for expression of a transgene and generally harbors at least one promoter sequence that drives expression of the transgene. Expression as used herein refers to transcription of a transgene or transcription and translation of an open reading frame and can occur in a cell-free environment such as a cell-free expression system or in a host cell. In embodiments expression of an open reading frame or a gene results in the production of a polypeptide or protein. An expression vector is typically designed to contain one or more regulatory sequences such as enhancer, promoter and terminator regions that control expression of the inserted transgene. Suitable expression vectors include, without limitation, plasmids and viral vectors. Vectors and expression systems for various applications are available from commercial suppliers such as Novagen (Madison, WI), Clontech (Palo Alto, CA), Stratagene (La Jolla, CA), and Life Technologies Corp. (Carlsbad, CA). In embodiments an expression vector is engineered for expression of a TAL effector fusion.

A "viral vector" generally relates to a genetically-engineered noninfectious virus containing modified viral nucleic acid sequences. In embodiments, a viral vector contains at least one viral promoter and is designed for insertion of one or more transgenes or DNA fragments. In embodiments a viral vector is delivered to a target host together with a helper virus providing packaging or other functions. In embodiments viral vectors are used to stably integrate transgenes into the genome of a host cell. A viral vector may be used for delivery and/or expression of transgenes.

Viral vectors may be derived from bacteriophage, baculoviruses, tobacco mosaic virus, vaccinia virus, retrovirus (avian leukosis-sarcoma, mammalian C-type, B-type viruses, D type viruses, HTLV-BLV group, lentivirus, spumavirus), adenovirus, parvovirus (e.g., adenoassociated viruses), coronavirus, negative strand RNA viruses such as orthomyxovirus (e.g., influenza virus) or sendai virus, rhabdovirus (e.g., rabies and vesicular stomatitis virus), paramyxovirus (e.g., measles and Sendai), positive strand RNA viruses such as picornavirus and alphavirus (such as Semliki Forest virus), and double-stranded DNA viruses including adenovirus, herpes virus (e.g., Herpes Simplex virus types 1 and 2, Epstein-Barr virus, cytomegalovirus), and poxvirus (e.g., vaccinia, fowlpox and canarypox). Other viruses include without limitation Norwalk virus, togavirus, flavivirus, reoviruses, papovavirus, hepadnavirus, and hepatitis virus. For example common viral vectors used for gene delivery are lentiviral vectors based on their relatively large packaging capacity, reduced immunogenicity and their ability to stably transduce with high efficiency a large range of different cell types. Such lentiviral vectors can be "integrative" (i.e., able to integrate into the genome of a target cell) or "non-integrative" (i.e., not integrated into a target cell genome). Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and generally known in the art.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor et al., *Science* 251:767-773 (1991); Johnston, *Curr. Biol.* 8:R171-R174 (1998); Schummer, *Biotechniques* 23:1087-1092 (1997); Kern, *Biotechniques* 23:120-124 (1997); U.S. Pat. No. 5,143,854).

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells, are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

A "wild-type sequence" as used herein refers to any given sequence (e.g., an isolated sequence) that can be used as template for subsequent reactions or modifications. As understood by the skilled artisan, a wild-type sequence may include a nucleic acid sequence (such as DNA or RNA or combinations thereof) or an amino acid sequence or may be composed of different chemical entities. In some embodiments, the wild-type sequence may refer to an in silico sequence which may be the sequence information as such or sequence data that can be stored in a computer readable medium in a format that is readable and/or editable by a mechanical device. A wild-type sequence (reflecting a given order of nucleotide or amino acid symbols) can be entered, e.g., into a customer portal via a web interface. In embodiments, the sequence initially provided by a customer would be regarded as wild-type sequence in view of downstream processes based thereon—irrespective of whether the sequence itself is a natural or modified sequence, i.e., it was modified with regard to another wild-type sequence or is completely artificial.

In embodiments wild-type sequence may also refer to a physical molecule such as a nucleic acid molecule (such as RNA or DNA or combinations thereof) or a protein, polypeptide or peptide composed of amino acids. Methods to obtain a wild-type sequence by chemical, enzymatic or other means are known in the art. In one embodiment, a physical nucleic acid wild-type sequence may be obtained by PCR amplification of a corresponding template region or may be synthesized de novo based on assembly of synthetic oligonucleotides. A wild-type sequence as used herein can encompass naturally occurring as well as artificial (e.g., chemically or enzymatically modified) parts or building blocks. A wild-type sequence can be composed of two or multiple sequence parts. A wild-type sequence can be, e.g., a coding region, an open reading frame, an expression cassette, an effector domain, a repeat domain, a promoter/enhancer or terminator region, an untranslated region (UTR) but may also be a defined sequence motif, e.g., a binding, recognition or cleavage site within a given sequence. A wild-type sequence can be both, DNA or RNA of any length and can be linear, circular or branched and can be either single-stranded or double stranded.

As used herein, the term "conjugate" refers to the association between atoms or molecules. The association can be direct or indirect. For example, a conjugate between a first moiety (e.g., nuclease domain) and a second moiety (DNA binding domain) provided herein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first moiety (e.g., nuclease moiety) is non-covalently attached to the second moiety (DNA binding moiety) through a non-covalent chemical reaction between a component of the first moiety (e.g., nuclease moiety) and a component of the second moiety (DNA binding moiety). In other embodiments, the first moiety (e.g., nuclease moiety) includes one or more reactive moieties, e.g., a covalent reactive moiety, as described herein (e.g., alkyne, azide, maleimide or thiol reactive moiety). In other embodiments, the first moiety (e.g., nuclease moiety) includes a linker with one or more reactive moieties, e.g., a covalent reactive moiety, as described herein (e.g., alkyne, azide, maleimide or thiol reactive moiety). In other embodiments, the second moiety (DNA binding moiety) includes one or more reactive moieties, e.g., a covalent reactive moiety, as described herein (e.g., alkyne, azide, maleimide or thiol reactive moiety). In other embodiments, the second moiety (DNA binding moiety) includes a linker with one or more reactive moieties, e.g., a covalent reactive moiety, as described herein (e.g., alkyne, azide, maleimide or thiol reactive moiety).

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms apply to macrocyclic peptides, peptides that have been modified with non-peptide functionality, peptidomimetics, polyamides, and macrolactams. A "fusion protein" refers to a chimeric protein encoding two or more separate protein sequences that are recombinantly expressed as a single moiety.

The term "peptidyl", "peptide moiety", "protein moiety" and "peptidyl moiety" means a monovalent peptide or protein.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Contacting" is used in accordance with its plain ordinary meaning and refers to the process of allowing at least two distinct species to become sufficiently proximal to react, interact or physically touch. It should be appreciated, however, that the resulting reaction product can be produced directly from a reaction between the added reagents or from an intermediate from one or more of the added reagents which can be produced in the reaction mixture. In embodiments contacting includes, for example, allowing a ribonucleic acid as described herein to interact with an endonuclease and an enhancer agent.

A "control" sample or value refers to a sample that serves as a reference, usually a known reference, for comparison to a test sample. For example, a test sample can be taken from a test condition, e.g., in the presence of a test compound (e.g., a first or second DNA-binding modulation-enhancing agent), and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

"Biological sample" or "sample" refers to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate, e.g., chimpanzee or human; cow; dog; cat; a rodent, e.g., guinea pig, rat, mouse; rabbit; or a bird; reptile; or fish.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *Spodoptera*) and human cells.

The term "gene" means the segment of DNA involved in producing a protein; it includes regions preceding and following the coding region (enhancer, promoter, leader and trailer) as well as intervening sequences (introns) between individual coding segments (exons). The enhancer, promoter, leader, trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, Molecular Cloning: A Laboratory Manual, 18.1-18.88).

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "plasmid" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

The term "episomal" refers to the extra-chromosomal state of a plasmid in a cell. Episomal plasmids are nucleic acid molecules that are not part of the chromosomal DNA and replicate independently thereof.

The term "exogenous" refers to a molecule or substance (e.g., nucleic acid or protein) that originates from outside a given cell or organism. Conversely, the term "endogenous" refers to a molecule or substance that is native to, or originates within, a given cell or organism.

A "cell culture" is an in vitro population of cells residing outside of an organism. The cell culture can be established from primary cells isolated from a cell bank or animal, or secondary cells that are derived from one of these sources and immortalized for long-term in vitro cultures. A cell culture as provided herein further refers to an environment including appropriate cellular nutrients and capable of maintaining cells in vitro. The environment may be a liquid environment, a solid environment and/or a semisolid environment (e.g., agar, gel etc.) in an appropriate vessel (e.g., cell culture dish). A cell culture medium may be employed. A "cell culture medium" as used herein, is used according to its generally accepted meaning in the art. A cell culture medium (also referred to in the art and herein as a "culture medium") includes liquids (e.g., growth factors, minerals, vitamins etc.) or gels designed to support the growth (e.g., division, differentiation, maintenance etc.) of cells. In embodiments, the compositions provided herein including embodiments, further include a physiologically acceptable solution. A "physiologically acceptable solution" as provided herein refers to any acceptable aqueous solution (e.g., buffer) in which the compositions provided herein may be contained without losing their biological properties. In embodiments, the physiologically acceptable solution is a cell culture medium.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al., Gene Therapy 8:1-4 (2001) and Prochiantz, *Nat. Methods* 4:119-120 (2007).

As used herein, the terms "specific binding" or "specifically binds" refer to two molecules forming a complex (e.g., DNA-binding enhancing agent and an enhancer binding sequence) that is relatively stable under physiologic conditions.

A "ribonucleoprotein complex," "ribonucleoprotein particle", "deoxyribonucleoprotein complex," or "deoxyribonucleoprotein particle" as provided herein refers to a complex or particle including a nucleoprotein and a ribonucleic acid or a deoxyribonucleic acid. A "nucleoprotein" as provided herein refers to a protein capable of binding a nucleic acid (e.g., RNA, DNA). Where the nucleoprotein binds a ribonucleic acid it is referred to as "ribonucleoprotein." Where the nucleoprotein binds a deoxyribonucleic acid it is referred to as "deoxyribonucleoprotein." The interaction between the ribonucleoprotein and the ribonucleic acid or the deoxyribonucleoprotein and the deoxyribonucleic acid may be direct, e.g., by covalent bond, or indirect, e.g., by non-covalent bond (e.g., electrostatic interactions (e.g. ionic bond, hydrogen bond, halogen bond), van der Waals interactions (e.g., dipole-dipole, dipole-induced dipole, London dispersion), ring stacking (pi effects), hydrophobic interactions and the like). In embodiments, the ribonucleoprotein includes an RNA-binding motif non-covalently bound to the ribonucleic acid. In embodiments, the deoxyribonucleoprotein includes a DNA-binding motif non-covalently bound to the deoxyribonucleic acid. For example, positively charged aromatic amino acid residues (e.g., lysine residues) in the RNA-binding motif or the DNA-binding motif may form electrostatic interactions with the negative nucleic acid phosphate backbones of the RNA or DNA, thereby forming a ribonucleoprotein complex or a deoxyribonucleoprotein complex (e.g., an Argonaute complex referred to herein). Non-limiting examples of ribonucleoproteins include ribosomes, telomerase, RNAseP, hnRNP, CRISPR associated protein 9 (Cas9) and small nuclear RNPs (snRNPs). An example of a deoxyribonucleoprotein is Argonaute. The ribonucleoprotein or deoxyribonucleoprotein may be an enzyme. In embodiments, the ribonucleoprotein or deoxyribonucleoprotein is an endonuclease. Thus, in embodiments, the ribonucleoprotein complex includes an endonuclease and a ribonucleic acid. In embodiments, the endonuclease is a CRISPR associated protein 9. In embodiments, the deoxyribonucleoprotein complex includes an endonuclease and a deoxyribonucleic acid. In embodiments, the endonuclease is an Argonaute nuclease.

A "guide RNA" or "gRNA" as provided herein refers to a ribonucleotide sequence capable of binding a nucleoprotein, thereby forming ribonucleoprotein complex. Likewise a "guide DNA" or "gDNA" as provided herein refers to a deoxyribonucleotide sequence capable of binding a nucleoprotein, thereby forming deoxyribonucleoprotein complex. In embodiments, the guide RNA includes one or more RNA molecules. In embodiments, the guide DNA includes one or more DNA molecules. In embodiments, the gRNA includes a nucleotide sequence complementary to a target site (e.g., a modulator binding sequence). In embodiments, the gDNA includes a nucleotide sequence complementary to a target site (e.g., a modulator binding sequence). The complementary nucleotide sequence may mediate binding of the ribonucleoprotein complex or the deoxyribonucleoprotein complex to said target site thereby providing the sequence specificity of the ribonucleoprotein complex or the deoxyribonucleoprotein complex. Thus, in embodiments, the guide RNA or the guide DNA is complementary to a target nucleic acid (e.g., a modulator binding sequence). In embodiments, the guide RNA binds a target nucleic acid sequence (e.g., a modulator binding sequence). In embodiments, the guide DNA binds a target nucleic acid sequence (e.g., a modulator binding sequence). In embodiments, the guide RNA is complementary to a CRISPR nucleic acid sequence. In embodiments, the complement of the guide RNA or guide DNA has a sequence identity of about 50%, 55%, 60%, 65%, 70%, 75%, 80%, 85%, 90%, 95%, 96%, 97%, 98% or 99% to a target nucleic acid (e.g., a modulator binding sequence). A target nucleic acid sequence as provided herein is a nucleic acid sequence expressed by a cell.

In embodiments, the target nucleic acid sequence is an exogenous nucleic acid sequence. In embodiments, the target nucleic acid sequence is an endogenous nucleic acid sequence. In embodiments, the target nucleic acid sequence (e.g., a modulator binding sequence) forms part of a cellular gene. Thus, in embodiments, the guide RNA or guide DNA is complementary to a cellular gene or fragment thereof. In embodiments, the guide RNA or guide DNA is about 50%, 55%, 60%, 65%, 70%, 75%, 80%, 85%, 90%, 95%, 96%, 97%, 98% or 99% to the target nucleic acid sequence (e.g., a modulator binding sequence). In embodiments, the guide RNA or guide DNA is about 50%, 55%, 60%, 65%, 70%, 75%, 80%, 85%, 90%, 95%, 96%, 97%, 98% or 99% complementary to the sequence of a cellular gene. In embodiments, the guide RNA or the guide DNA binds a cellular gene sequence. The term "target nucleic acid sequence" refers to a modulator binding sequence as provided herein.

In embodiments, the guide RNA or guide DNA is a single-stranded ribonucleic acid. In embodiments, the guide RNA or guide DNA is about 10, 20, 30, 40, 50, 60, 70, 80, 90, 100 or more nucleic acid residues in length. In embodiments, the guide RNA or guide DNA is from about 10 to about 30 nucleic acid residues in length. In embodiments, the guide RNA or guide DNA is about 20 nucleic acid residues in length. In embodiments, the length of the guide RNA or the guide DNA can be at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. In embodiments, the guide RNA or guide DNA is from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. In embodiments, the guide RNA or guide DNA is from 10 to 15, 10 to 20, 10 to 30, 10 to 40, or 10 to 50 residues in length.

PAM refers to "protospacer adjacent motif". These sites are generally 2-6 base pair DNA sequences that are adjacent to DNA sequence bound by Cas9. Thus, in some instances, DNA-binding modulation-enhancing agents other than Cas9 might be used and in other instances a single Cas9/RNA complex might be used as a DNA-binding modulation-enhancing agent (either alone or in conjunction with a different DNA-binding modulation-enhancing agent).

For specific proteins described herein (e.g., Cas9, Argonaute), the named protein includes any of the protein's naturally occurring forms, or variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment or homolog thereof.

Thus, a "CRISPR associated protein 9," "Cas9" or "Cas9 protein" as referred to herein includes any of the recombinant or naturally-occurring forms of the Cas9 endonuclease or variants or homologs thereof that maintain Cas9 endonuclease enzyme activity (e.g. within at least 50%, 80%, 90%, 95%, 96%, 97%, 98%, 99% or 100% activity compared to Cas9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 protein. In embodiments, the Cas9 protein is substantially identical to the protein identified by the Uni-Prot reference number Q99ZW2 or a variant or homolog having substantial identity thereto. Cas9 refers to the protein also known in the art as "nickase". In embodiments, Cas9 binds a CRISPR (clustered regularly interspaced short palindromic repeats) nucleic acid sequence. In embodiments, the CRISPR nucleic acid sequence is a prokaryotic nucleic acid sequence. Examples of Cas9 proteins useful for the invention provided herein include without limitation, cas9 mutant proteins such as, HiFi Cas9 as described by Kleinstiver, Benjamin P., et al. ("High-fidelity CRISPR-Cas9 nucleases with no detectable genome-wide off-target effects." Nature (2016). PubMed PMID: 26735016); Cas9 proteins binding modified PAMs and orthologous Cas9 proteins such as CRISPR from *Prevotella* and *Francisella* 1 (Cpf1). Any of the mutant Cas9 forms commonly known and described in the art may be used for the methods and compositions provided herein. Non-limiting examples of mutant Cas9 proteins contemplated for the methods and compositions provided herein are described in Slaymaker, Ian M., et al. ("Rationally engineered Cas9 nucleases with improved specificity." Science (2015): aad5227. PubMed PMID: 26628643) and Kleinstiver, Benjamin P., et al. ("High-fidelity CRISPR-Cas9 nucleases with no detectable genome-wide off-target effects." Nature (2016). PubMed PMID: 26735016).

The term "Argonaute (AGO) protein," "NgAgo," or "*Natronobacterium gregoryi* Argonaute," "*N. gregoryi* SP2 Argonaute" as referred to herein includes any of the recombinant or naturally-occurring forms of the NgAgo or variants or homologs thereof that maintain NgAgo endonuclease enzyme activity (e.g., within at least 50%, 80%, 90%, 95%, 96%, 97%, 98%, 99% or 100% activity compared to wild type NgAgo). In embodiments, the variants or homologs have at least 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring NgAgo protein. In embodiments, the NgAgo protein is substantially identical to the protein identified by the National Center for Biotechnology Information (NCBI) protein identifier AFZ73749.1 or a variant or homolog having at least 70%, 75%, 80%, 85%, 90%, 95%, 96%, 97%, 98%, 99% or 100% amino acid sequence identity thereto. In embodiments, Argonaute proteins can also include nuclease domains (i.e., DNase or RNase domains), additional DNA binding domains, helicase domains, protein-protein interaction domains, dimerization domains, as well as other domains.

Argonaute protein also refers to proteins that form a complex that binds a nucleic acid molecule. Thus, one Argonaute protein may bind to, for example, a guide DNA and another protein may have endonuclease activity. These are all considered to be Argonaute proteins because they function as part of a complex that performs the same functions as a single protein such as NgAgo.

As used herein the term "Argonaute system" refers to a collection of Argonaute proteins and nucleic acid that, when combined, result in at least Argonaute associated activity (e.g., the target locus specific, double-stranded cleavage of double-stranded DNA).

As used herein the term "Argonaute complex" refers to the Argonaute proteins and nucleic acid (e.g., DNA) that has associate with each other to form an aggregate that has functional activity. An example of an Argonaute complex is a wild-type *Natronobacterium gregoryi* Argonaute (NgAgo) protein that is bound to a guide DNA specific for a target locus.

In embodiments, "Argonaute (AGO) protein," "NgAgo," or "*Natronobacterium gregoryi* Argonaute," "*N. gregoryi* SP2 Argonaute" referred herein includes any of the recombinant or naturally-occurring forms of the NgAgo or variants or homologs thereof that maintain NgAgo endonuclease enzyme activity (e.g., within at least 50%, 80%, 90%, 95%, 96%, 97%, 98%, 99% or 100% activity compared to wild type NgAgo). In embodiments, the variants or homologs have at least 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring NgAgo protein. In embodiments, the NgAgo protein is substantially identical to the protein identified by the National Center for Biotechnology Information (NCBI) protein identifier AFZ73749.1 or a variant or homolog having at least 70%, 75%, 80%, 85%, 90%, 95%, 96%, 97%, 98%, 99% or 100% amino acid sequence identity thereto. In embodiments, Argonaute proteins can also include nuclease domains (i.e., DNase or RNase domains), additional DNA binding domains, helicase domains, protein-protein interaction domains, dimerization domains, as well as other domains.

Argonaute protein also refers to proteins that form a complex that binds a nucleic acid molecule. Thus, one Argonaute protein may bind to, for example, a guide DNA and another protein may have endonuclease activity. These are all considered to be Argonaute proteins because they function as part of a complex that performs the same functions as a single protein such as NgAgo.

As used herein, the term "transcriptional regulatory sequence" refers to a functional stretch of nucleotides contained on a nucleic acid molecule, in any configuration or geometry, that act to regulate the transcription of (1) one or more structural genes (e.g., two, three, four, five, seven, ten, etc.) into messenger RNA or (2) one or more genes into untranslated RNA. Examples of transcriptional regulatory sequences include, but are not limited to, promoters, enhancers, repressors, and the like.

As used herein the term "nucleic acid targeting capability" refers to the ability of a molecule or a complex of molecule to recognize and/or associate with nucleic acid on a sequence specific basis. As an example, binding of a modulating protein o modulating complex to a modulator binding sequence or the hybridization region on a guide DNA (gDNA) molecule confers nucleic acid targeting capability to an Argonaute complex.

As used herein "TAL effector" or "TAL effector protein" as provided herein refers to a protein including more than one TAL repeat and capable of binding to nucleic acid in a sequence specific manner. In embodiments, TAL effector protein Includes at least six (e.g., at least 8, at least 10, at least 12, at least 15, at least 17, from about 6 to about 25, from about 6 to about 35, from about 8 to about 25, from about 10 to about 25, from about 12 to about 25, from about 8 to about 22, from about 10 to about 22, from about 12 to about 22, from about 6 to about 20, from about 8 to about 20, from about 10 to about 22, from about 12 to about 20, from about 6 to about 18, from about 10 to about 18, from about 12 to about 18, etc.) TAL repeats. In embodiments, the TAL effector protein includes 18 or 24 or 17.5 or 23.5 TAL nucleic acid binding cassettes. In embodiments, the TAL effector protein includes 15.5, 16.5, 18.5, 19.5, 20.5, 21.5, 22.5 or 24.5 TAL nucleic acid binding cassettes. A TAL effector protein includes at least one polypeptide region which flanks the region containing the TAL repeats. In embodiments, flanking regions are present at the amino and/or the carboxyl termini of the TAL repeats.

"Regulatory sequence" as used herein refers to nucleic acid sequences that influence transcription and/or translation initiation and rate, stability and/or mobility of a transcript or polypeptide product. Regulatory sequences include, without limitation, promoter sequences or control elements, enhancer sequences, response elements, protein recognition sites, inducible elements, protein binding sequences, transcriptional start sites, termination sequences, polyadenylation sequences, introns, 5' and 3' untranslated regions (UTRs) and other regulatory sequences that can reside within coding sequences, such as splice sites, inhibitory sequence elements (often referred to as CNS or INS such known from some viruses), secretory signals, Nuclear Localization Signal (NLS) sequences, inteins, translational coupler sequences, protease cleavage sites as described in more detail elsewhere herein. A 5' untranslated region (UTR) is transcribed, but not translated, and is located between the start site of the transcript and the translation initiation codon and may include the +1 nucleotide. A 3' UTR can be positioned between the translation termination codon and the end of the transcript. UTRs can have particular functions such as increasing mRNA message stability or translation attenuation. Examples of 3' UTRs include, but are not limited to polyadenylation signals and transcription termination sequences. Regulatory sequences may be universal or host- or tissue-specific.

A "promoter" as used herein is a transcription regulatory sequence which is capable of directing transcription of a nucleic acid segment (e.g., a transgene comprising, for example, an open reading frame) when operably connected thereto. A promoter is a nucleotide sequence which is positioned upstream of the transcription start site (generally near the initiation site for RNA polymerase II). A promoter typically comprises at least a core, or basal motif, and may include or cooperate with at least one or more control elements such as upstream elements (e.g., upstream activation regions (UARs)) or other regulatory sequences or synthetic elements. A basal motif constitutes the minimal sequence necessary for assembly of a transcription complex required for transcription initiation. In embodiments, such minimal sequence includes a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site. The transcription of an adjacent nucleic acid segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

The choice of a promoter to be included in an expression vector depends upon several factors, including without limitation efficiency, selectability, inducibility, desired expression level, and cell or tissue specificity. For example, tissue-, organ- and cell-specific promoters that confer transcription only or predominantly in a particular tissue, organ, and cell type, respectively, can be used. In embodiments, promoters that are essentially specific to seeds ("seed-preferential promoters") can be useful. In embodiments, constitutive promoters are used that can promote transcription in most or all tissues of a specific species. Other classes of promoters include, but are not limited to, inducible promoters, such as promoters that confer transcription in response to external stimuli such as chemical agents, developmental stimuli, or environmental stimuli. Inducible promoters may be induced by pathogens or stress like cold, heat, UV light, or high ionic concentrations or may be induced by chemicals. Examples of inducible promoters are the eukaryotic metallothionein promoter, which is induced by increased levels of heavy metals; the prokaryotic lacL promoter, which is induced in response to isopropyl-β-D-thiogalacto-pyranoside (IPTG); and eukaryotic heat shock promoters, which are induced by raised temperature. Numerous additional bacterial and eukaryotic promoters suitable for use with the invention are known in the art and described in, e.g., in Sambrook et al., Molecular Cloning, A Laboratory Manual (2nd ed. 1989; 3rd ed., 2001); Kriegler, Gene Transfer and Expression: A Laboratory Manual (1990); and Ausubel et al., Current Protocols in Molecular Biology. Bacterial expression systems for expressing the ZFP are available in, e.g., *E. coli, Bacillus* sp., and *Salmonella* (Palva et al., *Secretion of interferon by Bacillus subtilis. Gene* 22:229-235 (1983)). Kits for such expression systems are commercially available. Eukaryotic expression systems for mammalian cells, yeast, and insect cells are well known by those of skill in the art and are also commercially available.

Common promoters for prokaryotic protein expression are e.g., lac promoter or trc and tac promoter (IPTG induction), tetA promoter/operator (anhydrotetracyclin induction), PPBAD promoter (L-arabinose induction), r/zaPBAD promoter (L-rhamnose induction) or phage promoters such as phage promoter pL (temperature shift sensitive), T7, T3, SP6, or T5.

Common promoters for mammalian protein expression are, e.g., Cytomegalovirus (CMV) promoter, SV40 promoter/enhancer, Vaccinia virus promoter, Viral LTRs (MMTV, RSV, HIV etc.), E1B promoter, promoters of constitutively expressed genes (actin, GAPDH), promoters of genes expressed in a tissue-specific manner (albumin, NSE), promoters of inducible genes (Metallothionein, steroid hormones).

Numerous promoters for expression of nucleic acids in plants are known and may be used in the practice of the invention. Such promoter may be constitutive, regulatable, and/or tissue-specific (e.g., seed specific, stem specific, leaf specific, root specific, fruit specific, etc.). Exemplary promoters which may be used for plant expression include the Cauliflower mosaic virus 35 S promoter and promoter for the following genes: the ACT 11 and CAT 3 genes from *Arabidopsis*, the gene encoding stearoyl-acyl carrier protein desaturase from *Brassica napus* (GenBank No. X74782), and the genes encoding GPC1 (GenBank No. X15596) and GPC2 (GenBank No. U45855) from maize. Additional promoters include the tobamovirus subgenomic promoter, the cassaya vein mosaic virus (CVMV) promoter (which exhibits high transcriptional activity in vascular elements, in leaf mesophyll cells, and in root tips), the drought-inducible promoter of maize, and the cold, drought, and high salt inducible promoter from potato. A number of additional promoters suitable for plant expression are found in U.S. Pat. No. 8,067,222, the disclosure of which is incorporated herein by reference.

Heterologous expression in chloroplast of microalgae such as, e.g., *Chlamydomonas reinhardtii* can be achieved using, for example, the psbA promoter/5' untranslated region (UTR) in a psbA-deficient genetic background (due to psbA/DI-dependent auto-attenuation) or by fusing the strong 16S rRNA promoter to the 5' UTR of the psbA and atpA genes to the expression cassette as, for example, disclosed in Rasala et al, "Improved heterologous protein expression in the chloroplast of *Chlamydomonas reinhardtii* through promoter and 5' untranslated region optimization", Plant Biotechnology Journal, Volume 9, Issue 6, pages 674-683, (2011). The promoter used to direct expression of a TAL effector encoding nucleic acid depends on the particular application. For example, a strong constitutive promoter is typically used for expression and purification of TAL-effector fusion proteins. In contrast, when a TAL effector nuclease fusion protein is administered in vivo for gene regulation, it may be desirable to use either a constitutive or an inducible promoter, depending on the particular use of the TAL effector nuclease fusion protein and other factors. In addition, a promoter suitable for administration of a TAL effector nuclease fusion protein can be a weak promoter, such as HSV thymidine kinase or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard. Tight control of gene expression in mammalian cells by tetracycline-responsive promoters. Proc. Natl. Acad. Sci. USA 89:5547 (1992); Oligino et al. *Drug inducible transgene expression in brain using a herpes simplex virus vector. Gene Ther.* 5:491-496 (1998); Wang et al. *Positive and negative regulation of gene expression in eukaryotic cells with an inducible transcriptional regulator. Gene Ther.* 4:432-441 (1997); Necring et al. *Transduction of primitive human hematopoietic cells with recombinant adenovirus vectors. Blood* 88:1147-1155 (1996); and Rendahl et al., *Regulation of gene expression in vivo following transduction by two separate rAAV vectors Nat. Biotechnol.* 16:151-161 (1998)). The MNDU3 promoter can also be used, and is preferentially active in CD34+ hematopoietic stem cells.

By "host" is meant a cell or organism that supports the replication of a vector or expression of a protein or polypeptide encoded by a vector sequence. Host cells may be prokaryotic cells such as *E. coli*, or eukaryotic cells such as yeast, fungal, protozoal, higher plant, insect, or amphibian cells, or mammalian cells such as CHO, HeLa, 293, COS-1, and the like, e.g., cultured cells (in vitro), explants and primary cultures (in vitro and ex vivo), and cells in vivo.

As used herein, the phrase "recombination proteins" includes excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707

(1993)), or mutants, derivatives (e.g., fusion proteins containing the recombination protein sequences or fragments thereof), fragments, and variants thereof. Examples of recombination proteins include Cre, Int, IHF, Xis, Flp, Fis, Hin, Gin, Phi-C31, Cin, Tn3 resolvase, TndX, XerC, XerD, TnpX, Hjc, SpCCE1, and Par A.

A used herein, the phrase "recombination site" refers to a recognition sequence on a nucleic acid molecule which participates in an integration/recombination reaction by recombination proteins. Recombination sites are discrete sections or segments of nucleic acid on the participating nucleic acid molecules that are recognized and bound by a site-specific recombination protein during the initial stages of integration or recombination. For example, the recombination site for Cre recombinase is loxV which is a 34 base pair sequence comprised of two 13 base pair inverted repeats (serving as the recombinase binding sites) flanking an 8 base pair core sequence (see FIG. 1 of Sauer, B. Site-specific recombination: developments and applications. Curr. Opin. Biotech. 5:521-527 (1994)). Other examples of recognition sequences include the attB, attP, attL, and attR sequences described herein, and mutants, fragments, variants and derivatives thereof, which are recognized by the recombination protein lambda phage Integrase and by the auxiliary proteins integration host factor (IHF), Fis and excisionase (lamda phage is).

As used herein, the phrase "recognition sequence" refers to a particular sequence to which a protein, chemical compound, DNA, or RNA molecule (e.g., restriction endonuclease, a modification methylase, or a recombinase) recognizes and binds. In the present invention, a recognition sequence will usually refer to a recombination site. For example, the recognition sequence for Cre recombinase is loxP which is a 34 base pair sequence comprising two 13 base pair inverted repeats (serving as the recombinase binding sites) flanking an 8 base pair core sequence (see FIG. 1 of Sauer, B. Current Opinion in Biotechnology 5:521-527 (1994)). Other examples of recognition sequences are the attB, attP, attL, and attR sequences which are recognized by the recombinase enzyme lamda phage Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS and excisionase (lamda phage is). (See Landy, Current Opinion in Biotechnology 3:699-707 (1993).)

Throughout this document, unless the context requires otherwise, the words "comprise," "comprises" and "comprising" or "contain", "contains" or "containing" will be understood to imply the inclusion of a stated step or element or group of steps or elements but not the exclusion of any other step or element or group of steps or elements.

As used herein the term "homologous recombination" refers to a mechanism of genetic recombination in which two DNA strands comprising similar nucleotide sequences exchange genetic material. Cells use homologous recombination during meiosis, where it serves to rearrange DNA to create an entirely unique set of haploid chromosomes, but also for the repair of damaged DNA, in particular for the repair of double strand breaks. The mechanism of homologous recombination is well known to the skilled person and has been described, for example by Paques and Haber (Paques F, Haber J E.; *Microbial. Mal. Biol. Rev.* 63:349-404 (1999)). In the method of the present invention, homologous recombination is enabled by the presence of said first and said second flanking element being placed upstream (5') and downstream (3'), respectively, of said donor DNA sequence each of which being homologous to a continuous DNA sequence within said target sequence.

As used herein the term "non-homologous end joining" (NHEJ) refers to cellular processes that join the two ends of double-strand breaks (DSBs) through a process largely independent of homology. Naturally occurring DSBs are generated spontaneously during DNA synthesis when the replication fork encounters a damaged template and during certain specialized cellular processes, including V(D)J recombination, class-switch recombination at the immunoglobulin heavy chain (IgH) locus and meiosis. In addition, exposure of cells to ionizing radiation (X-rays and gamma rays), UV light, topoisomerase poisons or radiomimetic drugs can produce DSBs. NHEJ (non-homologous end-joining) pathways join the two ends of a DSB through a process largely independent of homology. Depending on the specific sequences and chemical modifications generated at the DSB, NHEJ may be precise or mutagenic (Lieber M. R., *The mechanism of double-strand DNA break repair by the nonhomologous DNA end-joining pathway. Annu. Rev. Biochem.* 79:181-211).

As used herein the term "donor DNA" or "donor nucleic acid" refers to nucleic acid that is designed to be introduced into a locus by homologous recombination. Donor nucleic acid will have at least one region of sequence homology to the locus. In embodiments, donor nucleic acid will have two regions of sequence homology to the locus. These regions of homology may be at one of both termini or may be internal to the donor nucleic acid. In embodiments, an "insert" region with nucleic acid that one desires to be introduced into a nucleic acid molecules present in a cell will be located between two regions of homology.

Donor nucleic acid molecules (e.g., donor DNA molecules) may be double-stranded, single-stranded, or partially double-stranded and single-stranded and, thus, may have overhanging termini on one or both ends (e.g., two 5' overhangs, two 3' overhangs, a 5' and a 3' overhang, a single 3' overhang, or a single 5' overhang). Further, nucleic acid molecules may be linear nucleic acid molecules of circular nuclei acid molecules (closed circular or nicked nucleic acid molecules.

As used herein the term "homologous recombination system or "HR system" refers components of systems set out herein that maybe used to alter cells by homologous recombination. In particular, zinc finger nucleases, TAL effector nucleases, CRISPR endonucleases, homing endonucleases, and Argonaute editing systems.

As used herein the term "nucleic acid cutting entity" refers to a single molecule or a complex of molecules that has nucleic acid cutting activity (e.g., double-stranded nucleic acid cutting activity). Exemplary nucleic acid cutting entities include Argonuate complexes, zinc finger proteins, transcription activator-like effectors (TALEs), CRISPR complexes, and homing meganucleases. In embodiments, nucleic acid cutting entities will have an activity that allows them to be nuclear localized (e.g., will contain nuclear localization signals (NLS)).

As used herein, the term "double-stranded break site" refers to a location in a nucleic acid molecule where a double-stranded break occurs. In embodiments, this will be generated by the nicking of the nucleic acid molecule at two close locations (e.g., within from about 3 to about 50 base pairs, from about 5 to about 50 base pairs, from about 10 to about 50 base pairs, from about 15 to about 50 base pairs, from about 20 to about 50 base pairs, from about 3 to about 40 base pairs, from about 5 to about 40 base pairs, from about 10 to about 40 base pairs, from about 15 to about 40 base pairs, from about 20 to about 40 base pairs, etc.). Typically, nicks may be further apart in nucleic acid regions that contain higher AT content, as compared to nucleic acid regions that contain higher GC content.

As used herein, the term "matched termini" refers to termini of nucleic acid molecules that share sequence identity of greater than 90%. A matched terminus of a DS break at a target locus may be double-stranded or single-stranded. A matched terminus of a donor nucleic acid molecule will generally be single-stranded.

As used herein, "homology directed repair" or "HDR" is a mechanism in cells to repair double-stranded breaks (DSBs) in DNA. In some embodiments, the HDR is greater than or equal to 10%, 25%, 50%, 75%, 90%, 95%, 98%, 99%, or 100%.

A common form of HDR is "homologous recombination," which refers to a mechanism of genetic recombination in which two DNA strands comprising similar nucleotide sequences exchange genetic material. Cells use homologous recombination during meiosis, where it serves to rearrange DNA to create an entirely unique set of haploid chromosomes, but also for the repair of damaged DNA, in particular, for the repair of double stranded breaks. The mechanism of homologous recombination is well known to the skilled person and has been described, for example by Paques F., Haber J. E., *Microbiol. Mol. Biol. Rev.* 63:349-404 (1999). In some embodiments, homologous recombination is enabled by the presence of matched termini being placed upstream (5') and downstream (3'), respectively, in a donor nucleic acid molecule, each of which are homologous to a continuous DNA sequence within the cleaved nucleic acid molecule.

Some embodiments include compositions and methods designed to result in high efficiency of homologous recombination in cells (e.g., eukaryotic cells such as plant cells and animal cells, such as insect cells and mammalian cells, including mouse, rat, hamster, rabbit and human cells). In some embodiments, homologous recombination efficiency is such that greater than 20% of cells in a population will have underdone homologous recombination at the desired target locus or loci. In some embodiments, homologous recombination may occur within from 10% to 65%, 15% to 65%, 20% to 65%, 30% to 65%, 35% to 65%, 10% to 55%, 20% to 55%, 30% to 55%, 35% to 55%, 40% 55%, 10% 45%, 20% to 45%, 30% to 45%, 40% to 45%, 30% to 50%, etc., of cells in a population.

Further, some embodiments include compositions and methods for increasing the efficiency of homologous recombination within cells. For example, if homologous recombination occurs in 10% of a cell population under one set of conditions and in 40% of a cell population under another set of conditions, then the efficiency of homologous recombination has increased by 300%. In some embodiments, the efficiency of homologous recombination may increase by 100% to 500% (e.g., 100% to 450%, 100% to 400%, 100% to 350%, 100% to 300%, 200% to 500%, 200% to 400%, 250% to 500%, 250% to 400%, 250% to 350%, 300% to 500%, etc.).

As used herein, "double-stranded break" or "DSB" refers to a double-stranded break in a nucleic acid molecule. In many embodiments, the DSB will be generated by the nicking of the nucleic acid molecule at two close locations (e.g., within 3 to 50 base pairs, 5 to 50 base pairs, 10 to 50 base pairs, 15 to 50 base pairs, 20 to 50 base pairs, 3 to 40 base pairs, 5 to 40 base pairs, 10 to 40 base pairs, 15 to 40 base pairs, 20 to 40 base pairs, etc.). Nicks may be further apart in nucleic acid regions that contain higher AT content, as compared to nucleic acid regions that contain higher GC content. In some embodiments, the double-stranded break is less than or equal to 250 bp from the ATG start codon for N-terminal tagging a nucleic acid molecule, or less than or equal to 250 bp from the stop codon for C-terminal tagging of a nucleic acid molecule.

As used herein, "donor nucleic acid molecule" or "donor DNA" refers to a nucleic acid that is designed to be introduced into a cleaved nucleic acid molecule by homologous recombination. A donor nucleic acid molecule will have at least one region of sequence homology to the cleaved nucleic acid molecule. In many embodiments, the donor nucleic acid molecule will have two regions of sequence homology to the locus. These regions of homology may be at one or both termini or may be internal to the donor nucleic acid molecule.

As used herein, "integration efficiency" refers to the frequency with which a segment of foreign DNA of interest is incorporated into an initial nucleic acid molecule. In some embodiments, integration efficiency of the donor nucleic acid molecule is greater than or equal to 50%, 75%, 90%, 95%, 98%, 99%, or 100%.

Table 1 shows that near 100% integration efficiency and up to 100% precise HDR was found at four different genomic loci in three different mammalian cell lines. At some loci, deletion and insertion at the junction or at the Cas9 cleavage site was observed.

TABLE 1

| | | | Integration efficiency of exogenous DNA molecules into human genome | | | | |
|---|---|---|---|---|---|---|---|
| | | | Efficiency at allele 1 | | Efficiency at allele 2 | | % of |
| Locus | Position | insert/size | Precise HDR | HDR/ Indel | Precise HDR | No HDR/ Indel | functional Cells |
| Beta-actin SEQ ID NO: 3 | N-terminus | puromycin-P2A-OFP/1.4 kb | 68 | 32 | 0 | 100 | 80%[a] |
| Beta-actin SEQ ID NO: 3 | N-terminus | puromycin-CMV-HC-LC/4.2 kb | 36 | 64 | 0 | 100 | 70%[b] |
| LRRK2 SEQ ID NO: 4 | N-terminus | puromycin-P2A-EmGFP/1.4 kb | 100 | 0 | 20 | 80 | not determined[c] |
| FAK SEQ ID NO: 1 | C-terminus | EmGFP-P2A-puromycin/1.4 kb | 70 | 30 | 30 | 70 | not determined[c] |

TABLE 1-continued

| Integration efficiency of exogenous DNA molecules into human genome | | | | | | |
|---|---|---|---|---|---|---|
| | | | Efficiency at allele 1 | | Efficiency at allele 2 | | % of |
| Locus | Position | insert/size | Precise HDR | HDR/ Indel | Precise HDR | No HDR/ Indel | functional Cells |
| EGFR SEQ ID NO: 2 | C-terminus | EmGFP-P2A- puromycin/1.4 kb | 100 | 0 | 17 | 83 | not determined[c] |

[a]determined by flow cytometry;
[b]determined by ELISA assay;
[c]not able to determine by flow cytometry due to low expression level of chimeric protein.

In some embodiments, end modification of donor DNA with phosphorothioate or amine groups and/or treatment with non-homologous end joining inhibitor (NHEJ) inhibitors can further improve the efficiency of HDR.

As used herein, "matched termini" refers to termini of a nucleic acid molecule that share sequence identity of greater than or equal to 90%. In some embodiments, the matched termini on the 5' and 3' ends have a length of 12 bp to 250 bp, 12 bp to 200 bp, 12 bp to 150 bp, 12 bp to 100 bp, 12 bp to 50 bp, or 12 bp to 40 bp. In some embodiments, the matched termini have a length of 35 bp. In some embodiments, the matched termini will share sequence identity greater than or equal to 90%, 91%, 92%, 93%, 94%, 95%, 96%, 97%, or 99%, or equal to 100%. A matched terminus of a double-stranded break at a target locus may be double-stranded or single-stranded DNA. In some embodiments, a matched terminus of a donor nucleic acid molecule will be single-stranded.

The amount of sequence identity the matched termini share with the nucleic acid at the target locus, typically the higher the homologous recombination efficiency. High levels of sequence identity are especially desired when the homologous regions are fairly short (e.g., 50 bases). In some embodiments, the amount of sequence identity between the target locus and the matched termini will be greater than 90% (e.g., from 90% to 100%, 90% to 99%, 90% to 98%, 95% to 100%, 95% to 99%, 95% to 98%, 97% to 100%, etc.).

As used herein, "percentage of sequence identity" means the value determined by comparing two optimally aligned nucleotide sequences over a comparison window, wherein the portion of the nucleotide sequence in the comparison window may comprise additions or deletions (i.e., sequence alignment gaps) as compared to the reference sequence (which does not comprise additions or deletions) for optimal alignment of the two sequences. In other words, sequence alignment gaps are removed for quantification purposes. The percentage of sequence identity is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

One method for determining sequence identity values is through the use of the BLAST 2.0 suite of programs using default parameters (Altschul et al., *Nucleic Acids Res.* 25:3389-3402 (1997)). Software for performing BLAST analyses is publicly available, e.g., through the National Center for Biotechnology-Information.

In some embodiments, termini may differ in one or more features related to homologous recombination. For example, the lengths of the terminal "matched" regions of sequence complementarity to the target locus may be different. Thus, one terminus may have forty nucleotides of sequence complementarity and the other terminus may have only fifteen nucleotides of sequence complementarity. In some embodiments, one or both termini of donor nucleic acid molecules will be partially or fully single-stranded.

As used herein, "promoterless selection marker" refers to a foreign gene of interest having no promoter, such that it expresses only after insertion into a genomic locus containing a promoter. In some embodiments, the promoterless selection marker is protein, antibiotic resistance selection marker, cell surface marker, cell surface protein, metabolite, or active fragment thereof. In some embodiments, the promoterless selection marker is a label (e.g. EmGFP or OFP). In one embodiment, the promoterless selection marker is puromycin, dihydrofolate reductase, or glutamine synthetase.

The promoterless selection marker can be linked directly to the reporter gene or, alternatively, the donor nucleic acid molecule can contain an additional amino acid sequence acting as a "linker" between the promoterless selection marker and the reporter gene. The linker can be a polypeptide or any other suitable linker that is known in the art. In some embodiments, the linker comprises greater than or equal to 2, 3, 5, 10, 15, 20, 30, 40, 50, 60, 70, 80, or 90 amino acids. In some embodiments, the linker comprises 100 amino acids. In some embodiments, the linker comprises greater than or equal to two amino acids selected from the group consisting of glycine, serine, alanine and threonine. In some embodiments, the linker is a polyglycine linker. In some embodiments, the polyglycine linker comprises 3, 4, 5, 6, 7, 8, 9, 10, 11, 12, 13, 14, 15, 16, 17, 18, 19, or 20 glycine residues. In one embodiment, the linker is a 6-residue polyglycine. In some embodiments, the distance between the promoterless selection marker and the reporter gene is less than or equal to 300 nt, 240 nt, 180 nt, 150 nt, 120 nt, 90 nt, 60 nt, 30 nt, 15 nt, 12 nt, or 9 nt.

As used herein, "reporter gene" refers to a gene whose product can be readily assayed, and can be used as a marker for screening successfully modified cells, for studying regulation of gene expression, or serve as controls for standardizing recombination efficiencies. In some embodiments, the reporter gene is a selectable marker. In some embodiments, the reporter gene is a fluorescent reporter, such as emerald green fluorescent protein (EmGFP) reporter or orange fluorescent protein (OFP) reporter. In some embodiments, the reporter gene is a luminescent reporter, such as a luciferase (e.g., *P. pyralis* luciferase). Other commonly used reporter genes are β-glucuronidase and β-galactosidase. Ideally, the reporter gene should be absent from the cells used in the study or easily distinguishable from the native form of the gene, assayed conveniently, have a broad linear detection range, and not affect the normal physiology and general health of the cells.

As used herein, "self-cleaving peptide" refers to a peptide that dissociates into component proteins on translation. In some embodiments, the self-cleaving peptide links the promoterless selection marker and the reporter gene, and enables the promoterless selection marker to dissociate from the reporter gene during translation after recombination into an initial nucleic acid molecule. In some embodiments, the self-cleaving peptide is self-cleaving 2A peptide or other self-cleaving peptides known to a skilled person.

In some embodiments, "loxP" or "locus of X-over P1" is placed on either side of the promoterless selection marker as an alternative or addition to a self-cleaving peptide. LoxP may be used as part of the Cre-lox strategy for recombination to facilitate the replication of the promoterless selection marker. A Cre-lox strategy requires at least two components: 1) Cre recombinase, an enzyme that catalyzes recombination between two loxP sites; and 2) loxP sites (e.g. a specific 34-base pair by sequence consisting of an 8-bp core sequence, where recombination takes place, and two flanking 13-bp inverted repeats) or mutant lox sites. (Sec, e.g. Araki et al., PNAS 92:160-4 (1995); Nagy, A., et al. Genesis 26:99-109 (2000); Araki et al., Nuc Acids Res 30(19):e103 (2002); and US20100291626A1, all of which are herein incorporated by reference). Exemplary loxP sites include, but are not limited to, wild-type, lox511, lox5171, lox2272, M2, M3, M7, M11, lox71 and lox66. The loxP allows for the ability to remove the promoterless selection marker at a later time. That way one could select for the edited population and then remove the promoterless selection marker. This allows for additional use of the promoterless selection markers if further editing is required.

As used herein, "non-homologous end joining" (NHEJ) refers to cellular processes that join the two ends of double-strand breaks (DSBs) through a process largely independent of homology. Naturally occurring DSBs are generated spontaneously during DNA synthesis when the replication fork encounters a damaged template and during certain specialized cellular processes, including V(D)J recombination, class-switch recombination at the immunoglobulin heavy chain (IgH) locus and meiosis. In addition, exposure of cells to ionizing radiation (X-rays and gamma rays), UV light, topoisomerase poisons, or radiomimetic drugs can produce DSBs. Depending on the specific sequences and chemical modifications generated at the DSB, NHEJ may be precise or mutagenic (Lieber, M. R., *Annu. Rev. Biochem.* 79:181-211 (2010)).

As used herein, "non-homologous end joining inhibitor" or "NHEJ inhibitor" refers to molecules that inhibit non-homologous end joining processes. In some embodiments, the donor nucleic acid molecule is treated with at least one NHEJ inhibitor. Examples of NHEJ inhibitors include, but are not limited to, DNA-dependent protein kinase (DNA-PK), DNA ligase IV, DNA polymerase 1 or 2 (PARP-1 or PARP-2), or combinations thereof. Exemplary DNA-PK inhibitors include Nu7206 (2-(4-Morpholinyl)-4H-naphthol[1,2-b]pyran-4-one), Nu7441 (8-(4-Dibenzothienyl)-2-(4-morpholinyl)-4H-1-benzopyran-4-one), Ku-0060648 (4-Ethyl-N-[4-[2-(4-morpholinyl)-4-oxo-4H-1-benzopyran-8-yl]-1-dibenzothienyl]-1-piperazineacetamide), Compound 401 (2-(4-Morpholinyl)-4H-pyrimido[2,1-a]isoquinolin-4-one), DMNB (4,5-Dimethoxy-2-nitrobenzaldehyde), ETP 45658 (3-[1-Methyl-4-(4-morpholinyl)-1H-pyrazolo[3,4-d]pyrimidin-6-ylphenol), LTURM 34 (8-(4-Dibenzothienyll)-2-(4-morpholinyl)-4H-1,3-benzoxazin-4-one), and Pl 103 hydrochloride (3-[4-(4-Morpholinylpyrido[3',2':4,5]furo[3,2-d]pyrimidin-2-yl]phenol hydrochloride).

As used herein, "target locus" refers to a site within a nucleic acid molecule that is recognized and cleaved by a nucleic acid cutting entity. When, for example, a single CRISPR complex is designed to cleave double-stranded nucleic acid, then the target locus is the cut site and the surrounding region recognized by the CRISPR complex. When, for example, two CRISPR complexes are designed to nick double-stranded nucleic acid in close proximity to create a double-stranded break, then the region surrounding recognized by both CRISPR complexes and including the break point is referred to as the target locus.

As used herein, "nuclease-resistant group" refers to a chemical group that may be incorporated into nucleic acid molecules and can inhibit by enzymes (exonucleases and/or endonucleases) degradation of nucleic acid molecules containing the group. Examples of such groups are phosphorothioate groups, amine groups, 2'-O-methyl nucleotides, 2'-deoxy-2'-fluoro nucleotides, 2'-deoxy nucleotides, and 5-C-methyl nucleotides. Nuclease resistant groups may be located at a number of places in the donor nucleic acid molecules. In some embodiments, cellular nucleases will digest this portion of the donor nucleic acid molecule. These nucleases will either stop or be slowed down by the nuclease resistant group, thereby stabilizing the structure of donor nucleic acid molecule.

Embodiments of the invention include compositions comprising nucleic acid molecules containing one or more (e.g., one, two, three, four, five, six, seven, etc.) nuclease resistant groups, as well as methods for making and using such donor nucleic acid molecules. In many embodiments, nuclease resistant groups will be located at one or both termini of donor nucleic acid molecules. Donor nucleic acid molecules may contain groups interior from one or both termini. In many embodiments, some or all of such donor nucleic acid molecules will be processed within cells to generate termini that match DS break sites.

As used herein, the term "intracellular targeting moiety" refers to a chemical entity (e.g., a polypeptide) that facilitates localization to an intracellular location. Examples of intracellular targeting moieties include nuclear localization signals, chloroplast targeting signals, and mitochondrial targeting signals.

As used herein, "subject" refers to a human or non-human animal (e.g., a mammal), or a plant.

As used herein, "treating" refers to reducing at least one symptom of a disease, disorder, or condition of a subject by administrating an affective amount of the promoterless selection marker to the subject.

As used herein, "nucleic acid cutting entity" refers to one or more molecules, enzymes, or complex of molecules with nucleic acid cutting activity (e.g., double-stranded nucleic acid cutting activity). In most embodiments, nucleic acid cutting entity components will be either proteins or nucleic acids or a combination of the two but they may be associated with cofactors and/or other molecules. The nucleic acid cutting entity will typically be selected based upon a number of factors, such as efficiency of DS break generation at target loci, the ability to generate DS break generation at suitable locations at or near target loci, low potential for DS break generation at undesired loci, low toxicity, and cost issues. A number of these factors will vary with the cell employed and target loci. A number of nucleic acid cutting entities are known in the art. For example, in some embodiments the nucleic acid cutting entity includes one or more zinc finger proteins, transcription activator-like effectors (TALEs), CRISPR complex (e.g., Cas9 or CPF1), homing endonucleases or meganucleases, argonaute-nucleic acid complexes, or macronucleases. In some embodiments, the nucleic acid cutting entity will have an activity that allows them to be nuclear localized (e.g., will contain nuclear localization signals (NLS)). In some embodiments, a single strand DNA donor could work with a nick or combination of nicks.

Zinc Finger Proteins (ZFPs)

As used herein, "zinc finger protein" (ZFP) refers to a chimeric protein comprising a nuclease domain and a nucleic acid (e.g., DNA) binding domain that is stabilized by zinc. The individual DNA binding domains are typically referred to as "fingers," such that a zinc finger protein or polypeptide has at least one finger, more typically two fingers, or three fingers, or even four or five fingers, to at least six or more fingers. In some embodiments, ZFPs will contain three or four zinc fingers. Each finger typically binds from two to four base pairs of DNA. Each finger may comprise about 30 amino acids zinc-chelating, DNA-binding region (see, e.g., U.S. Pat. Publ. No. 2012/0329067 A1, the disclosure of which is incorporated herein by reference).

One example of a nuclease domain is the non-specific cleavage domain from the type IIs restriction endonuclease FokI (Kim, Y. G., et al., *Proc. Natl. Acad. Sci.* 93:1156-60 (1996)) typically separated by a linker sequence of 5-7 base pairs. A pair of the FokI cleavage domain is generally required to allow for dimerization of the domain and cleavage of a non-palindromic target sequence from opposite strands. The DNA-binding domains of individual $Cys_2His_2$ ZFNs typically contain between 3 and 6 individual zinc-finger repeats and can each recognize between 9 and 18 base pairs.

One problem associated with ZFPs is the possibility of off-target cleavage which may lead to random integration of donor DNA or result in chromosomal rearrangements or even cell death which still raises concern about applicability in higher organisms (Radecke, S., et al., *Mol. Ther.* 18:743-753 (2010)).

Transcription Activator-Like Effectors (TALEs)

As used herein, "transcription activator-like effectors" (TALEs) refer to proteins composed of more than one TAL repeat and is capable of binding to nucleic acid in a sequence specific manner. TALEs represent a class of DNA binding proteins secreted by plant-pathogenic bacteria of the species, such as *Xanthomonas* and *Ralstonia*, via their type III secretion system upon infection of plant cells. Natural TALEs specifically have been shown to bind to plant promoter sequences thereby modulating gene expression and activating effector-specific host genes to facilitate bacterial propagation (Römer, P., et al., *Science* 318:645-648 (2007); Boch, J., et al., *Annu. Rev. Phytopathol.* 48:419-436 (2010); Kay, S., et al., *Science* 318:648-651 (2007); Kay, S., et al., *Curr. Opin. Microbiol.* 12:37-43 (2009)).

Natural TALEs are generally characterized by a central repeat domain and a carboxyl-terminal nuclear localization signal sequence (NLS) and a transcriptional activation domain (AD). The central repeat domain typically consists of a variable amount of between 1.5 and 33.5 amino acid repeats that are usually 33-35 residues in length except for a generally shorter carboxyl-terminal repeat referred to as half-repeat. The repeats are mostly identical but differ in certain hypervariable residues. DNA recognition specificity of TALEs is mediated by hypervariable residues typically at positions 12 and 13 of each repeat—the so-called repeat variable diresidue (RVD) wherein each RVD targets a specific nucleotide in a given DNA sequence. Thus, the sequential order of repeats in a TAL protein tends to correlate with a defined linear order of nucleotides in a given DNA sequence. The underlying RVD code of some naturally occurring TALEs has been identified, allowing prediction of the sequential repeat order required to bind to a given DNA sequence (Boch, J., et al., Science 326:1509-1512 (2009); Moscou, M. J., et al., Science 326:1501 (2009)). Further, TAL effectors generated with new repeat combinations have been shown to bind to target sequences predicted by this code. It has been shown that the target DNA sequence generally start with a 5' thymine base to be recognized by the TAL protein.

The modular structure of TALs allows for combination of the DNA binding domain with effector molecules such as nucleases. In particular, TALE nucleases allow for the development of new genome engineering tools.

TALEs used in some embodiments may generate DS breaks or may have a combined action for the generation of DS breaks. For example, TAL-FokI nuclease fusions can be designed to bind at or near a target locus and form double-stranded nucleic acid cutting activity by the association of two FokI domains.

In some embodiments, TALEs will contain greater than or equal to 6 (e.g., greater than or equal to 8, 10, 12, 15, or 17, or from 6 to 25, 6 to 35, 8 to 25, 10 to 25, 12 to 25, 8 to 22, 10 to 22, 12 to 22, 6 to 20, 8 to 20, 10 to 22, 12 to 20, 6 to 18, 10 to 18, 12 to 18, etc.) TAL repeats. In some embodiments, a TALE may contain 18 or 24 or 17.5 or 23.5 TAL nucleic acid binding cassettes. In additional embodiments, a TALE may contain 15.5, 16.5, 18.5, 19.5, 20.5, 21.5, 22.5 or 24.5 TAL nucleic acid binding cassettes. TALEs will generally have at least one polypeptide region which flanks the region containing the TAL repeats. In many embodiments, flanking regions will be present at both the amino and carboxyl termini of the TAL repeats. Exemplary TALEs are set out in U.S. Pat. Publ. No. 2013/0274129 A1, the disclosure of which is incorporated herein by reference, and may be modified forms on naturally occurring proteins found in bacteria of the genera *Burkholderia, Xanthamonas* and *Ralstonia*.

In some embodiments, TALE proteins will contain nuclear localization signals (NLS) that allow them to be transported to the nucleus.

CRISPR Based Systems

The term "CRISPR" or "Clustered Regularly Interspaced Short Palindromic Repeats" is a general term that applies to three types of systems, and system sub-types. In general, the term CRISPR refers to the repetitive regions that encode CRISPR system components (e.g., encoded crRNAs). Three types of CRISPR systems (see Table 2) have been identified, each with differing features.

TABLE 2

| CRISPR System Types Overview | | |
| --- | --- | --- |
| System | Features | Examples |
| Type I | Multiple proteins (5-7 proteins typical), crRNA, requires PAM. DNA Cleavage is catalyzed by Cas3. | *Staphylococcus epidermidis* (Type IA) |
| Type II | 3-4 proteins (one protein (Cas9) has nuclease activity) two RNAs, requires PAMs. Target DNA cleavage catalyzed by Cas9 and RNA components. | *Streptococcus pyogenes* CRISPR/Cas9, *Francisella novicida* U112 Cpf1 |

TABLE 2-continued

CRISPR System Types Overview

| System | Features | Examples |
|---|---|---|
| Type III | Five or six proteins required for cutting, number of required RNAs unknown but expected to be 1, PAMs not required. Type IIIB systems have the ability to target RNA. | *S. epidermidis* (Type IIIA); *P. furiosus* (Type IIIB). |

As used herein, "CRISPR complex" refers to the CRISPR proteins and nucleic acid (e.g., RNA) that associate with each other to form an aggregate that has functional activity. An example of a CRISPR complex is a wild-type Cas9 (sometimes referred to as Csn1) protein that is bound to a guide RNA specific for a target locus.

As used herein, "CRISPR protein" refers to a protein comprising a nucleic acid (e.g., RNA) binding domain nucleic acid and an effector domain (e.g., Cas9, such as *Streptococcus pyogenes* Cas9, or CPF1 (cleavage and polyadenylation factor 1)). The nucleic acid binding domains interact with a first nucleic acid molecules either having a region capable of hybridizing to a desired target nucleic acid (e.g., a guide RNA) or allows for the association with a second nucleic acid having a region capable of hybridizing to the desired target nucleic acid (e.g., a crRNA). CRISPR proteins can also comprise nuclease domains (i.e., DNase or RNase domains), additional DNA binding domains, helicase domains, protein-protein interaction domains, dimerization domains, as well as other domains.

CRISPR protein also refers to proteins that form a complex that binds the first nucleic acid molecule referred to above. Thus, one CRISPR protein may bind to, for example, a guide RNA and another protein may have endonuclease activity. These are all considered to be CRISPR proteins because they function as part of a complex that performs the same functions as a single protein, such as Cas9 or CPF1.

In some embodiments, CRISPR proteins will contain nuclear localization signals (NLS) that allow them to be transported to the nucleus.

CRISPRs used in some embodiments may generate DS breaks or may have a combined action for the generation of DS breaks. For example, mutations may be introduced into CRISPR components that prevent CRISPR complexes from making DS breaks but still allow for these complexes to nick DNA. Mutations have been identified in Cas9 proteins that allow for the preparation of Cas9 proteins that nick DNA rather than making double-stranded cuts. Thus, some embodiments include the use of Cas9 proteins that have mutations in RuvC and/or HNH domains that limit the nuclease activity of this protein to nicking activity.

The term "dCas9" as provided herein refers to a nuclease inactivated Cas9. In embodiments, the DNA-binding modulation-enhancing agent may be a guide RNA bound to a dCas9 domain. In other embodiments, the modulation complex is a Cas9 domain bound to a gRNA, wherein the modulation complex further includes a VP16 transcriptional activation domain operably linked to the Cas9 domain. Such a system could be used to induce expression of, for example, an endogenous gene in a mammalian cell. A person of ordinary skill in the art will immediately recognize that the types of DNA-binding modulation-enhancing agents used will vary depending on the cell type and specific application.

In many instances, dCas9 proteins will have at least one mutation in each of the RuvC and HNH domains which inactivate the nuclease activity of the protein.

CRISPR systems that may be used vary greatly. These systems will generally have the functional activities of a being able to form complex comprising a protein and a first nucleic acid where the complex recognizes a second nucleic acid. CRISPR systems can be a type I, a type II, or a type III system. Non-limiting examples of suitable CRISPR proteins include Cas3, Cas4, Cas5, Cas5c (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Csc2 (or CasB), Cse3 (or CasE), Csc4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

In some embodiments, the CRISPR protein (e.g., Cas9) is derived from a type II CRISPR system. In some embodiments, the CRISPR system is designed to acts as an oligonucleotide (e.g., DNA or RNA)-guided endonuclease derived from a Cas9 protein. The Cas9 protein for this and other functions set out herein can be from *Streptococcus pyogenes*, *Streptococcus thermophilus*, *Streptococcus* sp., *Nocardiopsis dassonvillei*, *Streptomyces pristinaespiralis*, *Streptomyces viridochromogenes*, *Streptomyces viridochromogenes*, *Streptosporangium roseum*, *Alicyclobacillus acidocaldarius*, *Bacillus pseudomycoides*, *Bacillus selenitireducens*, *Exiguobacterium sibiricum*, *Lactobacillus delbrueckii*, *Lactobacillus salivarius*, *Microscilla marina*, *Burkholderiales* bacterium, *Polaromonas naphthalenivorans*, *Polaromonas* sp., *Crocosphaera watsonii*, *Cyanothece* sp., *Microcystis aeruginosa*, *Synechococcus* sp., *Acetohalobium arabaticum*, *Ammonifex degensii*, *Caldicelulosiruptor becscii*, *Candidatus Desulforudis*, *Clostridium botulinum*, *Clostridium difficile*, *Finegoldia magna*, *Natranaerobius thermophilus*, *Pelotomaculum thermopropionicum*, *Acidithiobacillus caldus*, *Acidithiobacillus ferrooxidans*, *Allochromatium vinosum*, *Marinobacter* sp., *Nitrosococcus halophilus*, *Nitrosococcus watsoni*, *Pseudoalteromonas haloplanktis*, *Ktedonobacter racemifer*, *Methanohalobium evestigatum*, *Anabaena variabilis*, *Nodularia spumigena*, *Nostoc* sp., *Arthrospira maxima*, *Arthrospira platensis*, *Arthrospira* sp., *Lyngbya* sp., *Microcoleus chthonoplastes*, *Oscillatoria* sp., *Petrotoga mobilis*, *Thermosipho africanus*, or *Acaryochloris marina*.

Argonaute Gene Editing Systems

The argonaute family of proteins are endonucleases that use 5' phosphorylated single-stranded nucleic acids as guides to cleave nucleic acid targets. These proteins, like Cas9, are believed to have roles in gene expression repression and defense against exogenous nucleic acids.

Argonaute proteins differ from Cas9 in a number of ways. Unlike Cas9, which exist only in prokaryotes, argonaute proteins are evolutionarily conserved and are present in almost all organisms. Some argonaute proteins have been found to bind single-stranded DNAs and cleave target DNA molecules. Further, no specific consensus secondary structure of guides is required for argonaute binding and no sequence like a CRISPR system PAM site is required. It has been shown that the argonaute protein of *Natronobacterium gregoryi* can be programmed with single-stranded DNA guides and used as a genome editing in mammalian cells (Gao, F., et al., *Nat. Biotechnol.* 34:768-73 (2016)).

Argonaute proteins require a 5' phosphorylated single-stranded guide DNA molecule that is about 24 nucleotides in length. See, for example, the amino acid sequence of an argonaute at SEQ ID NO: 6 in Table 12.

Introduction of Materials into Cells

Introduction of a various molecules into cells may be done in a number of ways, including by methods described in many standard laboratory manuals, such as Davis, L. et al., Basic Methods in Molecular Biology, New York: Elsevier (1986) and Sambrook, J., et al., Molecular Cloning: A laboratory manual vol. 1, 2nd ed., Cold Spring Harbour Lab. Press, N.Y. (1989). Examples include, but are not limited to, calcium phosphate transfection, DEAE-dextran mediated transfection, transfection, microinjection, cationic lipid-mediated transfection, electroporation, transduction, scrape loading, ballistic introduction, nucleoporation, hydrodynamic shock, and infection.

Different components of nucleic acid cutting entities and/or donor nucleic acid molecules can be introduced into cells by different means. In some embodiments, a single type of nucleic acid cutting entity molecule may be introduced into a cell but some nucleic acid cutting entity molecules may be expressed within the cell. One example is where two zinc finger-FokI fusions are used to generate a double-stranded break in intracellular nucleic acid. In some instance, only one of the zinc finger-FokI fusions may be introduced into the cell and the other zinc finger-FokI fusion may be produced intracellularly.

Suitable transfection agents include transfection agents that facilitate the introduction of RNA, DNA and proteins into cells. Exemplary transfection reagents include, but are not limited to, TurboFect Transfection Reagent (Thermo Fisher Scientific), Pro-Ject Reagent (Thermo Fisher Scientific), TRANSPASS™ P Protein Transfection Reagent (New England Biolabs), CHARIOT™ Protein Delivery Reagent (Active Motif), PROTEOJUICE™ Protein Transfection Reagent (EMD Millipore), 293fectin, LIPOFECTAMINE™ 2000, LIPOFECTAMINE™ 3000 (Thermo Fisher Scientific), LIPOFECTAMINE™ (Thermo Fisher Scientific), LIPOFECTIN™ (Thermo Fisher Scientific), DMRIE-C, CELLFECTIN™ (Thermo Fisher Scientific), Oligofectamine™ (Thermo Fisher Scientific), LIPOFECTACE™, Fugene™ (Roche, Basel, Switzerland), Fugene™ HD (Roche), Transfectam™ (Transfectam, Promega, Madison, Wis.), Tfx-10™ (Promega), Tfx-20™ (Promega), Tfx-50™ (Promega), Transfectin™ (BioRad, Hercules, Calif.), SilentFect™ (BioRad), Effectene™ (Qiagen, Valencia, Calif.), DC-chol (Avanti Polar Lipids), GENEPORTER™ (Gene Therapy Systems, San Diego, Calif.), DHARMAFECT 1™ (Dharmacon, Lafayette, Colo.), DHARMAFECT 2™ (Dharmacon), DHARMAFECT 3™ (Dharmacon), DHARMAFECT 4™ (Dharmacon), ESCORT™ III (Sigma, St. Louis, Mo.), and Escort™ IV (Sigma Chemical Co.).

Compositions and methods of the invention include can be used in high throughput screening methods. One example of such a method is reverse transfection. For purposes of illustration, assume that a library of gRNA molecules and corresponding NLS-conjugated donor DNA molecules have been generated. Further assume that each library composition contains (1) a gRNA molecule with sequence homology to a particular locus in a cellular genome and (2) an NLS-conjugated donor DNA molecule with regions of homology that flank the intended genomic cleavage site. Also assume that three hundred such library compositions have been generated and each of these compositions is spotted at a separate location on a glass slide. Finally, a 293FT cell line which expresses Cas9 protein is overlaid onto the glass slide under conditions that allow for (1) uptake of the library compositions and (2) gene editing to occur at the gRNA specified target locus. Of course numerous variations of such methods are possible, including variations where the gene editing reagents used differ (e.g., TAL-FokI mRNA instead of gRNA) and where the array format differs (e.g., wells of a 96 well plate instead of the surface of a glass slide).

The invention thus includes libraries of gene editing reagents (e.g., gRNA, TAL mRNA, donor nucleic acid molecules, etc.) and high throughput methods for modifying various target loci in cells.

Nucleic Acid Localization and Gene Editing Efficiency

The invention also includes compositions and methods for increasing gene editing efficiency. In some embodiments, such compositions and methods relate to nucleic acid molecules that are connected to one or more intracellular targeting moiety that localize the nucleic acid molecules to an intracellular location where gene editing is desired (e.g., cell nuclei, mitochondria, chloroplasts, etc.). Some embodiments will employ intracellular targeting moieties to facilitate increased local concentration of nucleic acid molecules at one or more intracellular location. While not wishing to be bound by theory, it is believed that the increased gene editing efficiency results from an increase in donor nucleic acid concentration at the location where gene editing is desired.

One embodiment is shown in FIG. 9. This figure shows a nuclear localization signal (NLS) (an example of an intracellular targeting moiety) connected to a single-stranded donor DNA molecule via two different linkers. Constructs of this type may be used to facilitate delivery of nucleic acid to the nucleus. A number of variations of such constructs are possible.

As set out in FIGS. 11 and 13 and as discussed in the nuclear localization example below, it has been found that constructs such as those shown in FIG. 9 can significantly increase the efficiency of intracellular gene editing and allow for the use of less donor nucleic acid. In particular, the date referred to above demonstrates that the use of NLS modified donor DNA can increase the efficiency of genome engineering at nucleic acid cut sites (e.g., chromosomal loci cut with gRNA/Cas9).

Figure 13:
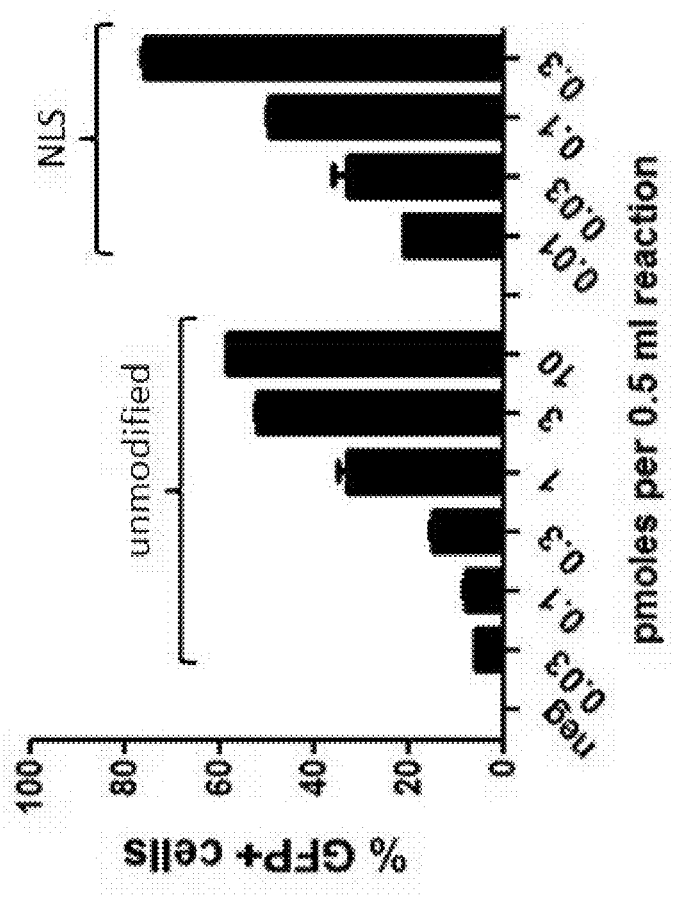
FIG. 13. Dose response of a PS oligo donor DNA com-
pared to an NLS modified donor DNA to edit a single base
to convert BFP expressing cells to GFP expressing cells.
Dose response of PS oligo donor DNA compared to SMCC
linked NLS modified donor DNA.

The data in FIGS. 11 and 13 show gene editing efficiencies approaching 80%. Further, this is seen with as little as 0.03 picomoles of NLS-donor DNA conjugate per around $2 \times 10^5$ cells. Embodiments thus include compositions and methods for intracellular gene engineering wherein a specific target locus is modified in at least 75% (e.g., at least 80%, at least 85%, at least 90%, at least 95%, from 50% to 75%, 50% to 80%, 50% to 85%, 50% to 95%, 60% to 95%, 70% to 95%, 70% to 90%, 75% to 90%, 80% to 99%, 80% to 97%, 80% to 99%, 80% to 96%, 88% to 98%, etc.) of the cells. Further, some embodiments include compositions and methods where at least 50% of the transfected cells in a reaction mixture are modified at the target locus when the cells are contacted with 0.3 picomoles or less (e.g., from 0.001 to 0.3, 0.005 to 0.3, 0.01 to 0.3, 0.05 to 0.3, 0.001 to 0.2, 0.005 to 0.2, 0.001 to 0.15, 0.001 to 0.1, etc., picomoles) of donor DNA per $2 \times 10^5$ cells. This assumes 100% transfection. For example, with 50% transfection one would obtain approximately half of the total number of cells and at least 75% of the transfected cells.

Some embodiments also relate to compositions and methods for increasing the local concentration of donor nucleic acid at locations where intracellular nucleic acid molecules for which alteration is desired are present (e.g., the nucleus). Some embodiments include compositions and methods for using intracellular targeting moieties for increasing the concentration of at an intracellular location, wherein the amount of increase in localized nucleic acid concentration is at least 10 (e.g., 10 to 1,000, 10 to 800, 10 to 600, 10 to 1,000, 10 to 1,000, 10 to 1,000, 10 to 400, 50 to 1,000, 50 to 600, 100 to 1,000, 100 to 700, etc.) fold higher that when intracellular targeting moieties are not used. As an example, the fold increase in intracellular localization of nucleic acid molecules may be measure using, for example, fluorescently labeled nucleic acid molecules. By way of illustration, both NLS conjugated and unconjugated nucleic acid molecules could be used for comparison in such an assay.

One variation of the construct shown in FIG. 9 is where an NLS is located at the 3' terminus of the donor DNA molecule, instead of the 5' terminus, at both termini, placed in the middle of the donor DNA molecule, etc. Further, more than one NLS may be present at one or both termini. Also, the nucleic acid molecule may be: (1) DNA or RNA; (2) single-stranded or double-stranded; (3) linear, circular, or molecules with a stem or hairpin loop; and/or (4) chemically modified (e.g., contain phosphorothioate linkages, 2'-O-methyl bases, etc.). Additionally, as set out below, the NLS may be replaced with as intracellular targeting moiety that directs localization to a cellular space other than the nucleus (e.g., mitochondria, chloroplast, etc.). Some embodiments thus include nucleic acid molecules operably linked to one or more intracellular targeting moiety that localizes to an intracellular location where gene editing is desired, as well as methods for using such nucleic acid molecules (e.g., for genome engineering). The amino acid sequences of some exemplary intracellular targeting moieties that may be used in some embodiments are set out in Table 3.

TABLE 3

Exemplary Sub-Cellular/Organelle Localization Sequences

| | SEQ ID |
|---|---|
| Nuclear Localization Signals | |
| PKKKRKV | 7 |
| AVKRPAATKKAGQAKKKKLD | 99 |
| MSRRRKANPTKLSENAKKLAKEVEN | 100 |
| PAAKRVKLD | 101 |
| Chloroplast Targeting Signals | |
| LIAHPQAFPGAIAAPISYAYAVKGRKPRFQTAKGSVRI | 11 |
| Mitochondrial Targeting Signal | |
| MLSLRQSIRFFKPATRTLCSSRYLL | 12 |

Further, in many instances when intracellular targeting moieties (e.g., polypeptides) are use, these targeting moieties may be designed to localize nucleic acid molecules to a location where intracellular nucleic acid is expected to be present (e.g., the nucleus, the stroma of chloroplasts, the matrix of mitochondria, etc.). In other words, in many instances, it may be desirable to direct localization of nucleic acid to a specific sub-space within in a cell. Some embodiments include compositions and methods for localizing donor nucleic acid molecules in locations within cells, as well as for enhancing the efficiency of genome engineering reactions at locations within cells where the donor nucleic acid molecules are localized.

Any number of methods may be used to connect intracellular targeting moieties to nucleic acid molecules in the practice of the invention. Two methods set out in the examples are succinimidyl 4-(N-maleimidomethyl) cyclohexane-1-carboxylate (SMCC) linkers and the Click-iT® system (Thermo Fisher Scientific). In any event, the linker used to connect intracellular targeting moieties to nucleic acid molecules will typically have certain characteristics, some of those characteristics are (1) low cellular toxicity, (2) facilitation of or, at least, low levels of interference with cellular uptake, and (3) low molecular weight (mwt) (e.g., less than 500 mwt). The connection of intracellular targeting moieties to nucleic acid molecules may be carried out by PCR amplification with NLS-conjugated DNA oligonucleotide as primer. Also, the NLS-conjugated DNA oligonucleotide may serve as a universal primer, in which the nucleic acid moieties are linked to a gene-specific region for PCR amplification. Further, instead of covalent conjugation of intracellular targeting moieties, the NLS-conjugated DNA oligonucleotide may anneal to a single-stranded DNA donor or double-stranded DNA donor with a single-stranded overhang and then carry the donor into an intracellular compartment.

The size, type and other characteristics of nucleic acid molecule component of the conjugate will often vary with the application, with SNP alteration generally being shorter than coding region insertion. Further, the lengths regions of homology (when present) with endogenous nucleic acid will also vary with the application. The nucleic acid molecule component (e.g., donor DNA) of the conjugate can be from 1 to 2000 or greater (e.g., less than or equal to 1500, 1000, 750, 500, 300, 250, 200, 150, 100, 75, 50, 40, 35, 30, 25, 20, 15, 10, 5, 4, 3, 2, or 1) nucleotides or base pairs in length (depending on whether they are single-stranded or double-stranded. In some embodiments, the nucleic acid molecule component is from 1 to 500, 10 to 400, 20 to 300, 30 to 250, 30 to 200, or 30 to 100, etc., nucleotides or base pairs in length.

The invention also includes compositions and methods comprising gene editing proteins (e.g., Cas9 proteins, TAL proteins, etc.), wherein the gene editing proteins are operably linked to one or more intracellular targeting moiety capable of localizing the donor nucleic acid molecule to a location in the cell where the endogenous nucleic acid molecule is located one or more intracellular targeting moiety is associated with the gene editing proteins.

Nuclear localization signals that may be used in the practice of the invention may have various structures and may be, for examples, monopartite or bipartite. Monopartite NLSs typically consists of a single cluster of basic residues. Bipartite NLSs typically consists of two clusters of basic residues separated by 10-12 residues. Exemplary NLS amino acid sequences are set out below in Tables 4, 5 and 6.

TABLE 4

Exemplary Classical Based NLS Amino Acid Sequences

| | Monopartite | SEQ ID No. |
|---|---|---|
| SV40 | PKKKRKV | 7 |
| Myc | PAAKRVKLD | 101 |
| | Bipartite | SEQ ID No. |
| Nucleoplasmin | KRPAATKKAGQAKKKKL | 102 |
| BP-SV40 | KRTADGSEFESPKKKRKVE | 48 |
| BP-SV40A4 | KRTADGSEFESPKKARKVE | 49 |

TABLE 4-continued

Exemplary Classical Based NLS Amino Acid Sequences

| | | |
|---|---|---|
| BP-SV40A5 | KR*TADGSEFES*PKKKAKVE | 50 |
| BP-SV40C | KRX$_{5-15}$KKN$_1$N$_2$KV | 142 |

Underlined amino acid sequences are believed to associate with importin α, linker sequences are italicized. BP-SV40C is a BP-SV40 bipartite NLS consensus sequence. In some instances N$_1$ may be lysine or alanine and N$_2$ may be lysine, arginine, or alanine.

TABLE 5

Exemplary Non-Classical/Other NLS Amino Acid Sequences

| | SEQ ID No. |
|---|---|
| ASPEYVNLPINGNG | 103 |
| LSPSLSPL | 104 |
| MVQLRPRASR | 105 |
| PPARRRRL | 106 |
| TLSPASSPSSVSCPVIPASTDESPGSALNI | 107 |

TABLE 6

Additional NLS Sequences and Consensus Sequences

| | | SEQ ID No |
|---|---|---|
| Non-Naturally Occurring NLSs | | |
| BP-Myc Variant | KRTADGSEFEPAAKRVKLDE | 108 |
| BP-SV40 Variant | KRTADGSEFESPKKKRKVE | 48 |
| Naturally Occurring NLSs | | |
| Bipartite NLS1 | SAARKRNSATVHLCPVPRKRSG | 109 |
| Bipartite NLS2 | AAAKRPADDDDNASPAAKRRSG | 110 |
| Bi-partite NLS3 | SAAKRPSATVHLCDVPTKKTKRSG | 111 |
| Consensus Sequences | | |
| Consensus 1 | KRX$_{(10-12)}$K(K/R)(K/R)$_n$ | 112 |
| Consensus 2 | KRX$_{(10-12)}$K(K/R)X(K/R)$_n$ | 113 |
| Consensus 3 | KRX$_{(5-15)}$K(K/R)(K/R)$_{1-2}$ | 114 |
| Consensus 4 | KRX$_{(5-15)}$K(K/R)X(K/R)$_{1-2}$ | 115 |

Figure 39:
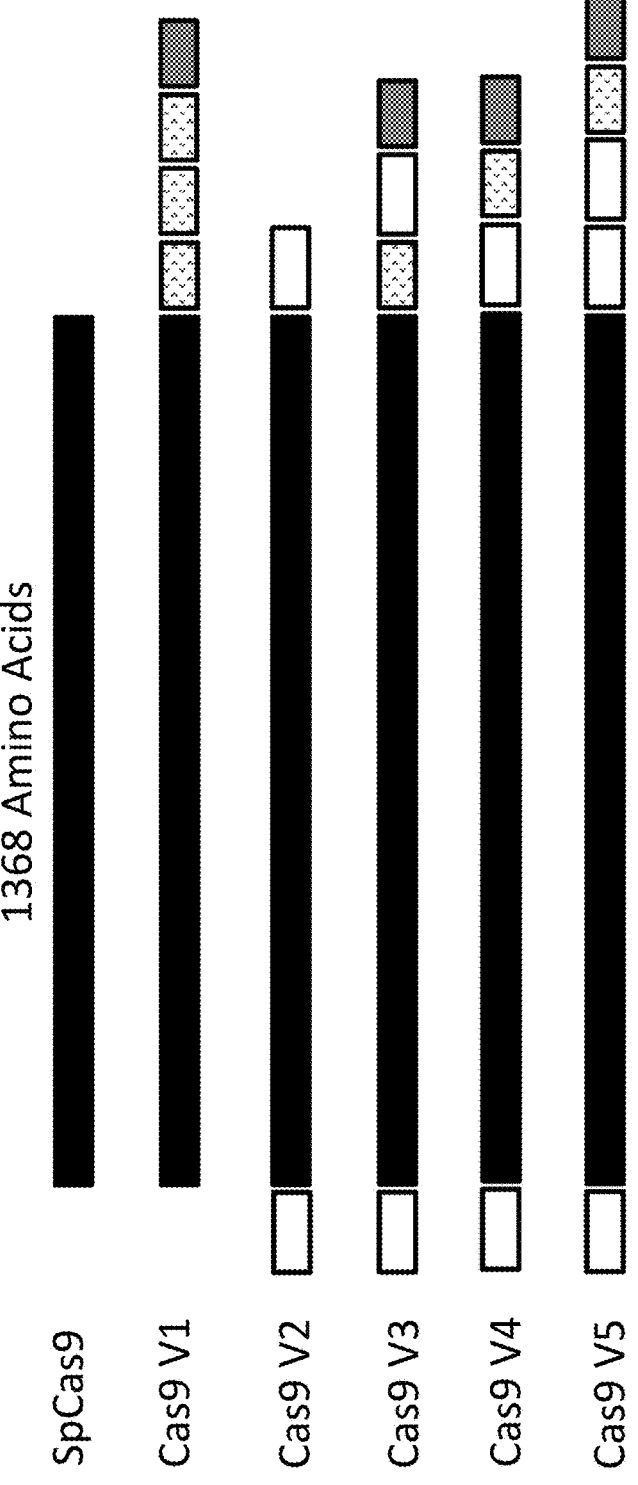
FIG. 39 is a schematic representation of exemplary Cas9 formats, based upon a model Cas9 protein, *Streptococcus pyogenes* Cas9. This 1368 amino acid protein is represented by the solid top line of the figure. The Cas9 proteins designated as V1-V5 are fusion proteins with nuclear localization signals (NLSs) as components. The dotted boxes represent monopartite NLSs and the open boxes represent bipartite NLSs. The grey box represents an affinity tag (e.g., a six histidine tag (SEQ ID NO: 129)).
Figure 40:
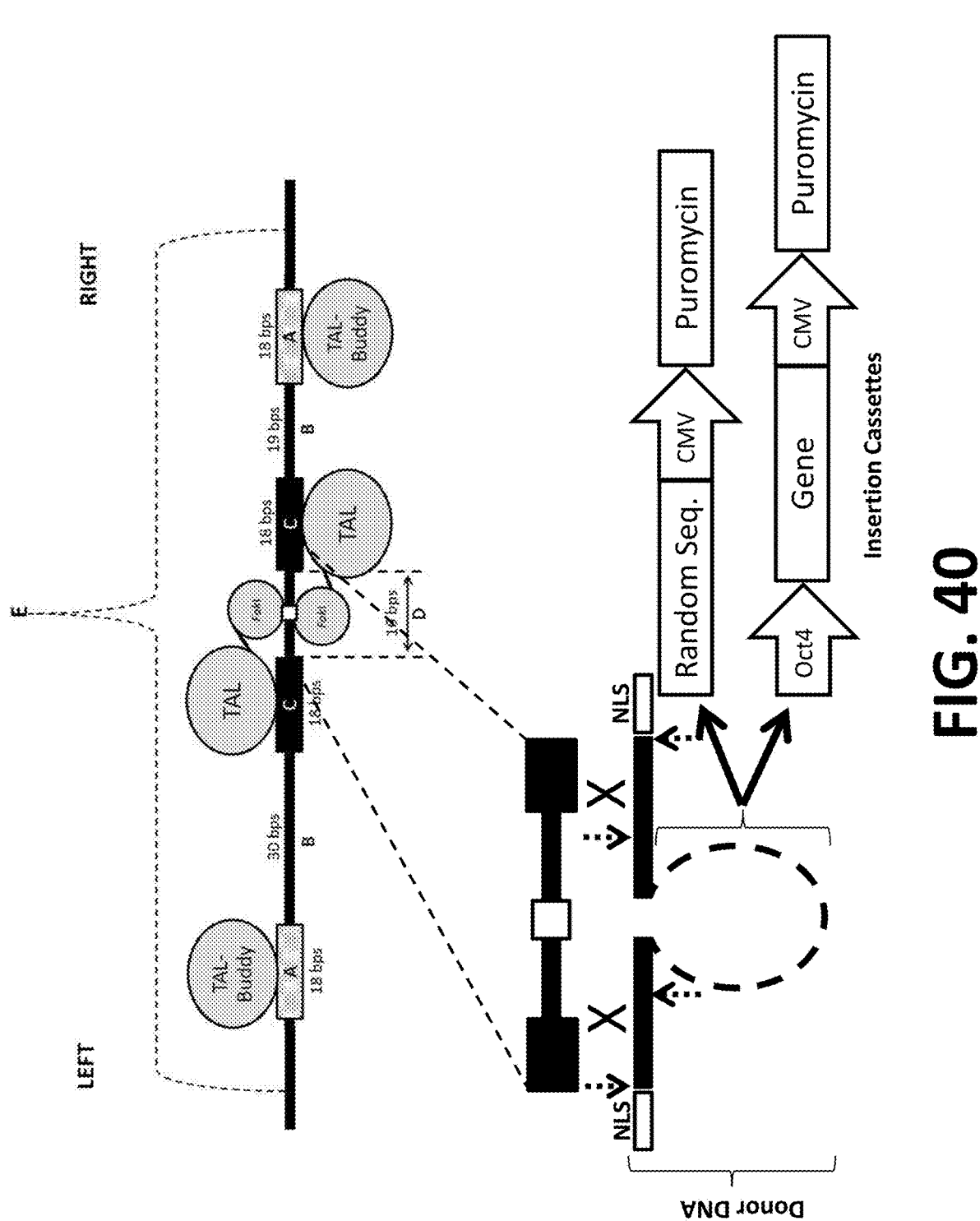
FIG. 40 is a schematic similar to FIG. 36 that add more detailed view of both the TAL cleavage locus and schematics over of donor DNA molecules. A line representation schematic of donor DNA is shown on the lower left. The solid straight lines represent the regions of homology with the target locus. The dashed, circular line represents an insertion cassette. The "X" symbols represent regions of sequence homology. The dashed up and down arrows represent two phosphorothioate linkages in the 5' and 3' strands of the donor DNA homology arms. Upon nuclease digestion, these phosphorothioate linkages are positions so as to result in the generation of 5' overhanging termini ten nucleotides in length. The open boxes on the left and the right represent bipartite NLSs. To the right of the line representation schematic are two examples of insertion cassettes. The upper insertion cassette is designed to both disrupt functionality at the insert locus and to express a puromycin resistance marker. The lower insertion cassette is similar to the upper insertion cassette but is also designed to insert a gene of interest operably linked to a tissue specific promoter into the locus.

X = Any amino acid, n = an integer, sequences believed to be conserved are underlined, linker sequences are italicized FIG. 39 shows a series of schematic drawings of Cas9 proteins operably linked to NLSs. Any number and type of NLSs may be used and their location in proteins or nucleic acid molecules will vary with the specifics of both the molecule to which the NLSs are linked to and the intended purpose. With respect to a protein such as Cas9 or a TAL effector, it will generally be desirable to introduce substantial quantities of the proteins into cells, followed by the proteins being retained in the cytoplasm for a relatively short period of time with the majority of the protein being localized to the nucleus. This is so because it is believed that the longer the protein remains in the cytoplasm, the more of the protein will be degraded. It is also believed that the higher the concentration of Cas9 in the nucleus, the higher the cutting efficiency, assuming of course that all of the Cas9 has cutting activity (e.g., is associated with gRNA). Thus, the amount of NLS associated proteins (as well as other molecules) that "collect" in the nucleus is based upon: (1) the amount of protein that is introduced into the cell and (2) the rate of which the protein proceeds to the nucleus.

Figure 45:
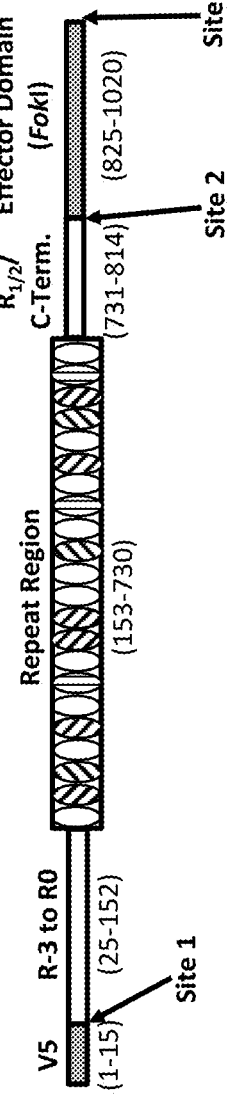
FIG. 45 is a schematic showing a common TALE structural format. Sites 1, 2, and 3 are located outside of the TALE regions believed to be involved in DNA recognition and binding.

FIG. 45 is a schematic showing a common TALE structural format. In many instances, TALEs operate by innervating DNA present in a specified location within a cell (e.g., the nucleus, mitochondria, chloroplast, etc.). In many instances, interruption of regions of TALE proteins involved in DNA recognition and binding will result in either decreased or elimination of DNA recognition and/or binding activity(ies). Sites 1, 2, and 3 are located outside of the TALE regions believed to be involved in DNA recognition and binding. These are thus suitable sites for the placement of NLSs when high levels of target DNA binding are desired.

Using FIG. 45 as a point of reference, NLS placement at Site 1 may occur at any location to the left (N-terminal direction) of amino acid 25. NLS placement at Sites 2 and 3 may occur at any location to the Right (N-terminal direction) of amino acid 814. This includes instances where longer naturally occurring TALE protein regions are included beyond amino acids 25 on the left and 814 on the right of FIG. 45. Further, Site 3 is located at the C-terminus of the Effector Domain.

One or more NLSs may be located at one or more of Sites 1, 2, and/or 3. Further, when multiple NLSs are present (at one of more of these sites), they may be of the same type or of different types.

In many instances, the locations (e.g., Sites 1, 2, and/or 3 in FIG. 45) and types of NLSs will be selected in a manner that result in (1) high levels of localization of the gene editing reagent to the nucleus and/or (2) high levels of functional activity in the nucleus. These two effects will generally be related with nuclear functional activity generally being lower than the amount of nuclear localization. This is so because, in many instances, not all of the gene editing reagents that enter the nucleus will bind to the target locus they have specificity for and those that do bind, may not always act on the target locus nucleic acid in the matter they are designed for (e.g., nucleic acid cleavage, activation of transcription, etc.). One exemplary reason for this is that nuclear nucleic acid may be more accessible in one cell type than another cells type. Also, even within cells of the same cell type, variations exist that may render a target locus more or less accessible in one cell in a population than another cell in the same population.

Both nuclear localization assays and functional assays (e.g., Genomic Cleavage Detection) are set out elsewhere herein. In order to correct for differences in target loci and cell types, typically the same target locus and cell type will be used for comparative assays.

Further, gene editing efficiency will often vary with the locus being edited and the cell type. This is so due to a number of factors, including accessible of the target locus to gene editing reagents and the efficiency of the cell type with respect to homology directed repair (HDR). With respect to HDR, cells that have higher HDR efficiencies (e.g., 293FT and U2OS cells) will generally exhibit higher gene editing rates than cell with lower levels of HDR efficiency (e.g., A549 cells).

A number of formats of TALE proteins, with respect to the location and type of NLSs are set out below in Table 7.

TABLE 7

| | | | C-Terminus- | C-Terminus of Effector |
| No. | N-Terminus (SEQ ID NO) | Repeat Region | Effector Domain (SEQ ID NO) | Domain (SEQ ID NO) |
| --- | --- | --- | --- | --- |
| 1 | XXKRPAATKKAGQAKKKK (116) | | | |
| 2 | PKKKRVD (98) | | | PKKKRVD (98) |
| 3 | | | PKKKRVD (98) | PKKKRVD (98) |
| 4 | PKKKRVD (98) | | PKKKRV (126) | PKKKRVD (98) |
| 5 | PKKKRVDX$_{1-20}$PKKKRVD (117) | | | |
| 6 | XXKRPAATKKAGQAKKKK (116) | | | XXKRPAATKKAGQAKKKK (116) |
| 7 | One NLS | | One NLS | One NLS |
| 8 | | | | Two NLSs |

X = Any amino acid
X$_{1-20}$ = From 1 to 20 of any amino acids

The exemplary TALE/NLS format set out in Table 7 vary in the type of NLSs and NLS location within TALE proteins. In some instances, TALE proteins will contain from about 1 to about 15 (e.g., from about 2 to about 14, from about 3 to about 14, from about 4 to about 14, from about 2 to about 10, from about 2 to about 8, from about 2 to about 6, from about 3 to about 5, from about 3 to about 4, etc.). Further, when multiple NLSs are present in a TALE protein, these NLSs may be monopartite or bipartite.

Also, two or more NLSs may be located in the same region of a TALE protein (e.g., the N-terminal region, etc.). When more than one NLS is located in a TALE protein (e.g., within the same region of a TALE proteins, two or more of these NLSs may be located within about 1 to about 50 (e.g., from about 2 to about 50, from about 3 to about 50, from about 5 to about 50, from about 10 to about 50, from about 15 to about 50, from about 2 to about 30, from about 5 to about 50, from about 5 to about 25, etc.) amino acids from each other. In some instances, two NLSs may be separated from each other by two amino acids. Further, these amino acids may be of a type intended to form a flexible linker (e.g., Gly-Gly, Gly-Ser, etc.).

Table 7 sets out six specific TALE/NLS formats, with respect to regional locations and amino acid sequences of NLSs. Further set out are two more general TALE/NLS formats. Any number of such formats are possible. For example, the various regions of a TALE protein may independently comprise from about 1 to about 5 NLSs.

FIGS. 46 and 47 show the amino acid sequences of two different TALEN proteins with NLSs at different locations. Both Cas9 and TALEN proteins may vary in the number, type and locations of NLSs that present in the molecules. With respect to the amino acid sequence set out in FIG. 46, when NLSs are located N-terminal with respect to the repeat region, the NLSs will often be located further to the N-terminus than the R-3 region. Further, when NLSs are located C-terminal with respect to the repeat region, the NLSs will often be located further to the C-terminus than amino acids H R V A (amino acid 811-814 in FIG. 46) ("H R V A" disclosed as residues 811-814 of SEQ ID NO: 95), which lies between the repeat region and the effector domain (FokI in the amino acid sequence set out in FIG. 46). Thus, using the amino acid sequence in FIG. 46 for reference, NLSs may be located in three general locations: (1) N-terminal to the Repeat Region, (2) between the Repeat Region and the effector domain, and (3) after the effector domain.

In some instance, one or more NLSs may be located in the region from amino acid 768 to 814, using the amino acid sequence set out in FIG. 46 for reference. As example, one or more NLS may be present immediately after one or more of the following amino acids in FIG. 45: 768, 777, 779, 788, and/or 789.

In particular, FIG. 46 shows, amongst other things, a TAL protein region (amino acids 18 to 153 in FIG. 46) located to the left of the N-terminal end of the Repeat Region. This TAL protein region is typically conserved amongst *Xanthomonas* species, with over 90% identity at the amino acid level. Further, this region contains four regions (R0, R-1, R-2, and R-3) that have some sequence homology to TAL repeats. NLSs will normally be positioned outside of this region and, typically, will be placed further towards the N-terminal end of the TAL protein.

Additional, the amino acid sequence shown in FIG. 46, for example, contains only 153 amino acids N-terminal to the Repeat Region. This N-terminal region may be different lengths and may be, for example, from about 140 to about 400 (e.g., from about 150 to about 350, from about 150 to about 300, from about 150 to about 250, from about 150 to about 200, from about 180 to about 350, from about 185 to about 300, from about 200 to about 350, from about 200 to about 300, etc.) amino acids in length.

Further, again using amino acid sequence shown in FIG. 46 for the region C-terminal to the Repeat Region of amino acids is also typically conserved amongst *Xanthomonas* species. Again, NLSs will normally be positioned outside of this region and, typically, will be placed further towards the C-terminal end of the TAL protein.

Depending on the desired intracellular level of the gene editing molecule (e.g., TAL protein, CRISPR protein, gRNA, etc.) and the desired duration of gene editing activity, gene editing molecules may be introduced into cells as RNA/mRNA or by DNA which encodes the RNA or protein gene editing reagent. Further, when nucleic acid encoding gene editing molecules are located in cells, the coding regions will often be operably linked to an expression control sequence, such as a promoter (e.g., a constitutive promoter, an inducible promoter, a repressible promoter, etc.).

Provided herein are TAL proteins (as well as other gene editing molecules) of various format, nucleic acid molecules encoding these proteins, and methods of using these proteins to modify the genomes of cells.

Assays for measuring the nuclear uptake of proteins and other molecules are known. Such assays may be based upon measurement of functional activity in the nucleus (e.g., the GCD assay set out in Example 1). Other assays directly measure molecular uptake and include fluorescence based assays. Such assays typically require that the molecule being measured exhibit fluorescence. The fluorescence may be naturally resident in the molecule or the fluorescence may result from association with a fluorescent molecule (e.g., GFP, OFP, chemical label (e.g., a dye), etc.).

One suitable assay is set out in Wu et al., *Biophysical Journal,* 96:3840-3849 (2009), where two-photon fluorescence corresponding microscopy was used to measure nuclear import. These methods were based upon measurement by microscope of the average fluorescent intensity at multiple points inside the cytoplasm and nucleus, followed by determining the ratio. While some gene editing reagents may become trapped in membranes and endosomes, the cytoplasmic fluorescence level may be compared to the nuclease fluorescence level to determine the rate of entry of a gene editing reagent into the nucleus and the amount of gene editing reagent present in the nucleus at one or more time points.

Methods such as those set out in Wu et al. may be used to measure uptake and location based concentration of fluorescently labeled gene editing reagents. One exemplary method is where two-photon fluorescence corresponding microscopy is used to measure nuclear localization of a Cas9 protein. In this illustration of a method, a series of different Cas9-NLS-GFP fusion protein/gRNA complex are introduced into a cell line and fluorescent measurements are taken at 50 points with the cells, half being in the cytoplasm and half being in the nucleus. Steady state nuclear to cytoplasmic ratios are then determined for each Cas9-NLS-GFP fusion protein/gRNA complex. Provided herein are compositions and methods that allow for the generation of cells where the nuclear to cytoplasmic ratio of a gene editing reagent within the cells is, on average, from about 5 to about 120 (e.g., from about 5 to about 100, from about 15 to about 100, from about 20 to about 100, from about 25 to about 100, from about 30 to about 100, from about 35 to about 100, from about 40 to about 100, from about 50 to about 100, from about 60 to about 100, from about 70 to about 100, from about 40 to about 120, from about 50 to about 120, etc.).

Also provided herein are compositions and methods that allow for the generation of a cell population wherein, with respect to diploid cells, at least one of the two target loci is cleaved in at least 90% (e.g., from about 90% to about 100%, from about 90% to about 98%, from about 90% to about 96%, from about 93% to about 100%, from about 95% to about 100%, from about 92% to about 96%, etc.) of the members of the population. In some instances, the above cleavage percentages will apply when conditions are adjust such that 50,000 (+/−10%) are contacted with from about to about 0.5 to about 200 ng (e.g., from about to about 0.5 to about 150, from about to about 0.5 to about 100, from about to about 0.5 to about 90, from about to about 0.5 to about 75, from about to about 1 to about 200, from about to about 1.5 to about 200, from about to about 3 to about 200, from about to about 1 to about 50 ng, from about to about 10 to about 45, from about to about 12 to about 60, etc.) of Cas9/gRNA complex under conditions set out in Example 7.

Compositions and methods of the invention where intracellular targeting moieties are employed may be used to alter endogenous nucleic acid molecules by way of any number of methods. For example, these compositions and methods may be sued to facilitate homologous recombination at locations where the endogenous nucleic acid is "intact". By this it is meant that the endogenous nucleic acid has not been cut by gene editing reagents (e.g., CRISPRs, TALs, zinc finger-FokI fusions, etc.). In some instances, however, the site for genetic alteration will be either nicked or have a double-stranded break.

Methods

Methods and compositions provided herein are, inter alia, useful to modulate a target locus (e.g., a gene, genomic region, or a transcriptional regulatory sequence (e.g., a promoter, enhancer)) including chromatin (histone proteins associated with DNA), DNA, proteins bound to DNA or a combination thereof. As used herein the term "target locus" refers to a region within the genome of a cell. A target locus includes one or more binding sequences binding proteins or nucleic acids the binding of which results in structural and or chemical modification of the target locus. Using methods and compositions provided herein a target locus may be structurally or chemically modified by binding of one or more DNA binding agents (e.g., a first or a second DNA-binding modulation-enhancing agent) to specific sites which form part of the target locus. Binding of said DNA binding agents (e.g., a first or a second DNA-binding modulation-enhancing agent) may result, for example, in displacing or restructuring chromatin at the target locus, and/or it may increase the accessibility of the target locus to further modifications by additional endogenous or exogenous modulating agents. For example, methods provided herein are useful to increase efficiency and specificity of a nuclease (TALEN, Cas9) at a genomic locus, by increasing accessibility of the DNA at the cleavage site and surrounding sequences at the locus. Thus, methods and compositions provided herein are, inter alia, useful for genome editing and enhancing enzymatic processes involved therein.

Thus, in one aspect, a method of increasing accessibility of a target locus in a cell is provided. The method includes (1) introducing into a cell including a nucleic acid encoding a target locus a first DNA-binding modulation-enhancing agent, wherein the first DNA-binding modulation-enhancing agent is not endogenous to the cell; and (2) allowing the first DNA-binding modulation-enhancing agent to bind a first enhancer binding sequence of the target locus, thereby increasing accessibility of the target locus relative to the absence of the first DNA-binding modulation-enhancing agent.

The accessibility of a target locus may be enhanced upstream or downstream of an enhancer binding sequence provided herein. Therefore, the chromatin located 5' and 3' of an enhancer binding sequence may be more accessible upon binding of a DNA-binding modulation-enhancing agent to the enhancer binding site relative to the absence of the DNA-binding modulation-enhancing agent.

In embodiments, the target locus includes a plurality of DNA-binding modulation-enhancing agents binding to a plurality of enhancer binding sequences (e.g., 2, 4, 6, 8, 10 enhancer binding sequences) of the target locus. Each of the plurality of enhancer binding sequences may be separated from each other by a sequence of 20-60 nucleotides in length. In embodiments, the target locus includes a first, a second, a third, a fourth, a fifth and a sixth enhancer binding sequence, wherein the first enhancer binding sequence is connected to the third enhancer binding sequence through the second enhancer binding sequence, the third enhancer binding sequence is connected to the fifth enhancer binding sequence through the fourth enhancer binding sequence and the fourth enhancer binding sequence is connected to the sixth enhancer binding sequence through the fifth enhancer binding sequence. The first and second enhancer binding sequence, the second and third enhancer binding sequence, the third and fourth enhancer binding sequence, the fourth and fifth enhancer binding sequence and the fifth and sixth enhancer binding sequence may each be separated by 20-50 nucleotides. In embodiments, the first and second enhancer binding sequence, the second and third enhancer binding sequence, the third and fourth enhancer binding sequence, the fourth and fifth enhancer binding sequence and the fifth and sixth enhancer binding sequence are each separated by 50 nucleotides.

In another aspect, a method of displacing chromatin of a target locus in a cell is provided. The method includes (1) introducing into a cell including a nucleic acid encoding a target locus a first DNA-binding modulation-enhancing agent, wherein the first DNA-binding modulation-enhancing agent is not endogenous to the cell; and (2) allowing the first DNA-binding modulation-enhancing agent to bind a first enhancer binding sequence of the target locus, thereby displacing chromatin of the target locus.

In another aspect, a method of restructuring chromatin of a target locus in a cell is provided. The method includes (1) introducing into a cell including a nucleic acid encoding a target locus a first DNA-binding modulation-enhancing agent, wherein the first DNA-binding modulation-enhancing agent is not endogenous to the cell; and (2) allowing the first DNA-binding modulation-enhancing agent to bind a first enhancer binding sequence of the target locus, thereby restructuring chromatin of the target locus.

As described above, methods and compositions provided herein may include binding of one or more DNA binding agents (e.g., a first or second DNA-binding modulation-enhancing agent) to accomplish modulation of a target locus. Thus, in another aspect, a method of increasing accessibility of a target locus in a cell is provided. The method includes (1) introducing into a cell including a nucleic acid encoding a target locus (i) a first DNA-binding modulation-enhancing agent, wherein the first DNA-binding modulation-enhancing agent is not endogenous to the cell; and (ii) a second DNA-binding modulation-enhancing agent, wherein the second DNA-binding modulation-enhancing agent is not endogenous to the cell. (2) The first DNA-binding modulation-enhancing agent is allowed to bind a first enhancer binding sequence of the target locus; and (3) the second DNA-binding modulation-enhancing agent is allowed to bind a second enhancer binding sequence of the target locus, thereby increasing accessibility of the target locus relative to the absence of the first DNA-binding modulation-enhancing agent or the second DNA-binding modulation-enhancing agent. Enhancing (increasing) the accessibility of a target locus as provided herein refers to the structural modulation of a target locus, which results in enhancement of the functional activity of a modulating protein or complex, for example an enzyme (e.g., nuclease), at the target locus. The target locus is cleared off of chromatin and/or the DNA at the target locus is restructured to enable better binding and/or enhanced activity of the modulating protein. The term enhancing (increasing) the accessibility of a target locus therefore includes modulating the structure of the target locus to allow for increased activity of the modulating protein, where the activity includes, for example, enzymatic activity, DNA binding activity, transcriptional activity.

In one aspect, a method of displacing chromatin of a target locus in a cell is provided. The method includes (1) introducing into a cell including a nucleic acid encoding a target locus: (i) a first DNA-binding modulation-enhancing agent, wherein the first DNA-binding modulation-enhancing agent is not endogenous to the cell; and (ii) a second DNA-binding modulation-enhancing agent, wherein the second DNA-binding modulation-enhancing agent is not endogenous to the cell. (2) The first DNA-binding modulation-enhancing agent is allowed to bind a first enhancer binding sequence of the target locus; and (3) the second DNA-binding modulation-enhancing agent is allowed to bind a second enhancer binding sequence of the target locus, thereby displacing chromatin of the target locus.

In one aspect, a method of restructuring chromatin of a target locus in a cell is provided. The method includes (1) introducing into a cell including a nucleic acid encoding a target locus: (i) a first DNA-binding modulation-enhancing agent, wherein the first DNA-binding modulation-enhancing agent is not endogenous to the cell; and (ii) a second DNA-binding modulation-enhancing agent, wherein the second DNA-binding modulation-enhancing agent is not endogenous to the cell. (2) The first DNA-binding modulation-enhancing agent is allowed to bind a first enhancer binding sequence of the target locus; and (3) the second DNA-binding modulation-enhancing agent is allowed to bind a second enhancer binding sequence of the target locus, thereby restructuring chromatin of the target locus.

As described above, methods and compositions provided herein may increase accessibility of a target locus and thereby may allow recruitment of a modulating activity the target locus. Thus, a method of modulating a target locus in a cell is provided. The method includes (1) introducing into a cell including a nucleic acid encoding a target locus: (i) a first modulating protein or a first modulating complex capable of binding a modulator binding sequence of the target locus, wherein the modulator binding sequence includes a modulation site; and (ii) a first DNA-binding modulation-enhancing agent capable of binding a first enhancer binding sequence of the target locus. And (2) allowing the first modulating protein or the first modulating complex to modulate the modulation site, thereby modulating the target locus in a cell.

Due to binding of the one or more DNA binding agent (e.g., first or second DNA-binding modulation-enhancing agent) to the target locus, the target locus becomes more accessible thereby allowing for enhanced efficiency and/or specificity of a modulating protein or modulating complex at the target locus. For example, using methods and compositions provided herein may enhance the efficiency of gene editing reactions via, for example, homologous recombination. In embodiments, nuclease activity of a nuclease is enhanced at the target locus due to the presence of the one or more DNA binding agent (e.g., first or second DNA-binding modulation-enhancing agent).

Thus in one aspect, a method of enhancing activity of a modulating protein or a modulating complex at a target locus in a cell is provided. The method includes (1) introducing into a cell including a nucleic acid encoding a target locus: (i) a first modulating protein or a first modulating complex capable of binding a modulator binding sequence of the target locus, wherein the modulator binding sequence includes a modulation site; and (ii) a first DNA-binding modulation-enhancing agent capable of binding a first enhancer binding sequence of the target locus. And (2) allowing the first DNA-binding modulation-enhancing agent to bind the first enhancer binding sequence, thereby enhancing activity of the first modulating protein or the first modulating complex at a target locus in a cell.

Also provided herein are compositions and methods for generating regions of chromatin structure that is accessible to gene editing reagents using DNA binding protein-transcriptional activator fusion proteins. In some aspects, provided herein are the use of DNA binding protein-transcriptional activator fusion proteins and methods for using such fusion proteins for the remodeling of chromatin to allow for enhanced site specific nucleic acid cleavage. Variations of some aspects of this are set out in FIG. 51.

It is known that transcriptional activation remodels chromatin and disrupts what is often a defined pattern of nucleosomes at specific genetic loci. (See, e.g., Gilbert and Ramsahoye, "The relationship between chromatin structure and transcriptional activity in mammalian genomes", BRIEFINGS IN FUNCTIONAL GENOMICS AND PROTEOMICS, 4:129-142 (2005).)

Figure 51:
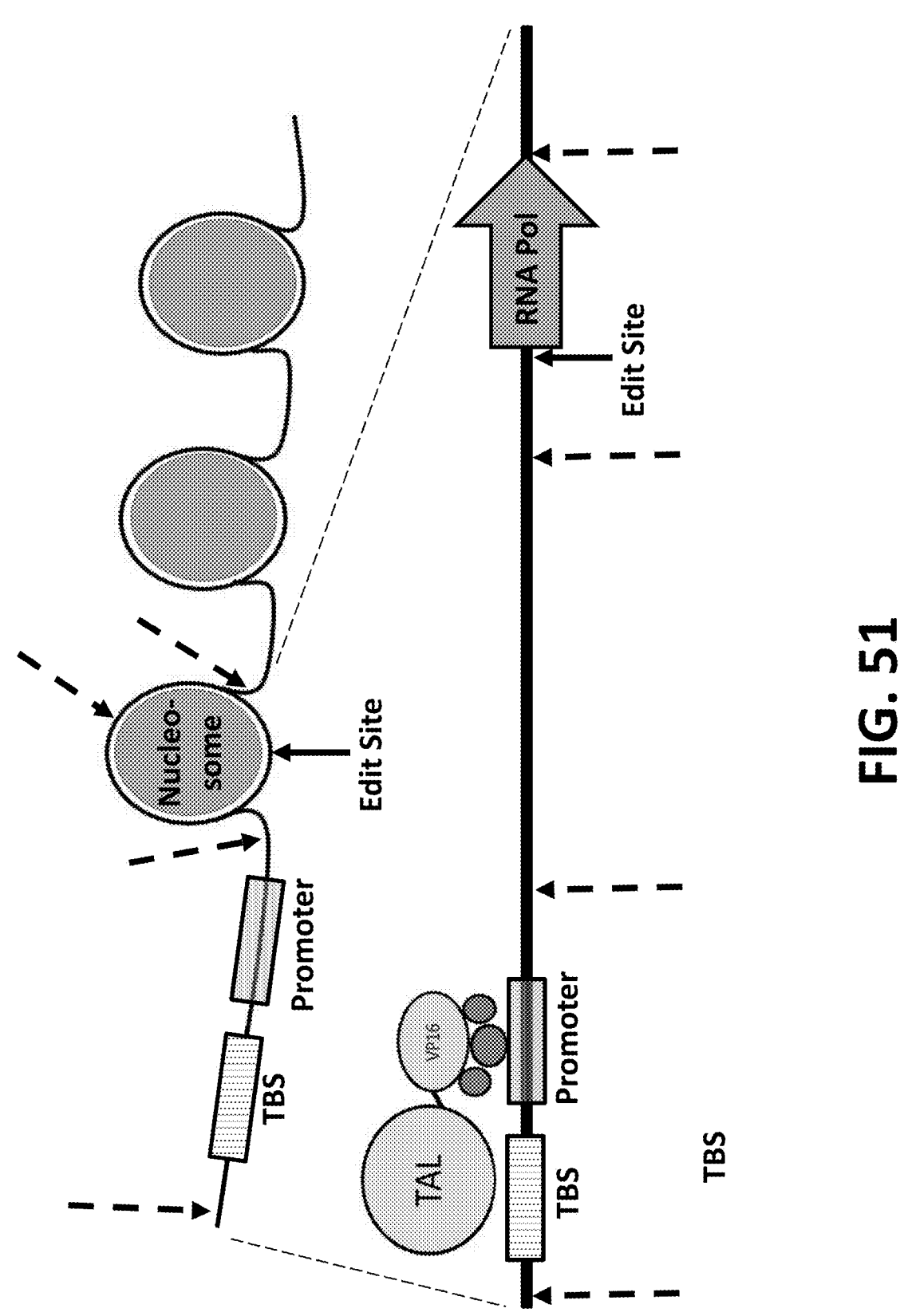
FIG. 51 is a schematic of some uses of TALs for opening and maintaining opened chromatin. The upper portion of the schematic shows an intracellular nucleic acid region where the nucleic acid is associated with histone octamers to form chromatin. About 145 base pairs of DNA are wound around each octamer is about 1.6 turns. Histone H1 is not represented in this schematic. The dashed arrows indicate Buddy-TAL binding loci. The box with the vertical lines labeled "TBS" refers to TAL binding site. "RNA Pol" refers to an RNA polymerase molecule transcribing nucleic acid "downstream" from the "Promoter".

The upper portion of FIG. 51 shows a schematic of an intracellular nucleic acid region where the nucleic acid is in the form of chromatin 10 nm fiber. The upper portion of FIG. 51 shows a promoter, nucleosomes, a desired Edit Site, and potential Buddy-TAL binding sites. The locations of the nucleosomes may vary with the nucleic acid regions and/or the specific cells a particular nucleic acid region is located in. For example, in any particular cells, the promoter nucleic acid may be fully or partially located in a nucleosome or entirely outside of a nucleosome. Further, the location of a specific nucleic acid region (e.g., an Edit Site), with respect to nucleosomes, in a particular cell may vary with factors such as a specific time point, transcriptional status, stage of cell cycle, etc.

Using the schematic of FIG. 51 for purposes of illustration, TAL-transcriptional activator fusion protein binds to a TAL binding site ("TBS"), resulting in transcriptional activation. This results in chromatin remodeling in the nucleic acid region that is transcribed, as well as in the surrounding local area. This chromatin remodeling results in increased accessibility of the nucleic acid to gene editing reagents with nucleic acid cutting activity (e.g., TAL-FokI fusion proteins). The net result is improved nucleic acid cutting activity by gene editing reagents.

FIG. 51 also shows an "Edit Site". As used here, "Edit Site" refers to a nucleic acid site where one or more gene editing reagents are designed to cleave for alteration of the locus at the nucleotide sequence level (e.g., deletion, insertion and/or substitution). In this schematic, transcription is used to increase accessibility of the Edit Site to gene editing reagents.

Buddy-TALs, also referred to as DNA-binding modulation-enhancing agents, may also be used in conjunction with DNA binding protein-transcriptional activator fusion proteins. These Buddy-TALs may be used to enhance binding of DNA binding protein-transcriptional activator fusion proteins to the TAL Binding Site ("TBS") and/or enhance accessibility of gene editing reagents with nucleic acid cutting activity to the Edit Site. Thus, provided herein are compositions and methods enhancing nucleic acid cleavage using DNA binding protein-transcriptional activator fusion proteins both alone and in conjunction with Buddy-TALs.

In some aspects, provided herein are methods for editing a first nucleic acid locus in a cell, the method comprising: (A) contacting a second nucleic acid locus with a DNA binding protein-transcriptional activator fusion protein under conditions which allow for nucleic acid transcription and (B) contacting the first nucleic acid locus with one or more gene editing reagents with nucleic acid cutting activity under conditions that allow for cleavage of the nucleic acid at the first nucleic acid locus, wherein the nucleic acid transcription alters the chromatin structure of the first nucleic acid locus. In some instances, one or more DNA-binding modulation-enhancing agents designed to bind to one or more nucleic acid locations within two hundred (e.g., from about 30 to about 200, from about 50 to about 200, from about 60 to about 200, from about 30 to about 180, from about 30 to about 130, from about 45 to about 150, etc.) base pairs of the (a) first nucleic acid locus and/or (b) the second nucleic acid locus may also be used. In some instances, one or more DNA-binding modulation-enhancing agents designed to bind to a nucleic acid locations within two hundred base pairs upstream from the second nucleic acid locus and/or downstream form the first nucleic acid locus. In some instances, the DNA binding protein-transcriptional activator fusion protein may be a TAL-transcriptional activation domain (e.g., p53, NFAT, NF-κB, VP16, VP32, VP64, etc.) fusion protein. In some instances, at least one of the one or more DNA-binding modulation-enhancing agents may be a TAL-nuclease fusion protein (e.g., a TAL-FokI fusion protein).

DNA Binding Modulation-Enhancing Agent

A "DNA-binding modulation-enhancing agent" as provided herein is an agent capable of binding a corresponding sequence (enhancer binding sequence) of a target locus in a cell and thereby chemically or structurally modulating the target locus. Upon binding to a target locus, the DNA binding modulation-enhancing agent provided herein including embodiments thereof may modulate chromatin at the locus. Upon binding of the DNA binding modulation-enhancing agent may transform a densely packed heterochromatic region upstream (5') or downstream (3') of the enhancer binding sequence into a less densely packed euchromatic region. The transformation may be achieved by dissociating histones from the DNA they are bound to (chromatin displacing) at the target locus. Alternatively, histones may be rearranged within the chromatin at the target locus (chromatin restructuring). Upon changing the chromatin structure at the target locus the DNA becomes more accessible for subsequent modification of the target locus. This effect may be achieved by binding of one or more DNA binding modulation-enhancing agents (e.g., a first or a second DNA binding modulation-enhancing agent). Thus, in embodiments, methods set out herein include introducing a second DNA-binding modulation-enhancing agent capable of binding a second enhancer binding sequence of the target locus.

For the methods provided herein the enhancing agents and modulating proteins or complexes may be introduced to a cell in various ways. The enhancing agents and modulating proteins or complexes may be introduced by way of transfecting a nucleic acid (vector) encoding the enhancing agents and modulating proteins or complexes. Alternatively, the enhancing agents and modulating proteins or complexes may be introduced by way of transfecting an mRNA encoding the enhancing agents and modulating proteins or complexes may. The enhancing agents and modulating proteins or complexes may further be introduced by transfecting the actual agent, modulating protein or modulating complex directly. A person of ordinary skill in the art will immediately recognize the half-life (time an agent is active and/or expressed in a cell) of an agent, modulating protein or complex in a cell is determined by the physical form it is delivered to a cell. Without being bound to any specific scientific theory, delivery of a nucleic acid encoding an enhancing agent, modulating protein or complex, will result in the enhancing agent, modulating protein or complex being expressed/present in the cell longer compared to the enhancing agent and modulating protein or complex being transfected as actual protein or complex.

In embodiments, the introducing a first DNA-binding modulation-enhancing agent includes introducing a vector encoding the first DNA-binding modulation-enhancing agent. In embodiments, the introducing a first DNA-binding modulation-enhancing agent includes introducing an mRNA encoding the first DNA-binding modulation-enhancing agent. In embodiments, the introducing a first DNA-binding modulation-enhancing agent includes introducing a first DNA binding protein or a first DNA binding nucleic acid.

In embodiments, the introducing a second DNA-binding modulation-enhancing agent includes introducing a vector encoding the second DNA-binding modulation-enhancing agent. In embodiments, the introducing a second DNA-binding modulation-enhancing agent includes introducing an mRNA encoding the second DNA-binding modulation-enhancing agent. In embodiments, the introducing a second DNA-binding modulation-enhancing agent includes introducing a second DNA binding protein or a second DNA binding nucleic acid.

In embodiments, the introducing a first modulating protein includes introducing a vector encoding the first modulating protein. In embodiments, the introducing a first modulating protein includes introducing an mRNA encoding the first modulating protein. In embodiments, the introducing a first modulating protein includes introducing a first modulating protein. In embodiments, the introducing a first modulating complex includes introducing a vector encoding the first modulating complex. In embodiments, the introducing a first modulating complex includes introducing an mRNA encoding the first modulating complex. In embodiments, the introducing a first modulating complex includes introducing a first modulating complex.

In embodiments, the introducing a second modulating protein includes introducing a vector encoding the second modulating protein. In embodiments, the introducing a second modulating protein includes introducing an mRNA encoding the second modulating protein. In embodiments, the introducing a second modulating protein includes introducing a second modulating protein. In embodiments, the introducing a second modulating complex includes introducing a vector encoding the second modulating complex. In embodiments, the introducing a second modulating complex includes introducing an mRNA encoding the second modulating complex. In embodiments, the introducing a second modulating complex includes introducing a second modulating complex.

Exemplary DNA binding modulation-enhancing agents useful for methods and compositions provided herein include DNA binding proteins or a DNA binding nucleic acids. The first DNA-binding modulation-enhancing agent and second DNA-binding modulation-enhancing agent may be the same or chemically different. In embodiments, the first DNA-binding modulation-enhancing agent is not endogenous to the cell. In embodiments, the second DNA-binding modulation-enhancing agent is not endogenous to the cell. In embodiments, the first DNA-binding modulation-enhancing agent is a first DNA binding protein or a first DNA binding nucleic acid. In embodiments, the first DNA-binding modulation-enhancing agent is a first transcription activator-like (TAL) effector protein or a first truncated guide RNA (gRNA). In embodiments, the first DNA-binding modulation-enhancing agent is a first zinc finger DNA binding protein. In embodiments, the second DNA-binding modulation-enhancing agent is a second DNA binding protein or a second DNA binding nucleic acid. In embodiments, the second DNA-binding modulation-enhancing agent is a TAL effector protein or a truncated gRNA.

A "truncated gRNA" or "truncated guide RNA" is a ribonucleic acid corresponding to a wildtype guide RNA, but including fewer nucleotides compared to said wild-type guide RNA. As provided herein a truncated gRNA may be bound to a Cas9 protein. Thus, a truncated guide RNA as provided herein may be an RNA bound to a Cas9 protein and capable of binding a modulator binding sequence. A Cas9 protein bound to a truncated gRNA is incapable of cleaving a modulator binding sequence. Thus, in embodiments, the DNA-binding modulation-enhancing agent is a truncated gRNA bound to a Cas9 protein. In embodiments, the Cas9 protein bound to the truncated gRNA is a *Streptococcus pyogenes* Cas9 protein. A *Streptococcus pyogenes* Cas9 protein as provided herein is a Cas9 protein derived from the bacterium *Streptococcus pyogenes*.

The truncated gRNA provided herein may be less than 16 nucleotides in length. In embodiments, the truncated gRNA is no more than 15 nucleotides in length. In embodiments, the truncated gRNA is 10 to 15 nucleotides in length. In embodiments, the truncated gRNA is 11 to 15 nucleotides in length. In embodiments, the truncated gRNA is 12 to 15 nucleotides in length. In embodiments, the truncated gRNA is 13 to 15 nucleotides in length. In embodiments, the truncated gRNA is 10 to 14 nucleotides in length. In embodiments, the truncated gRNA is 10 to 13 nucleotides in length. In embodiments, the truncated gRNA is 10 to 12 nucleotides in length. In embodiments, the truncated gRNA is 16 nucleotides in length. In embodiments, the truncated gRNA is less than 15 nucleotides in length. In embodiments, the truncated gRNA is 15 nucleotides in length. In embodiments, the truncated gRNA is less than 14 nucleotides in length. In embodiments, the truncated gRNA is 14 nucleotides in length. In embodiments, the truncated gRNA is less than 13 nucleotides in length. In embodiments, the truncated gRNA is 13 nucleotides in length. In embodiments, the truncated gRNA is less than 12 nucleotides in length. In embodiments, the truncated gRNA is 12 nucleotides in length. In embodiments, the truncated gRNA is less than 11 nucleotides in length. In embodiments, the truncated gRNA is 11 nucleotides in length. In embodiments, the truncated gRNA is less than 10 nucleotides in length. In embodiments, the truncated gRNA is 10 nucleotides in length. In embodiments, the truncated gRNA is less than 9 nucleotides in length. In embodiments, the truncated gRNA is 9 nucleotides in length. In embodiments, the truncated gRNA is less than 8 nucleotides in length. In embodiments, the truncated gRNA is 8 nucleotides in length. In embodiments, the truncated gRNA is less than 7 nucleotides in length. In embodiments, the truncated gRNA is 7 nucleotides in length. In embodiments, the truncated gRNA is less than 6 nucleotides in length. In embodiments, the truncated gRNA is 6 nucleotides in length. In embodiments, the truncated gRNA is less than 5 nucleotides in length. In embodiments, the truncated gRNA is 5 nucleotides in length. In embodiments, the truncated gRNA is less than 4 nucleotides in length. In embodiments, the truncated gRNA is 4 nucleotides in length.

Enhancer Binding Sequences

An "enhancer binding sequence" as provided herein is a nucleic acid sequence that forms part of the target locus and is bound by a DNA-binding modulation-enhancing agent. In embodiments, the enhancer binding sequence is a TAL nucleic acid binding cassette. As used herein a "TAL nucleic acid binding cassette" (also referred to as a "TAL cassette") refers to a nucleic acid that encodes a polypeptide which allows for a protein including said polypeptide to bind a single base pair (e.g., A, T, C, or G) of a nucleic acid molecule. In embodiments, proteins will contain more than one polypeptide encoded by a TAL nucleic acid binding cassette. The individual amino acid sequences of the encoded multimer are referred to as "TAL repeats". In embodiments, TAL repeats will be between twenty-eight and forty amino acids in length and (for the amino acids present) will share at least 60% (e.g., at least about 65%, at least about 70%, at least about 75%, at least about 80%, from about 60% to about 95%, from about 65% to about 95%, from about 70% to about 95%, from about 75% to about 95%, from about 80% to about 95%, from about 85% to about 95%, from about 60% to about 90%, from about 60% to about 85%, from about 65% to about 90%, from about 70% to about 90%, from about 75% to about 90%, etc.) identity with the following thirty-four amino acid sequence: LTPDQVVAIA SXXGGKQALE TVQRLLPVLC QAHG (SEQ ID NO:118).

In embodiments, the two Xs at positions twelve and thirteen in the above sequence represent amino acid which also TAL nucleic acid binding cassettes to recognize a specific base in a nucleic acid molecule.

In embodiments, the final TAL repeat present at the carboxyl terminus of a series of repeats series will often be a partial TAL repeat in that the carboxyl terminal end may be missing (e.g., roughly the amino terminal 15 to 20 amino acids of this final TAL repeat).

In embodiments, the enhancer binding sequence is a nucleic acid sequence capable of binding (hybridizing to) a guide RNA binding sequence or guide DNA binding sequence. In embodiments, the first enhancer binding sequence has the sequence of SEQ ID NO:26, SEQ ID NO:28, SEQ ID NO:30, SEQ ID NO:32, SEQ ID NO:34, SEQ ID NO:36, SEQ ID NO:38, or SEQ ID NO:40. In embodiments, the second enhancer binding sequence has the sequence of SEQ ID NO:27, SEQ ID NO:29, SEQ ID NO:31, SEQ ID NO:33, SEQ ID NO:35, SEQ ID NO:37, SEQ ID NO:39, or SEQ ID NO:41.

Modulating Proteins and Modulating Complexes

The modulating proteins and modulating complexes provided herein may be endogenous to a cell or may not be endogenous to a cell. The terms "modulating protein" and "modulating complex" as provided herein refer to a molecule (e.g., protein or protein conjugate) or a complex of molecules (e.g., ribonucleoprotein complex), respectively, which are capable of structurally and/or chemically changing a target locus. The change in a target locus structure or chemical composition may include a change in the entire target locus or portions thereof. Examples of a modulating protein include without limitation, double-stranded nucleases, nickases, transcriptional activators, transcriptional repressors, nucleic acid methylases, nucleic acid demethylases, topoisomerases, gyrases, ligase, methyl-transferases, transposases, glycosylases, integrases, kinases, phosphatases, sulphurilases, polymerases, fluorescent activity and recombinases. Non-limiting examples of a modulating complex as provided herein includes a ribonucleoprotein complex and a deoxyribonucleoprotein complex.

In embodiments, the first modulating protein or the second modulating protein includes a DNA binding protein or a DNA modulating enzyme. The DNA binding protein may be a transcriptional repressor or a transcriptional activator. In embodiments, the DNA modulating enzyme is a nuclease, a deaminase, a methylase or a demethylase. In embodiments, the first modulating protein or the second modulating protein includes a histone modulating enzyme. In embodiments, the histone modulating enzyme is a deacetylase or an acetylase.

In embodiments, the first modulating protein or the second modulating protein includes a first DNA binding domain operably linked to a first DNA modifying domain. In embodiments, the first DNA binding domain is a TAL effector domain and the first DNA modifying domain is a transcriptional activator domain or a transcriptional repressor domain. In embodiments, the first DNA modifying domain is a VP16 domain. In embodiments, the first DNA modifying domain is a VP64 domain. In embodiments, the first DNA modifying domain is a VP16 domain, a VP32 domain or a VP64 transcriptional activator domain(s) or a KRAB transcriptional repressor domain.

In embodiments, the first modulating protein is a first DNA binding nuclease conjugate. In embodiments, the second modulating protein is a second DNA binding nuclease conjugate. As used herein a "DNA binding nuclease conjugate" refers to one or more molecules, enzymes, or complex of molecules with nucleic acid cutting activity (e.g., double-stranded nucleic acid cutting activity). In most embodiments, DNA binding nuclease conjugate components will be either proteins or nucleic acids or a combination of the two but they may be associated with cofactors and/or other molecules. The DNA binding nuclease conjugate will typically be selected based upon a number of factors, such as efficiency of DS break generation at target loci, the ability to generate DS break generation at suitable locations at or near target loci, low potential for DS break generation at undesired loci, low toxicity, and cost issues. A number of these factors will vary with the cell employed and target loci. A number of DNA binding nuclease conjugates are known in the art. For example, in some embodiments the DNA binding nuclease conjugate includes one or more zinc finger proteins, transcription activator-like effectors (TALEs), CRISPR complex (e.g., Cas9 or CPF1), homing endonucleases or meganucleases, argonaute-nucleic acid complexes, or macronucleases. In some embodiments, the DNA binding nuclease conjugate will have an activity that allows them to be nuclear localized (e.g., will contain nuclear localization signals (NLS)). In some embodiments, a single strand DNA donor could work with a nick or combination of nicks.

In embodiments, the DNA binding nuclease conjugate is a TAL effector fusion. A "TAL effector fusion" as provided herein refers to a TAL effector connected to another polypeptide or protein to which it is not naturally associated with in nature (e.g., an Argonaute protein). In embodiments, the non-TAL component of the TAL effector fusion will confer a functional activity (e.g., an enzymatic activity) upon the fusion protein. In embodiments, a TAL effector fusion may have binding activity or may have an activity that directly or indirectly triggers nucleic acid modification, such as, e.g., a nuclease activity.

In embodiments, the first DNA binding nuclease conjugate includes a first nuclease and the second DNA binding nuclease conjugate includes a second nuclease. In embodiments, the first nuclease and the second nuclease form a dimer. In embodiments, the first nuclease and the second nuclease are independently a transcription activator-like effector nuclease (TALEN). In embodiments, the first nuclease and the second nuclease are independently a FokI nuclease cleavage domain mutant KKR Sharkey. In embodiments, the first nuclease and the second nuclease are independently a FokI nuclease cleavage domain mutant ELD Sharkey.

In embodiments, the first DNA binding nuclease conjugate includes a first transcription activator-like (TAL) effector domain (e.g., DNA binding portion of a TAL protein) operably linked to a first nuclease (TALEN). In embodiments, the first DNA binding nuclease conjugate includes a first TAL effector domain operably linked to a first FokI nuclease. In embodiments, the second DNA binding nuclease conjugate includes a second TAL effector domain operably linked to a second nuclease (TALEN). In embodiments, the second DNA binding nuclease conjugate includes a second TAL effector domain operably linked to a second FokI nuclease. In embodiments, the first DNA binding nuclease conjugate includes a first zinc finger nuclease. In embodiments, the second DNA binding nuclease conjugate includes a first zinc finger nuclease.

As used herein the term "zinc finger nuclease" refers to a protein comprising a polypeptide having nucleic acid (e.g., DNA) binding domains that are stabilized by zinc. The individual DNA binding domains are typically referred to as "fingers," such that a zinc finger protein or polypeptide has at least one finger, more typically two fingers, or three fingers, or even four or five fingers, to at least six or more fingers. In some aspect, zinc finger nuclease will contain three or four zinc fingers. Each finger typically binds from two to four base pairs of DNA. Each finger usually comprises an about 30 amino acids zinc-chelating, DNA-binding region (see, e.g., U.S. Pat. Publ. No. 2012/0329067 A1, the disclosure of which is incorporated herein by reference).

One example of a nuclease protein forming part of the conjugates provided herein is the non-specific cleavage domain from the type IIS restriction endonuclease FokI (Kim, Y. G., et al., *Proc. Natl. Acad. Sci.* 93:1156-60 (1996)) typically separated by a linker sequence of 5-7 base pairs. A pair of the FokI cleavage domain is generally required to allow for dimerization of the domain and cleavage of a non-palindromic target sequence from opposite strands. The DNA-binding domains of individual $Cys_2His_2$ ZFNs typically contain between 3 and 6 individual zinc-finger repeats and can each recognize between 9 and 18 base pairs.

As used herein, "transcription activator-like effectors" (TALEs) refer to proteins composed of more than one TAL repeat and is capable of binding to a nucleic acid in a sequence specific manner. TALEs represent a class of DNA binding proteins secreted by plant-pathogenic bacteria of the species, such as *Xanthomonas* and *Ralstonia*, via their type III secretion system upon infection of plant cells. Natural TALEs specifically have been shown to bind to plant promoter sequences thereby modulating gene expression and activating effector-specific host genes to facilitate bacterial propagation (Römer, P., et al., *Science* 318:645-648 (2007); Boch, J., et al., *Annu. Rev. Phytopathol.* 48:419-436 (2010);

Kay, S., et al., *Science* 318:648-651 (2007); Kay, S., et al., *Curr. Opin. Microbiol.* 12:37-43 (2009)).

Natural TALEs are generally characterized by a central repeat domain and a carboxyl-terminal nuclear localization signal sequence (NLS) and a transcriptional activation domain (AD). The central repeat domain typically consists of a variable amount of between 1.5 and 33.5 amino acid repeats that are usually 33-35 residues in length except for a generally shorter carboxyl-terminal repeat referred to as half-repeat. The repeats are mostly identical but differ in certain hypervariable residues. DNA recognition specificity of TALEs is mediated by hypervariable residues typically at positions 12 and 13 of each repeat—the so-called repeat variable diresidue (RVD) wherein each RVD targets a specific nucleotide in a given DNA sequence. Thus, the sequential order of repeats in a TAL protein tends to correlate with a defined linear order of nucleotides in a given DNA sequence. The underlying RVD code of some naturally occurring TALEs has been identified, allowing prediction of the sequential repeat order required to bind to a given DNA sequence (Boch, J., et al., *Science* 326:1509-1512 (2009); Moscou, M. J., et al., *Science* 326:1501 (2009)). Further, TAL effectors generated with new repeat combinations have been shown to bind to target sequences predicted by this code. It has been shown that the target DNA sequence generally start with a 5' thymine base to be recognized by the TAL protein.

The modular structure of TALs allows for combination of the DNA binding domain with effector molecules such as nucleases. In particular, TALE nucleases allow for the development of new genome engineering tools. TALEs used in some embodiments may generate DS breaks or may have a combined action for the generation of DS breaks. For example, TAL-FokI nuclease fusions can be designed to bind at or near a target locus and form double-stranded nucleic acid cutting activity by the association of two FokI domains.

In some embodiments, TALEs will contain greater than or equal to 6 (e.g., greater than or equal to 8, 10, 12, 15, or 17, or from 6 to 25, 6 to 35, 8 to 25, 10 to 25, 12 to 25, 8 to 22, 10 to 22, 12 to 22, 6 to 20, 8 to 20, 10 to 22, 12 to 20, 6 to 18, 10 to 18, 12 to 18, etc.) TAL repeats. In some embodiments, a TALE may contain 18 or 24 or 17.5 or 23.5 TAL nucleic acid binding cassettes. In additional embodiments, a TALE may contain 15.5, 16.5, 18.5, 19.5, 20.5, 21.5, 22.5 or 24.5 TAL nucleic acid binding cassettes. TALEs will generally have at least one polypeptide region which flanks the region containing the TAL repeats. In many embodiments, flanking regions will be present at both the amino and carboxyl termini of the TAL repeats. Exemplary TALEs are set out in U.S. Pat. Publ. No. 2013/0274129 A1, the disclosure of which is incorporated herein by reference, and may be modified forms on naturally occurring proteins found in bacteria of the genera *Burkholderia*, *Xanthamonas* and *Ralstonia*. In some embodiments, TALE proteins will contain nuclear localization signals (NLS) that allow them to be transported to the nucleus.

For the methods and compositions provided herein the nucleic acid targeting capability of a modulating protein or a modulating complex is increased relative to the absence of the DNA-binding modulation-enhancing agent. In embodiments, the rate of homologous recombination at the target locus is increased relative to the absence of the DNA-binding modulation-enhancing agent.

In embodiments, the first modulating complex is a first ribonucleoprotein complex. In embodiments, the second modulating complex is a second ribonucleoprotein complex.

In embodiments, the first ribonucleoprotein complex includes a CRISPR associated protein 9 (Cas9) domain bound to a gRNA or an Argonaute protein domain bound to a guide DNA (gDNA). In embodiments, the second ribonucleoprotein complex includes a CRISPR associated protein 9 (Cas9) domain bound to a gRNA or an Argonaute protein domain bound to a guide DNA (gDNA).

In embodiments, the first DNA-binding modulation-enhancing agent is a first TAL effector protein and the second DNA-binding modulation-enhancing agent is a second TAL effector protein. In embodiments, the first DNA-binding modulation-enhancing agent is a TAL effector protein and the second DNA-binding modulation-enhancing agent is a truncated gRNA. In embodiments, the first DNA-binding modulation-enhancing agent is a first truncated gRNA and the second DNA-binding modulation-enhancing agent is a second truncated gRNA. In embodiments, the first DNA-binding modulation-enhancing agent is a truncated gRNA and the second DNA-binding modulation-enhancing agent is a TAL effector protein.

In embodiments, the first modulating protein is a first DNA binding nuclease conjugate and the second modulating protein is a second DNA binding nuclease conjugate. In embodiments, the first modulating protein is a DNA binding nuclease conjugate and the second modulating complex is a ribonucleoprotein complex. In embodiments, the first modulating complex is a first ribonucleoprotein complex and the second modulating complex is a second ribonucleoprotein complex. In embodiments, the first modulating complex is a ribonucleoprotein complex and the second modulating protein is a DNA binding nuclease conjugate.

Agents provided herein may be endogenous or not endogenous to the cell expressing them. Thus, in embodiments, the first modulating protein or the first modulating complex is not endogenous to the cell. In embodiments, the first modulating protein, the first modulating complex, the second modulating protein or the second modulating complex is not endogenous to the cell. In embodiments, the first modulating protein and the second modulating protein are not endogenous to the cell. In embodiments, the first modulating complex and the second modulating complex are not endogenous to the cell. In embodiments, the first DNA-binding modulation-enhancing agent or the second DNA-binding modulation-enhancing agent is not endogenous to the cell. In embodiments, the first DNA-binding modulation-enhancing agent and the second DNA-binding modulation-enhancing agent are not endogenous to the cell.

Applicants have surprisingly found that the distance of the first and/or second enhancer binding site relative to the modulator binding sequence impacts the effect the DNA-binding modulation-enhancing agent has on the activity of the modulating protein or modulating complex. The distance between the first enhancer binding site and the modulator binding sequence is the number of nucleotides connecting the most 3' nucleotide of the first DNA-binding modulation-enhancing agent and the most 5' nucleotide of the modulator binding sequence. Similarly, the distance between the second enhancer binding site and the modulator binding sequence is the number of nucleotides connecting the most 3' nucleotide of the modulator binding sequence and the most 5' nucleotide of the first DNA-binding modulation-enhancing agent. The modulator binding sequence may be bound by a protein (e.g., a DNA binding protein) or a nucleic acid (e.g., a gRNA or gDNA). The modulation site included in the modulator binding sequence is the position of a nucleotide in the modulator binding sequence, which is recognized by a modulating protein or modulating complex and which corresponds to the nucleotide whose bond to the remainder of the modulator binding sequence is hydrolyzed.

In embodiments, the first enhancer binding sequence or the second enhancer binding sequence is separated from the modulator binding sequence by less than 200 nucleotides. In embodiments, the first enhancer binding sequence or the second enhancer binding sequence is separated from the modulator binding sequence by less than 150 nucleotides. In embodiments, the first enhancer binding sequence or the second enhancer binding sequence is separated from the modulator binding sequence by less than 100 nucleotides. In embodiments, the first enhancer binding sequence or the second enhancer binding sequence is separated from the modulator binding sequence by less than 50 nucleotides. In embodiments, the first enhancer binding sequence or the second enhancer binding sequence is separated from the modulator binding sequence by 4 to 30 nucleotides. In embodiments, the first enhancer binding sequence or the second enhancer binding sequence is separated from the modulator binding sequence by 7 to 30 nucleotides. In embodiments, the first enhancer binding sequence or the second enhancer binding sequence is separated from the modulator binding sequence by 4 nucleotides. In embodiments, the first enhancer binding sequence or the second enhancer binding sequence is separated from the modulator binding sequence by 7 nucleotides. In embodiments, the first enhancer binding sequence or the second enhancer binding sequence is separated from the modulator binding sequence by 12 nucleotides. In embodiments, the first enhancer binding sequence or the second enhancer binding sequence is separated from the modulator binding sequence by 20 nucleotides. In embodiments, the first enhancer binding sequence or the second enhancer binding sequence is separated from the modulator binding sequence by 30 nucleotides.

In embodiments, the first enhancer binding sequence or the second enhancer binding sequence is separated from the modulation site by 10 to 40 nucleotides. In embodiments, the first enhancer binding sequence or the second enhancer binding sequence is separated from the modulation site by 33 nucleotides.

In embodiments, the first enhancer binding sequence is separated from the modulator binding sequence by 30 nucleotides and the second enhancer binding sequence is separated from the modulator binding sequence by 19 nucleotides. In further embodiments, the first enhancer binding sequence and the second enhancer binding sequence are independently 18 nucleotides in length. In another further embodiment, the modulator binding sequence includes a first binding sequence and a second binding sequence, wherein the first binding sequence and the second binding sequence are independently 18 nucleotides in length and are separated by a 16 nucleotide sequence.

In embodiments, the first DNA-binding modulation-enhancing agent or the second DNA-binding modulation-enhancing agent enhance activity of the first modulating protein, the first modulating complex, the second modulating protein or the second modulating complex at the modulation site.

Provided herein are multiple formats for increasing the accessibility of a target locus to other components present in cells (e.g., a donor DNA molecule, a modulating protein, a modulating complex, etc.). Accessibility is increased by binding of a modulation-enhancing agent, which binds a specific DNA sequence (enhancer binding sequence) in the target locus. The DNA-binding modulation enhancing agent may be a truncated gRNA or a TAL effector domain. In embodiments, two DNA-binding modulation enhancing agents (e.g., a first and a second DNA-binding modulation enhancing agent) bind the target locus. Where two DNA-binding modulation enhancing agents (e.g., two TAL effector domains or two truncated gRNAs) bind the target locus they may flank a modulation sequence including, for example, a nuclease cleavage site. Through binding of the DNA-binding modulation enhancing agents to their respective enhancer binding sequences the modulation sequence of the target locus may be more accessible relative to the absence of the DNA-binding modulation enhancing agents.

The invention provides, inter alia, for a target locus which includes two TAL effector domains each bound to their respective binding sequence (enhancer binding sequence), wherein the enhancer binding sequences flank a modulator binding sequence with a modulation site (e.g., a nuclease cleavage site). Where the enhancer binding sequences flank a modulator binding sequence a first enhancer binding sequence is linked to the second enhancer binding sequence through the modulator binding sequence. Thus, in a 5' to 3' direction the target locus may encode a first enhancer binding sequence connected to a modulator binding sequence which is connected to a second enhancer binding sequence. Binding of the two TAL effector domains to their respective binding sequences (enhancer binding sequence) allows for increased accessibility of the target locus to be bound and/or modified by, inter alia, two TALEN conjugates at the modulator binding sequence. Each of the two enhancer binding sequences may be separated from the modulator binding sequence by, for example, 7 nucleotides. Where each of the two enhancer binding sequences are separated from the modulator binding sequence by 7 nucleotides, the most 3' nucleotide (i.e., the last nucleotide) of the first enhancer binding sequence is linked through a sequence of 7 consecutive nucleotides to the most 5' nucleotide (i.e., the first nucleotide) of the modulator binding sequence. Similarly, the most 5' nucleotide (i.e., the first nucleotide) of the second enhancer binding sequence is linked through a sequence of 7 consecutive nucleotides to the most 3' nucleotide (i.e., the last nucleotide) of the modulator binding sequence. Where two modulating proteins or modulating complexes or combinations thereof bind the modulator binding sequence, they may do so by binding independent binding sequences, a first binding sequence and a second binding sequence, respectively. The first binding sequence may be included in the 5' portion of the modulator binding sequence, while the second binding sequence may form part of the 3' portion of the modulator binding sequence. Therefore, in a 5' to 3' direction the modulator binding sequence may include a first binding sequence connected by at least one nucleotide to a second binding sequence. In embodiments, the most 5' nucleotide (i.e., the first nucleotide) of the modulator binding sequence is the most 5' nucleotide of the first binding site, and the most 3' nucleotide (i.e., the last nucleotide) of the modulator binding sequence is the most 3' nucleotide of the first binding site.

Further, each of the two enhancer binding sequences may be separated from the cleavage site (modulation site) by 33 nucleotides. Where each of the two enhancer binding sequences are separated from the modulation site by 33 nucleotides, the most 3' nucleotide of the first enhancer binding sequence is linked through a sequence of 33 consecutive nucleotides to the nucleotide 5' of the modulation site. Similarly, the most 5' nucleotide of the second enhancer binding sequence is linked through a sequence of 33 consecutive nucleotides to the nucleotide 3' of the modulation site.

Thus, in one embodiment, the target locus includes a first enhancer binding sequence bound to a first TAL effector protein; a second enhancer binding sequence bound to a second TAL effector protein; a first DNA binding nuclease conjugate consisting of a first TAL effector domain operably linked to a first TALEN, wherein the first conjugate is bound to the modulator binding sequence at a first binding site; and a second DNA binding nuclease conjugate consisting of a second TAL effector domain operably linked to a second TALEN, wherein the second conjugate is bound to the modulator binding sequence at a second binding site. In one further embodiment, the first enhancer binding sequence is separated by 7 nucleotides from the modulator binding sequence and the second enhancer binding sequence is separated by 7 nucleotides from the modulator binding sequence. In one further embodiment, the first enhancer binding sequence is separated by 7 nucleotides from the first binding sequence of the modulator binding sequence and the second enhancer binding sequence is separated by 7 nucleotides from the second binding sequence of the modulator binding sequence. In another further embodiment, the first enhancer binding sequence is separated by 33 nucleotides from the modulation site and the second enhancer binding sequence is separated by 33 nucleotides from the modulation site. In one further embodiment, the first enhancer binding sequence is separated by 12 nucleotides from the modulator binding sequence and the second enhancer binding sequence is separated by 12 nucleotides from modulator binding sequence. In one further embodiment, the first enhancer binding sequence is separated by 4 nucleotides from the modulator binding sequence and the second enhancer binding sequence is separated by 4 nucleotides from modulator binding sequence.

In one embodiment, the target locus includes a first enhancer binding sequence bound to a first TAL effector protein; a second enhancer binding sequence bound to a second TAL effector protein; a first DNA binding nuclease conjugate consisting of a first TAL effector domain operably linked to a first TALEN, wherein the first conjugate is bound to the modulator binding sequence at a first binding site; and a second DNA binding nuclease conjugate consisting of a second TAL effector domain operably linked to a second TALEN, wherein the second conjugate is bound to the modulator binding sequence at a second binding site. In one further embodiment, the first enhancer binding sequence is separated by 30 nucleotides from the modulator binding sequence and the second enhancer binding sequence is separated by 19 nucleotides from the modulator binding sequence. In one further embodiment, the first enhancer binding sequence is separated by 30 nucleotides from the first binding sequence of the modulator binding sequence and the second enhancer binding sequence is separated by 19 nucleotides from the second binding sequence of the modulator binding sequence. In another further embodiment, the first enhancer binding sequence is 18 nucleotides in length and the second enhancer binding sequence 18 nucleotides in length. In one further embodiment, the first binding sequence of the modulator binding sequence is separated by 16 nucleotides from the second binding sequence of the modulator binding sequence.

In one embodiment, the target locus includes a first enhancer binding sequence bound to a first TAL effector protein; a second enhancer binding sequence bound to a second TAL effector protein; and a ribonucleoprotein complex consisting of a Cas9 domain bound to a guide RNA, wherein the ribonucleoprotein complex is bound to the modulator binding sequence. In one further embodiment, the first enhancer binding sequence is separated by 7 nucleotides from the modulator binding sequence and the second enhancer binding sequence is separated by 7 nucleotides from modulator binding sequence. In one other embodiment, the first enhancer binding sequence is separated by 20 nucleotides from the modulator binding sequence and the second enhancer binding sequence is separated by 20 nucleotides from modulator binding sequence.

In one embodiment, the target locus includes a first enhancer binding sequence bound to a first TAL effector protein; a second enhancer binding sequence bound to a second TAL effector protein; and a DNA binding conjugate consisting of a TAL effector domain operably linked to a transcriptional activator domain, wherein the DNA binding conjugate is bound to the modulator binding sequence. In one further embodiment, the first enhancer binding sequence is separated by 30 nucleotides from the modulator binding sequence and the second enhancer binding sequence is separated by 30 nucleotides from modulator binding sequence. In another further embodiment, the first enhancer binding sequence is 18 nucleotides in length and the second enhancer binding sequence 18 nucleotides in length. In one further embodiment, the modulator binding sequence is 18 nucleotides in length.

In one other embodiment, the target locus includes a first enhancer binding sequence bound to a first truncated guide RNA bound to a Cas9 protein; a second enhancer binding sequence bound to a second truncated guide RNA bound to a Cas9 protein; and a ribonucleoprotein complex consisting of a Cas9 domain bound to a guide RNA, wherein the ribonucleoprotein complex is bound to the modulator binding sequence. In one further embodiment, the first enhancer binding sequence is separated by 30 nucleotides from the modulator binding sequence and the second enhancer binding sequence is separated by 15 nucleotides from modulator binding sequence.

In one embodiment, the modulator binding sequence is 52 nucleotides in length. In one other embodiment, the first binding sequence is 18 nucleotides in length. In one other embodiment, the second binding sequence is 18 nucleotides in length.

In one embodiment, the first DNA-binding modulation-enhancing agent is a first TAL effector protein and the second DNA-binding modulation-enhancing agent is a second TAL effector protein.

In one embodiment, the first DNA-binding modulation-enhancing agent is a first TAL effector protein and the second DNA-binding modulation-enhancing agent is a truncated gRNA. In one further embodiment, the truncated gRNA is bound to a Cas9 protein.

In one embodiment, the first DNA-binding modulation-enhancing agent is a first truncated gRNA and the second DNA-binding modulation-enhancing agent is a second truncated gRNA. In one further embodiment, the first truncated gRNA is bound to a first Cas9 protein and the second truncated gRNA is bound to a second Cas9 protein.

In one embodiment, the first DNA-binding modulation-enhancing agent is a first TAL effector protein; the second DNA-binding modulation-enhancing agent is a second TAL effector protein; the first modulating protein is a first DNA binding nuclease conjugate consisting of a first TAL effector domain operably linked to a first TALEN; and the second modulating protein is a second DNA binding nuclease conjugate consisting of a second TAL effector domain operably linked to a second TALEN.

In one embodiment, the first DNA-binding modulation-enhancing agent is a first TAL effector protein; the second DNA-binding modulation-enhancing agent is a second TAL effector protein; and the modulating protein complex is a Cas9 domain bound to a guide RNA.

In one embodiment, the first DNA-binding modulation-enhancing agent is a first truncated gRNA bound to a Cas9 protein; the second DNA-binding modulation-enhancing agent is a second truncated gRNA bound to a Cas9 protein; and the modulating protein complex is a Cas9 domain bound to a guide RNA.

In one embodiment, the first DNA-binding modulation-enhancing agent is a first truncated gRNA bound to a Cas9 protein; the second DNA-binding modulation-enhancing agent is a second truncated gRNA bound to a Cas9 protein; the first modulating protein is a first DNA binding nuclease conjugate consisting of a first TAL effector domain operably linked to a first TALEN; and the second modulating protein is a second DNA binding nuclease conjugate consisting of a second TAL effector domain operably linked to a second TALEN.

Nucleic Acid Molecules for Intracellular Alteration

Donor nucleic acid molecules (e.g., donor DNA molecules) will typically contain at least one region of homology corresponding to nucleic acid at or near a target locus and an inert region designed for modification of the target locus. Donor nucleic acid molecules designed for homologous recombination will often have at least three regions in the following order: (1) A first region of homology corresponding to nucleic acid at or near a target locus, (2) an insert region, and (3) a second region of homology corresponding to nucleic acid at or near a target locus (see FIG. 38). Further, donor nucleic acid molecules may be single-stranded (SS) or double-stranded (DS) and they may be blunted ended on one or both ends or it may have overhangs on one or both ends. Overhangs, when present, may be 5', 3' or 3' and 5'. Also, the lengths of overhangs may vary. Donor nucleic acid molecules will often also contain an "insert" region that may be from about one nucleotide to about several thousand nucleotides.

As noted above, overhangs, when present may be of varying size. Overhangs may be from about 1 to about 1,000 nucleotides (e.g., from about 1 to about 1,000, from about 5 to about 1,000, from about 10 to about 1,000, from about 25 to about 1,000, from about 30 to about 1,000, from about 40 to about 1,000, from about 50 to about 1,000, from about 60 to about 1,000, from about 70 to about 1,000, from about 80 to about 1,000, from about 100 to about 1,000, from about 1 to about 800, from about 1 to about 700, from about 1 to about 500, from about 1 to about 400, from about 1 to about 300, from about 10 to about 600, from about 10 to about 400, from about 10 to about 250, from about 30 to about 700, from about 50 to about 600, from about 50 to about 250, from about 75 to about 800, from about 80 to about 500, from about 100 to about 800, from about 100 to about 600, etc. nucleotides).

The efficiency of homologous recombination is enhanced when one or both termini of donor nucleic acid molecules "matches" that of a double-stranded break into which it is designed to be introduced into. Further, upon entry into cells (as well as prior to cellular entry), donor nucleic acid molecules may be exposed to nucleases (e.g., endonucleases, endonucleases, etc.). In order to limit the action of endonucleases with respect to altering donor nucleic acid molecule, one or more nuclease resistant group may be present.

Intracellular nucleic acid molecules intended for modification may be any intracellular nucleic acid molecules, including chromosomes, nuclear plasmids, chloroplast genomes, and mitochondrial genomes. Further, intracellular nucleic acid molecule intended for modification may be located anywhere in a cell.

Figure 38:
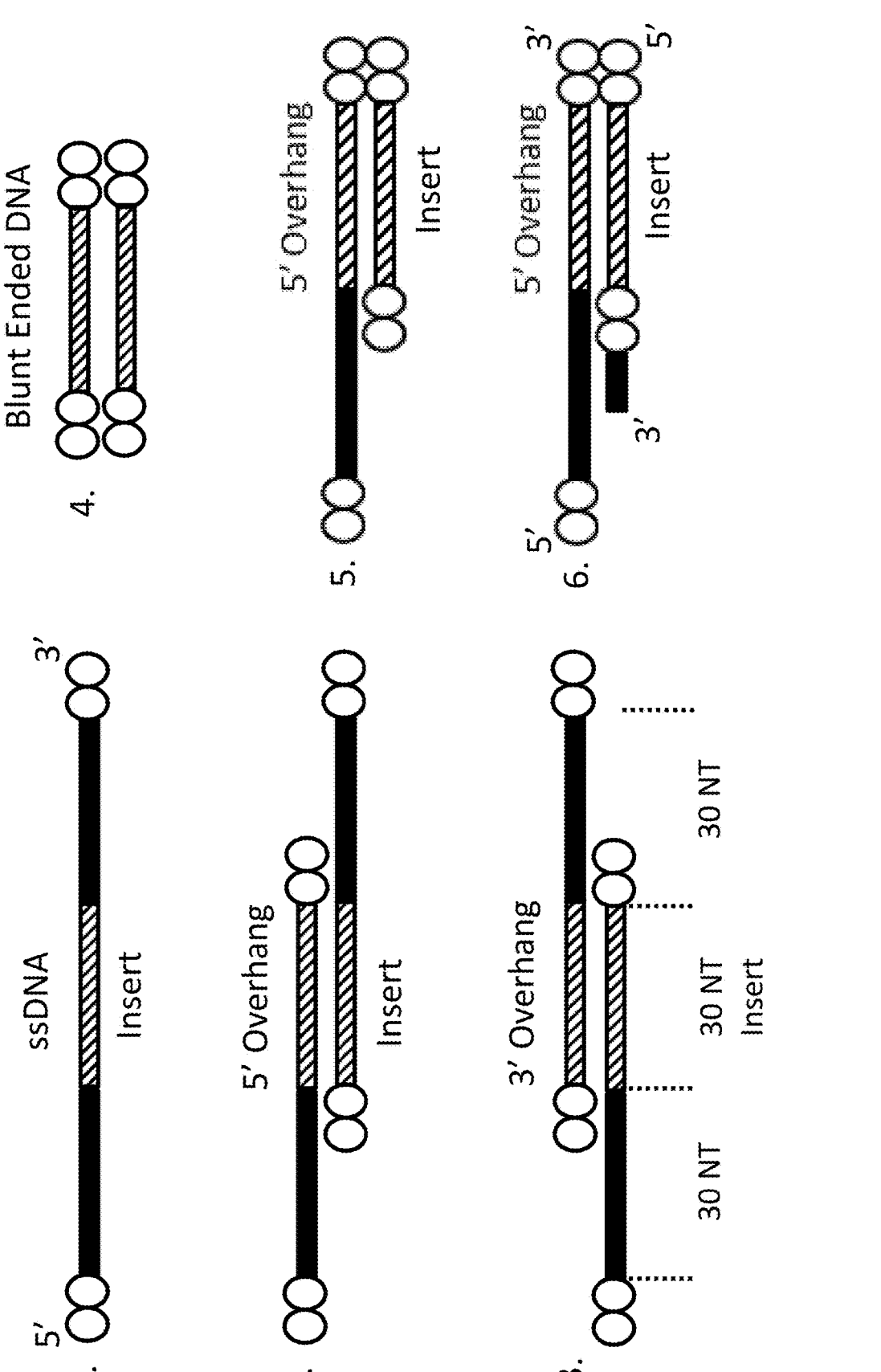
FIG. 38 shows a number of different formats of donor nucleic acid molecules that may be used in various embodiments set out herein. The open circles at the termini represent nuclease resistant groups. Two circles mean that there are two groups. The black areas represent regions of sequence homology/complementarity with one or more locus of another nucleic acid molecule (e.g., chromosomal DNA). The cross hatched areas represent nucleic acid located between regions of sequence homology/complementarity in the nucleic acid segments. This figure shows different variations of donor nucleic acid molecules that may be used in different aspects of the invention.

FIG. 38 shows a number of variations of donor nucleic acid molecules that may be used in methods set out herein. The open circles at the termini represent nuclease resistant groups. Such groups may be located at a number of places in the donor nucleic acid molecules. Donor nucleic acid molecule number 6 shows a 3' terminal region of the lower strand that is located past the nuclease resistant groups. In some instances, cellular nucleases will digest this portion of the donor nucleic acid molecule. These nucleases will either stop or be slowed down by the nuclease resistant group, thereby stabilizing the structure of the terminus of the 3' region of the lower strand.

Compositions comprising nucleic acid molecules containing one or more (e.g., one, two, three, four, five, six, seven, etc.) nuclease resistant groups may be used in the practice of methods set out herein. In many instances, nuclease resistant groups will be located or one or both termini of donor nucleic acid molecules. Donor nucleic acid molecules may contain groups interior from one or both termini. In many instances, some or all of such donor nucleic acid molecules will be processed within cells to generate termini that match double-stranded break sites.

The homology regions may be of varying lengths and may have varying amounts of sequence identity with nucleic acid at the target locus. Typically, homologous recombination efficiency increases with increased lengths and sequence identity of homology regions. The length of homology regions employed is often determined by factors such as fragility of large nucleic acid molecules, transfection efficiency, and case of generation of nucleic acid molecules containing homology regions.

Homology regions may be from about 20 bases to about 10,000 bases in total length (e.g., from about 20 bases to about 100 bases, from about 30 bases to about 100 bases, from about 40 bases to about 100 bases, from about 50 bases to about 8,000 bases, from about 50 bases to about 7,000 bases, from about 50 bases to about 6,000 bases, from about 50 bases to about 5,000 bases, from about 50 bases to about 3,000 bases, from about 50 bases to about 2,000 bases, from about 50 bases to about 1,000 bases, from about 50 bases to about 800 bases, from about 50 bases to about 600 bases, from about 50 bases to about 500 bases, from about 50 bases to about 400 bases, from about 50 bases to about 300 bases, from about 50 bases to about 200 bases, from about 100 bases to about 8,000 bases, from about 100 bases to about 2,000 bases, from about 100 bases to about 1,000 bases, from about 100 bases to about 700 bases, from about 100 bases to about 600 bases, from about 100 bases to about 400 bases, from about 100 bases to about 300 bases, from about 150 bases to about 1,000 bases, from about 150 bases to about 500 bases, from about 150 bases to about 400 bases, from about 200 bases to about 1,000 bases, from about 200 bases to about 600 bases, from about 200 bases to about 400 bases, from about 200 bases to about 300 bases, from about 250 bases to about 2,000 bases, from about 250 bases to about 1,000 bases, from about 350 bases to about 2,000 bases, from about 350 bases to about 1,000 bases, etc.).

In some instances, it may be desirable to use regions of sequence homology that are less than 200 bases in length. This will often be the case when the donor nucleic acid molecule contains a small insert (e.g., less than about 300 bases) and/or when the donor nucleic acid molecule has one or two overhanging termini that match the double-stranded break site.

Overhanging termini may be of various lengths and may be of different lengths at each end of the same donor nucleic acid molecules. In many instances, these overhangs will form the regions of sequence homology. FIG. 38, for example, shows a series of donor nucleic acid molecule that have 30 nucleotide single-stranded overhangs. These donor nucleic acid molecules are shown as single-stranded and double-stranded. Donor nucleic acid molecule number 1 in FIG. 38 is a single-stranded molecule that has 30 nucleotides of sequence homology with an intended double-stranded break site, a 30 nucleotide insert, and two nuclease resistant groups at each terminus.

The amount of sequence identity the homologous regions share with the nucleic acid at the target locus, typically the higher the homologous recombination efficiency. High levels of sequence identity are especially desired when the homologous regions are fairly short (e.g., 50 bases). Typically, the amount of sequencer identity between the target locus and the homologous regions will be greater than 90% (e.g., from about 90% to about 100%, from about 90% to about 99%, from about 90% to about 98%, from about 95% to about 100%, from about 95% to about 99%, from about 95% to about 98%, from about 97% to about 100%, etc.).

The insert region of donor nucleic acid molecules may be of a variety of lengths, depending upon the application that it is intended for. In many instances, donor nucleic acid molecules will be from about 1 to about 4,000 bases in length (e.g., from about 1 to 3,000, from about 1 to 2,000, from about 1 to 1,500, from about 1 to 1,000, from about 2 to 1,000, from about 3 to 1,000, from about 5 to 1,000, from about 10 to 1,000, from about 10 to 400, from about 10 to 50, from about 15 to 65, from about 2 to 15, etc. bases).

Also provided herein are compositions and methods for the introduction into intracellular nucleic acid of a small number of bases (e.g., from about 1 to about 10, from about 1 to about 6, from about 1 to about 5, from about 1 to about 2, from about 2 to about 10, from about 2 to about 6, from about 3 to about 8, etc.). For purposes of illustration, a donor nucleic acid molecule may be prepared that is fifty-one bases pairs in length. This donor nucleic acid molecule may have two homology regions that are 25 base pairs in length with the insert region being a single base pair. When nucleic acid surrounding the target locus essentially matches the regions of homology with no intervening base pairs, homologous recombination will result in the introduction of a single base pair at the target locus. Homologous recombination reactions such as this can be employed, for example, to disrupt protein coding reading frames, resulting in the introduction of a frame shift in intracellular nucleic acid. The invention thus provides compositions and methods for the introduction of one or a small number of bases into intracellular nucleic acid molecules.

The invention further provides compositions and methods for the alteration of short nucleotide sequences in intracellular nucleic acid molecules. One example of this would be the change of a single nucleotide position, with one example being the correction or alteration of a single-nucleotide polymorphism (SNP). Using SNP alteration for purposes of illustration, a donor nucleic acid molecule may be designed with two homology regions that are 25 base pairs in length. Located between these regions of homology is a single base pair that is essentially a "mismatch" for the corresponding base pair in the intracellular nucleic acid molecules. Thus, homologous recombination may be employed to alter the SNP by changing the base pair to either one that is considered to be wild-type or to another base (e.g., a different SNP). Cells that have correctly undergone homologous recombination may be identified by later sequencing of the target locus.

The invention also includes compositions and methods for the alteration of genomes for therapeutic applications, including SNP alterations. Two genetic afflictions resulting from SNP alterations are set out below for purposes of illustration.

The most common SNP associated with sickle cell anemia is rs334, which results in the alteration of a change of a single codon from GAG to GTG. This change results in the replacement of a glutamic acid residue with a valine residue. Compositions and methods set out herein are suited for altering this SNP from GTG to GAG, especially in individual homozygous for SNP rs334. One of these reasons relates to the introduction of nucleic acid molecules into cells can inducing toxicity related effects. Further, these effects are graded in that they increase with the amount of nucleic acid introduced into the cells. As shown in the examples below, the efficiency of genome insertion is such that relatively small amounts of donor DNA need be introduced into the cells (see, e.g., the donor DNA-NLS conjugate data in FIGS. 11 and 13).

One exemplary ex vivo workflow for altering SNP rs334 in a patient would include the removal of bone marrow tissue from the patient, alteration of SNP rs334, followed by reintroduction of the editing cells back into the patient.

One of the most common genome alterations associated with cystic fibrosis is based upon a three base pair deletion (SNP rs199826652) in the cystic fibrosis transmembrane conductance regulator (CFTR), resulting in the deletion of the amino acid phenylalanine at position 508.

An in vivo workflow for altering SNP rs199826652 in a patient would include delivery of donor DNA molecules to airway cells of the patient, under conditions where a three base pair insertion would occur to correct SNP rs199826652.

The low dosage of donor nucleic acid required for efficient gene editing is also useful for systemic delivery. This is so because low dosage correlates with decreased toxicity. Low donor DNA molecule levels are especially important when modified nucleic acid molecules (e.g., nucleic acid molecules with phosphorothioate linkages) are used.

Donor nucleic acid molecules may be conjugated to extracellular targeting moieties, as well as intracellular targeting moiety. An "extracellular targeting moiety" is a molecule that directs the donor nucleic acid molecule to one or more cell type. Such moieties include cell surface receptor ligands and antibodies. Domain II of *Pseudomonas* has been shown to be involved in translocation across cell membranes. (Jinno et al., *J. Biol. Chem.* 263:13203-13207 (1988)). Thus, one exemplary system for delivery of nucleic acid molecules to subcellular locations in an organism could involve the following components: (1) The donor DNA molecule, (2) a nuclear conjugation signal (NLS), and (3) a fusion protein comprising an antibody that binds to a cell surface receptor and Domain II of *Pseudomonas* exotoxin, wherein the NLS and fusion protein are covalently bound to the donor DNA molecule. Donor DNA molecules of this type allow for the systemic delivery of donor DNA molecules, wherein the donor DNA molecule would be delivered to a subcellular location within cells containing the cell surface receptor.

In each of the two instances above, only one copy of the allele needs to be altered in order for patients to receive substantial benefit. In many of the cells, however, both copies of the SNP would be altered. Thus, the invention includes the treatment of afflictions resulting from both homozygous and heterozygous genetic components.

Donor nucleic acid molecules may also be designed to introduce functional coding regions chromosomal open reading frames. One example of this is the removal of stop codons at the end of open reading frames. Such stop codons may be removed because they are not present in a wild-type open reading frame (i.e., represent an alteration from "wild-type") or they may be naturally present at the end of an open reading frame. Stop codons may also be introduced into coding regions. This is especially useful when one seeks to disrupt an open reading frame.

Further, tag coding regions may be introduced such that protein expression results in tagged protein. Such tags may be introduced in to intracellular nucleic acid such that the tags are present at one or more of the amino terminus, the carboxy terminus, or interior in the protein. Examples of tags include epitope tags (e.g., His tags, Maltose-Binding Protein (MBP) tags, Cellulose-Binding Domain (CBD) tags, and Glutathione S-Transferase (GST) tags, etc.) and enzymatic tags (e.g., horseradish peroxidase (HRP) tags and alkaline phosphatase (AP) tags, etc.).

The invention thus includes compositions and methods for producing non-naturally occurring proteins without cloning nucleic acid molecules encoding the non-naturally occurring proteins. These methods are based, in part, on introducing polypeptide coding regions into intracellular nucleic acid molecules at locations that result in fusion proteins being encoded by the modified intracellular nucleic acid molecules, followed by expression of the encoded fusion proteins and separation of the fusion proteins from the cells.

Cells

Cells provided herein including embodiments thereof include complexes capable of increasing accessibility of a genomic locus in a cell. Complexes provided may enhance the activity of modulating proteins or complexes at a genomic (target) locus by including enhancer proteins which increase the accessibility for the modulating proteins at the locus. For example, upon binding of a DNA-binding modulation-enhancing agent as provided herein to the genomic locus (target locus) the locus is made more accessible to a nuclease or other enzymatic activity and thereby enhancing the efficiency and effectivity of said nuclease or other enzymatic activity.

In one aspect, a cell including a nucleic acid encoding a target locus modulating complex is provided. The complex includes, (i) a target locus including a first enhancer binding sequence and a modulator binding sequence including a modulation site; (ii) a first modulating protein or a first modulating complex bound to the modulator binding sequence; and (iii) a first DNA-binding modulation-enhancing agent bound to the first enhancer binding sequence.

In embodiments, the target locus further includes a second enhancer binding sequence linked to the first enhancer binding sequence by the modulator binding sequence.

In embodiments, the cell includes a second DNA-binding modulation-enhancing agent bound to the second enhancer binding sequence.

In one aspect, a cell including a nucleic acid encoding a target locus complex is provided. The complex includes (i) a target locus including a first enhancer binding sequence; and (ii) a first DNA-binding modulation-enhancing agent bound to the first enhancer binding sequence, wherein the first DNA-binding modulation-enhancing agent is not endogenous to the cell and wherein the first DNA-binding modulation-enhancing agent is capable of increasing accessibility of the target locus relative to the absence of the first DNA-binding modulation-enhancing agent.

In one aspect, a cell including a nucleic acid encoding a target locus complex is provided. The complex includes (1) a target locus including: (i) a first enhancer binding sequence; and (ii) a second enhancer binding sequence. (2) A first DNA-binding modulation-enhancing agent bound to the first enhancer binding sequence of the target locus, wherein the first DNA-binding modulation-enhancing agent is not endogenous to the cell; and (3) a second DNA-binding modulation-enhancing agent bound to the second enhancer binding sequence of the target locus, wherein the second DNA-binding modulation-enhancing agent is not endogenous to the cell, wherein the first DNA-binding modulation-enhancing agent and the second DNA-binding modulation-enhancing agent are capable of increasing accessibility of the target locus relative to the absence of the first DNA-binding modulation-enhancing agent and the second DNA-binding modulation-enhancing agent.

Compositions and methods of the invention may be used to generate cell lines useful for any number of purposes. For example, a single locus or multiple loci may be altered. One example of a cell line that may be generated are CHO cell lines used to produce humanized antibodies. To produce such a cell line, donor nucleic acid molecules encoding the humanized antibody sequences are introduced into a CHO cell line under conditions where insertion into the CHO cell genome is designed to occur. Typically a selectable marker would also be introduced into the genome to allow for the selection of modified cells. Of course, any suitable cell line and essentially any desirable coding sequence could be used. The invention thus includes compositions and methods for the generation of cells useful for the bioproduction of gene products (e.g., proteins).

Compositions and methods of the invention may also be used to generate uniform pools of primary cells or cancer cells. Along these lines, high efficiency gene editing allows for the alteration of cells that may be used for "downstream" applications either directly or after a minimal selection.

One exemplary workflow involves the synthesis of a simvastatin precursor, monacolin J. Simvastatin precursor can made chemically by a multi-step process involving the alkaline hydrolysis of lovastatin, a fungal polyketide produced by *Aspergillus terreus*. A lovastatin hydrolase found in *Penicillium chrysogenum* has been identified and characterized. This hydrolase is highly efficient in the hydrolysis of lovastatin to monacolin J but has no detectable activity for simvastatin (see Huang et al., *Single-step production of the simvastatin precursor monacolin J by engineering of an industrial* strain *of Aspergillus terreus, Metabolic Engineering*, 42:109-114 (2017).

In this workflow, an *A. terreus* production cell line is developed by the stable introduction of the *P. chrysogenum* lovastatin hydrolase into the *A. terreus* genome. Since lovastatin is natural polyketide product produced by *A. terreus*, the engineered cells will then convert lovastatin intracellularly to monacolin J. Thus, one workflow is where *A. terreus* cells are engineered using methods set out herein, where a sufficient percentage of the cell population (e.g., over 60%) expresses lovastatin hydrolase that the cell population may be directly used for monacolin J production. An alternate workflow would be one where selection for engineered *A. terreus* cells or selection against engineered *A. terreus* cells occurs prior to use.

Workflows similar to the above may be used to produce cells (e.g., primary mammalian cell, immortalized mammalian cells, etc.) for use in screening assays. One example would be where primary hepatocytes are modified and then used to screen for drug related hepatotoxicity.

Kits

The invention also provides kits for, in part, the assembly and/or storage of nucleic acid molecules and for the editing of cellular genomes. As part of these kits, materials and instruction are provided for both the assembly of nucleic acid molecules and the preparation of reaction mixtures for storage and use of kit components.

Kits of the invention will often contain one or more of the following components:

1. One or more DNA-binding modulation-enhancing agents (e.g. a TAL effector protein or a truncated gRNA bound to a Cas9 protein), 2. One or more modulating proteins (e.g., a DNA binding nuclease conjugate including a TAL effector domain linked to a nuclease), 3. One or more modulating complexes (e.g., one or more Cas9 domain bound to gRNA, an Argonaute protein domain bound to a guide DNA etc.), and 4. Instructions for how to use kits components.

Kit reagents may be provided in any suitable container. A kit may provide, for example, one or more reaction or storage buffers. Reagents may be provided in a form that is usable in a particular reaction, or in a form that requires addition of one or more other components before use (e.g., in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10.

EXAMPLES

The following examples are provided to illustrate certain disclosed embodiments and are not to be construed as limiting the scope of this disclosure in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Promoter Insertion

Materials

GENEART™ PLATINUM™ Cas9 Nuclease, GENEART™ CRISPR gRNA Design Tool, GENEART™ Precision gRNA Synthesis Kit, 293FT cells, Dulbecco's Modified Eagle Medium (DMEM) medium, Fetal Bovine Serum (FBS), TRYPLE™ Express Enzyme, 2% E-Gel® EX Agarose Gels, TranscriptAid T7 High Yield Transcription Kit, MEGA-CLEAR™ Transcription Clean-Up Kit, ZERO BLUNT® TOPO® PCR Cloning Kit, PURELINK® Pro Quick96 Plasmid Purification Kit, PURELINK™ PCR Purification Kit, QUBIT® RNA BR Assay Kit, NEON® Transfection System 10 μL Kit, GIBCOR OPTMIZER™ CTS™ T-Cell Expansion SFM, recombinant human IL-2 (Interleukin 2) CTS™, DYNA-BEADS™ MYONE™ Streptavidin C1, DYNABEADS™ Human T-Expander CD3/CD28, DYNABEADS™ UNTOUCHED™ Human T Cells Kit, IgG (Total) Human ELISA Kit, polyclonal beta-actin antibody, polyclonal epidermal growth factor (EGFR) antibody, and Phusion Flash High-Fidelity PCR Master Mix were from Thermo Fisher Scientific. Ficoll-Paque PLUS was purchased from GE Healthcare Life Sciences. NU 7026 was ordered from Tocris Bioscience. The sequences of DNA oligonucleotides and donor DNA used in this study were listed in Table 12.

Synthesis of gRNA

DNA oligonucleotides and primers used for gRNA synthesis were designed by GENEART™ CRISPR gRNA Design Tool. The gRNAs were then synthesized using the GENEART™ Precision gRNA Synthesis Kit. The concentration of gRNA was determined by QUBIT® RNA BR Assay Kit.

Generation of Long Single-Stranded DNA Via Asymmetric PCR

The donor DNA template was first amplified with a forward primer and a biotinylated reverse primer. The resulting PCR product (20 ng) was added to a Phusion Flash High-Fidelity PCR Master Mix containing 0.2 µM forward primer and 0.01 µM biotinylated reverse primer in a total volume of 50 µl. A total of 24 reactions were set up and the following PCR program was used: 98° C. for 30 seconds for one cycle, then 98° C. for 5 seconds, 55° C. for 10 seconds, and 72° C. for 45 seconds for a total of 24 cycles. Final extension was incubated at 72° C. for 3 minutes. To remove double-stranded DNA template, the PCR products were combined and incubated with 300 µl of DYNABEADS™ MYONE™ Streptavidin C1 for 20 minutes at room temperature with gentle rotation. The magnetic beads were removed with a magnet and the supernatant was subjected to PURE-LINK™ PCR Purification with 4 columns then concentrated using a speed vac. Approximately 5 µg single stranded-DNA was obtained.

Genomic Cleavage and Detection Assay

The genomic cleavage efficiencies were determined by GENEART® Genomic Cleavage Detection kit (Thermo Fisher Scientific, cat. no. A24372) according to manufacturer's instructions. The primer sequences for PCR amplification of each genomic locus are described in Table 12. Cells were analyzed at 48 to 72 hours post transfection. The cleavage efficiencies were calculated based on the relative agarose gel band intensity, which were quantified using an ALPHAIMAGER® gel documentation system running ALPHAVIEW®, Version 3.4.0.0. ProteinSimple (San Jose, CA, USA).

Isolation of Human Primary T Cells

Human peripheral blood mononuclear cells (PBMCs) were isolated from peripheral blood using Ficoll-Paque PLUS density gradient according to manufacturer's instructions. The human primary T cells were then isolated using DYNABEADS™ UNTOUCHED™ Human T Cells Kit and expanded using OPTMIZER™ CTS™ T-Cell Expansion SFM supplemented with 200 IU/mL of IL-2. The activation and expansion of human T cells were carried out using DYNABEADS™ Human T-Expander CD3/CD28 kit. On day 3 of activation, T cells were harvested for transfection.

Cell Transfection

293FT or A549 cells were maintained in DMEM medium supplemented with 10% FBS. On the day of transfection, cells were detached from the culture flask and counted. For each electroporation, 1.5 µg of Cas9 protein and 360 ng of gRNA were added to Resuspension Buffer R to a final volume of 7 µl, but the total volume of Cas9 protein plus gRNA added was less than 1 µl. Upon mixing, the sample was incubated at room temperature for 5 to 10 minutes to form Cas9 RNPs complex. Meanwhile, aliquots of $1 \times 10^6$ cells were washed once with DPBS without $Ca^{2+}$ and $Mg^{2+}$ and the cell pellets were resuspended in 50 µl of Resuspension Buffer R. A 5 µl aliquot of cell suspension was then mixed with 7 µl of Cas9 RNPs, followed by addition of 1 µl indicated amount of donor DNA. 10 µl of cell suspension containing Cas9 RNP and donor was applied to NEON® electroporation (Thermo Fisher Scientific, cat. no. MPK5000) with voltage set at 1150V, pulse width set at 20 ms, and the number of pulses set at 2, respectively. The electroporated cells were transferred to a 48-well plate containing 0.5 ml culture media. Samples without either gRNA or donor DNA served as controls. At 48 hours post transfection, the cells were analyzed by flow cytometry. Alternatively, the genomic loci were PCR-amplified with the corresponding primers. The resulting PCR fragments were analyzed using the GENEART® Genomic Cleavage Detection assay. The edited cells were further subjected to limiting dilution, followed by clonal cell isolation. The clonal cells were characterized by PCR amplification of both the N- and C-terminal junctions and sequencing. The sequencing data were analyzed using VECTOR NTI ADVANCE® 11.5 software (Thermo Fisher Scientific).

For transfection of primary T cells, $1 \times 10^5$ cells were used per NEON® electroporation with voltage set at 1700V, pulse width set at 20 ms, and the number of pulses set at 1, respectively. To evaluate the effects of chemical modification on HDR efficiency, phosphorothioate or amine-modified nucleotides were added at specific positions of the oligonucleotides during chemical synthesis. The resulting modified oligonucleotides were then used to amplify the donor DNA. For cell treatment with NU 7026 inhibitor, cells were transfected as described above and then added to cell culture medium containing 30 µM Nu 7026. Cells were analyzed at 48 hours post transfection.

Strategies for Protein Tagging

Protein tagging allows researchers to visualize the subcellular localization of proteins and study their functions. The strategies for tagging endogenous cellular proteins are depicted in FIG. 1. A promoterless puromycin selection marker is linked to a reporter gene via a self-cleaving 2A peptide. The puromycin gene is placed at either the 5' end of the fusion protein for N-terminal tagging or at the 3' end for C-terminal tagging. The 35 nt homology arms are added to 5' and 3' ends of the donor DNA by PCR amplification. The expression of puromycin is driven by endogenous promoter whereas the reporter gene is fused in-frame to the endogenous gene. TALEN or CRISPR are designed to target the genomic locus near the ATG start codon for N-terminal tagging or the stop codon for C-terminal tagging. The resulting TALEN or CRISPR and donor DNA are then delivered into cells via lipid-mediated transfection or electroporation. Upon 48 hours post transfection, the cells are treated with puromycin for 7 days, and then visualized by fluorescence microscopy or analyzed by junction PCR and sequencing.

Examples of N-Terminal Protein Tagging

Figure 2A:
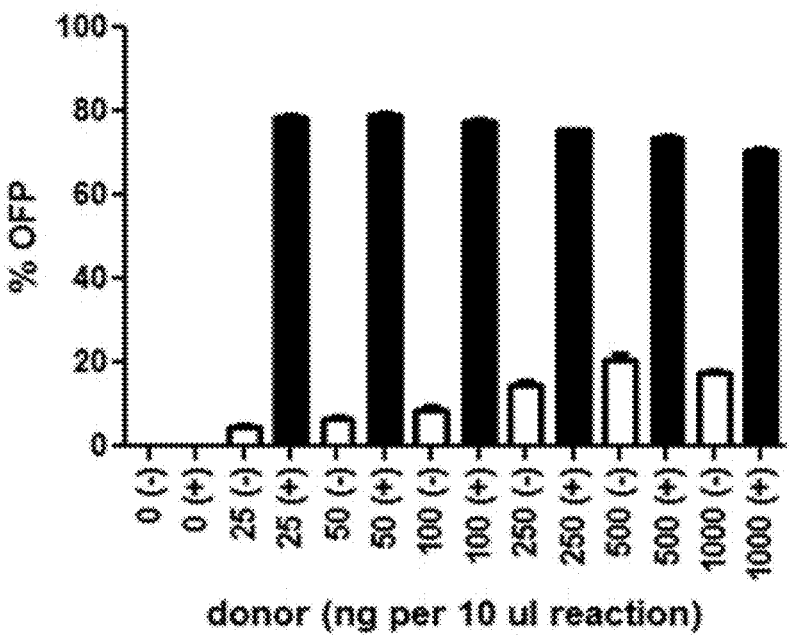
FIG. 2A to 2D show the effect of donor format and dosage as well as homology arm length on HDR efficiency.
Figure 2B:
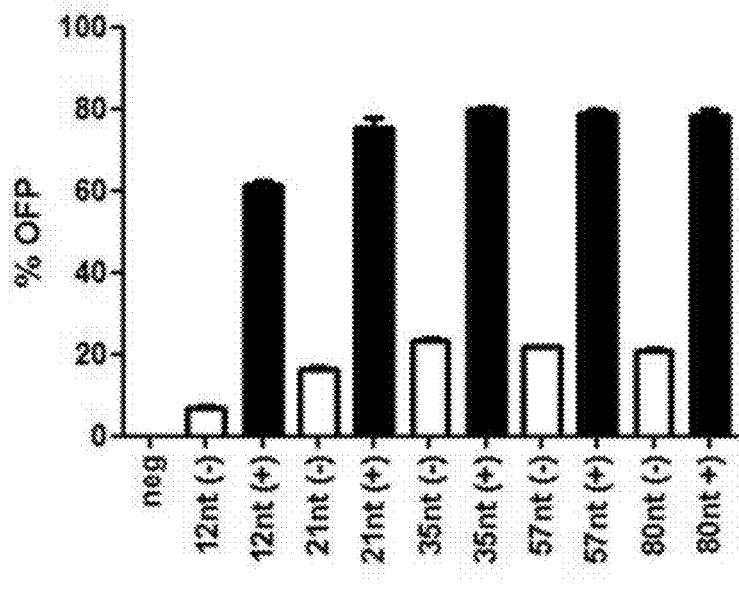
Figure 2C:
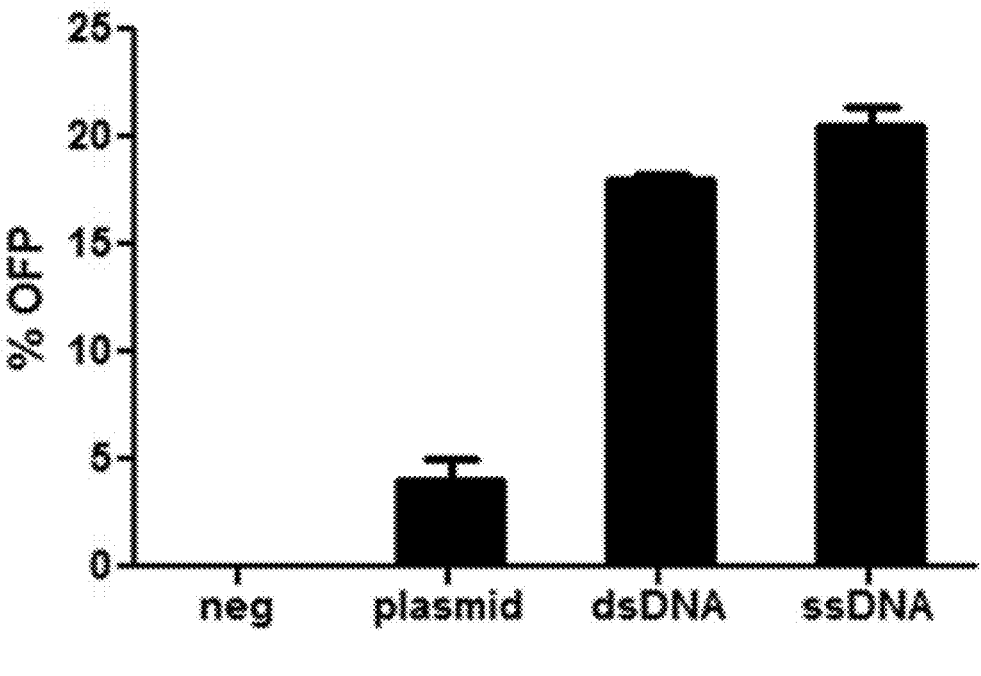
Figure 2D:
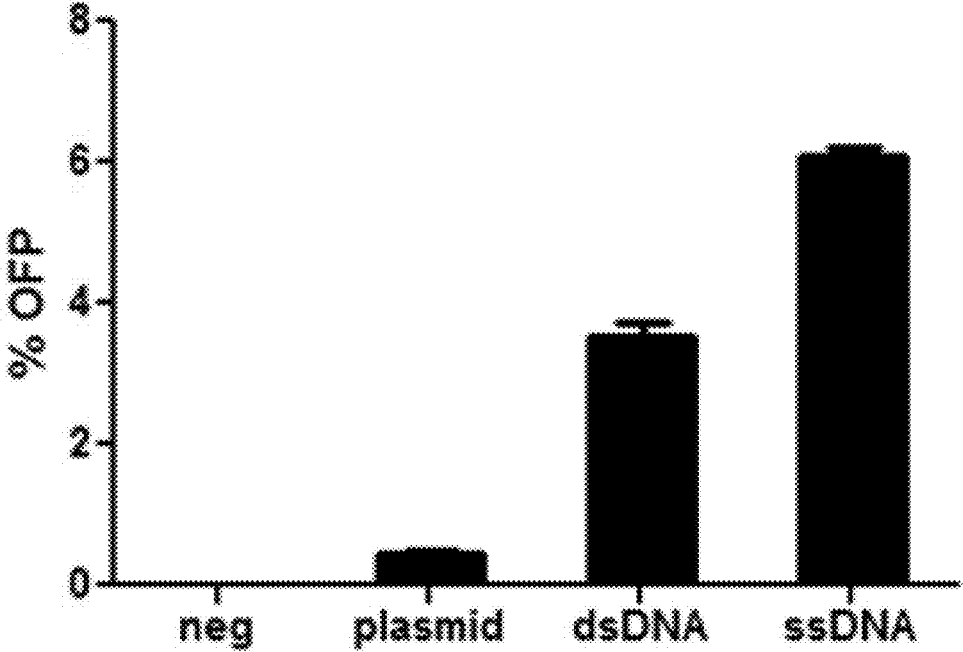

To evaluate the strategy of tagging endogenous protein, we fused the OFP gene to the N-terminus of beta-actin. Beta-actin is one of the most abundant proteins in eukaryotes, so it is easy to monitor using fluorescence microscopy. A gRNA was designed and synthesized to target the genomic locus of beta-actin near the ATG start codon (Table 12) and then complexed with Cas9 nuclease to form RNPs. The relevant 35 nt homology arms were added to a sequence-verified promoterless puromycin-P2A-OFP DNA fragment by PCR amplification. The resulting donor PCR fragments were purified using PureLink™ PCR Purification Kit and then concentrated using a speed-vac to a final concentration of around 1 µg/µl. To examine the effect of donor dosage on HDR efficient, we kept the amount of Cas9 RNP constant and varied the amount of donor DNA. The Cas9 RNP and donor DNA were transfected into 293 FT via electroporation. At 48 hours post transfection, the cells were analyzed by fluorescence microscope. When the cells were transfected with Cas9 RNP alone or Cas9 protein with donor DNA, no OFP-positive cells were detected, whereas OFP-positive cells were observed when cells were transfected with Cas9 RNP and donor DNA. The percentages of OFP-positive cells were determined by flow cytometric analysis. Without selection, the percentage of OFP-positive cells increased from approximately 5% to 20% when the amount of donor DNA increased from 25 ng to 500 ng (FIG. 2A). The optimal amount of donor DNA was around 500 ng per reaction. On the other hand, after treatment of transfected cells with 1 µg/ml puromycin for 7 days, approximately 80% of cells were OFP-positive. There was no significant difference in the percentage of OFP-positive cells between different amounts of donor DNA (FIG. 2A). Next, we examined the effect of homology arm length on HDR efficiency. Various lengths of homology arms were added to the promoterless puromycin-P2A-OFP DNA fragment by PCR amplification. As depicted in FIG. 2B, when the homology arm length increased from 12 nt to 80 nt, the percentage of OFP-positive cells increased and then plateaued at around 35 nt.

Traditionally, a plasmid donor was used to incorporate large DNA molecules into the genome. For comparison, we constructed a donor plasmid containing approximately 500 nt homology arms. Also, we prepared a long single-stranded DNA donor harboring 35 nt homology arms via asymmetric PCR. The Cas9 RNP and various forms of donor DNA were delivered into either 293FT cells or human primary T cells via electroporation. At 48 hours post transfection, we analyzed the percentages of OFP-positive cells using flow cytometry. As depicted in FIGS. 1C and 1D, the percentages of OFP-positive cells using single-stranded (ss) or double-stranded DNA (ds) fragments with 35 nt homology arms were significantly higher than that using a donor plasmid with long homology arms in both 293FT and primary T cells. The efficiency using ssDNA donor was higher than that using dsDNA donor in primary T cells, although their efficiencies were similar in 293FT.

Figure 3A:
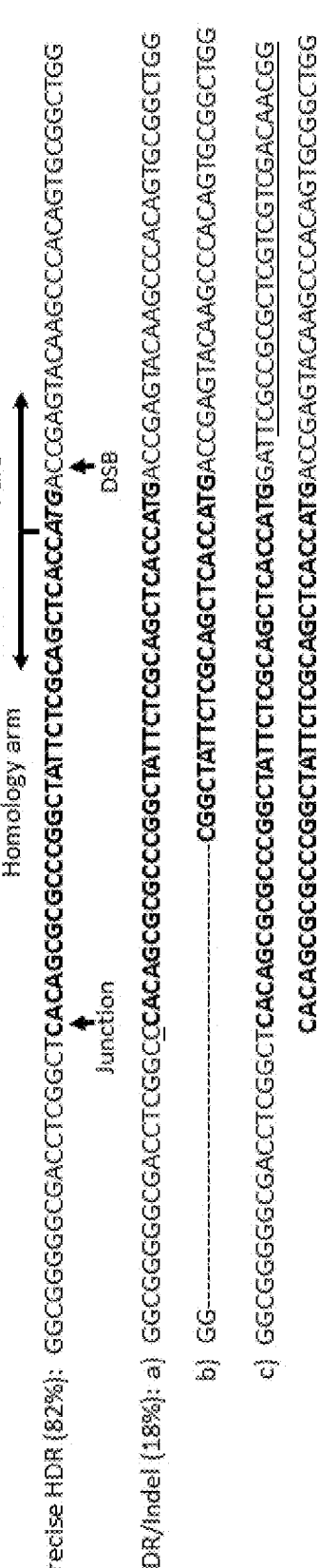
FIG. 3A to 3E show characterization of clonal cells with OFP integrated into beta-actin locus. Cas9 RNP and donor DNA with 35 nt homology arms were delivered into 293FT cells via electroporation, followed by clonal cell isolation after puromycin selection. The clonal cells were analyzed by junction PCR using one inner primer and one outer primer or a pair of outer primers. The resulting PCR products were analyzed by sequencing.
Figure 3B:
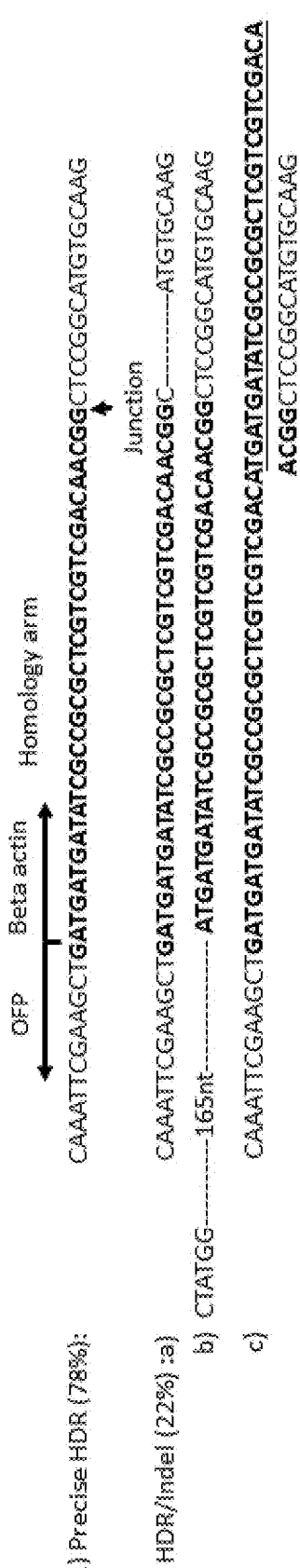
Figure 3C:
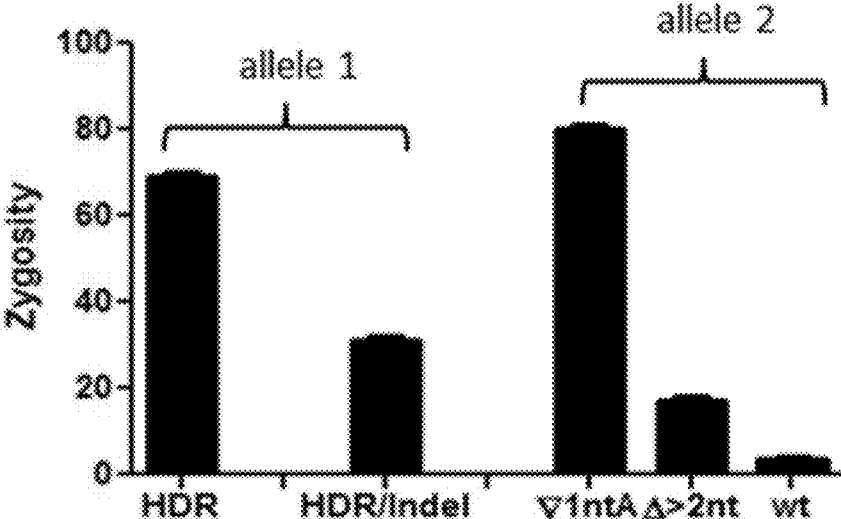

To examine the identity of integration sites, cells transfected with Cas9 RNP and donor DNA were subjected to puromycin selection, limiting dilution, and clonal cell isolation. A total of 48 colonies were randomly picked for junction PCR analysis. Among the 48 colonies, only one failed to grow and produce PCR products. All the other 47 colonies gave rise to PCR products for both N- and C-terminal junctions when one outer primer and one inner primer were used. The PCR product was also observed when a pair of outer primers was used with the size of about 420 bp, which corresponded to the genomic DNA fragment without an insert. The reason why a large PCR product containing the insert was not observed was because the smaller DNA fragment without the insert was preferentially amplified. Sequencing analysis of the PCR products confirmed that approximately 82% of the N-terminal junctions exhibited precise HDR at the junction between genomic DNA and donor DNA (FIG. 3A(1)). The other 18% of clonal cells also contained the insert but had mutations at the junction areas (FIG. 3A(2)). Most of the mutations were deletion and insertion. Sometimes a duplicate sequence of a partial or full-length homology arm was inserted at the junction. At the C-terminal junction, approximately 78% of the clonal cells harbored precise HDR (FIG. 3B(1)) whereas the other 22% of cells had Indel formation at the junction (FIG. 3B(2)). Rarely, a relatively large piece of donor DNA (up to 165 nt) was deleted at the C-terminal junction. Overall, all the clonal cells contained one copy of donor DNA at the right genomic locus in one of the alleles with 68% of cells harbored precise HDR at both N- and C-termini and 32% of cells harbored imperfect HDR at either N- or C-terminus or both. The other allele did not contain any insert. Instead, approximately 80% of the clones had one "A" insertion at the Cas9 cleavage site and 20% of the clones harbored more than 2 nt deletion. Only one wild type clone was detected at the second allele (FIG. 3C). Most of the clones expressed both wild type beta-actin and OFP fusion of beta-actin as confirmed by Western Blot analysis.

Figure 3D:
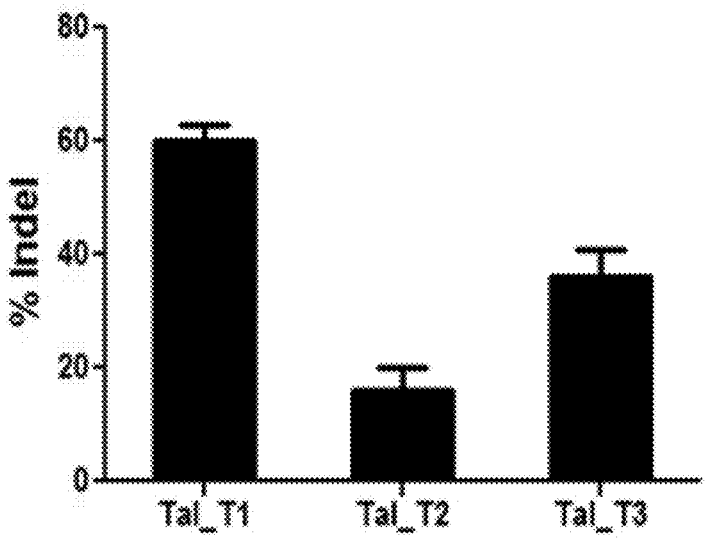
Figure 3E:
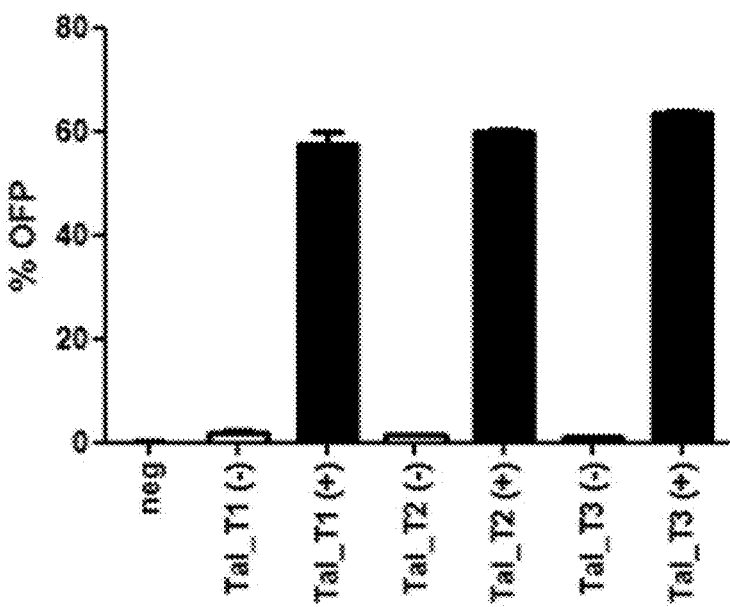

TALEN (TAL effector nuclease) is an alternative approach to introduce double-stranded breaks in the mammalian genome. Three pairs of TALEN mRNA to target the regions near the ATG codon of beta-actin were designed and synthesized. The TALEN mRNA alone or TALEN mRNA with donor DNA were transfected into HEK293FT cells via NEON® electroporation using 1150 volts, 20 milliseconds (ms) and two pulses. At 48 hours post transfection, the cells were lyzed to measure genome editing efficiency (FIG. 3D) or analyzed by flow cytometry (FIG. 3E) to determine the percentages of OFP-positive cells (−). Alternatively, the cells were treated with puromycin for 7 days prior to flow cytometric analysis (+) (FIG. 3E). As depicted in FIG. 3D, without puromycin selection, the percentages of OFP-positive cells were very low although TI and T3 targets produced approximately 60% and 35% Indel frequencies. However, upon puromycin selection, the percentages of OFP-positive went up to approximately 60% for all three different targets (FIG. 3E).

Figure 4A:
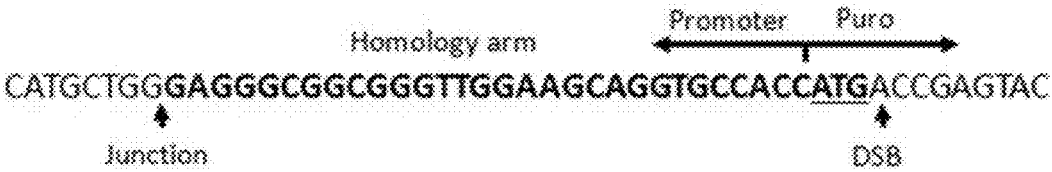
FIGS. 4A, 4B, and 4C show N-terminal tagging of EmGFP to LRRK2 in A549 cells. Cas9 RNP and donor DNA containing a promoterless puromycin-P2A-EmGFP fragment and approximately 35 nt homology arms were delivered into cells via electroporation. At 48 hours post transfection, the cells were subjected to clonal cell isolation. Upon expansion, the clonal cells were lysed and analyzed by junction PCR using one inner primer and one outer primer for either N-terminus (FIG. 4A) or C-terminus (FIG. 4B).
Figure 4B:
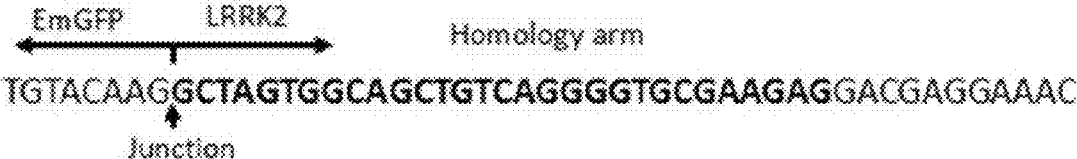
Figure 4C:
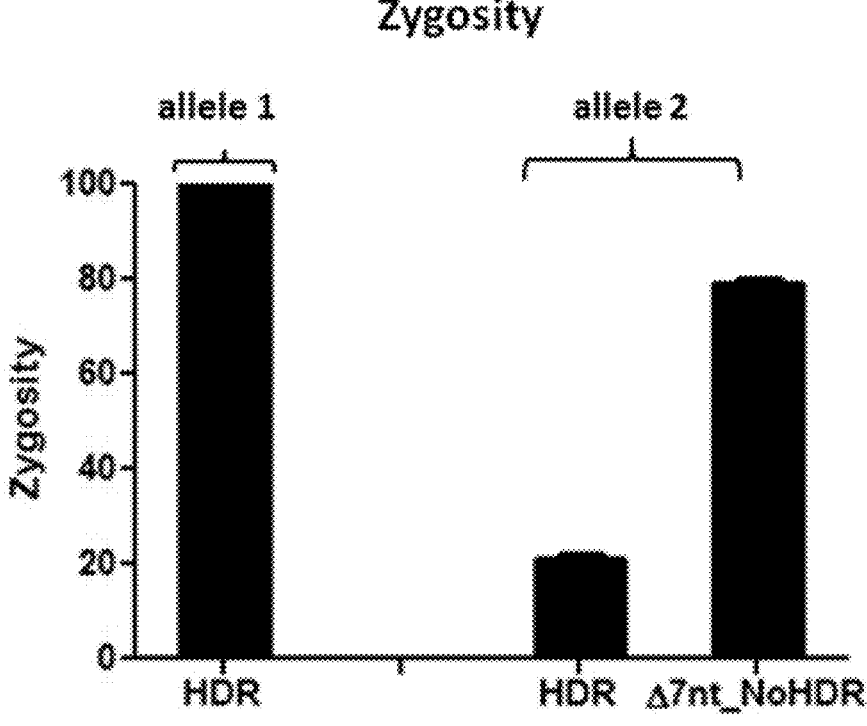

Besides beta-actin, we also evaluated a different protein in a different cell line. LRRK2 protein is related to Parkinson's disease with a molecular weight of approximately 280 kd. A gRNA was designed to target the LRRK2 genomic locus near the start codon. Approximately 35 nt homology arms were added to a sequence-verified promoterless puromycin-P2A-EmGFP DNA fragment via PCR amplification. The Cas9 RNP and donor DNA were co-delivered into A549 cells via NEON® electroporation using 1050 volts, 30 milliseconds and 2 pulses. Because LRRK2 is relatively low abundant protein, we were not able to detect EmGFP signal inside the cells. Also, a few commercial antibodies failed to detect the endogenous wild type LRRK2 protein in whole cell lysate by Western Blotting. To examine the integration efficiency, the cells were treated with 0.75 µg/ml puromycin for 7 days at 48 hours post transfection, followed by limiting dilution and clonal cell isolation. The junctions were analyzed by PCR using one inner primer and one outer primer, or a pair of outer primers. The resulting PCR products were analyzed by sequencing to determine the precision of integration. Surprisingly, all 86 colonies contained at least one copy of the insert. For all the colonies, both N- and C-termini harbored precise HDR with correct junctions between genomic DNA and donor DNA (FIGS. 4A and 4B). Upon isolation of genomic DNA, we were able to detect two PCR products for heterozygotes and one large PCR product for homozygotes. Based on sequencing analysis, about 20% of the colonies had precise integration of donor DNA in both alleles whereas the second allele in the remaining 80% of the colonies did not contain any insert but with 7 nt deletion exclusively (FIG. 4C). These results indicated that 100% integration efficiency with 100% precise HDR can be achieved.

Examples of C-Terminal Protein Tagging

Figure 5A:
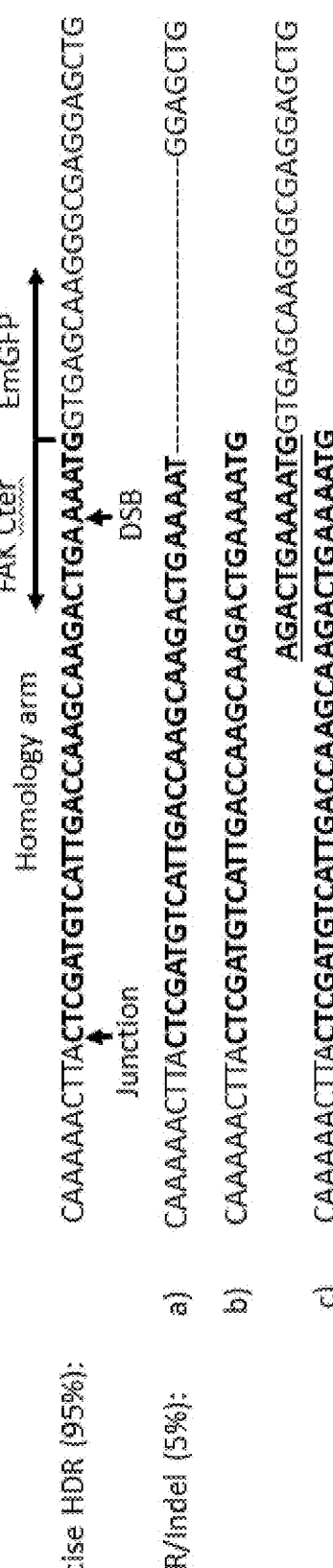
In FIG. 5A (SEQ ID NOs: 56-62), 5B (SEQ ID NOs: 63-69), and 5C, FAK was C-terminal tagged with EmGFP. Cas9 RNP and donor DNA with short homology arms were transfected into 293FT via electroporation. Upon puromycin selection, the cells were subjected to clonal cell isolation. The junctions were amplified by PCR, followed by sequencing analysis of N-terminal junction (FIG. 5A) or C-terminal junction (FIG. 5B). Arrows indicate the double-stranded breaks (DSBs) or junctions between genomic DNA and donor DNA. Short homology arms (bold) and stop codon (underline) were also indicated in the case of precise HDR. Examples of HDR with Indel were also shown in FIGS. 5A and 5B.
Figure 5B:
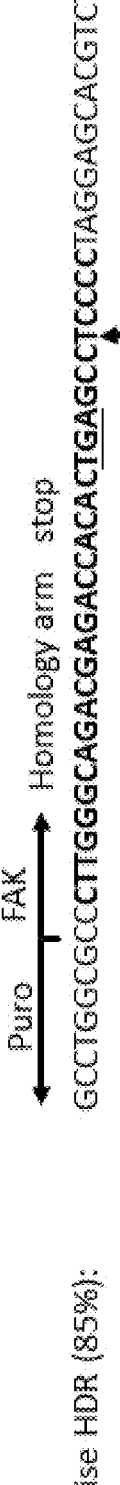
FIG. 5C shows genome modification analysis on both alleles.
Figures 5C, 6A, 6B:
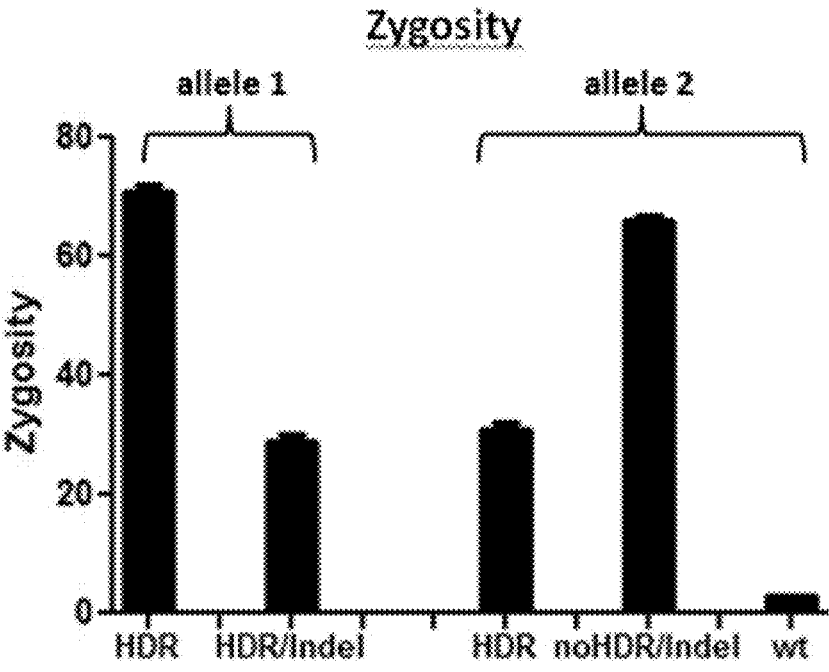
In FIGS. 6A, 6B, and 6C, EGFR was C-terminal tagged with EmGFP. A gRNA was designed to target the genomic locus of EGFR near the stop codon. The Cas9 RNP complexes and donor DNA were delivered into 293FT cells via electroporation. The clonal cells were analyzed by junction PCR and sequencing.

The promoter trapping strategy for C-terminal protein tagging is slightly different from that of N-terminal protein tagging, in which the promoterless selection marker is placed after the reporter gene for C-terminal tagging whereas it is placed before the reporter gene for N-terminal tagging (FIG. 1). As an example, we fused an EmGFP tag to the C-terminus of focal adhesion kinase (FAK). A gRNA was designed and synthesized to target the genomic locus of FAK near the stop codon (Table 12). The short homology arms were added to the sequenced-verified EmGFP-2A-puromycin cassette by PCR. The Cas9 RNP and the donor DNA were delivered to 293FT cells via Neon® electroporation. At 48 hours post transfection, the cells were selected with 0.75 µg/ml puromycin for 7 days, followed by limiting dilution and clonal cell isolation. The junctions were analyzed by PCR and sequencing. As depicted in FIGS. 5A and 5B, approximately 95% and 85% of the clones had the correction junction at either the N-terminus or C-terminus, respectively. Other clones also contained the insertion cassette but had Indel formation at the junctions or at the Cas9 cleavage site. Again, we observed duplicate sequence of partial or full-length homology arm was inserted into the genome. Overall, all the clones examined contained at least one copy of donor DNA with approximately 70% of the clones harbored precise HDR at both the N-terminus and C-terminus and the other 30% of the clones contained imprecise HDR in one of the alleles. Approximately 30% of the clonal cells had the donors integrated into both alleles. About 70% of cells did not have the insert at the second allele but had Indel formation at the junctions of the Cas9 cleavage site. Only one wild type clone was detected in the second allele (FIG. 5C).

Figure 6C:
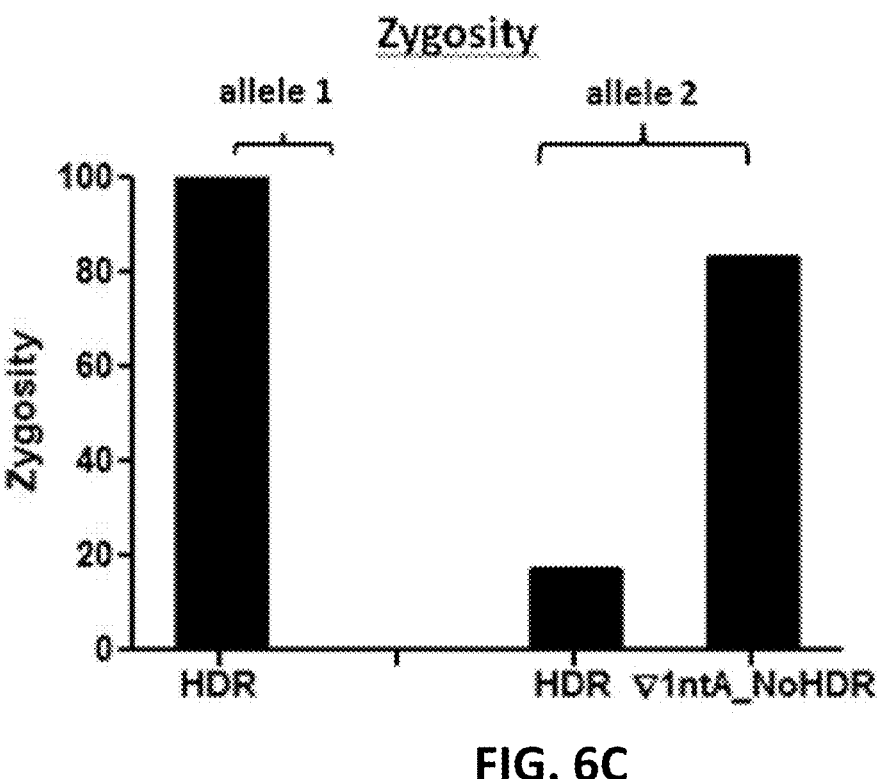

Besides FAK, we also examined other proteins, such as the epidermal growth factor receptor (EGFR). EGFR has a couple of isoforms. In this study, we fused EmGFP to the C-terminus of EGFR isoform 1. A gRNA was designed to cleave the genomic locus of EGFR near the stop codon. Short homology arms were added to the insertion cassette by PCR. The Cas9 RNP and donor DNA were electroporated into 293FT cells. After puromycin selection, the cells were subjected to clonal isolation. Surprisingly, all 19 colonies harbored an insertion cassette at one of the alleles with 100% correct junctions at both the N- and C-termini. Approximately 17% of the colonies had biallelic integration, whereas 83% of the colonies did not contain the insert at the second allele but had an "A" insertion at the Cas9 cleavage site exclusively (FIG. 6). The genome modification of EGFR with EmGFP was detected by Western Blotting.

Effect of End Modification of DNA Donor and NHEJ Inhibitor on HDR Efficiency

Linear ds- or ss-DNA donor could be degraded in vivo by exonucleases. The end modification of donor DNA might be able to prevent them from degradation. To test this hypothesis, DNA primers were chemically synthesized with different modification at their 5' end (Table 12). The modified DNA primers were then used to prepare donor DNA containing a promoterless puromycin-P2A-OFP fragment via PCR amplification. The resulting PCR products were purified using PureLink™ PCR Purification Kit, followed by concentration using a speed vac. The Cas9 RNP targeting the genomic locus of beta-actin was co-delivered with various forms of donor DNA into primary T cells via electroporation. At 48 hours post transfection, the percentages of OFP-positive cells were determined by flow cytometric analysis. As described in FIG. 7A, the phosphorothioate-modified DNA donor increased HDR efficiency by approximately 2-fold when compared to the unmodified donor DNA. Interestingly, the amine-modified donors also improved the HDR efficiency, especially when the modification occurred on the reverse primer that modified the 5'-end of antisense strand. Using donor DNA with amine-modification on both ends, the percentage of OFP-positive cells increased by approximately 4-fold. The end modification of ssDNA donors also improved the HDR efficiency. However, the efficiency using amine-modified dsDNA donor was approximately 2-fold higher than that using modified ssDNA donor.

Figure 7B:
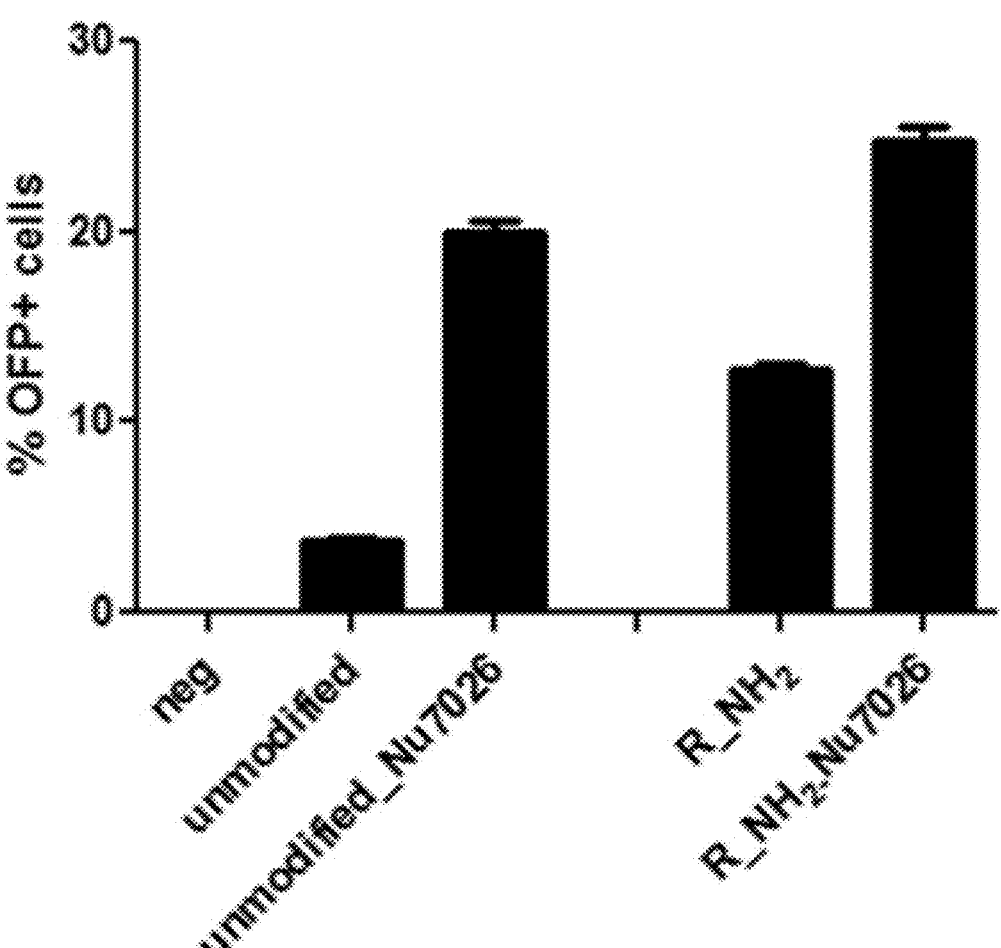

The disruption of NHEJ repair pathway is known to improve HDR efficiency. Here we examined how those NHEJ inhibitors affected the integration of relative large DNA molecule into human primary T cells. Immediately after electroporation of Cas9 RNP and donor DNA into primary T cells, we transferred the cells into culture medium containing 30 µM Nu7026. At 48 hours post transfection, we analyzed the cells by flow cytometry. As shown in FIG. 7B, the treatment of cells with Nu7026 increased the percentage of OFP-positive cells by approximately 5-fold for unmodified donor DNA and 2-fold for amine-modified donor DNA. Similar results were obtained for other DNAPK inhibitors, including Nu7441 and Ku-0060648.

Potential Applications

Using the method described above, we could easily integrate a large piece of DNA into mammalian genome with near 100% integration efficiency, which allows researchers to clone foreign DNA of interest directly into the mammalian genome and express protein for therapeutic applications.

Example Expression Cassette

Figure 8A:
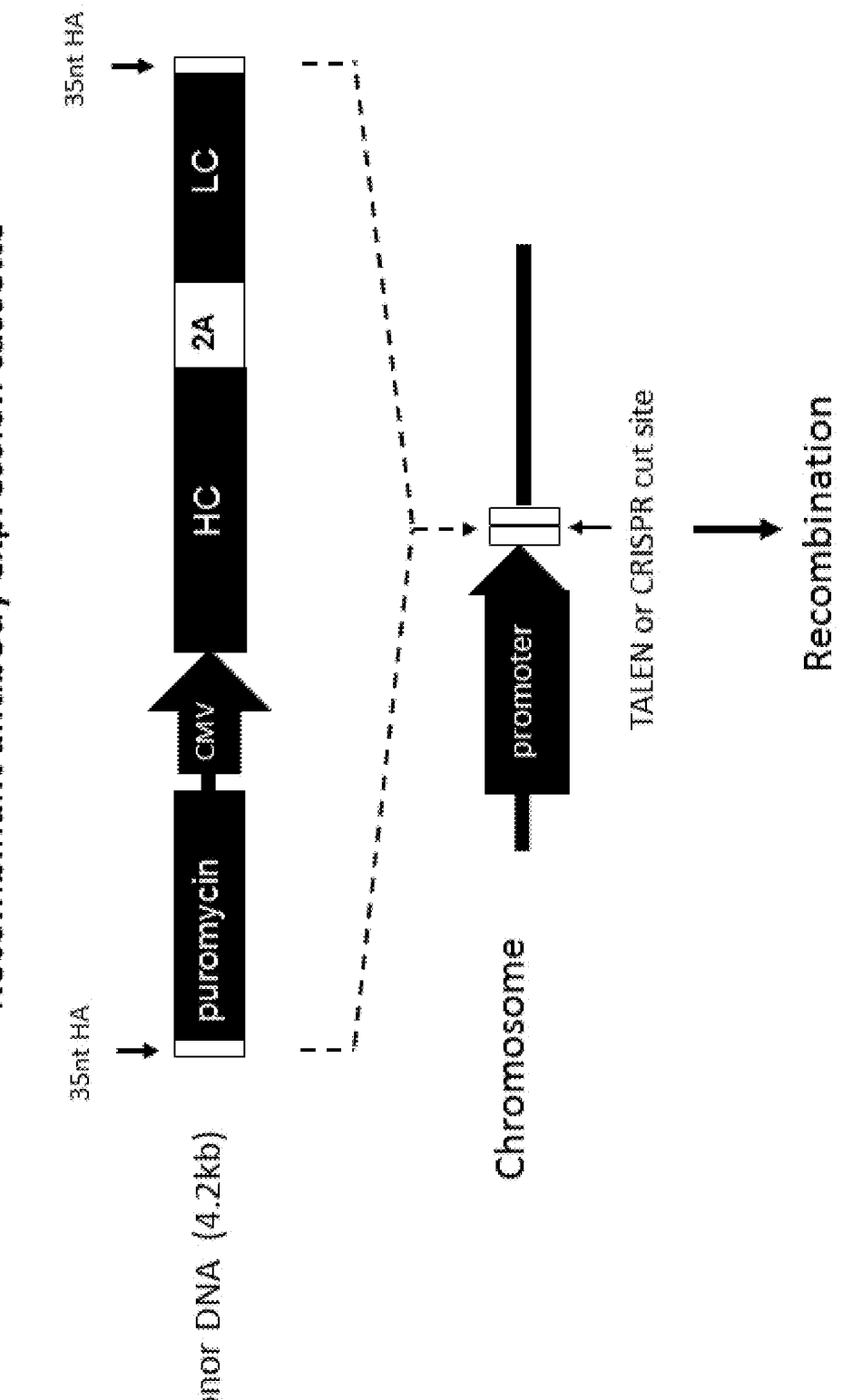

As an example, we prepared an approximately 4.2 kb human IgG expression cassette which contained a promoterless selection marker, cytomegalovirus (CMV) promoter, IgG heavy chain, IgG light chain, and WPRE (Woodchuck Hepatitis Virus Posttranscriptional Regulatory Element). The CMV promoter drives the expression of heavy and light chains of IgG, which is linked via a 2A self-cleaving peptide (FIG. 8A). The 35 nt short homology arms were added to the expression cassette by PCR, followed by PCR column purification. The expression cassette was inserted into the beta-actin locus in 293FT cells as described above. Upon puromycin selection for 7 days, we measured the titer of IgG production in the stable cell pool using ELISA assays. As a control, plasmid DNAs containing IgG heavy chain and light chain expression cassettes were transiently co-transfected into cells. The culture media were harvested at Day 5 after transfection. The expression level of IgG in the engineered cell pool was approximately 0.5 gram/liter, whereas the level of IgG in transient plasmid expression system was around 0.3 gram/liter.

To characterize each clonal cell in the stable pool, we performed limiting dilution and clonal cell isolation. The junctions of integration were analyzed by PCR and sequencing. As depicted in FIGS. 8B and 8C, approximately 88% of clonal cells harbored precise integration at N-terminal junction whereas 12% of clonal cells had some extra sequences inserted at the junction. On the other hand, approximately 41% of clonal cells had correct junction at the C-terminus, whereas 59% of the clonal cells harbored small mutations at the junction. For example, we observed base substitution, one or a few nucleotides insertion occurred at the WPRE polyA tail region. The small mutations happened after the stop codon, which might not affect the expression of IgG. To confirm this, we examined the titer of IgG for each clonal cell. As shown in FIG. 8D, approximately 70% of the clonal cells were able to produce antibodies.

In this study, endogenous proteins were tagged. The expression level of chimeric protein is dependent on the abundance of endogenous protein inside the cells. For abundant proteins, such as beta-actin, the chimeric fusion protein was easily detected using conventional widefield fluorescence microscopy. However, for low abundant protein, such as LRRK2, the conventional wide field fluorescence microscopy was insufficient for detection. The use of high resolution fluorescent techniques, such as fluorescence resonance energy transfer (FRET) and continuous-wave ultrasound-switchable fluorescence (CW-USF), may allow visualization of the fluorescent molecules inside living cells with improved spatial and temporal resolution (Sekar, et al., *"Fluorescence resonance energy transfer (FRET) microscopy imaging of live cell protein localizations", J. Cell Biol.* 160:629-33 (2003), and Cheng, et al., *"High-resolution ultrasound-switchable fluorescence imaging in centimeter-deep tissue phantoms with high signal-to-noise ratio and high sensitivity via novel contrast agents", PLOS One.* 11:e0165963 (2016)). While it is not fully understood why the expression level of chimeric protein in one allele is significantly lower than that of another wild type allele, it is possible that some transcriptional or translational regulatory elements get disrupted when a transgene is inserted into the genome.

Example 2: Increasing Rates of Homology Based Editing in Mammalian Cells Via Attachment of a Nuclear Localization Signal to the Donor DNA It was postulated that donor DNA (single strand or double strand, linear or circular) delivery to the nucleus would increase the local concentration of the donor DNA near where editing would be occurring and, hence, bias the repair to using this donor DNA over NHEJ.

Zanta, M. A., et al., Proc. Natl. Acad. Sci. (USA) 96:91-96 (1999), demonstrated that an NLS conjugated to a DNA segment could increase delivery of the DNA segment to the nucleus. It was thus reasoned that a similar approach could be used to enhance delivery of a donor ssDNA to the nucleus and that an increased in donor DNA within the nucleus may increase the integration frequency of the donor DNA at a "cut site."

Figure 10:
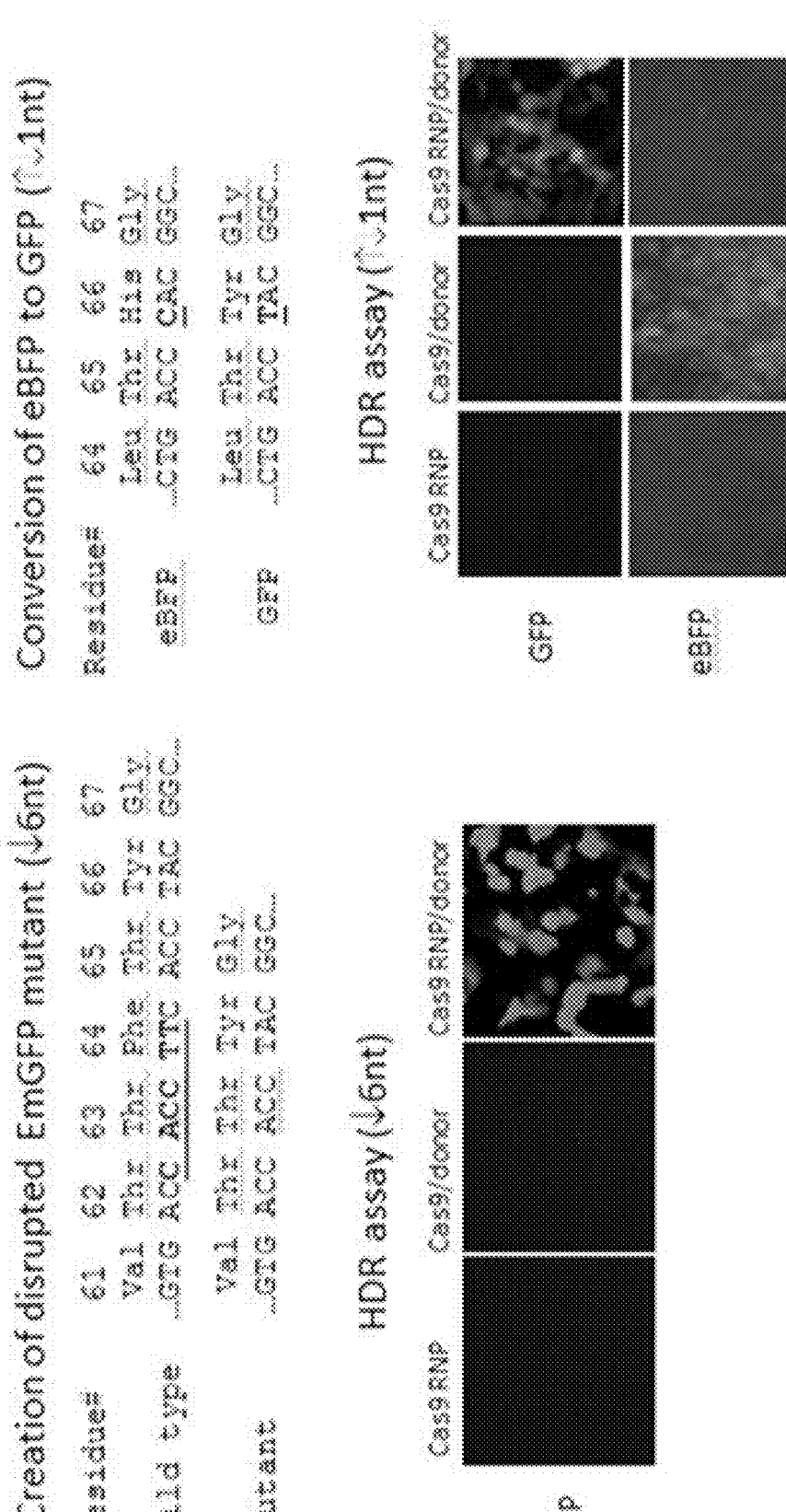
FIG. 10 (SEQ ID NO8: 85-92). HEK 293 lines modified
with NLS-donor DNA constructs. On the left side, a GFP
gene was disrupted by the deletion of 6 nucleotides that
constitute the fluorophore. Addition of a donor containing
the 6 bases restored GFP fluorescence. On the right side is
a similar BFP gene disruption. Addition of a donor with a
single nucleotide polymorphism (SNP) converted the BFP
coding sequence to a GFP coding sequence.

For the NLS, an evolved SV40 NLS was used (BP-SV40, KRTADGSEFESPKKKRKVEGG) (SEQ ID NO: 13). Hodel, M. R., et al., J. Biol. Chem. 276(2): 1317-1325 (2001), reported that this sequence efficiently localizes to the nucleus. Both succinimidyl 4-(N-maleimidomethyl) cyclohexane-1-carboxylate (SMCC) or Click-iT® chemistry to conjugate the NLS peptide to ssDNA donor sequences were used. The resulting NLS-oligo conjugate was purified by HPLC. The mass of the NLS-oligo was determined by MALDI-TOF. Two constructs as shown in FIG. 9 were made. As shown in FIG. 10, these donor DNAs allow for screening by fluorescence.

Part 1: Conversion of a 6 Base Deleted GFP to a Functional GFP Using NLS-Conjugated Oligonucleotide Donor.

The carboxy end of NLS peptide BP-SV40 (SEQ ID NO.: 13) was conjugated to the 5' end of the oligonucleotide: 5'CGGGGTAGCGGCT-GAAGCACTGCACGCCGTAGGTCAGGGTGGT-CACGAG GGTGGGCCAGGGCACGGGCAGCTTGCCGGTG-GTGCAGATGAACTTCAG-3' (SEQ ID NO.: 14) through CLICK-IT® chemistry. The resulting NLS-oligonucleotide conjugate was purified by HPLC. The mass of the NLS-oligonucleotide was determined by MALDI-TOF.

On the day before transfection, a disrupted EmGFP GRIP-TITE™ 293 cell line was seeded on 24-well plates at a cell density of 1×10⁵ per well. On the day of transfection, 0.5 µg Cas9 mRNA and ng gRNA 150 targeting disrupted EmGFP gene (GCACGCCGTAGGTGGTCACGAGG) (SEQ ID NO.: 15) were added to 25 µl OPTI-MEM® in a sterile test tube. NLS-oligonucleotide conjugate was dissolved in water and various amount of NLS-oligonucleotide was added to the test tube containing Cas9 and gRNA. The phosphorothioate-modified (PS) oligonucleotide was used as controls, having two phosphorothioates at the 5' end and two phosphorothioates at the 3' end of the oligonucleotide. In a separate tube, 1.5 µl of LIPOFECTAMINE™ MESSENGERMAX™ was added to a 25 µl OPTI-MEM® medium. The diluted LIPOFECTAMINE™ MESSENGERMAX™ was then transferred to the test tube containing Cas9, gRNA and indicated amount of NLS-oligonucleotide or PS-oligonucleotide. After incubation at room temperature for 5 minutes, the mixture was added to a 24-well containing 0.5 ml growth medium. At 48 hours post transfection, the cells were analyzed by flow cytometry to determine the percentage of EmGFP-positive cells.

Figure 12:
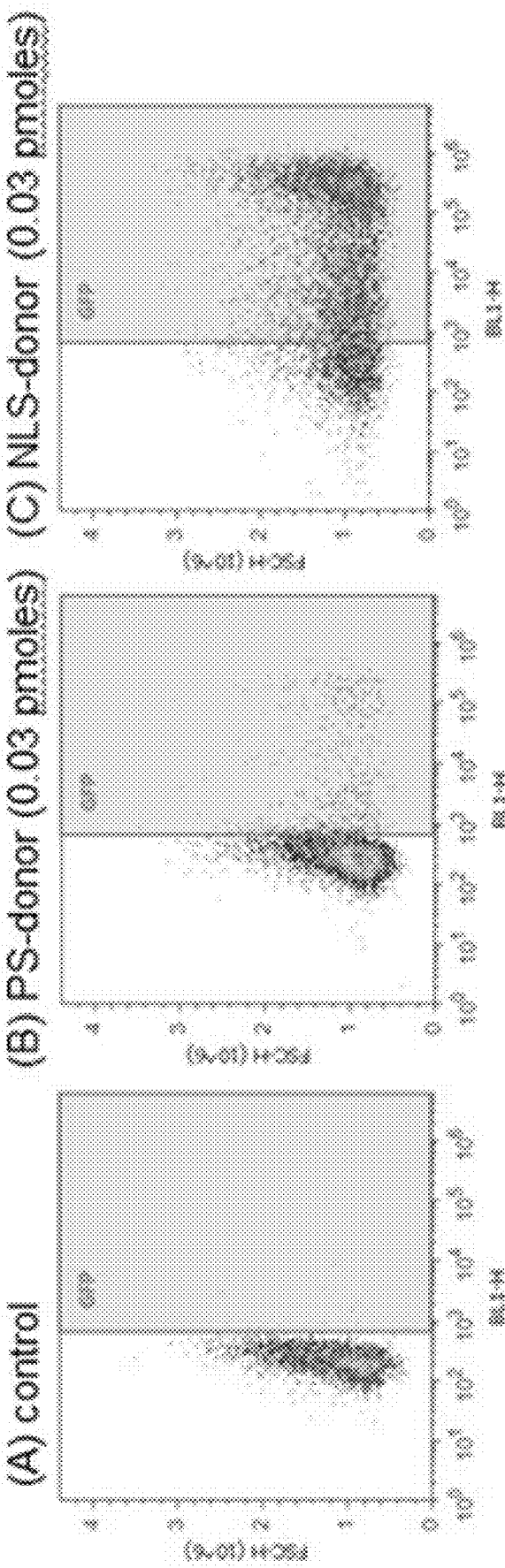
FIG. 12. Flow cytometry analysis of cells edited using
either the PS or NLS oligo donor DNA at equal concentra-
tion.

As shown in FIG. 11, the NLS-donor resulted in significantly higher editing of the cell line. Up to 52% of cells were GFP positive at the optimal dose of 0.1 pmoles NLS-donor compared to the standard PS-donor requiring 3 pmoles for optimal editing up to 36% which is 30× more material. FIG. 12 demonstrates that at equal low dose of 0.03 pmoles, the conversion to GFP+ cells is much high for the NLS-donor. In summary, a higher conversion of editing, as measured by GFP positive cells at a much lower dose with the NLS-donor, was seen.

Part 2: Conversion of a BFP to a Functional GFP by Changing a Single Base Using NLS-Conjugated Oligonucleotide Donor.

The carboxy end of NLS peptide BP-SV40 (SEQ ID NO.: 13) was conjugated to the 5' end of the oligonucleotide: 5'-GCTGCCCGTGCCCTGGCCCACCCTCGTGAC-CACCCTGACCT ACGGCGTGCAGTGCTTCAGCCGC-TACCCCGACCACATGA-3' (SEQ ID NO.: 16) through SMCC chemistry. The resulting NLS-oligo conjugate was purified by HPLC. The mass of the NLS-oligo was determined by MALDI-TOF.

On the day before transfection, eBFP 293 FT stable cell line was seeded on 24-well plates at a cell density of 1×10⁵ per well. On the day of transfection, 0.5 µg Cas9 mRNA and 150 ng gRNA targeting eBFP gene (CTCGTGAC-CACCCTGACCCACGG) (SEQ ID NO:17) were added to 25 µl Opti-MEM® in a sterile test tube. NLS-oligonucleotide was dissolved in water and various amount of NLS-oligonucleotide was added to the test tube containing Cas9 and gRNA. An unmodified oligonucleotide was used as controls. In a separate tube, 1.5 µl of LIPOFECTAMINE™ MESSENGERMAX™ was added to a 25 µl OPTI-MEM® medium. The diluted LIPOFECTAMINE™ MESSENGERMAX™ was then transferred to the test tube containing Cas9, gRNA and indicated amount of NLS-oligo or unmodified oligonucleotide. After incubation at room temperature for 5 minutes, the mixture was added to a 24-well containing 0.5 ml growth medium. At 48 hours post transfection, the cells were analyzed by flow cytometry to determine the percentage of GFP-positive cells.

As shown in FIG. 13, the NLS-donor again resulted in significantly higher editing of the cell line. Up to 76% of cells were converted from BFP to GFP positive at the optimal dose of 0.3 pmoles compared to 58.5% with the control PS oligonucleotide at 10 pmoles. Again, higher editing at a 30× lower dose of NLS-donor were seen. As the dose was lowered, it was possible to maintain a high level of editing with the NLS-oligonucleotide with 21% cells being edited at 0.01 pmoles compared to 6% at 0.03 pmoles with the control PS oligonucleotide.

The methods described herein have broad applications in cell engineering, cell therapy, and bioproduction, etc. Unlike transient plasmid expression, a relatively large expression cassette can be inserted directly into the genome at a specific locus for bioproduction. Safe harbor regions can be targeted using an endogenous promoter of the desired relative strength. Repetitive regions can also be potentially targeted to incorporate multiple copies of the payload to obtain higher expression levels. Independent of the selection marker, a strong promoter can be used to drive the expression of the foreign gene of interest. Because of the high integration efficiency and specificity, a stable cell pool can be used directly for protein production without the need of clonal cell isolation which saves time and cost. In some embodiments, this method is used for recombinant antibody production in ExpiCHO cells.

References

Liang, et al., "*Enhanced CRISPR/Cas9-mediated precise genome editing by improved design and delivery of gRNA, Cas9 nuclease, and donor DNA*", J. Biotechnol, 241:136-146 (2017).

Figure 14:
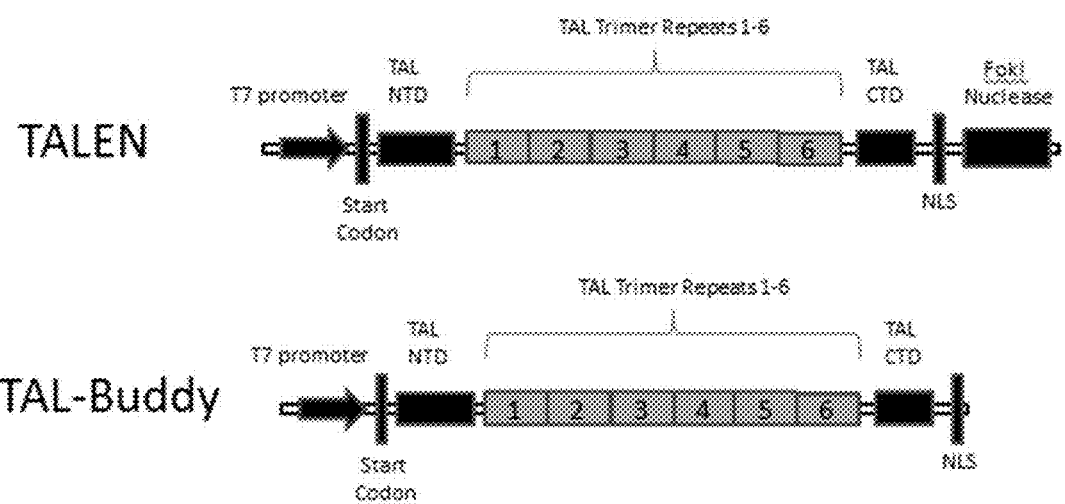
FIG. 14. The figure shows a schematic of an exemplary
architecture of TALEN and TAL-Buddy (no nuclease) con-
structs. The TAL-Buddy construct is shown with no nuclease
domain. In some instances, a nuclease domain may be
present but disrupted (e.g., by insertions deletions and/or
substitutions).

Example 3. Binding of DNA in Proximity of the Targeted dsDNA Break May Facilitate Displacement of Chromatin and/or DNA Un-Winding and Promote Improved Access of Designer Nucleases TAL-Buddy" consists of an 18-repeat TAL binder. "TAL-Buddy" was designed at close proximity of the designer nuclease binding region, one at each side (left=Lt, right=Rt, TALEN pair and TAL-Buddy binding sequences are listed in Table 12). "TAL-Buddy" was made by assembling N-terminal fragment containing T7 promoter and transcription/translation start elements and the amino terminal fragment of the TAL, six TAL RVD trimers, and the C-terminal fragment containing C-terminal domain, nuclear localization signal, and stop codon (shown in FIG. 14) via Golden Gate assembly reaction using BsaI. An example of "TAL-Buddy" (CMPK1-TALEN2_7 nt_TAL-Buddy_Lt) nucleotide sequence is listed in SEQ ID NO:35. The adjacent genomic sequence of CMPK1-C target is shown in SEQ ID NO:36; and the relative positions of TALEN and TAL Buddy is shown in SEQ ID NO:20 and SEQ ID NO:21. Further description of this example is provided in FIGS. 14-18, 22, and 32-36.

Figure 15:
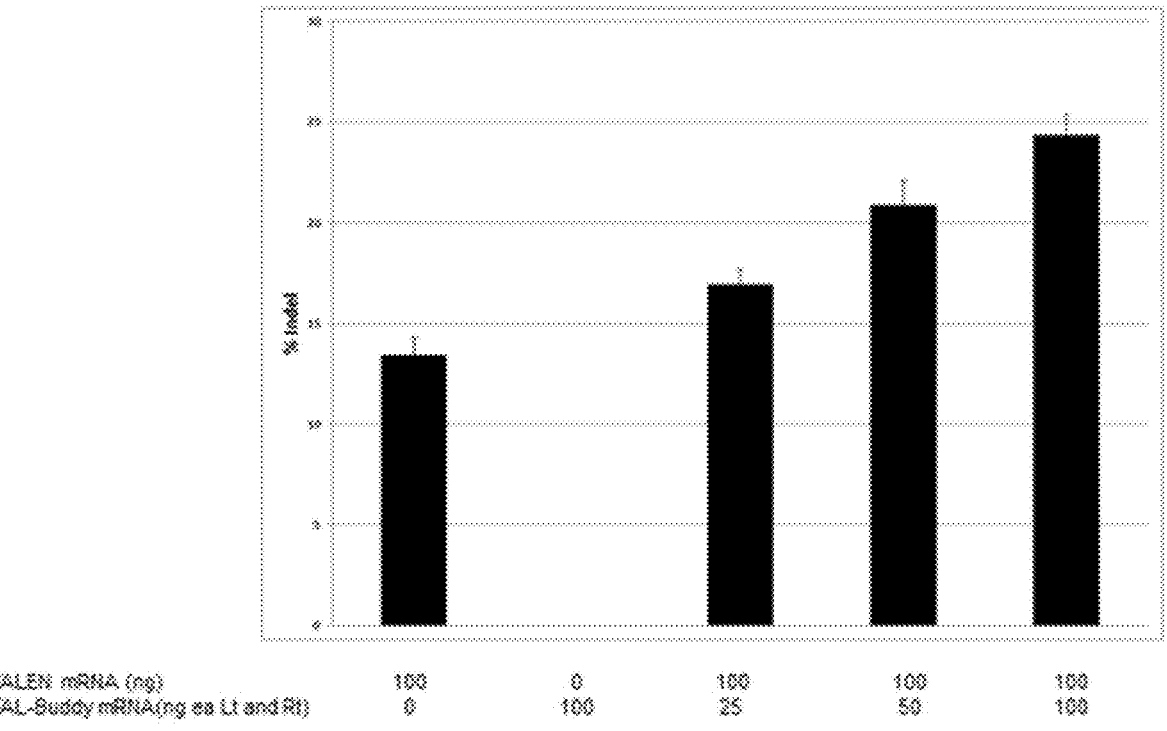
FIG. 15. Indel formation at CMPK1-C target improved ~2
fold when "TAL-Buddy" designed at 7 nt spacing relative to
TALEN binding sequence was added.

The full-length "TAL-Buddy" was enriched by amplification using primer pair TD1-F2 and TD8-R2 (SEQ ID NOs:22-23), and further used as template for making mRNA using mMESSAGE mMACHINE™ T7 ULTRA Transcription Kit (Thermo Fisher Scientific). 0, 25, 50, or 100 ng of Lt and Rt "TAL-Buddy" mRNA was added together with 100 ng of TALEN mRNA pair for transfection into ~50,000 of 293 human embryonic kidney cells (293FT) with NEON® electroporation apparatus (Thermo Fisher Scientific) at 1300 pulse voltage, 20 pulse width, and 2 pulse number. Cells were harvested and lysed 48 to 72 hours post transfection. Indel formation was assayed with GENEART™ Genomic Cleavage Detection Kit (Thermo Fisher Scientific, cat. no. A24372). (FIG. 15)

One collection of methods that may be used for the assembly of TALs is by the Golden Gate process.

In Golden Gate assembly and cloning is based upon the generation of nucleic acid segments with "sticky" ends that produced by cleavage with one or more Type IIs restriction endonucleases, typically followed by introduction of the assembled nucleic acid molecule into a suitable host cell. Type IIs restriction endonucleases are used because they recognize asymmetric sequences and cleave these sequences at a defined distance from the recognition site. Further, the ends of DNA molecules can be designed to be flanked by a Type IIs restriction site such that digestion of the fragments removes the enzyme recognition sites and generates complementary overhangs. Such ends can be ligated seamlessly, creating a junction that lacks the original site or scars.

Further, Type IIs restriction endonucleases may be, and have been, used to generate repeat regions of TAL effectors. Type IIs restriction endonucleases may also be used to connect suitable terminal protein coding nucleic acid to the flanks of TAL effector repeat regions and to connect TAL effector coding regions to additional nucleic acid molecules (e.g., a vector wherein TAL effector coding nucleic acid is operably linked to a promoter). Type IIs restriction endonuclease TAL effector assembly methods are set out in, for example, Morbitzer et al., "Assembly of custom TALE-type DNA binding domains by modular cloning", Nucleic Acids Res. 39:5790-9 (2011).

Result: Indel formation at CMPK1-C target was improved ~2 fold when "TAL-Buddy" was designed at 7 nt spacing relative to TALEN binding sequence (i.e., 33 nt relative to TALEN cleavage site) (FIG. 15).

Example 4. "TAL-Buddies" Designed for Different Spacing Relative to TALEN Binding Sequence (Table 12) and Tested in 293FT Cells Using Same Method Described in Example 3

Figure 16:
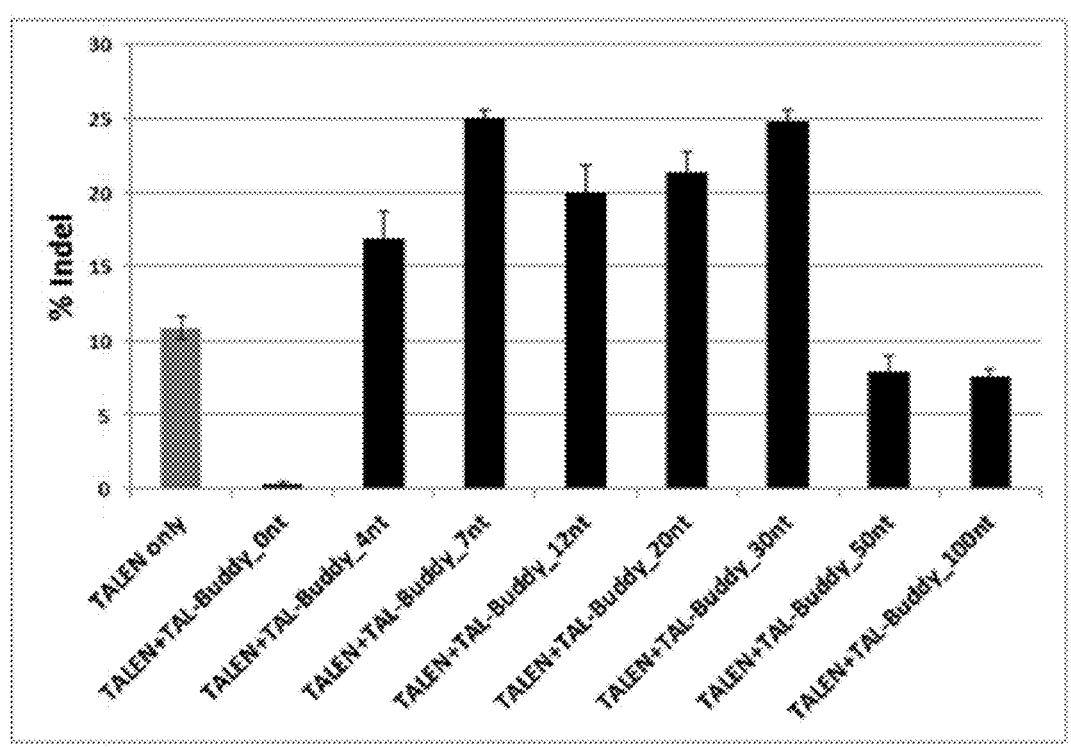
FIG. 16. "TAL-Buddy" at up to 100 nt spacing relative to
TALEN binding sequence tested for improving TALEN
cleavage.
Figure 17:
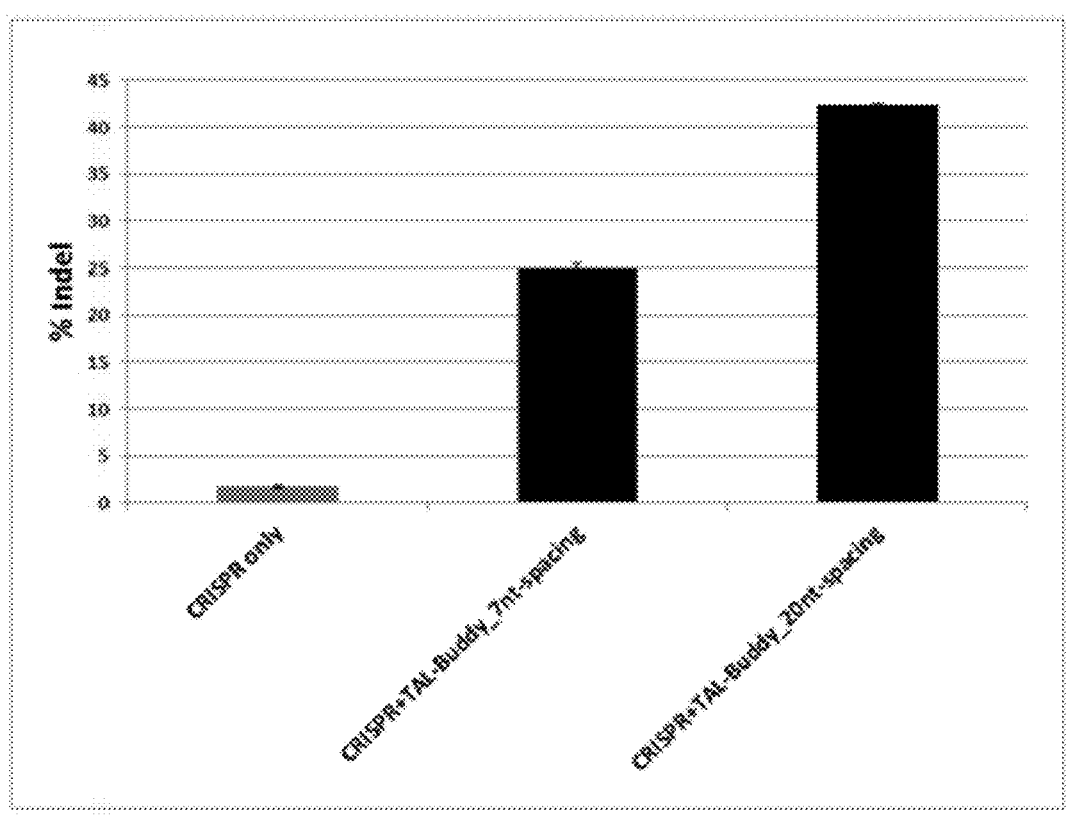
FIG. 17. "TAL-Buddy" at 20 nt spacing relative to
CRISPR sgRNA binding sequence improved indel forma-
tion of CRISPR-RNP≥20 fold at UFSP2-SNP target.

Result: "TAL-Buddy" was functional when spacing 7-30 nt relative to TALEN binding sequence (FIG. 16). The best enhancement of TALEN cutting occurred when the TAL-buddies were from 4 to 30 nt away from the TALENs. Having TAL-buddies immediately next to the TALENs or greater than 50 nts away resulted in no enhancement of the TALEN cutting (FIG. 16 and FIG. 17).

Example 5. "TAL-Buddy" in Close Proximity to CRISPR sgRNA Targeting UFSP2-SNP Site was Designed at 7 nt or 20 nt Spacing Relative to a CRISPR sgRNA Binding Sequence The genomic sequence of UFSP2-SNP target is listed in SEQ ID NO:25 and SEQ ID NO:43.

Result: A 10 to 20 fold increase of indel formation was obtained when "TAL-Buddy" was designed at 7 nt or 20 nt spacing relative to a poorly performing CRISPR sgRNA binding sequence (i.e., 23 nt and 37 nt relative to CRISPR cleavage site respectively). Results are shown in FIG. 17.

Example 6. To Minimize Off-Target Effect of Wild-Type SpCas9, Mutant Forms were Tested By way of increasing the accessibility of the DNA target locus the activity of poorly performing cas9 proteins (e.g., HiFi Cas9 described by Kleinstiver, Benjamin P., et al.

("High-fidelity CRISPR-Cas9 nucleases with no detectable genome-wide off-target effects." Nature (2016). PubMed PMID: 26735016; Cas9 proteins binding modified PAMs and other orthologous Cas9 proteins such as CRISPR from *Prevotella* and *Francisella* 1 (Cpf1) can be increased. Any of the mutant Cas9 forms commonly known and described in the art may be used for the methods and compositions provided herein. Non-limiting examples of mutant Cas9 proteins contemplated for the methods and compositions provided herein are described in Slaymaker, Ian M., et al. ("Rationally engineered Cas9 nucleases with improved specificity." Science (2015): aad5227. PubMed PMID: 26628643) and Kleinstiver, Benjamin P., et al. ("High-fidelity CRISPR-Cas9 nucleases with no detectable genome-wide off-target effects." Nature (2016). PubMed PMID: 26735016) which are incorporated by reference in their entirety and for all purposes. The on-target cleavage efficiency of these two mutant forms was also compromised. "TAL-Buddy" at 20 nt spacing relative to sgRNA binding sequence was tested in combination with RNP formed with sgRNA and either eSpCas9 or SpCas9-HF1. 100 ng of Lt and Rt "TAL-Buddy" mRNA was added together with CRISPR-RNP (1000 ng of either SpCas9-HF1 or eSpCas9 protein and 200 ng sgRNA) for transfection into ~50,000 of 293 human embryonic kidney cells (293FT) with NEON® electroporation apparatus (Thermo Fisher Scientific) at 1150 pulse voltage, 20 pulse width, and 2 pulse number. Cells were harvested and lysed 48 to 72 hours post transfection. Indel formation was assayed with the GENEART™ Genomic Cleavage Detection Kit (Thermo Fisher Scientific, cat. no. A24372).

Figure 18:
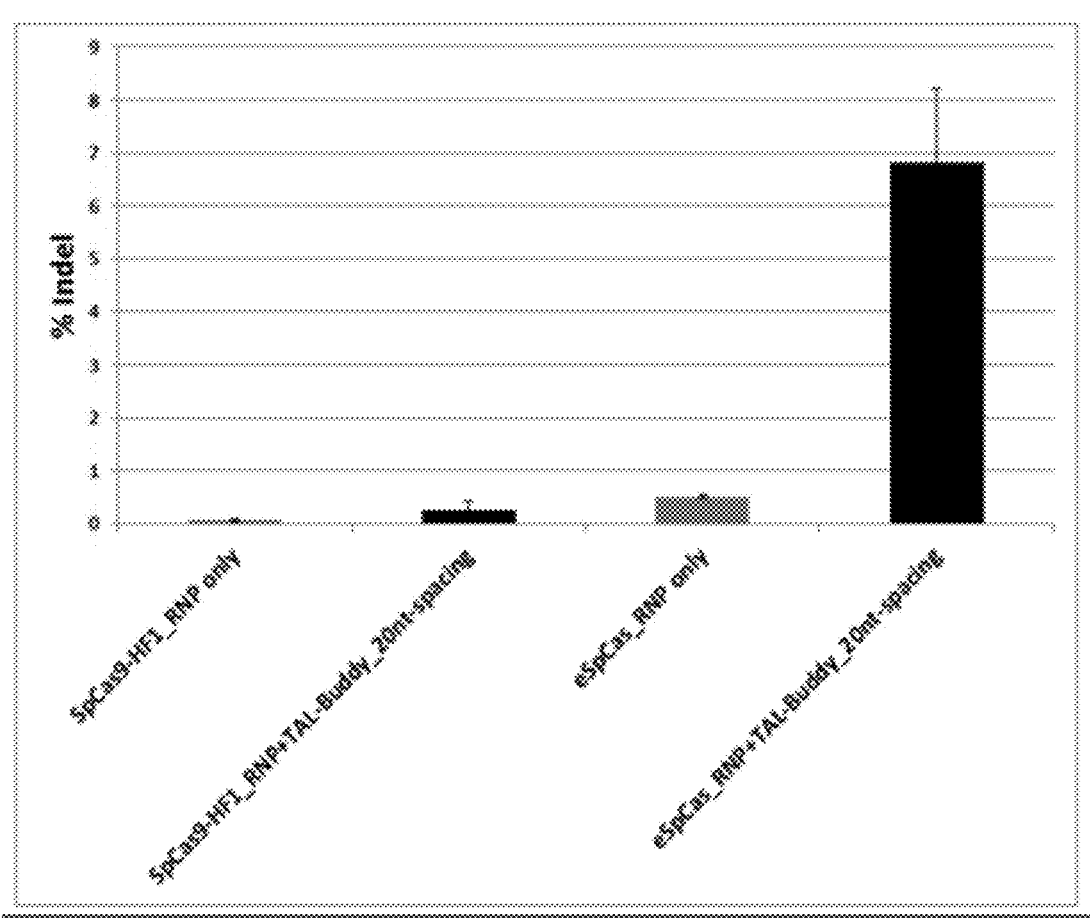
FIG. 18. "TAL-Buddy" improved indel formation with
RNP formed with sgRNA and either SpCas9-HF1 or eSp-
Cas9.

Results: 5 and 14 fold indel formation were obtained for CRISPR-RNP formed with sgRNA and either SpCas9-HF1 or eSpCas9 respectively when "TAL-Buddy" at 20 nt spacing relative to sgRNA binding sequence was added (FIG. 18).

Figure 19:
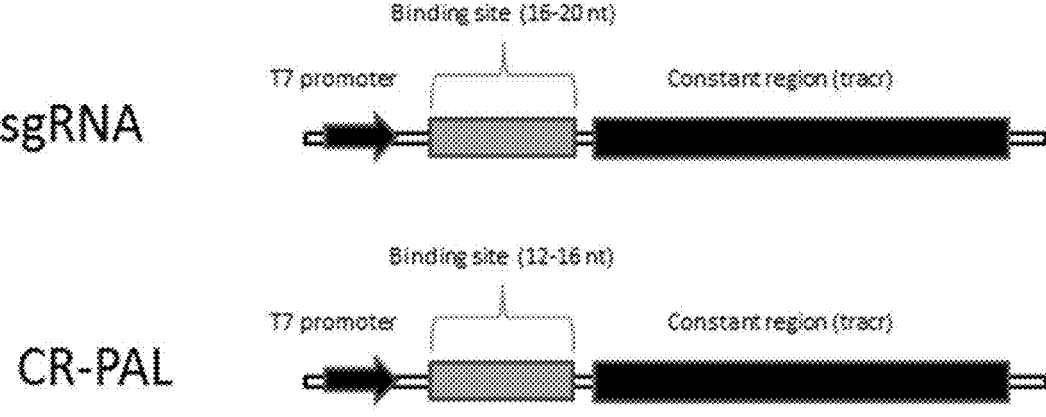
FIG. 19. Illustration of templates for making sgRNA and
"CR-PAL" gRNA.
Figure 20:
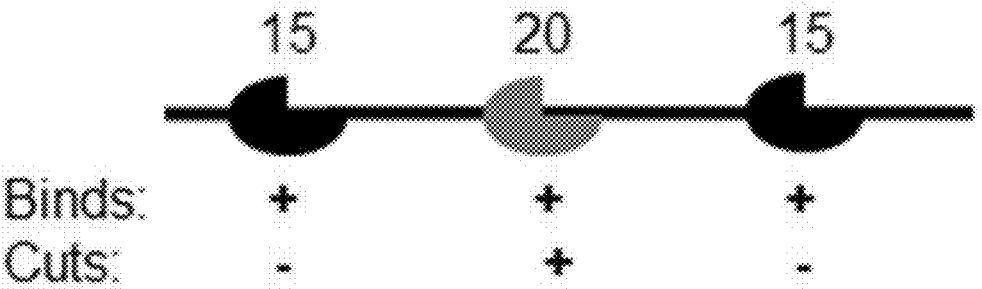
FIG. 20. Illustration of the function of "CR-PAL". Black
indicates "CR-PAL" with 15 nt binding capacity; Grey
indicates sgRNA with 20 nt binding capacity.

Example 7. Truncated gRNA at 15 nt in Length ("CR-PAL") has Shown dsDNA Binding Activity but No Cleavage Activity when Wild-Type Cas9 is Present The architecture of templates for making sgRNA and "CR-PAL" are illustrated in FIG. 19. The function of CR-PAL is illustrated in FIG. 20. 15-mer gRNA ("CR-PAL") at proximity of CRISPR cleavage site was designed and made by in vitro transcription. The genomic DNA sequence and relative positions of full-length sgRNA binding sequence is listed in SEQ ID NO:44 and SEQ ID NO:45. FIG. 19 and FIG. 20.

Figure 21:
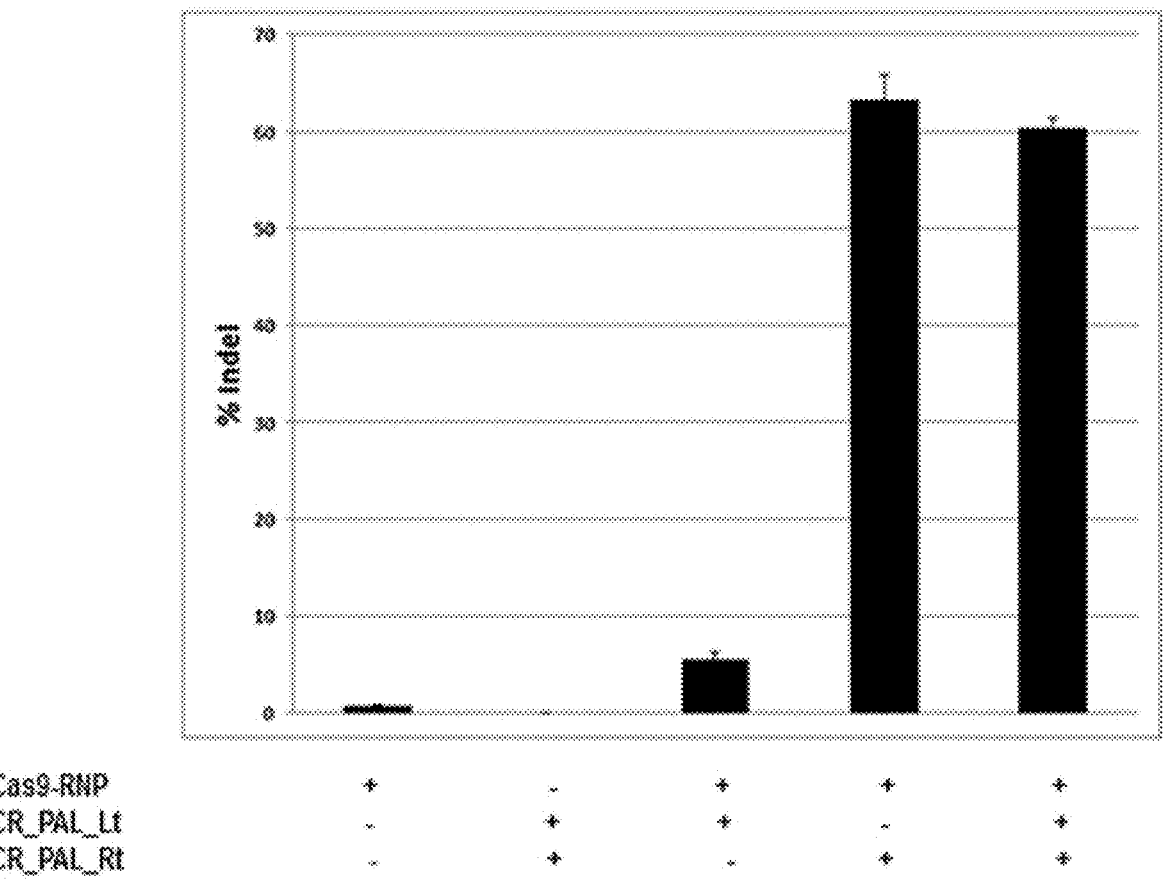
FIG. 21. More than 60 fold increase of indel formation
obtained when "CR-PAL" was used together with Cas9-
RNP at UFSP2-SNP target.
Figure 26:
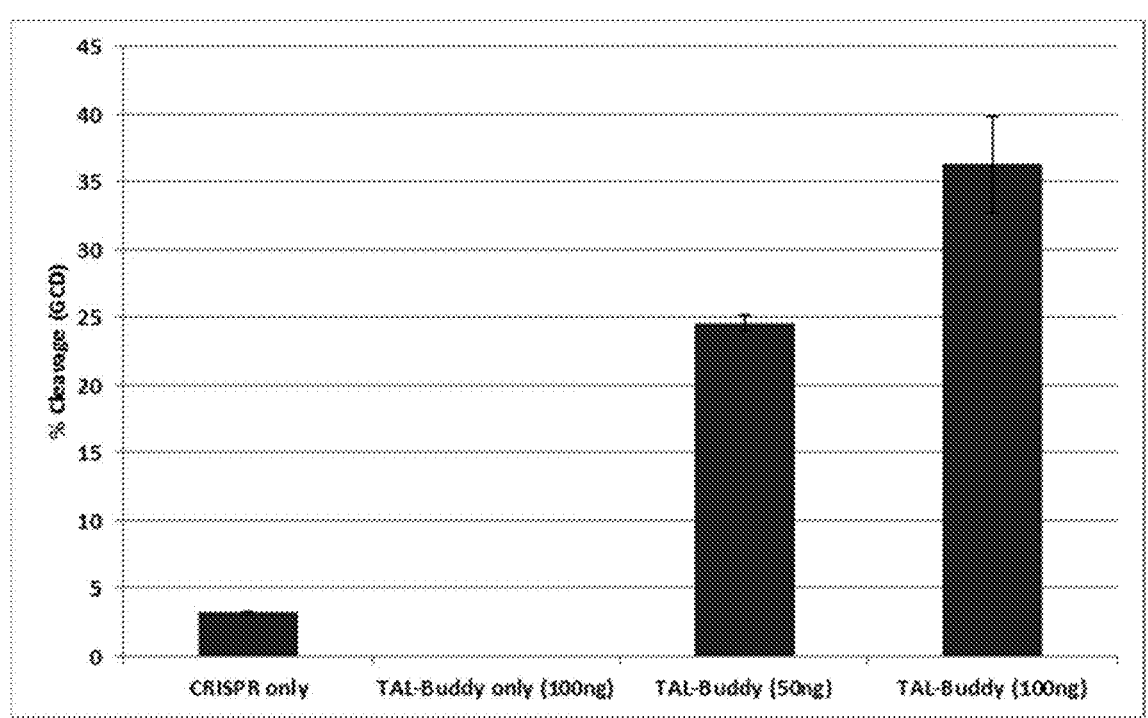
FIG. 26. The figure shows repeat TAL-buddy for editing
with CRISPR. 293FT cells; CRISPR target: USFP2; TAL-
Buddy: 20 nt spacing; NEON®: 1150/20/2. Repeat.
Figure 27:
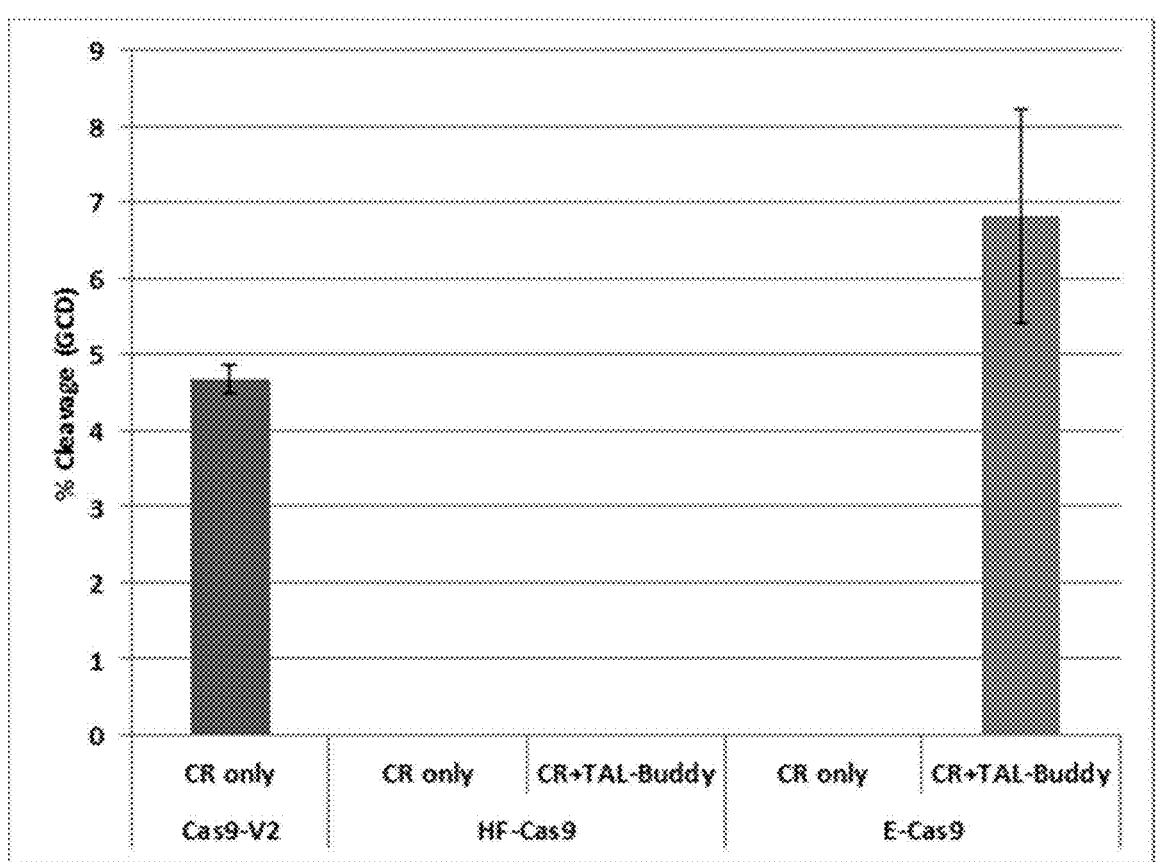
FIG. 27. The figure shows test TAL-Buddy on high
fidelity Cas9—recover activity in low performing mutants.
Target: UFSP2; Cell: 293FT; NEON®: 1150/20/2; TAL-
Buddy: 20 nt spacing. HF-cas9 had no detectable activity,
our analysis suggests that it is more crippled than eCas9.
eCas9 1.1 had no detectable activity w/o TAL. With TAL,
could get wt level of activity. This is important because you
get the high fidelity activity only localized to the desired
target site (Super high fidelity).
Figure 28:
FIG. 28. The figure shows test CRISPR-PAL with stan-
dard active cas9 and truncated gRNAs. Target: UFSP2; Cell:
293FT; NEON®: 1150/20/2; CR-PAL: 15mer gRNA;
CR_PAL-Left spacing: 36 nt; CR_PAL-Right spacing: 15 nt.
Cas9 will bind but not cut with a truncated gRNA (15mer).
(Church et al., 2014 Kiani et al., *Cas9 gRNA engineering for
genome editing, activation and repression. Nat. Methods*,
doi: 10.1038 (Sep. 7, 2015)). Use truncated gRNAs to
bracket the cut site and open up the DNA so the standard
gRNA (20mer) can cut better. 5% alone to >50% with
15mers. Cas9 v2+20mer gRNA+L/R 15mer gRNA.
Figure 29:
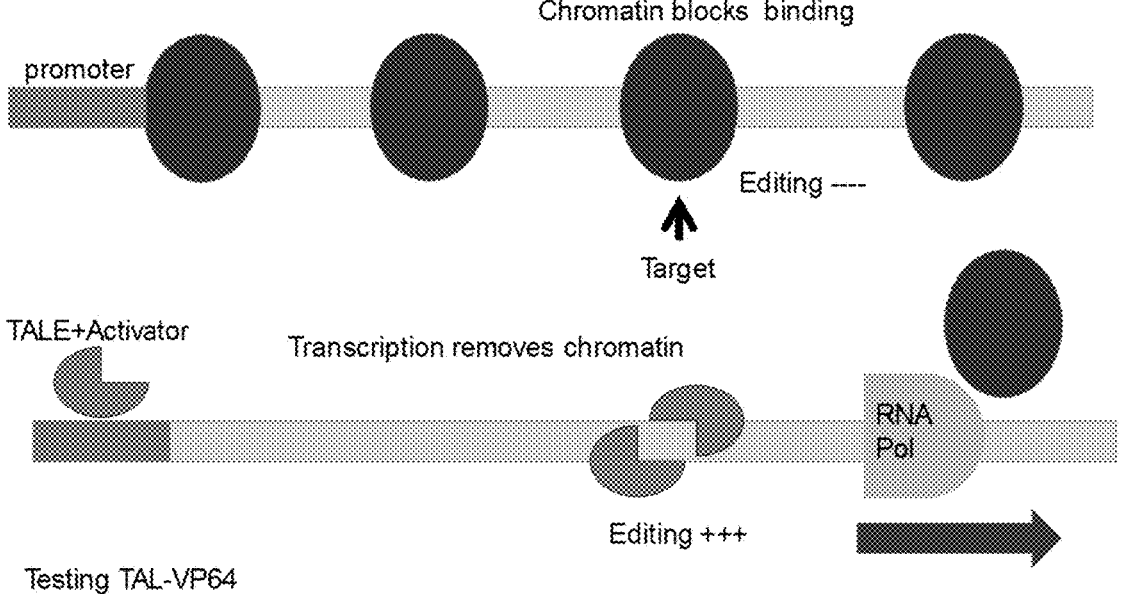
FIG. 29. The figure shows Buddy TAL activator concept.
Binding of TAL with activation domain, such as VP64,
promotes active gene expression which opens up the DNA
to enhance editing by a nuclease (TALEN, Cas9, etc.).
Figure 30:
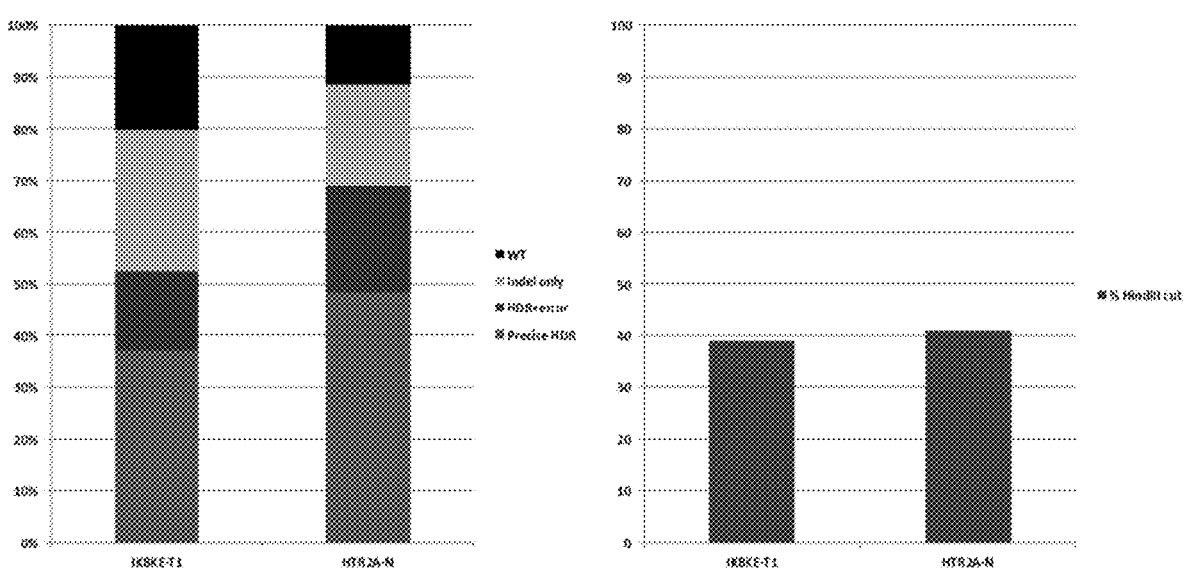
FIG. 30. This figure shows HDR in U2OS (sequence verification). Donor has a HindIII site insertion; NEON®: 1300/20/2.
Figure 31:
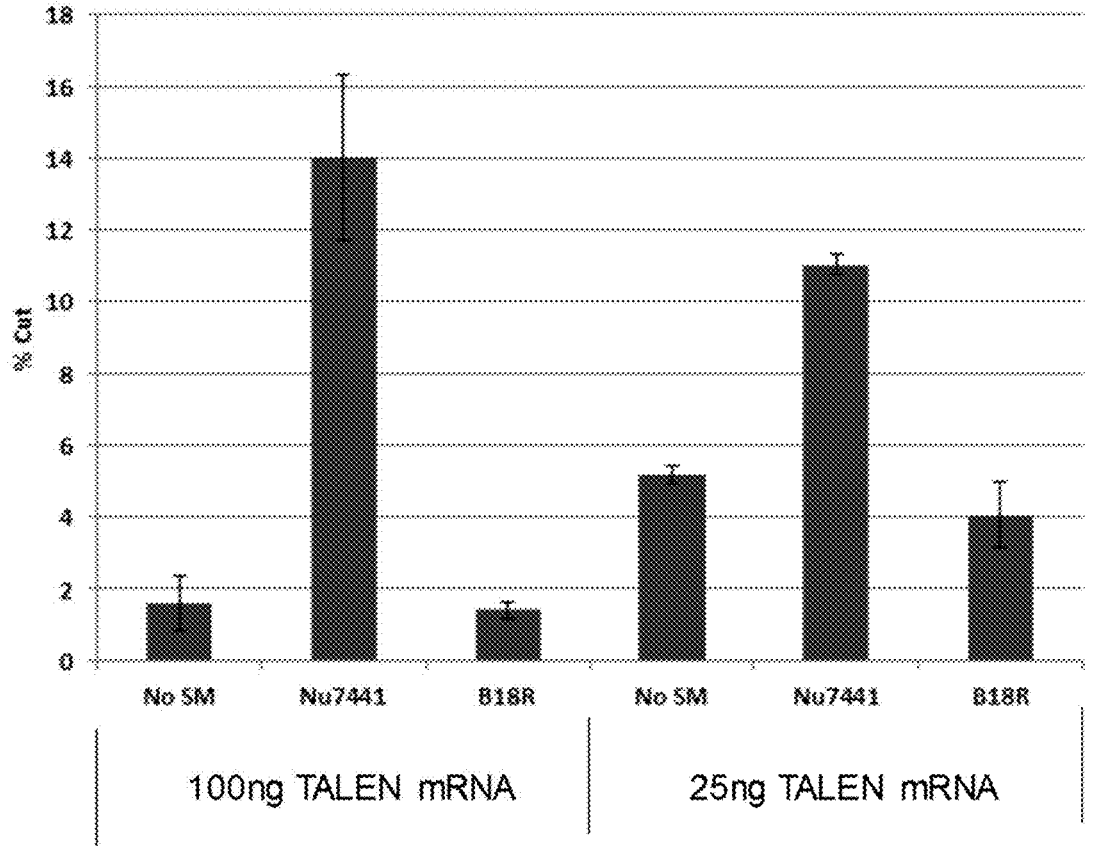
FIG. 31. This figure shows effect of small molecule/additives on TALEN editing in A549 cells. Target: HTR2A-N; Donor has a HindIII site insertion; NEON® condition: 1200/20/4; Media changed 24 hours; HindIII cut shown on graph. NU7441 (DNAPK inhibitor) and B18R (immune response repressor).
Figure 32:
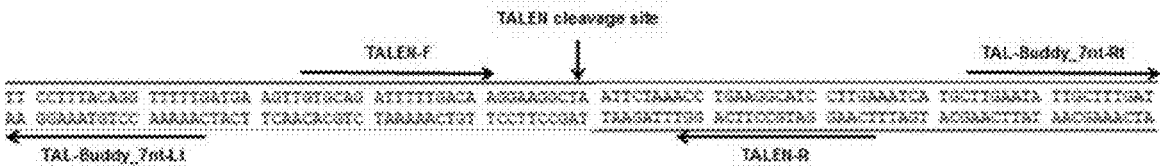
FIG. 32. This figure shows an example of relative positions of TALEN and TAL-Buddy. Then TALEN pair are space at 8 bases on each side of the target site. In this example, the TAL-buddies are at 7 nt spacing from the TALENs. The upper strand is SEQ ID NO:20 and the lower strand is SEQ ID NO:21.
Figure 33:
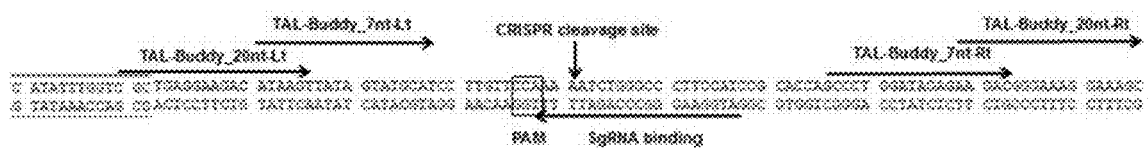
FIG. 33. This figure shows "TAL-Buddy" designed in proximity to CRISPR cleavage site in UFSP2-SNP target. 100 ng of Lt and Rt "TAL-Buddy" mRNA was added together with CRISPR-RNP (1000 ng of Cas9 protein and 200 ng sgRNA) for transfection into ~50,000 of 293 human embryonic kidney cells (293FT) with NEON® electroporation apparatus (Thermo Fisher Scientific, cat. no. MPK5000) at 1150 pulse voltage, 20 pulse width, and 2 pulse number. Cells were harvested and lysed 48 to 72 hours post transfection. Indel formation was assayed with GENEART™ Genomic Cleavage Detection Kit (Thermo Fisher Scientific, cat. no. A24372). The upper strand is SEQ ID NO:42 and the lower strand is SEQ ID NO:43.
Figure 34:
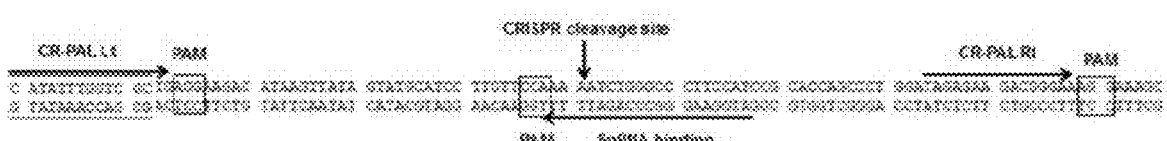
FIG. 34. This figure shows "CR-PAL" designed to proximity of CRISPR cleavage site in UFSP2-SNP target. 200 ng of CR-PAL_Lt and CR-PAL_Rt was incubated with wild-type Cas9-RNP and transfected into ~50,000 of 293 human embryonic kidney cells (293FT) with NEON® electroporation apparatus (Thermo Fisher Scientific, cat. no. MPK5000) at 1150 pulse voltage, 20 pulse width, and 2 pulse number. Cells were harvested and lysed 48 to 72 hours post transfection. Indel formation was assayed with "GENEART™ Genomic Cleavage Detection Kit" (Thermo Fisher Scientific, cat. no. A24372). The upper strand is SEQ ID NO:44 and the lower strand is SEQ ID NO:45.
Figure 35:
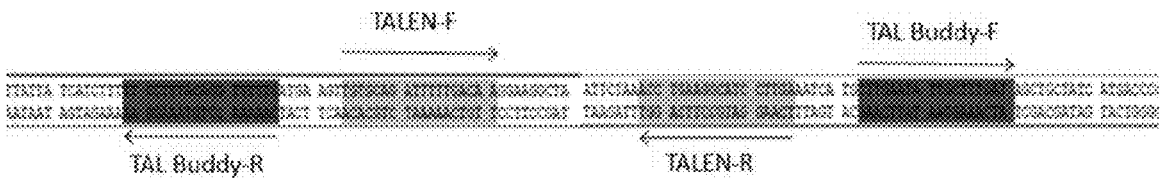
FIG. 35. This figure shows test "Buddy TAL" (293FT). The upper strand is SEQ ID NO:46 and the lower strand is SEQ ID NO:47.
Figures 36, 37:
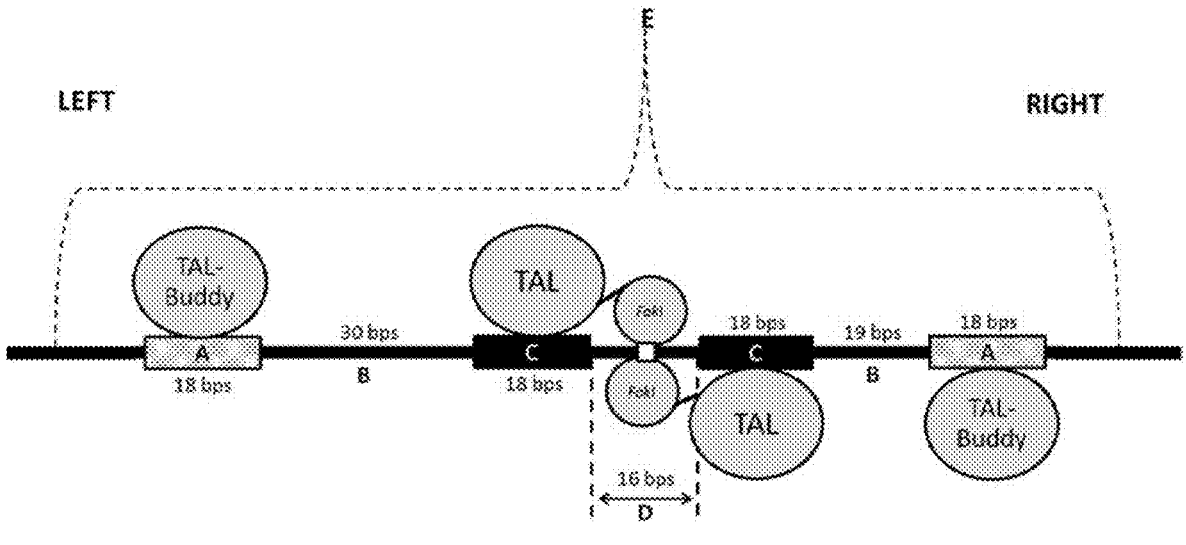
FIG. 36 is a schematic representation of the use of a pair of TAL-Buddys (also referred to herein as first and second DNA-binding modulation-enhancing agent) in conjunction with a pair of TAL-FokI nuclease fusions (also referred to herein as a first and second DNA binding nuclease conjugate). The right and the left sides of the figure are indicated with the left TAL-Buddy binding on the left side and the right TAL-Buddy binding on the right side. The long solid line represents a portion of an intracellular nucleic acid molecule (e.g., a chromosome; also referred to herein as target locus). Regions A (shown at the left and right ends) of the represented nucleic acid molecule are binding sites (also referred to herein as first and second enhancer binding sequence) for the two TAL-Buddy proteins. Regions B represent the distances between the TAL-Buddy binding sites (e.g., first and second enhancer binding sequence) and the TAL-FokI fusion protein binding sites (also referred to herein as first and second binding sequence). Region D represents the nucleic acid segment between the two TAL-FokI fusion protein binding sites. The white box in Region D represents the site where the nucleic acid is cleaved (also referred to herein as modulation site) by the pair of TAL- FokI fusion proteins. Region E represents the portion of the nucleic acid molecule in which accessibility is potentially enhanced.
FIG. 37 is a schematic similar to that of FIG. 36, except that a single TAL-VP16 fusion (also referred to herein as modulating protein) is used instead of a pair of TAL-FokI nuclease fusions. The unlabeled circles represent components of a VP16 recruited transcriptional complex. Further, there is only one Region C because a single TAL-VP16 fusion is employed. Also, the Regions B are formed is formed by the intervening base pairs between the Regions A (also referred to herein as first and second enhancer binding sequence) and Region C (also referred to herein as modulation binding sequence).

Results: more than 60 fold increase of indel formation was obtained with both left (Lt) and right (Rt) CR_PAL (FIG. 21 and FIG. 34).

Example 8: Cas9 NLS Variants

Cas9 v2 (BPsv40 tag/nucleoplasmin), IDT (cat. no. 1074181), and Cas9 v1 (−/3×sv40) were compared in A549 cells against two targets (HPRT and PRKCG), a 4× dilution series was done to determine how functional performance was affected by protein concentration. HPRT is considered an easy to modify target, while PRKCG has been more difficult to modify.

RNP complexes were formed using 1 µg of Cas9 protein (from the various sources) and 250 ng of the gRNA (either HPRT or PRKCG). After a 10 minute incubation, a 4× dilution series of the RNP complex was made by diluting the initial concentration in the appropriate volume of OPTI-MEM™. Each dilution series was mixed with LIPO-FECTAMINE™ CRISPRMAX™ according to the manual and then added to ~50,000 293FT cells. The transfected cells were grown out for 3 days and the editing efficiency was measure by the Genomic Cleavage Detection assay.

A number of different formats of spy Cas9 backbone variants were also tested (see FIG. 43, data not shown), with various NLS or affinity tags added to the N or C termini.

Figure 44A:
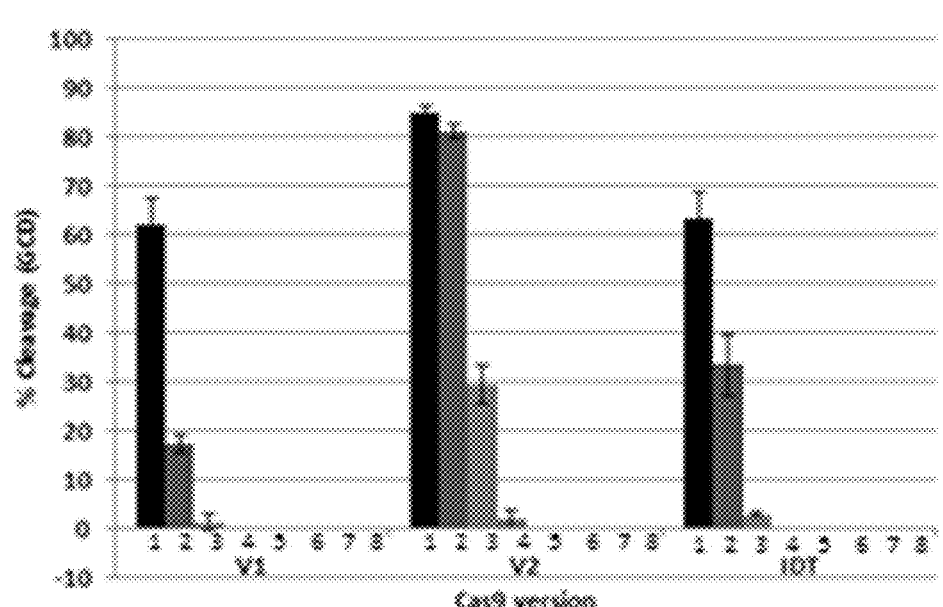
FIGS. 44A and 44B show GCD data obtained using different Cas9-NLS combination with two different cell types.
Figure 44B:
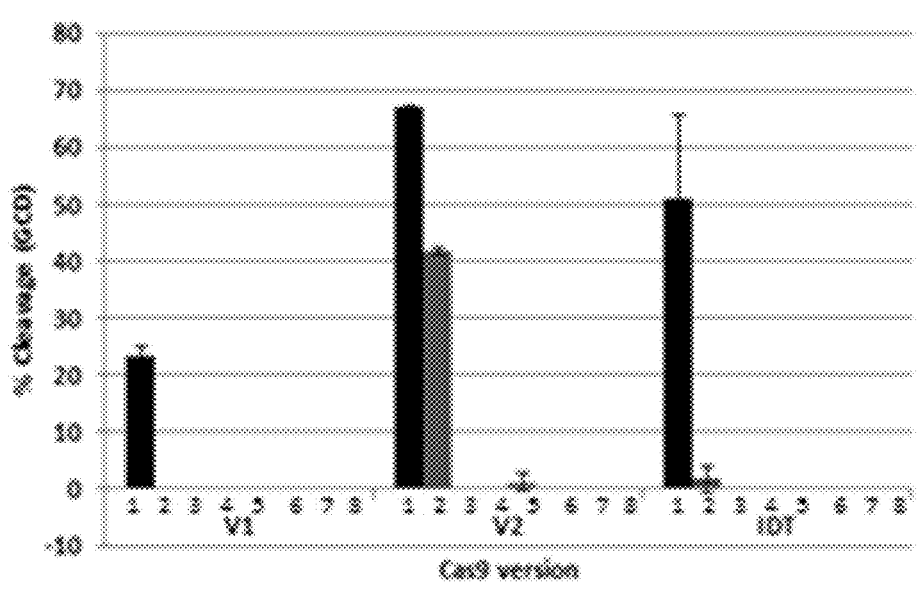

Of the three formats represented in the data shown in FIG. 44, the Cas9 v2 has significantly the highest activity over the dilution range.

Example 9: TALEN Efficiency of Cleavage and Homology Directed Repair

Figure 48:
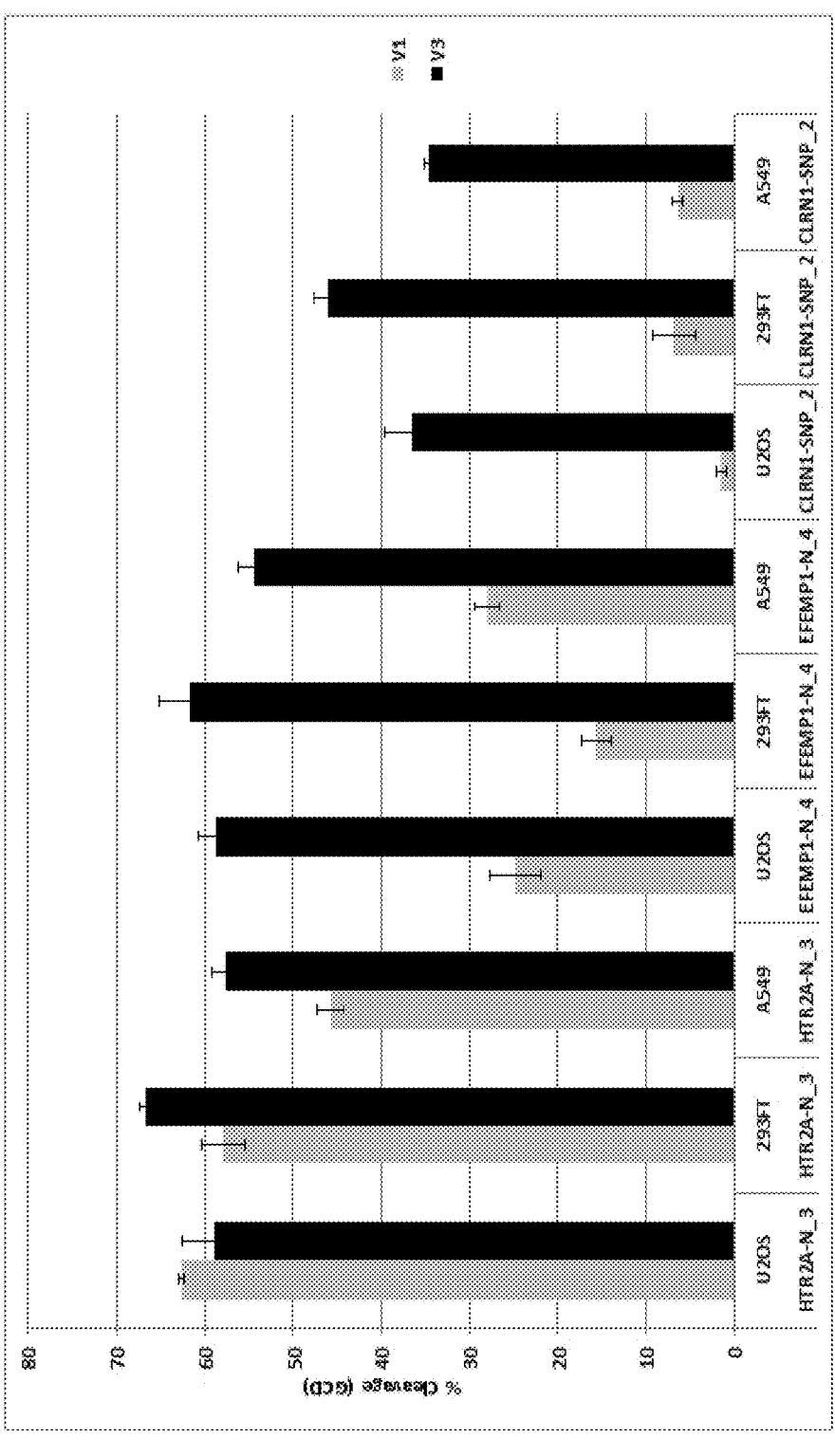
FIG. 48 shows genomic cleavage detection data, generated as set out below in Example 8, for three different genomic loci in three different cell types.

TALEN design shown below for the targets used to generate data set out on in FIGS. 48-50 are set out in Table 8 below. The data used to generate FIGS. 48-50 are set out in Tables 9-11 below.

TABLE 8

|  | SEQ ID NO |
| --- | --- |
| HTR2A_3 target: | |
| TALEN-F binding | |
| TGTTTTGCTG ACTTCAAAAA CTGCATGCAA GAGCTGAGCC AGCTCCCGCA CT | 119 |
| ACAAAACGAC TGAAGTTTTT GACGTACGTT CTCGACTCGG TCGAGGGCGT GA | 120 |
| TALEN-R binding | |
| EFEMP1_4 target: | |
| TALEN-F binding | |
| AGTTAGGAAA AGGGCTTTCA ACATTGTGAA TCTCAAAGAA AATACAGGAC AA | 121 |
| TCAATCCTTT TCCCGAAAGT TGTAACACTT AGAGTTTCTT TTATGTCCTG TT | 123 |
| TALEN-R binding | |

TABLE 8-continued

| | SEQ ID NO |
|---|---|
| CLRN1_2 target: | |

TALEN-F binding →

```
GCCCTGAGGC ATTGACGAGC AGAGCTCCCG TTTTGCAGAG GACAGTGGCT TT     124
CGGGACTCCG TAACTGCTCG TCTCGAGGGC AAAACGTCTC CTGTCACCGA AA     125
                                          ← TALEN-R binding
```

For each 50,000 cells grown in 96-well culture plate, 100 ng forward and 100 ng reverse TALEN mRNA and/or 10 pmol of donor single-stranded oligo which contains a 6 nucleotide HindIII recognition site in the middle and 35 nucleotide homology arms on both 5' and 3' ends. The two distal end nucleotides on both 5' and 3' ends have phosphorothioate bonds to protect from nuclease degradation.

On the day of transfection, prepare cells were prepared as following: (1) Total number of cells needed was calculated (50,000 cells each), (2) the cells were detached and the cell number was counted, (3) the desired number of cells were spun down at 1,000 rpm for 5 min., (4) the cell pellet was washed with one time DPBS, then spin down at 1,000 rpm for 5 min., (5), the cell pellet was resuspended in 5 μl of Neon® resuspension buffer R (Thermo Fisher Scientific, NEON® Transfection System 100 μL Kit, cat. no. MPK10096) per 50,000 cells, and (6) 100 ng of Forward TALEN primer, 100 ng Reverse TALEN primer, 10 pmol donor single-stranded oligo, and 5 μl R Buffer was added to each 5 μl of cells in R buffer.

A 10 μl Neon® pipet was used for electroporation (Thermo Fisher Scientific, cat. no. MPK5000). Electroporation conditions were as follows: 1300 (pulse voltage), 20 (Pulse width), 2 (Pulse no.) for 293FT cells; 1400 (pulse voltage), 20 (Pulse width), 2 (Pulse no.) for U2OS cells; 1150 (pulse voltage), 30 (Pulse width), 2 (Pulse no.) for A549 cells.

Electroporated cells were then transferred into 100 μl of pre-warmed growth media in 96 well culture plate. Cells were harvested 48-72 hours post transfection and analyze for cleavage efficiency using the GeneArt® Genomic cleavage detection kit (Thermo Fisher Scientific, cat. no. A24372), and HDR efficiency was determined using HindIII digestion.

TABLE 9

| | | FIG. 48 GCD Data | | | |
|---|---|---|---|---|---|
| Gene | Cell Type | Ave V1 | SD | Ave V3 | SD |
| HTR2A-N_3 | U2OS | 62.675 | 0.304 | 58.900 | 3.620 |
| HTR2A-N_3 | 293FT | 57.895 | 2.482 | 66.830 | 0.608 |

TABLE 9-continued

| | | FIG. 48 GCD Data | | | |
|---|---|---|---|---|---|
| Gene | Cell Type | Ave V1 | SD | Ave V3 | SD |
| HTR2A-N_3 | A549 | 45.780 | 1.513 | 57.675 | 1.435 |
| EFEMP1-N_4 | U2OS | 24.830 | 2.885 | 58.665 | 2.001 |
| EFEMP1-N_4 | 293FT | 15.630 | 1.669 | 61.725 | 3.486 |
| EFEMP1-N_4 | A549 | 28.01 | 1.400 | 54.420 | 1.824 |
| CLRN1-SNP_2 | U2OS | 1.465 | 0.477 | 36.535 | 3.048 |
| CLRN1-SNP_2 | 293FT | 6.905 | 2.368 | 46.070 | 1.499 |
| CLRN1-SNP_2 | A549 | 6.470 | 0.622 | 34.615 | 0.615 |

TABLE 10

| | | FIG. 49 HDR Data | | | |
|---|---|---|---|---|---|
| Gene | Cell Type | Ave V1 | SD | Ave V3 | SD |
| HTR2A-N_3 | 293FT | 16.570 | 0.3818 | 22.000 | 2.164 |
| | U2OS | 24.540 | 3.691 | 22.000 | 1.365 |
| EFEMP1-N_4 | 293FT | 2.635 | 0.417 | 33.755 | 0.615 |
| | U2OS | 6.775 | 0.912 | 31.040 | 0.990 |
| CLRN1-SNP_2 | 293FT | 1.970 | 0.976 | 22.400 | 2.461 |
| | U2OS | 0.250 | 0.0990 | 15.415 | 0.728 |

TABLE 11

| | FIG. 50 HDR Data (A549 Cells) | | | |
|---|---|---|---|---|
| | Ave | | SD | |
| Gene | V1 | V3 | V1 | V3 |
| HTR2A-N_3 | 4.485 | 7.925 | 0.557 | 0.304 |
| EFEMP1-N_4 | 0.855 | 11.785 | 0.926 | 1.874 |
| CLRN1-SNP_2 | 0 | 6.975 | 0 | 0.167 |

Description of Amino Acid and Nucleotide Sequences

Table 12 provides a listing of certain sequences referenced herein.

TABLE 12

| Various Nucleotide and Amino Acid Sequences Referred to Herein | | |
|---|---|---|
| Description | Sequences | SEQ ID NO |
| FAK | CTCGATGTCATTGACCAAGCAAGACTGAAAATGGTGAGCAAGGGCG AGGAGCTGTTCACCGGGGTGGTGCCCATCCTGGTCGAGCTGGACGG CGACGTAAACGGCCACAAGTTCAGCGTGTCCGGCGAGGGCGAGGGC GATGCCACCTACGGCAAGCTGACCCTGAAGTTCATCTGCACCACCGG CAAGCTGCCCGTGCCCTGGCCCACCCTCGTGACCACCTTCACCTACG | 1 |

TABLE 12-continued

Various Nucleotide and Amino Acid Sequences Referred to Herein

| Description | Sequences | SEQ ID NO |
|---|---|---|
| | GCGTGCAGTGCTTCGCCCGCTACCCCGACCACATGAAGCAGCACGA<br>CTTCTTCAAGTCCGCCATGCCCGAAGGCTACGTCCAGGAGCGCACCA<br>TCTTCTTCAAGGACGACGGCAACTACAAGACCCGCGCCGAGGTGAA<br>GTTCGAGGGCGACACCCTGGTGAACCGCATCGAGCTGAAGGGCATC<br>GACTTCAAGGAGGACGGCAACATCCTGGGGCACAAGCTGGAGTACA<br>ACTACAACAGCCACAAGGTCTATATCACCGCCGACAAGCAGAAGAA<br>CGGCATCAAGGTGAACTTCAAGACCCGCCACAACATCGAGGACGGC<br>AGCGTGCAGCTCGCCGACCACTACCAGCAGAACACCCCCATCGGCG<br>ACGGCCCCGTGCTGCTGCCCGACAACCACTACCTGAGCACCCAGTCC<br>GCCCTGAGCAAAGACCCCAACGAGAAGCGCGATCACATGGTCCTGC<br>TGGAGTTCGTGACCGCCGCCGGGATCACTCTCGGCATGGACGAGCT<br>GTACAAGGGAAGCGGAGCTACTAACTTCAGCCTGCTGAAGCAGGCT<br>GGAGACGTGGAGGAGAACCCTGGACCTATGACCGAGTACAAGCCCA<br>CAGTGCGGCTGGCCACCAGGGACGATGTGCCTAGAGCTGTGCGGAC<br>ACTGGCCGCTGCCTTCGCCGATTACCCTGCCACCAGACACACCGTGG<br>ACCCCGACAGACACATCGAGAGAGTGACCGAGCTGCAGGAACTGTT<br>TCTGACCAGAGTGGGCCTGGACATCGGCAAAGTGTGGGTGGCCGAT<br>GATGGCGCCGCTGTGGCTGTGTGGACAACCCCTGAGTCTGTGGAAG<br>CCGGCGCTGTGTTCGCCGAGATCGGACCTAGAATGGCCGAGCTGAG<br>CGGCTCTAGACTGGCTGCCCAGCAGCAGATGGAAGGCCTGCTGGCC<br>CCCCACAGACCTAAAGAGCCTGCCTGGTTTCTGGCCACCGTGGGCGT<br>GTCACCTGACCACCAGGGCAAGGGACTGGGATCTGCTGTGGTGCTG<br>CCTGGCGTGGAAGCTGCTGAAAGGGCTGGCGTGCCCGCCTTCCTGG<br>AAACAAGCGCCCCCAGAAACCTGCCCTTCTACGAGAGACTGGGCTT<br>CACCGTGACCGCCGACGTGGAAGTGCCTGAGGGCCCTAGAACCTGG<br>TGCATGACCAGAAAGCCTGGCGCCCTTGGGCAGACGAGACCACACT<br>GAGCCTCCCC | |
| EGFR | GGTCGCGCCACAAAGCAGTGAATTTATTGGAGCATGGGTGAGCAAG<br>GGCGAGGAGCTGTTCACCGGGGTGGTGCCCATCCTGGTCGAGCTGG<br>ACGGCGACGTAAACGGCCACAAGTTCAGCGTGTCCGGCGAGGGCGA<br>GGGCGATGCCACCTACGGCAAGCTGACCCTGAAGTTCATCTGCACC<br>ACCGGCAAGCTGCCCGTGCCCTGGCCCACCCTCGTGACCACCTTCAC<br>CTACGGCGTGCAGTGCTTCGCCCGCTACCCCGACCACATGAAGCAGC<br>ACGACTTCTTCAAGTCCGCCATGCCCGAAGGCTACGTCCAGGAGCGC<br>ACCATCTTCTTCAAGGACGACGGCAACTACAAGACCCGCGCCGAGG<br>TGAAGTTCGAGGGCGACACCCTGGTGAACCGCATCGAGCTGAAGGG<br>CATCGACTTCAAGGAGGACGGCAACATCCTGGGGCACAAGCTGGAG<br>TACAACTACAACAGCCACAAGGTCTATATCACCGCCGACAAGCAGA<br>AGAACGGCATCAAGGTGAACTTCAAGACCCGCCACAACATCGAGGA<br>CGGCAGCGTGCAGCTCGCCGACCACTACCAGCAGAACACCCCCATC<br>GGCGACGGCCCCGTGCTGCTGCCCGACAACCACTACCTGAGCACCC<br>AGTCCGCCCTGAGCAAAGACCCCAACGAGAAGCGCGATCACATGGT<br>CCTGCTGGAGTTCGTGACCGCCGCCGGGATCACTCTCGGCATGGACG<br>AGCTGTACAAGGGAAGCGGAGCTACTAACTTCAGCCTGCTGAAGCA<br>GGCTGGAGACGTGGAGGAGAACCCTGGACCTATGACCGAGTACAAG<br>CCCACAGTGCGGCTGGCCACCAGGGACGATGTGCCTAGAGCTGTGC<br>GGACACTGGCCGCTGCCTTCGCCGATTACCCTGCCACCAGACACACC<br>GTGGACCCCGACAGACACATCGAGAGAGTGACCGAGCTGCAGGAAC<br>TGTTTCTGACCAGAGTGGGCCTGGACATCGGCAAAGTGTGGGTGGC<br>CGATGATGGCGCCGCTGTGGCTGTGTGGACAACCCCTGAGTCTGTGG<br>AAGCCGGCGCTGTGTTCGCCGAGATCGGACCTAGAATGGCCGAGCT<br>GAGCGGCTCTAGACTGGCTGCCCAGCAGCAGATGGAAGGCCTGCTG<br>GCCCCCCACAGACCTAAAGAGCCTGCCTGGTTTCTGGCCACCGTGGG<br>CGTGTCACCTGACCACCAGGGCAAGGGACTGGGATCTGCTGTGGTG<br>CTGCCTGGCGTGGAAGCTGCTGAAAGGGCTGGCGTGCCCGCCTTCCT<br>GGAAACAAGCGCCCCCAGAAACCTGCCCTTCTACGAGAGACTGGGC<br>TTCACCGTGACCGCCGACGTGGAAGTGCCTGAGGGCCCTAGAACCT<br>GGTGCATGACCAGAAAGCCTGGCGCCTACCACGGAGGATAGTATGA<br>GCCCTAAAAATCCAG | 2 |
| Beta Actin | CACAGCGCGCCCGGCTATTCTCGCAGCTCACCATGACCGAGTACAA<br>GCCCACAGTGCGGCTGGCCACCAGGGACGATGTGCCTAGAGCTGTG<br>CGGACACTGGCCGCTGCCTTCGCCGATTACCCTGCCACCAGACACAC<br>CGTGGACCCCGACAGACACATCGAGAGAGTGACCGAGCTGCAGGAA<br>CTGTTTCTGACCAGAGTGGGCCTGGACATCGGCAAAGTGTGGGTGG<br>CCGATGATGGCGCCGCTGTGGCTGTGTGGACAACCCCTGAGTCTGTG<br>GAAGCCGGCGCTGTGTTCGCCGAGATCGGACCTAGAATGGCCGAGC<br>TGAGCGGCTCTAGACTGGCTGCCCAGCAGCAGATGGAAGGCCTGCT<br>GGCCCCCCACAGACCTAAAGAGCCTGCCTGGTTTCTGGCCACCGTGG<br>GCGTGTCACCTGACCACCAGGGCAAGGGACTGGGATCTGCTGTGGT<br>GCTGCCTGGCGTGGAAGCTGCTGAAAGGGCTGGCGTGCCCGCCTTCC<br>TGGAAACAAGCGCCCCCAGAAACCTGCCCTTCTACGAGAGACTGGG<br>CTTCACCGTGACCGCCGACGTGGAAGTGCCTGAGGGCCCTAGAACC<br>TGGTGCATGACCAGAAAGCCTGGCGCCGGAAGCGGAGCTACTAACT | 3 |

TABLE 12-continued

Various Nucleotide and Amino Acid Sequences Referred to Herein

| Description | Sequences | SEQ ID NO |
|---|---|---|
| | TCAGCCTGCTGAAGCAGGCTGGAGACGTGGAGGAGAACCCTGGACC<br>TAACCTGAGCAAAAACGTGAGCGTGAGCGTGTATATGAAGGGGAAC<br>GTCAACAATCATGAGTTTGAGTACGACGGGGAAGGTGGTGGTGATC<br>CTTATACAGGTAAATATTCCATGAAGATGACGCTACGTGGTCAAAAT<br>TCCCTACCCTTTTCCTATGATATCATTACCACGGCATTTCAGTATGGT<br>TTCCGCGTATTTACAAAATACCCTGAGGGAATTGTTGACTATTTTAA<br>GGATTCGCTTCCCGACGCATTCCAGTGGAACAGACGAATTGTGTTTG<br>AAGATGGTGGAGTACTAAACATGAGCAGTGATATCACATATAAAGA<br>TAATGTTCTGCATGGTGACGTCAAGGCTGAGGGAGTGAACTTCCCGC<br>CGAATGGGCCAGTGATGAAGAATGAAATTGTGATGGAGGAACCGAC<br>TGAAGAAACATTTACTCCAAAAAACGGGGTTCTTGTTGGCTTTTGTC<br>CCAAAGCGTACTTACTTAAAGATGGTTCCTATTACTATGGAAATATG<br>ACAACATTTTACAGATCCAAGAAATCTGGCCAGGCACCTCCTGGGTA<br>TCACTTTGTTAAGCATCGTCTCGTCAAGACCAATGTGGGACATGGAT<br>TTAAGACGGTTGAGCAGACTGAATATGCCACTGCTCATGTCAGTGAT<br>CTTCCCAAATTCGAAGCTGATGATGATATCGCCGCGCTCGTCGTCGA<br>CAACGG | |
| LRRK2 | GAGGGCGGCGGGTTGGAAGCAGGTGCCACCATGACCGAGTACAAG<br>CCCACAGTGCGGCTGGCCACCAGGGACGATGTGCCTAGAGCTGTGC<br>GGACACTGGCCGCTGCCTTCGCCGATTACCCTGCCACCAGACACACC<br>GTGGACCCCGACAGACACATCGAGAGAGTGACCGAGCTGCAGGAAC<br>TGTTTCTGACCAGAGTGGGCCTGGACATCGGCAAAGTGTGGGTGGC<br>CGATGATGGCGCCGCTGTGGCTGTGTGGACAACCCCTGAGTCTGTGG<br>AAGCCGGCGCTGTGTTCGCCGAGATCGGACCTAGAATGGCCGAGCT<br>GAGCGGCTCTAGACTGGCTGCCCAGCAGCAGATGGAAGGCCTGCTG<br>GCCCCCCACAGACCTAAAGAGCCTGCCTGGTTTCTGGCCACCGTGGG<br>CGTGTCACCTGACCACCAGGGCAAGGGACTGGGATCTGCTGTGGTG<br>CTGCCTGGCGTGGAAGCTGCTGAAAGGGCTGGCGTGCCCGCCTTCCT<br>GGAAACAAGCGCCCCCAGAAACCTGCCCTTCTACGAGAGACTGGGC<br>TTCACCGTGACCGCCGACGTGGAAGTGCCTGAGGGCCCTAGAACCT<br>GGTGCATGACCAGAAAGCCTGGCGCCGGAAGCGGAGCTACTAACTT<br>CAGCCTGCTGAAGCAGGCTGGAGACGTGGAGGAGAACCCTGGACCT<br>GTGAGCAAGGGCGAGGAGCTGTTCACCGGGGTGGTGCCCATCCTGG<br>TCGAGCTGGACGGCGACGTAAACGGCCACAAGTTCAGCGTGTCCGG<br>CGAGGGCGAGGGCGATGCCACCTACGGCAAGCTGACCCTGAAGTTC<br>ATCTGCACCACCGGCAAGCTGCCCGTGCCCTGGCCCACCCTCGTGAC<br>CACCTTCACCTACGGCGTGCAGTGCTTCGCCCGCTACCCCGACCACA<br>TGAAGCAGCACGACTTCTTCAAGTCCGCCATGCCCGAAGGCTACGTC<br>CAGGAGCGCACCATCTTCTTCAAGGACGACGGCAACTACAAGACCC<br>GCGCCGAGGTGAAGTTCGAGGGCGACACCCTGGTGAACCGCATCGA<br>GCTGAAGGGCATCGACTTCAAGGAGGACGGCAACATCCTGGGGCAC<br>AAGCTGGAGTACAACTACAACAGCCACAAGGTCTATATCACCGCCG<br>ACAAGCAGAAGAACGGCATCAAGGTGAACTTCAAGACCCGCCACAA<br>CATCGAGGACGGCAGCGTGCAGCTCGCCGACCACTACCAGCAGAAC<br>ACCCCCATCGGCGACGGCCCCGTGCTGCTGCCCGACAACCACTACCT<br>GAGCACCCAGTCCGCCCTGAGCAAAGACCCCAACGAGAAGCGCGAT<br>CACATGGTCCTGCTGGAGTTCGTGACCGCCGCCGGGATCACTCTCGG<br>CATGGACGAGCTGTACAAGGCTAGTGGCAGCTGTCAGGGGTGCGAA<br>GAGGAC | 4 |
| Human IgG expression cassette | CGACCCTCTTTTGTGCCCTGATATAGTTCGCCATGACCGAGTACAAG<br>CCCACAGTGCGGCTGGCCACCAGGGACGATGTGCCTAGAGCTGTGC<br>GGACACTGGCCGCTGCCTTCGCCGATTACCCTGCCACCAGACACACC<br>GTGGACCCCGACAGACACATCGAGAGAGTGACCGAGCTGCAGGAAC<br>TGTTTCTGACCAGAGTGGGCCTGGACATCGGCAAAGTGTGGGTGGC<br>CGATGATGGCGCCGCTGTGGCTGTGTGGACAACCCCTGAGTCTGTGG<br>AAGCCGGCGCTGTGTTCGCCGAGATCGGACCTAGAATGGCCGAGCT<br>GAGCGGCTCTAGACTGGCTGCCCAGCAGCAGATGGAAGGCCTGCTG<br>GCCCCCCACAGACCTAAAGAGCCTGCCTGGTTTCTGGCCACCGTGGG<br>CGTGTCACCTGACCACCAGGGCAAGGGACTGGGATCTGCTGTGGTG<br>CTGCCTGGCGTGGAAGCTGCTGAAAGGGCTGGCGTGCCCGCCTTCCT<br>GGAAACAAGCGCCCCCAGAAACCTGCCCTTCTACGAGAGACTGGGC<br>TTCACCGTGACCGCCGACGTGGAAGTGCCTGAGGGCCCTAGAACCT<br>GGTGCATGACCAGAAAGCCTGGCGCCTGAGTTGACATTGATTATTGA<br>CTAGTTATTAATAGTAATCAATTACGGGGTCATTAGTTCATAGCCCA<br>TATATGGAGTTCCGCGTTACATAACTTACGGTAAATGGCCCGCCTGG<br>CTGACCGCCCAACGACCCCCGCCCATTGACGTCAATAATGACGTATG<br>TTCCCATAGTAACGCCAATAGGGACTTTCCATTGACGTCAATGGGTG<br>GAGTATTTACGGTAAACTGCCCACTTGGCAGTACATCAAGTGTATCA<br>TATGCCAAGTACGCCCCCTATTGACGTCAATGACGGTAAATGGCCCG<br>CCTGGCATTATGCCCAGTACATGACCTTATGGGACTTTCCTACTTGG<br>CAGTACATCTACGTATTAGTCATCGCTATTACCATGGTGATGCGGTT<br>TTGGCAGTACATCAATGGGCGTGGATAGCGGTTTGACTCACGGGGA<br>TTTCCAAGTCTCCACCCCATTGACGTCAATGGGAGTTTGTTTTGGCA | 5 |

TABLE 12-continued

Various Nucleotide and Amino Acid Sequences Referred to Herein

| Description | Sequences | SEQ ID NO |
|---|---|---|
| | CCAAAATCAACGGGACTTTCCAAAATGTCGTAACAACTCCGCCCCAT TGACGCAAATGGGCGGTAGGCGTGTACGGTGGGAGGTCTATATAAG CAGAGCTCGTTTAGTGAACCGTCAGATCGCCTGGAGACGCCATCCAC GCTGTTTTGACCTCCATAGAAGACACCGGGACCGATCCAGCCTCCGG ACTCTAGAGGATCGAACCCTTGCCACCATGGGTTGGAGCCTCATCTT GCTCTTCCTTGTCGCTGTTGCTACGCGTGTCCTGTCCCAGGTACAACT GCAGCAGCCTGGGGCTGAGCTGGTGAAGCCTGGGGCCTCAGTGAAG ATGTCCTGCAAGGCTTCTGGCTACACATTTACCAGTTACAATATGCA CTGGGTAAAACAGACACCTGGTCGGGGCCTGGAATGGATTGGAGCT ATTTATCCCGGAAATGGTGATACTTCCTACAATCAGAAGTTCAAAGG CAAGGCCACATTGACTGCAGACAAATCCTCCAGCACAGCCTACATG CAGCTCAGCAGCCTGACATCTGAGGACTCTGCGGTCTATTACTGTGC AAGATCGACTTACTACGGCGGTGACTGGTACTTCAATGTCTGGGGCG CAGGGACCACGGTCACCGTCTCTGCAGCTAGCACCAAGGGCCCATC GGTCTTCCCCCTGGCACCCTCCTCCAAGAGCACCTCTGGGGGCACCG CGGCCCTGGGCTGCCTGGTCAAGGACTACTTCCCCGAACCGGTGACG GTGTCGTGGAACTCAGGCGCCCTGACCAGCGGCGTGCACACCTTCCC GGCTGTCCTACAGTCCTCAGGACTCTACTCCCTCAGCAGCGTGGTGA CCGTGCCCTCCAGCAGCTTGGGCACCCAGACCTACATCTGCAACGTG AATCACAAGCCCAGCAACACCAAGGTGGACAAGAAAGCAGAGCCC AAATCTTGTGACAAAACTCACACATGCCCACCGTGCCCAGCACCTGA ACTCCTGGGGGGACCGTCAGTCTTCCTCTTCCCCCCAAAACCCAAGG ACACCCTCATGATCTCCCGGACCCCTGAGGTCACATGCGTGGTGGTG GACGTGAGCCACGAAGACCCTGAGGTCAAGTTCAACTGGTACGTGG ACGGCGTGGAGGTGCATAATGCCAAGACAAAGCCACGGGAGGAGC AGTACAACAGCACGTACCGTGTGGTCAGCGTCCTCACCGTCCTGCAC CAGGACTGGCTGAATGGCAAGGAGTACAAGTGCAAGGTCTCCAACA AAGCCCTCCCAGCCCCCATCGAGAAAACCATCTCCAAAGCCAAAGG GCAGCCCCGAGAACCACAGGTGTACACCCTGCCCCCATCCCGGGAT GAGCTGACCAAGAACCAGGTCAGCCTGACCTGCCTGGTCAAAGGCT TCTATCCCAGCGACATCGCCGTGGAGTGGGAGAGCAATGGGCAGCC GGAGAACAACTACAAGACCACGCCTCCCGTGCTGGACTCCGACGGC TCCTTCTTCCTCTACAGCAAGCTCACCGTGGACAAGAGCAGGTGGCA GCAGGGGAACGTCTTCTCATGCTCCGTGATGCATGAGGCTCTGCACA ACCACTACACGCAGAAGAGCCTCTCCCTGTCTCCGGGTAAACGTAA ACGAAGAGGCAGCGGGGCTACTAACTTCAGCCTGCTGAAGCAGGCT GGAGACGTGGAGGAGAACCCTGGACCTATGGATTTTCAGGTGCAGA TTATCAGCTTCCTGCTAATCAGTGCTTCAGTCATAATGTCCAGAGGA CAAATTGTTCTCTCCCAGTCTCCAGCAATCCTGTCTGCATCTCCAGG GGAGAAGGTCACAATGACTTGCAGGGCCAGCTCAAGTGTAAGTTAC ATCCACTGGTTCCAGCAGAAGCCAGGATCCTCCCCCAAACCCTGGAT TTATGCCACATCCAACCTGGCTTCTGGAGTCCCTGTTCGCTTCAGTG GCAGTGGGTCTGGGACTTCTTACTCTCTCACAATCAGCAGAGTGGAG GCTGAAGATGCTGCCACTTATTACTGCCAGCAGTGGACTAGTAACCC ACCCACGTTCGGAGGGGGGACCAAGCTGGAAATCAAACGTACGGTG GCTGCACCATCTGTCTTCATCTTCCCGCCATCTGATGAGCAGTTGAA ATCTGGAACTGCCTCTGTTGTGTGCCTGCTGAATAACTTCTATCCCA GAGAGGCCAAAGTACAGTGGAAGGTGGATAACGCCCTCCAATCGGG TAACTCCCAGGAGAGTGTCACAGAGCAGGACAGCAAGGACGACACC TACAGCCTCAGCAGCACCCTGACGCTGAGCAAAGCAGACTACGAGA AACACAAAGTCTACGCCTGCGAAGTCACCCATCAGGGCCTGAGCTC GCCCGTCACAAAGAGCTTCAACAGGGGAGAGTGTTGAAAGGGGTTCG ATCCCTACCGGTTAGTAATGAGTTTGATATCTCGACAATCAACCTCT GGATTACAAAATTTGTGAAAGATTGACTGGTATTCTTAACTATGTTG CTCCTTTTACGCTATGTGGATACGCTGCTTTAATGCCTTTGTATCATG CTATTGCTTCCCGTATGGCTTTCATTTTCTCCTCCTTGTATAAATCCT GGTTGCTGTCTCTTTATGAGGAGTTGTGGCCCGTTGTCAGGCAACGT GGCGTGGTGTGCACTGTGTTTGCTGACGCAACCCCCACTGGTTGGGG CATTGCCACCACCTGTCAGCTCCTTTCCGGGACTTTCGCTTTCCCCCT CCCTATTGCCACGGCGGAACTCATCGCCGCCTGCCTTGCCCGCTGCT GGACAGGGGCTCGGCTGTTGGGCACTGACAATTCCGTGGTGTTGTCG GGGAAGCTGACGTCCTTTCCATGGCTGCTCGCCTGTGTTGCCACCTG GATTCTGCGCGGGACGTCCTTCTGCTACGTCCCTTCGGCCCTCAATC CAGCGGACCTTCCTTCCCGCGGCCTGCTGCCGGCTCTGCGGCCTCTT CCGCGTCTTCGCCTTCGCCCTCAGACGAGTCGGATCTCCCTTTGGGC CGCCTCCCCGCCTGGATGACGATATCGCTGCGCTCGTTGTCGACAA CGG | |
| *Natronobacterium gregoryi* Argonaute Amino Acid Sequence | MTVIDLDSTT TADELTSGHT YDISVTLTGV YDNTDEQHPR MSLAFEQDNG ERRYITLWKN TTPKDVFTYD YATGSTYIFT NIDYEVKDGY ENLTATYQTT VENATAQEVG TTDEDETFAG GEPLDHHLDD ALNETPDDAE TESDSGHVMT SFASRDQLPE WTLHTYTLTA TDGAKTDTEY ARRTLAYTVR QELYTDHDAA PVATDGLMLL TPEPLGETPL DLDCGVRVEA DETRTLDYTT AKDRLLAREL VEEGLKRSLW DDYLVRGIDE VLSKEPVLTC | 6 |

TABLE 12-continued

---

Various Nucleotide and Amino Acid Sequences Referred to Herein

| Description | Sequences | SEQ ID NO |
|---|---|---|
| | DEFDLHERYD LSVEVGHSGR AYLHINFRHR FVPKLTLADI DDDNIYPGLR VKTTYRPRRG HIVWGLRDEC ATDSLNTLGN QSVVAYHRNN QTPINTDLLD AIEAADRRVV ETRRQGHGDD AVSFPQELLA VEPNTHQIKQ FASDGFHQQA RSKTRLSASR CSEKAQAFAE RLDPVRLNGS TVEFSSEFFT GNNEQQLRLL YENGESVLTF RDGARGAHPD ETFSKGIVNP PESFEVAVVL PEQQADTCKA QWDTMADLLN QAGAPPTRSE TVQYDAFSSP ESISLNVAGA IDPSEVDAAF VVLPPDQEGF ADLASPTETY DELKKALANM GIYSQMAYFD RFRDAKIFYT RNVALGLLAA AGGVAFTTEH AMPGDADMFI GIDVSRSYPE DGASGQINIA ATATAVYKDG TILGHSSTRP QLGEKLQSTD VRDIMKNAIL GYQQVTGESP THIVIHRDGF MNEDLDPATE FLNEQGVEYD IVEIRKQPQT RLLAVSDVQY DTPVKSIAAI NQNEPRATVA TFGAPEYLAT RDGGGLPRPI QIERVAGETD IETLTRQVYL LSQSHIQVHN STARLPITTA YADQASTHAT KGYLVQTGAF ESNVGFL | |
| Nuclear Localization Signal (NLS) | PKKKRKV | 7 |
| NLS | AVKRPAATKKAGQAKKKKLD | 8 |
| NLS | MSRRRKANPTKLSENAKKLAKEVEN | 9 |
| NLS | PAAKRVKLD | 10 |
| Chloroplast Targeting Signal | LIAHPQAFPGAIAAPISYAYAVKGRKPRFQTAKGSVRI | 11 |
| Mitochondrial Targeting Signal | MLSLRQSIRFFKPATRTLCSSRYLL | 12 |
| BP-SV40, NLES peptide | KRTADGSEFESPKKKRKVEGG | 13 |
| Example oligonucleotide | CGGGGTAGCGGCTGAAGCACTGCACGCCGTAGGTCA GGGTGGTCACGAGGGTGGGCCAGGGCACGGGCAGCT TGCCGGTGGTGCAGATGAACTTCAG | 14 |
| Disrupted EmGFP | GCACGCCGTAGGTGGTCACGAGG | 15 |
| Example oligonucleotide | GCTGCCCGTGCCCTGGCCCACCCTCGTGACCACCCTG ACCTACGGCGTGCAGTGCTTCAGCCGCTACCCCGACC ACATGA | 16 |
| eBFP | CTCGTGACCACCCTGACCCACGG | 17 |
| CMPK1- TALEN2_7 nt_ TAL- Buddy_Lt | CTGGCTAACTAGAGAACCCACTGCTTACTGGCTTATC GAAATTAATACGACTCACTATAGGGAGTCCCAAGCTG GCTAGCGTTTAAACTTCTGCGGCCGCGCCACCATGGG AAAACCTATTCCTAATCCTCTGCTGGGCCTGGATTCT ACCGGAGGCGTGGACCTGAGAACACTGGGATATTCTC AGCAGCAGCAGGAGAAGATCAAGCCCAAGGTGAGAT CTACAGTGGCCCAGCACCACGAAGCCCTGGTGGGAC ACGGATTTACACACGCCCACATTGTGGCCCTGTCTCA GCACCCTGCCGCCCTGGGAACAGTGGCCGTGAAATAT CAGGATATGATTGCCGCCCTGCCTGAGGCCACACACG AAGCCATTGTGGGAGTGGGAAAACGAGGCGCTGGAG CCAGAGCCCTGGAAGCCCTGCTGACAGTGGCCGGAG AACTGAGAGGACCTCCTCTGCAGCTGGATACAGGAC AGCTGCTGAAGATTGCCAAAAGGGGCGGAGTGACCG CGGTGGAAGCCGTGCACGCCTGGAGAAATGCCCTGA CAGGAGCCCCTCTGAACCTGACCCCCGAACAGGTGGT GGCCATTGCCAGCCACGACGGCGGCAAGCAGGCCCT GGAAACCGTGCAGAGACTGCTGCCCGTGCTGTGCCAG GCCCATGGCCTGACACCTGAACAGGTGGTGGCTATCG CCTCTAATATCGGAGGAAAACAGGCTCTGGAAACAG TGCAGCGGCTGCTGCCTGTGCTGTGTCAGGCTCACGG CTTGACTCCAGAACAGGTGGTGGCTATTGCTTCCAAT ATTGGGGGGAAACAGGCCCTGGAAACTGTGCAGCGC | 18 |

TABLE 12-continued

Various Nucleotide and Amino Acid Sequences Referred to Herein

| Description | Sequences | SEQ ID NO |
|---|---|---|
| | CTGCTGCCAGTGCTGTGCCAGGCTCACGGACTGACCC CCGAACAGGTGGTGGCCATTGCCAGCAACATCGGCG GCAAGCAGGCCCTGGAAACCGTGCAGAGACTGCTGC CCGTGCTGTGCCAGGCCCATGGCCTGACACCTGAACA GGTGGTGGCTATCGCCTCTAATATCGGAGGAAAACAG GCTCTGGAAACAGTGCAGCGGCTGCTGCCTGTGCTGT GTCAGGCTCACGGCTTGACTCCAGAACAGGTGGTGGC TATTGCTTCCAATATTGGGGGGAAACAGGCCCTGGAA ACTGTGCAGCGCCTGCTGCCAGTGCTGTGCCAGGCTC ACGGGCTGACCCCCGAACAGGTGGTGGCCATTGCCA GCCACGACGGCGGCAAGCAGGCCCTGGAAACCGTGC AGAGACTGCTGCCCGTGCTGTGCCAGGCCCATGGCCT GACACCTGAACAGGTGGTGGCTATCGCCTCTCACGAC GGAGGAAAACAGGCTCTGGAAACAGTGCAGCGGCTG CTGCCTGTGCTGTGTCAGGCTCACGGCTTGACTCCAG AACAGGTGGTGGCTATTGCTTCCAACGGCGGGGGGA AACAGGCCCTGGAAACTGTGCAGCGCCTGCTGCCAGT GCTGTGCCAGGCTCACGGCCTCACTCCCGAACAGGTG GTGGCCATTGCCAGCAACAACGGCGGCAAGCAGGCC CTGGAAACCGTGCAGAGACTGCTGCCCGTGCTGTGCC AGGCCCATGGCCTGACACCTGAACAGGTGGTGGCTAT CGCCTCTAACGGCGGAGGAAAACAGGCTCTGGAAAC AGTGCAGCGGCTGCTGCCTGTGCTGTGTCAGGCTCAC GGCTTGACTCCAGAACAGGTGGTGGCTATTGCTTCCA ATATTGGGGGGAAACAGGCCCTGGAAACTGTGCAGC GCCTGCTGCCAGTGCTGTGCCAGGCTCACGGACTGAC CCCCGAACAGGTGGTGGCCATTGCCAGCAACATCGGC GGCAAGCAGGCCCTGGAAACCGTGCAGAGACTGCTG CCCGTGCTGTGCCAGGCCCATGGCCTGACACCTGAAC AGGTGGTGGCTATCGCCTCTAATATCGGAGGAAAACA AGCACTCGAGACAGTGCAGCGGCTGCTGCCTGTGCTG TGTCAGGCTCACGGCTTGACTCCAGAACAGGTGGTGG CTATTGCTTCCAACAACGGGGGGAAACAGGCCCTGG AAACTGTGCAGCGCCTGCTGCCAGTGCTGTGCCAGGC TCACGGCCTGACCCCCGAACAGGTGGTGGCCATTGCC AGCAACAACGGCGGCAAGCAGGCCCTGGAAACCGTG CAGAGACTGCTGCCCGTGCTGTGCCAGGCCCATGGCC TGACACCTGAACAGGTGGTGGCTATCGCCTCTAATAT CGGAGGAAAACAGGCTCTGGAAACAGTGCAGCGGCT GCTGCCTGTGCTGTGTCAGGCTCACGGCTTGACTCCA CAGCAGGTCGTGGCAATTGCTAGCAATATCGGCGGAC GGCCCGCCCTGGAGAGCATTGTGGCCCAGCTGTCTAG ACCTGATCCTGCCCTGGCCGCCCTGACAAATGATCAC CTGGTGGCCCTGGCCTGTCTGGGAGGCAGACCTGCCC TGGATGCCGTGAAAAAAGGACTGCCTCACGCCCCTGC CCTGATCAAGAGAACAAATAGAAGAATCCCCGAGCG GACCTCTCACAGAGTGGCCGGATCCCCTAAGAAAA GCGGAAGGTGGGATCCTGAAAGCTTCTCGAGTCTAG AGGGCCCGTTTAAACCCGCTGATCAGCCTCGACTGTG CCTTCTAGTTGCCAGCCATCTGTTGTTTGCCCCTCCCC CGTGCC | |
| CMPK1-C target | AACTCAAGTGATCTGCCCGCCTCGACCTCCCAAAGTG CTGGGATTACAGATGTGAGCCACCGCGCCCCGCCAAA TTTGATTATTTTTAATAAGAACTTAGCTGTATGGTATT TTAACAGTACCTGCTTTTAAAATTATTATCATCTTT*TT CCTTTACAGGTTTTTG*ATGAAGT<u>TGTGCAGATTTTTGA</u> CAAGGAAGGCTAATTCTAAACCTGAAGGCATCCTTGA AATCATG*CTTGAATATTGCTTTGAT*AGCTGCTATCATG ACCCCTTTTTAAGGCAATTCTAATCTTTCATAACTACA TCTCAATTAGTGGCTGGAAAGTACATGGTAAAACAAA GTAAATTTTTTTATGTTCTTTTTTTTGGTCACAGGAGT AGACAGTGAATTCAGGTTTAACTTCACCTTAGTTATG GTGCTCACCAAACGAAGGGTATCAGCTATTTTTTTTA AAATTCAAAAAGAATATCCCTTTTATAGTTTGTGCCTT CTGTGAGCAAAACTTTTTAGTACGCGTATATATCCCT CTAGTAATCACAACATTTTAGGATTT | 19 |

TD1-F2, 5' primer for TALEN/TAL-Buddy full-length enrichment
CTGGCTAACTAGAGAACCCACTGCTTACTG                                                        22

TD8-R2, 3' primer for TALEN/TAL-Buddy full-length enrichment
GGCACGGGGGAGGGGCAAACAACAGATGGC                                                        23

TABLE 12-continued

Various Nucleotide and Amino Acid Sequences Referred to Herein

| Description Sequences | SEQ ID NO |
|---|---|
| CMPK1-TALEN2_F, Forward TALEN at CMPK1-C target<br>TGTGCAGATTTTTGACAA | 24 |
| CMPK1-TALEN2_R, Reverse TALEN at CMPK1-C target<br>TCAAGGATGCCTTCAGGT | 25 |
| CMPK1-TALEN2_7 nt_TAL-Buddy_Lt, Left TAL-Buddy at 7 nt spacing<br>CAAAAACCTGTAAAGGAA | 26 |
| CMPK1-TALEN2_7 nt_TAL-Buddy_Rt, Right TAL-Buddy at 7 nt spacing<br>CTTGAATATTGCTTTGAT | 27 |
| CMPK1-TALEN2_0 nt_TAL-Buddy_Lt, Left TAL-Buddy at 0 nt spacing<br>ACTTCATCAAAAACCTGT | 28 |
| CMPK1-TALEN2_0 nt_TAL-Buddy_Rt, Right TAL-Buddy at 0 nt spacing<br>AATCATGCTTGAATATTG | 29 |
| CMPK1-TALEN2_4 nt_TAL-Buddy_Lt, Left TAL-Buddy at 4 nt spacing<br>CATCAAAAACCTGTAAAG | 30 |
| CMPK1-TALEN2_4 nt_TAL-Buddy_Rt, Right TAL-Buddy at 4 nt spacing<br>ATGCTTGAATATTGCTTT | 31 |
| CMPK1-TALEN2_12 nt_TAL-Buddy_Lt, Left TAL-Buddy at 12 nt spacing<br>ACCTGTAAAGGAAAAAGA | 32 |
| CMPK1-TALEN2_12 nt_TAL-Buddy_Rt, Right TAL-Buddy at 12 nt spacing<br>ATATTGCTTTGATAGCTG | 33 |
| CMPK1-TALEN2_20 nt_TAL-Buddy_Lt, Left TAL-Buddy at 20 nt spacing<br>AGGAAAAAGATGATAATA | 34 |
| CMPK1-TALEN2_20 nt_TAL-Buddy_Rt, Right TAL-Buddy at 20 nt spacing<br>TTGATAGCTGCTATCATG | 35 |
| CMPK1-TALEN2_30 nt_TAL-Buddy_Lt, Left TAL-Buddy at 30 nt spacing<br>TGATAATAATTTTAAAAG | 36 |
| CMPK1-TALEN2_30 nt_TAL-Buddy_Rt, Right TAL-Buddy at 30 nt spacing<br>CTATCATGACCCCTTTTT | 37 |
| CMPK1-TALEN2_50 nt_TAL-Buddy_Lt, Left TAL-Buddy at 50 nt spacing<br>GGTACTGTTAAAATACCA | 38 |
| CMPK1-TALEN2_50 nt_TAL-Buddy_Rt, Right TAL-Buddy at 50 nt spacing<br>GGCAATTCTAATCTTTCA | 39 |
| CMPK1-TALEN2_100 nt_TAL-Buddy_Lt, Left TAL-Buddy at 100 nt spacing<br>TTGGCGGGGCGCGGTGGC | 40 |
| CMPK1-TALEN2_100 nt_TAL-Buddy_Rt, Right TAL-Buddy at 100 nt spacing<br>ATGGTAAAACAAAGTAAA | 41 |

The titles, headings and subheadings provided herein should not be interpreted as limiting the various aspects of the disclosure. Accordingly, the terms defined below are more fully defined by reference to the specification in its entirety.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. Definitions are provided herein to facilitate understanding of certain terms used frequently herein and are not meant to limit the scope of the present disclosure.

In this application, the use of "or" means "and/or" unless stated otherwise. In the context of a multiple dependent claim, the use of "or" refers back to more than one preceding independent or dependent claim in the alternative only. It is further noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

As described herein, any concentration range, percentage range, ratio range or integer range is to be understood to include the value of any integer within the recited range and, when appropriate, fractions thereof (such as one tenth and one hundredth of an integer), unless otherwise indicated.

Units, prefixes, and symbols are denoted in their Système International de Unites (SI) accepted form. Numeric ranges are inclusive of the numbers defining the range. Measured values are understood to be approximate, taking into account significant digits and the error associated with the measurement.

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof. This description and exemplary embodiments should not be taken as limiting.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

When terms, such as "less than or equal to" or "greater than or equal to," precede a list of numerical values or ranges, the terms modify all of the values or ranges provided in the list. In some embodiments, the numerical values are rounded to the nearest whole number or significant figure. Exemplary Subject Matter of the Invention is Represented by the Following Clauses:

Clause 1. A method for homologous recombination in an initial nucleic acid molecule, the method comprising: (a) generating a double-stranded break in the initial nucleic acid molecule to produce a cleaved nucleic acid molecule, and (b) contacting the cleaved nucleic acid molecule with a donor nucleic acid molecule, wherein the initial nucleic acid molecule comprises a promoter and a gene and wherein the donor nucleic acid molecule comprises: (i) matched termini on the 5' and 3' ends of 12 bp to 250 bp in length, (ii) a promoterless selection marker, (iii) a reporter gene, (iv) a self-cleaving peptide linking the promoterless selection marker and the reporter gene or LoxP on either side of the promoterless selection marker, and (iv) optionally a linker between the promoterless selection marker and the reporter gene.

Clause 2. The method of clause 1, wherein the double-stranded break in the nucleic acid molecule is: (i) less than or equal to 250 bp from the ATG start codon for N-terminal tagging of the cleaved nucleic acid molecule; or (ii) less than or equal to 250 bp from the stop codon for C-terminal tagging of the cleaved nucleic acid molecule.

Clause 3. The method of clause 1, wherein the double-stranded break is induced by at least one nucleic acid cutting entity or electroporation.

Clause 4. The method of clause 3, wherein the at least one nucleic acid cutting entity comprises a nuclease comprising one or more zinc finger protein, one or more transcription activator-like effectors (TALEs), one or more CRISPR complex, one or more argonaute-nucleic acid complex, or one or more macronuclease.

Clause 5. The method of clause 3, wherein the at least one nucleic acid cutting entity is administered using an expression vector, a plasmid, ribonucleoprotein complex (RNC), or mRNA.

Clause 6. The method of clause 1, wherein the promoterless selection marker comprises a protein, antibiotic resistance selection marker, cell surface marker, cell surface protein, metabolite, or active fragment thereof.

Clause 7. The method of clause 6, wherein the promoterless selection marker is a protein.

Clause 8. The method of clause 7, wherein the protein is focal adhesion kinase (FAK), angiopoietin-related growth factor (AGF) receptor, or epidermal growth factor receptor (EGFR).

Clause 9. The method of clause 6, wherein the promoterless selection marker is an antibiotic resistance selection marker.

Clause 10. The method of clause 9, wherein the antibiotic resistance selection marker is a recombinant antibody.

Clause 11. The method of clause 9, wherein the antibiotic resistance selection marker is a human IgG antibody.

Clause 12. The method of clause 1, wherein the reporter gene comprises a fluorescent protein reporter.

Clause 13. The method of clause 12, wherein the fluorescent protein reporter is emerald green fluorescent protein (EmGFP) reporter or orange fluorescent protein (OFP) reporter.

Clause 14. The method of clause 1, wherein the promoterless selection marker is: (i) linked to the 5' end of a reporter gene for N-terminal tagging of the cleaved nucleic acid molecule; or (ii) linked to the 3' end of the reporter gene for C-terminal tagging of the cleaved nucleic acid molecule.

Clause 15. The method of clause 1, wherein the donor nucleic acid molecule comprises the linker between the promoterless selection marker and the reporter gene.

Clause 16. The method of clause 15, wherein the distance between the promoterless selection marker and the reporter gene is less than or equal to 300 nt, 240 nt, 180 nt, 150 nt, 120 nt, 90 nt, 60 nt, 30 nt, 15 nt, 12 nt, or 9 nt.

Clause 17. The method of clause 16, wherein the distance is 6 nt.

Clause 18. The method of clause 15, wherein the linker is a polyglycine linker.

Clause 19. The method of clause 1, wherein the self-cleaving peptide is a self-cleaving 2A peptide.

Clause 20. The method of clause 1, wherein the matched termini are added to the 5' and 3' ends of the donor nucleic acid molecule by PCR amplification.

Clause 21. The method of clause 1, wherein the matched termini share a sequence identity greater than or equal to 95%.

Clause 22. The method of clause 1, wherein the matched termini comprise single-stranded DNA or double-stranded DNA.

Clause 23. The method of clause 1, wherein the matched termini on the 5' and 3' ends of the donor nucleic acid molecule have a length of 12 bp to 200 bp, 12 bp to 150 bp, 12 bp to 100 bp, 12 bp to 50 bp, or 12 bp to 40 bp.

Clause 24. The method of clause 23, wherein the matched termini have a length of 35 bp.

Clause 25. The method of clause 1, wherein the initial nucleic acid molecule is in a cell or a plasmid.

Clause 26. The method of clause 1, wherein the donor nucleic acid molecule comprises a length of less than or equal to 1 kb, 2 kb, 3 kb, 5 kb, 10 kb, 15 kb, 20 kb, 25 kb, or 30 kb.

Clause 27. The method of clause 1, wherein the donor nucleic acid molecule is integrated into the cleaved nucleic acid molecule by homology directed repair (HDR).

Clause 28. The method of clause 27, wherein the HDR is greater than or equal to 10%, 25%, 50%, 75%, 90%, 95%, 98%, 99%, or 100%.

Clause 29. The method of clause 1, wherein integration efficiency of the donor nucleic acid molecule is greater than or equal to 50%, 75%, 90%, 95%, 98%, 99%, or 100%.

Clause 30. The method of clause 1, further comprising modifying the donor nucleic acid molecule at the 5' end, the 3' end, or the 5' and 3' ends.

Clause 31. The method of clause 30, wherein the donor nucleic acid molecule is modified at the 5' and 3' ends.

Clause 32. The method of clause 30, wherein the donor nucleic acid molecule is modified with one or more nuclease resistant groups in at least one strand of at least one terminus.

Clause 33. The method of clause 32, wherein the one or more nuclease resistant groups comprises one or more phosphorothioate groups, one or more amine groups, 2'-O-methyl nucleotides, 2'-deoxy-2'-fluoro nucleotides, 2'-deoxy nucleotides, 5-C-methyl nucleotides, or a combination thereof.

Clause 34. The method of clause 1, further comprising treating the donor nucleic acid molecule with at least one non-homologous end joining (NHEJ) inhibitor.

Clause 35. The method of clause 34, wherein the at least one NHEJ inhibitor is a DNA-dependent protein kinase (DNA-PK), a DNA ligase IV, DNA polymerase 1 or 2 (PARP-1 or PARP-2), or combination thereof.

Clause 36. The method of clause 35, wherein the DNA-PK inhibitor is Nu7206 (2-(4-Morpholinyl)-4H-naphthol[1,2-b]pyran-4-one), Nu7441 (8-(4-Dibenzothienyl)-2-(4-morpholinyl)-4H-1-benzopyran-4-one), Ku-0060648 (4-Ethyl-N-[4-[2-(4-morpholinyl)-4-oxo-4H-1-benzopyran-8-yl]-1-dibenzothienyl]-1-piperazineacetamide), Compound 401 (2-(4-Morpholinyl)-4H-pyrimido[2,1-a]isoquinolin-4-one), DMNB (4,5-Dimethoxy-2-nitrobenzaldehyde), ETP 45658 (3-[1-Methyl-4-(4-morpholinyl)-1H-pyrazolo[3,4-d]pyrimidin-6-ylphenol), LTURM 34 (8-(4-Dibenzothienyl)-2-(4-morpholinyl)-4H-1,3-benzoxazin-4-one), or Pl 103 hydrochloride (3-[4-(4-Morpholinylpyrido[3',2':4,5]furo[3,2-d]pyrimidin-2-yl]phenol hydrochloride).

Clause 37. The method of clause 1, wherein the mammal is a human, a mammalian laboratory animal, a mammalian farm animal, a mammalian sport animal, or a mammalian pet.

Clause 38. The method of clause 37, wherein the mammal is a human.

Clause 39. A cell or plasmid made by the method of clause 1.

Clause 40. The cell of clause 39, wherein the cell is a eukaryotic cell.

Clause 41. The cell of clause 40, wherein the eukaryotic cell is a mammalian cell.

Clause 42. A method of cell therapy, comprising administering an effective amount of the cell of clause 41 to a subject in need thereof.

Clause 43. The method of clause 42, wherein the cell is a T-cell and the promoterless selection marker is a chimeric antigen receptor (CAR).

Clause 44. A method for producing a promoterless selection marker, comprising activating the promoter of a cell or plasmid made by the method of clause 1 to produce the promoterless selection marker.

Clause 45. A composition comprising a promoterless selection marker produced by the method of clause 44.

Clause 46. A method for therapeutic treatment of a subject in need thereof, comprising administering an effective amount of the promoterless selection marker produced by the method of clause 44.

Clause 47. A drug screening assay comprising the promoterless selection marker produced by the method of clause 44.

Clause 48. A kit for producing a promoterless selection marker, comprising a promoterless selection marker linked to a reporter gene by a self-cleaving peptide or LoxP on either side of the selection marker.

Clause 49. The kit of clause 48, wherein the reporter gene is GFP or OFP.

Clause 50. The kit of clause 48, further comprising at least one nucleic acid cutting entity.

Clause 51. The kit of clause 48, further comprising at least one NHEJ inhibitor.

Clause 52. The kit of clause 48, further comprising one or more nuclease resistant groups.

Clause 53. A recombinant antibody expression cassette comprising: (i) matched termini on the 5' and 3' ends of the cassette, wherein the matched termini are of less than or equal to 250 bp in length; (ii) a promoterless selection marker; (iii) a reporter gene; (iv) a self-cleaving peptide linking the promoterless selection marker and the reporter gene; and (v) optionally, a linker between the promoterless selection marker and the reporter gene, wherein the promoterless selection marker is linked at the 5' end of the reporter gene for N-terminal tagging of a cleaved nucleic acid molecule, or at the 3' end of the reporter gene for C-terminal tagging of a cleaved nucleic acid molecule.

Clause 54. A method of increasing accessibility of a target locus in a cell, said method comprising: (1) introducing into a cell comprising a nucleic acid encoding a target locus a first DNA-binding modulation-enhancing agent, wherein said first DNA-binding modulation-enhancing agent is not endogenous to said cell; and (2) allowing said first DNA-binding modulation-enhancing agent to bind a first enhancer binding sequence of said target locus, thereby increasing accessibility of said target locus relative to the absence of said first DNA-binding modulation-enhancing agent.

Clause 55. The method of clause 54, wherein said introducing a first DNA-binding modulation-enhancing agent comprises introducing a vector encoding said first DNA-binding modulation-enhancing agent.

Clause 56. The method of clause 54, wherein said introducing a first DNA-binding modulation-enhancing agent comprises introducing a mRNA encoding said first DNA-binding modulation-enhancing agent.

Clause 57. The method of clause 54, wherein said introducing a first DNA-binding modulation-enhancing agent comprises introducing a first DNA binding protein or a first DNA binding nucleic acid.

Clause 58. The method of clause 54, wherein the rate of homologous recombination at said target locus is increased relative to the absence of said first DNA-binding modulation-enhancing agent.

Clause 59. The method of clause 54, wherein said first DNA-binding modulation-enhancing agent is a first DNA binding protein or a first DNA binding nucleic acid.

Clause 60. The method of clause 54, wherein said first DNA-binding modulation-enhancing agent is a first transcription activator-like (TAL) effector protein or a first truncated guide RNA (gRNA).

Clause 61. The method of clause 54, wherein said first enhancer binding sequence has the sequence of SEQ ID NO:26, SEQ ID NO:28, SEQ ID NO:30, SEQ ID NO:32, SEQ ID NO:34, SEQ ID NO:36, SEQ ID NO:38, or SEQ ID NO:40.

Clause 62. A method of displacing chromatin of a target locus in a cell, said method comprising: (1) introducing into said cell comprising a nucleic acid encoding a target locus a first DNA-binding modulation-enhancing agent, wherein said first DNA-binding modulation-enhancing agent is not endogenous to said cell; and (2) allowing said first DNA-binding modulation-enhancing agent to bind a first enhancer binding sequence of said target locus, thereby displacing chromatin of said target locus.

Clause 63. The method of clause 62, wherein said introducing a first DNA-binding modulation-enhancing agent comprises introducing a vector encoding said first DNA-binding modulation-enhancing agent.

Clause 64. The method of clause 62, wherein said introducing a first DNA-binding modulation-enhancing agent comprises introducing a mRNA encoding said first DNA-binding modulation-enhancing agent.

Clause 65. The method of clause 62, wherein said introducing a first DNA-binding modulation-enhancing agent comprises introducing a first DNA binding protein or a first DNA binding nucleic acid.

Clause 66. The method of clause 62, wherein the rate of homologous recombination at said target locus is increased relative to the absence of said first DNA-binding modulation-enhancing agent.

Clause 67. The method of clause 62, wherein said first DNA-binding modulation-enhancing agent is a first DNA binding protein or a first DNA binding nucleic acid.

Clause 68. The method of clause 62, wherein said first DNA-binding modulation-enhancing agent is a first transcription activator-like (TAL) effector protein or a first truncated guide RNA (gRNA).

Clause 69. A method of restructuring chromatin of a target locus in a cell, said method comprising: (1) introducing into a cell comprising a nucleic acid encoding a target locus a first DNA-binding modulation-enhancing agent, wherein said first DNA-binding modulation-enhancing agent is not endogenous to said cell; and (2) allowing said first DNA-binding modulation-enhancing agent to bind a first enhancer binding sequence of said target locus, thereby restructuring chromatin of said target locus.

Clause 70. The method of clause 69, wherein said introducing a first DNA-binding modulation-enhancing agent comprises introducing a vector encoding said first DNA-binding modulation-enhancing agent.

Clause 71. The method of clause 69, wherein said introducing a first DNA-binding modulation-enhancing agent comprises introducing a mRNA encoding said first DNA-binding modulation-enhancing agent.

Clause 72. The method of clause 69, wherein said introducing a first DNA-binding modulation-enhancing agent comprises introducing a first DNA binding protein or a first DNA binding nucleic acid.

Clause 73. The method of clause 69, wherein the rate of homologous recombination at said target locus is increased relative to the absence of said first DNA-binding modulation-enhancing agent.

Clause 74. The method of clause 69, wherein said first DNA-binding modulation-enhancing agent is a first DNA binding protein or a first DNA binding nucleic acid.

Clause 75. The method of clause 69, wherein said first DNA-binding modulation-enhancing agent is a first transcription activator-like (TAL) effector protein or a first truncated guide RNA (gRNA).

Clause 76. A method of increasing accessibility of a target locus in a cell, said method comprising: (1) introducing into a cell comprising a nucleic acid encoding a target locus: (i) a first DNA-binding modulation-enhancing agent, wherein said first DNA-binding modulation-enhancing agent is not endogenous to said cell; and (ii) a second DNA-binding modulation-enhancing agent, wherein said second DNA-binding modulation-enhancing agent is not endogenous to said cell; (2) allowing said first DNA-binding modulation-enhancing agent to bind a first enhancer binding sequence of said target locus; and (3) allowing said second DNA-binding modulation-enhancing agent to bind a second enhancer binding sequence of said target locus, thereby increasing accessibility of said target locus relative to the absence of said first DNA-binding modulation-enhancing agent or said second DNA-binding modulation-enhancing agent.

Clause 77. The method of clause 76, wherein said introducing a first DNA-binding modulation-enhancing agent comprises introducing a vector encoding said first DNA-binding modulation-enhancing agent.

Clause 78. The method of clause 76, wherein said introducing a first DNA-binding modulation-enhancing agent comprises introducing a mRNA encoding said first DNA-binding modulation-enhancing agent.

Clause 79. The method of clause 76, wherein said introducing a first DNA-binding modulation-enhancing agent comprises introducing a first DNA binding protein or a first DNA binding nucleic acid.

Clause 80. The method of clause 76, wherein said introducing a second DNA-binding modulation-enhancing agent comprises introducing a vector encoding said second DNA-binding modulation-enhancing agent.

Clause 81. The method of clause 76, wherein said introducing a second DNA-binding modulation-enhancing agent comprises introducing a mRNA encoding said second DNA-binding modulation-enhancing agent.

Clause 82. The method of clause 76, wherein said introducing a second DNA-binding modulation-enhancing agent comprises introducing a second DNA binding protein or a second DNA binding nucleic acid.

Clause 83. The method of clause 76, wherein the rate of homologous recombination at said target locus is increased relative to the absence of said first DNA-binding modulation-enhancing agent.

Clause 84. The method of clause 76, wherein said first DNA-binding modulation-enhancing agent is a first DNA binding protein or a first DNA binding nucleic acid.

Clause 85. The method of clause 76, wherein said first DNA-binding modulation-enhancing agent is a first transcription activator-like (TAL) effector protein or a first truncated guide RNA (gRNA).

Clause 86. The method of clause 76, wherein said second DNA-binding modulation-enhancing agent is a second DNA binding protein or a second DNA binding nucleic acid.

Clause 87. The method of clause 76, wherein said second DNA-binding modulation-enhancing agent is a TAL effector protein or a truncated gRNA.

Clause 88. The method of clause 76, wherein said first DNA-binding modulation-enhancing agent is a first TAL effector protein and said second DNA-binding modulation-enhancing agent is a second TAL effector protein.

Clause 89. The method of clause 76, wherein said first DNA-binding modulation-enhancing agent is a TAL effector protein and said second DNA-binding modulation-enhancing agent is a truncated gRNA.

Clause 90. The method of clause 76, wherein said first DNA-binding modulation-enhancing agent is a first truncated gRNA and said second DNA-binding modulation-enhancing agent is a second truncated gRNA.

Clause 91. The method of clause 76, wherein said first DNA-binding modulation-enhancing agent is a truncated gRNA and said second DNA-binding modulation-enhancing agent is a TAL effector protein.

Clause 92. The method of clause 76, wherein said first enhancer binding sequence has the sequence of SEQ ID NO:26, SEQ ID NO:28, SEQ ID NO:30, SEQ ID NO:32, SEQ ID NO:34, SEQ ID NO:36, SEQ ID NO:38, or SEQ ID NO:40.

Clause 93. The method of clause 76, wherein said second enhancer binding sequence has the sequence of SEQ ID NO:27, SEQ ID NO:29, SEQ ID NO:31, SEQ ID NO:33, SEQ ID NO:35, SEQ ID NO:37, SEQ ID NO:39, or SEQ ID NO:41.

Clause 94. A method of displacing chromatin of a target locus in a cell, said method comprising: (1) introducing into a cell comprising a nucleic acid encoding a target locus: (i) a first DNA-binding modulation-enhancing agent, wherein said first DNA-binding modulation-enhancing agent is not endogenous to said cell; and (ii) a second DNA-binding modulation-enhancing agent, wherein said second DNA-binding modulation-enhancing agent is not endogenous to said cell; (2) allowing said first DNA-binding modulation-enhancing agent to bind a first enhancer binding sequence of said target locus; and (3) allowing said second DNA-binding modulation-enhancing agent to bind a second enhancer binding sequence of said target locus, thereby displacing chromatin of said target locus.

Clause 95. The method of clause 94, wherein said introducing a first DNA-binding modulation-enhancing agent comprises introducing a vector encoding said first DNA-binding modulation-enhancing agent.

Clause 96. The method of clause 94, wherein said introducing a first DNA-binding modulation-enhancing agent comprises introducing a mRNA encoding said first DNA-binding modulation-enhancing agent.

Clause 97. The method of clause 94, wherein said introducing a first DNA-binding modulation-enhancing agent comprises introducing a first DNA binding protein or a first DNA binding nucleic acid.

Clause 98. The method of clause 94, wherein said introducing a second DNA-binding modulation-enhancing agent comprises introducing a vector encoding said second DNA-binding modulation-enhancing agent.

Clause 99. The method of clause 94, wherein said introducing a second DNA-binding modulation-enhancing agent comprises introducing a mRNA encoding said second DNA-binding modulation-enhancing agent.

Clause 100. The method of clause 94, wherein said introducing a second DNA-binding modulation-enhancing agent comprises introducing a second DNA binding protein or a second DNA binding nucleic acid.

Clause 101. The method of clause 94, wherein the rate of homologous recombination at said target locus is increased relative to the absence of said first DNA-binding modulation-enhancing agent.

Clause 102. The method of clause 94, wherein said first DNA-binding modulation-enhancing agent is a first DNA binding protein or a first DNA binding nucleic acid.

Clause 103. The method of clause 94, wherein said first DNA-binding modulation-enhancing agent is a first transcription activator-like (TAL) effector protein or a first truncated guide RNA (gRNA).

Clause 104. The method of clause 94, wherein said second DNA-binding modulation-enhancing agent is a second DNA binding protein or a second DNA binding nucleic acid.

Clause 105. The method of clause 94, wherein said second DNA-binding modulation-enhancing agent is a TAL effector protein or a truncated gRNA.

Clause 106. The method of clause 94, wherein said first DNA-binding modulation-enhancing agent is a first TAL effector protein and said second DNA-binding modulation-enhancing agent is a second TAL effector protein.

Clause 107. The method of clause 94, wherein said first DNA-binding modulation-enhancing agent is a TAL effector protein and said second DNA-binding modulation-enhancing agent is a truncated gRNA.

Clause 108. The method of clause 94, wherein said first DNA-binding modulation-enhancing agent is a first truncated gRNA and said second DNA-binding modulation-enhancing agent is a second truncated gRNA.

Clause 109. The method of clause 94, wherein said first DNA-binding modulation-enhancing agent is a truncated gRNA and said second DNA-binding modulation-enhancing agent is a TAL effector protein.

Clause 110. The method of clause 94, wherein said first enhancer binding sequence has the sequence of SEQ ID NO:26, SEQ ID NO:28, SEQ ID NO:30, SEQ ID NO:32, SEQ ID NO:34, SEQ ID NO:36, SEQ ID NO:38, or SEQ ID NO:40.

Clause 111. The method of clause 94, wherein said second enhancer binding sequence has the sequence of SEQ ID NO:27, SEQ ID NO:29, SEQ ID NO:31, SEQ ID NO:33, SEQ ID NO:35, SEQ ID NO:37, SEQ ID NO:39, or SEQ ID NO:41.

Clause 112. A method of restructuring chromatin of a target locus in a cell, said method comprising: (1) introducing into a cell comprising a nucleic acid encoding a target locus: (i) a first DNA-binding modulation-enhancing agent, wherein said first DNA-binding modulation-enhancing agent is not endogenous to said cell; and (ii) a second DNA-binding modulation-enhancing agent, wherein said second DNA-binding modulation-enhancing agent is not endogenous to said cell; (2) allowing said first DNA-binding modulation-enhancing agent to bind a first enhancer binding sequence of said target locus; and (3) allowing said second DNA-binding modulation-enhancing agent to bind a second enhancer binding sequence of said target locus, thereby restructuring chromatin of said target locus.

Clause 113. The method of clause 112, wherein said introducing a first DNA-binding modulation-enhancing agent comprises introducing a vector encoding said first DNA-binding modulation-enhancing agent.

Clause 114. The method of clause 112, wherein said introducing a first DNA-binding modulation-enhancing agent comprises introducing a mRNA encoding said first DNA-binding modulation-enhancing agent.

Clause 115. The method of clause 112, wherein said introducing a first DNA-binding modulation-enhancing agent comprises introducing a first DNA binding protein or a first DNA binding nucleic acid.

Clause 116. The method of clause 112, wherein said introducing a second DNA-binding modulation-enhancing agent comprises introducing a vector encoding said second DNA-binding modulation-enhancing agent.

Clause 117. The method of clause 112, wherein said introducing a second DNA-binding modulation-enhancing agent comprises introducing a mRNA encoding said second DNA-binding modulation-enhancing agent.

Clause 118. The method of clause 112, wherein said introducing a second DNA-binding modulation-enhancing agent comprises introducing a second DNA binding protein or a second DNA binding nucleic acid.

Clause 119. The method of clause 112, wherein the rate of homologous recombination at said target locus is increased relative to the absence of said first DNA-binding modulation-enhancing agent.

Clause 120. The method of clause 112, wherein said first DNA-binding modulation-enhancing agent is a first DNA binding protein or a first DNA binding nucleic acid.

Clause 121. The method of clause 112, wherein said first DNA-binding modulation-enhancing agent is a first transcription activator-like (TAL) effector protein or a first truncated guide RNA (gRNA).

Clause 122. The method of clause 112, wherein said second DNA-binding modulation-enhancing agent is a second DNA binding protein or a second DNA binding nucleic acid.

Clause 123. The method of clause 112, wherein said second DNA-binding modulation-enhancing agent is a TAL effector protein or a truncated gRNA.

Clause 124. The method of clause 112, wherein said first DNA-binding modulation-enhancing agent is a first TAL effector protein and said second DNA-binding modulation-enhancing agent is a second TAL effector protein.

Clause 125. The method of clause 112, wherein said first DNA-binding modulation-enhancing agent is a TAL effector protein and said second DNA-binding modulation-enhancing agent is a truncated gRNA.

Clause 126. The method of clause 112, wherein said first DNA-binding modulation-enhancing agent is a first truncated gRNA and said second DNA-binding modulation-enhancing agent is a second truncated gRNA.

Clause 127. The method of clause 112, wherein said first DNA-binding modulation-enhancing agent is a truncated gRNA and said second DNA-binding modulation-enhancing agent is a TAL effector protein.

Clause 128. A method of enhancing activity of a modulating protein or a modulating complex at a target locus in a cell, said method comprising: (1) introducing into a cell comprising a nucleic acid encoding a target locus: (i) a first modulating protein or a first modulating complex capable of binding a modulator binding sequence of said target locus, wherein said modulator binding sequence comprises a modulation site; and (ii) a first DNA-binding modulation-enhancing agent capable of binding a first enhancer binding sequence of said target locus; and (2) allowing said first DNA-binding modulation-enhancing agent to bind said first enhancer binding sequence, thereby enhancing activity of said first modulating protein or said first modulating complex at a target locus in a cell.

Clause 129. The method of clause 128, further comprising introducing a second DNA-binding modulation-enhancing agent capable of binding a second enhancer binding sequence of said target locus.

Clause 130. The method of clause 128, wherein said introducing a first DNA-binding modulation-enhancing agent comprises introducing a vector encoding said first DNA-binding modulation-enhancing agent.

Clause 131. The method of clause 128, wherein said introducing a first DNA-binding modulation-enhancing agent comprises introducing a mRNA encoding said first DNA-binding modulation-enhancing agent.

Clause 132. The method of clause 128, wherein said introducing a first DNA-binding modulation-enhancing agent comprises introducing a first DNA binding protein or a first DNA binding nucleic acid.

Clause 133. The method of clause 129, wherein said introducing a second DNA-binding modulation-enhancing agent comprises introducing a vector encoding said second DNA-binding modulation-enhancing agent.

Clause 134. The method of clause 129, wherein said introducing a second DNA-binding modulation-enhancing agent comprises introducing a mRNA encoding said second DNA-binding modulation-enhancing agent.

Clause 135. The method of clause 129, wherein said introducing a second DNA-binding modulation-enhancing agent comprises introducing a second DNA binding protein or a second DNA binding nucleic acid.

Clause 136. The method of clause 128, wherein said first modulating protein or said first modulating complex is not endogenous to said cell.

Clause 137. The method of clause 128, wherein the rate of homologous recombination at said target locus is increased relative to the absence of said first DNA-binding modulation-enhancing agent.

Clause 138. The method of clause 129, wherein said second enhancer binding sequence is linked to said first enhancer binding sequence by said modulator binding sequence.

Clause 139. The method of clause 128, further comprising introducing a second modulating protein or a second modulating complex capable of binding said modulator binding sequence.

Clause 140. The method of clause 128, wherein said introducing a first modulating protein comprises introducing a vector encoding said first modulating protein.

Clause 141. The method of clause 128, wherein said introducing a first modulating protein comprises introducing a mRNA encoding said first modulating protein.

Clause 142. The method of clause 128, wherein said introducing a first modulating protein comprises introducing a first modulating protein.

Clause 143. The method of clause 128, wherein said introducing a first modulating complex comprises introducing a vector encoding said first modulating complex.

Clause 144. The method of clause 128, wherein said introducing a first modulating complex comprises introducing a mRNA encoding said first modulating complex.

Clause 145. The method of clause 128, wherein said introducing a first modulating complex comprises introducing a first modulating complex.

Clause 146. The method of clause 139, wherein said introducing a second modulating protein comprises introducing a vector encoding said second modulating protein.

Clause 147. The method of clause 139, wherein said introducing a second modulating protein comprises introducing a mRNA encoding said second modulating protein.

Clause 148. The method of clause 139, wherein said introducing a second modulating protein comprises introducing a second modulating protein.

Clause 149. The method of clause 139, wherein said introducing a second modulating complex comprises introducing a vector encoding said second modulating complex.

Clause 150. The method of clause 139, wherein said introducing a second modulating complex comprises introducing a mRNA encoding said second modulating complex.

Clause 151. The method of clause 139, wherein said introducing a second modulating complex comprises introducing a second modulating complex.

Clause 152. The method of clause 139, wherein said first modulating protein or said second modulating protein comprises a DNA binding protein or a DNA modulating enzyme.

Clause 153. The method of clause 152, wherein said DNA binding protein is a transcriptional repressor or a transcriptional activator.

Clause 154. The method of clause 152, wherein said DNA modulating enzyme is a nuclease, a deaminase, a methylase or a demethylase.

Clause 155. The method of clause 128, wherein said first modulating protein or said second modulating protein comprises a histone modulating enzyme.

Clause 156. The method of clause 155, wherein said histone modulating enzyme is a deacetylase or an acetylase.

Clause 157. The method of clause 128, wherein said first modulating protein is a first DNA binding protein nuclease conjugate.

Clause 158. The method of clause 139, wherein said second modulating protein is a second DNA binding protein nuclease conjugate.

Clause 159. The method of clause 158, wherein said first DNA binding protein nuclease conjugate comprises a first nuclease and said second DNA binding protein nuclease conjugate comprises a second nuclease.

Clause 160. The method of clause 159, wherein said first nuclease and said second nuclease form a dimer.

Clause 161. The method of clause 159, wherein said first nuclease and said second nuclease are independently a transcription activator-like effector nuclease (TALEN).

Clause 162. The method of clause 159, wherein said first DNA binding protein nuclease conjugate comprises a first transcription activator-like (TAL) effector domain operably linked to a first nuclease (TALEN).

Clause 163. The method of clause 159, wherein said first DNA binding protein nuclease conjugate comprises a first TAL effector domain operably linked to a first FokI nuclease.

Clause 164. The method of clause 159, wherein said second DNA binding protein nuclease conjugate comprises a second TAL effector domain operably linked to a second nuclease (TALEN).

Clause 165. The method of clause 159, wherein said second DNA binding protein nuclease conjugate comprises a second TAL effector domain operably linked to a second FokI nuclease.

Clause 166. The method of clause 159, wherein said first DNA binding protein nuclease conjugate comprises a first Zinc finger nuclease.

Clause 167. The method of clause 159, wherein said second DNA binding protein nuclease conjugate comprises a first Zinc finger nuclease.

Clause 168. The method of clause 128, wherein said first modulating complex is a first ribonucleoprotein complex.

Clause 169. The method of clause 139, wherein said second modulating complex is a second ribonucleoprotein complex.

Clause 170. The method of clause 168, wherein said first ribonucleoprotein complex comprises a CRISPR associated protein 9 (Cas9) domain bound to a gRNA or an Argonaute protein domain bound to a guide DNA (gDNA).

Clause 171. The method of clause 169, wherein said second ribonucleoprotein complex comprises a CRISPR associated protein 9 (Cas9) domain bound to a gRNA or an Argonaute protein domain bound to a guide DNA (gDNA).

Clause 172. The method of clause 139, wherein said first modulating protein, said first modulating complex, said second modulating protein or said second modulating complex is not endogenous to said cell.

Clause 173. The method of clause 139, wherein said first modulating protein and said second modulating protein are not endogenous to said cell.

Clause 174. The method of clause 139, wherein said first modulating complex and said second modulating complex are not endogenous to said cell.

Clause 175. The method of clause 168, wherein said first DNA-binding modulation-enhancing agent or said second DNA-binding modulation-enhancing agent is not endogenous to said cell.

Clause 176. The method of clause 129, wherein said first DNA-binding modulation-enhancing agent and said second DNA-binding modulation-enhancing agent are not endogenous to said cell.

Clause 177. The method of clause 128, wherein said first DNA-binding modulation-enhancing agent is a first DNA binding protein or a first DNA binding nucleic acid.

Clause 178. The method of clause 128, wherein said first DNA-binding modulation-enhancing agent is a first transcription activator-like (TAL) effector protein or a first truncated guide RNA (gRNA).

Clause 179. The method of clause 139, wherein said second DNA-binding modulation-enhancing agent is a second DNA binding protein or a second DNA binding nucleic acid.

Clause 180. The method of clause 129, wherein said second DNA-binding modulation-enhancing agent is a TAL effector protein or a truncated gRNA.

Clause 181. The method of clause 129, wherein said first DNA-binding modulation-enhancing agent is a first TAL effector protein and said second DNA-binding modulation-enhancing agent is a second TAL effector protein.

Clause 182. The method of clause 129, wherein said first DNA-binding modulation-enhancing agent is a TAL effector protein and said second DNA-binding modulation-enhancing agent is a truncated gRNA.

Clause 183. The method of clause 129, wherein said first DNA-binding modulation-enhancing agent is a first truncated gRNA and said second DNA-binding modulation-enhancing agent is a second truncated gRNA.

Clause 184. The method of clause 129, wherein said first DNA-binding modulation-enhancing agent is a truncated gRNA and said second DNA-binding modulation-enhancing agent is a TAL effector protein.

Clause 185. The method of clause 139, wherein said first modulating protein is a first DNA binding nuclease conjugate and said second modulating protein is a second DNA binding nuclease conjugate.

Clause 186. The method of clause 139, wherein said first modulating protein is a DNA binding nuclease conjugate and said second modulating complex is a ribonucleoprotein complex.

Clause 187. The method of clause 139, wherein said first modulating complex is a first ribonucleoprotein complex and said second modulating complex is a second ribonucleoprotein complex.

Clause 188. The method of clause 139, wherein said first modulating complex is a ribonucleoprotein complex and said second modulating protein is a DNA binding nuclease conjugate.

Clause 189. The method of clause 129, wherein said first enhancer binding sequence and/or second enhancer binding sequence are separated from said modulator binding sequence by less than 200 nucleotides, by less than 150 nucleotides, by less than 100 nucleotides, or by less than 50 nucleotides.

Clause 190. The method of clause 129, wherein said first enhancer binding sequence and/or second enhancer binding sequence are separated from said modulator binding sequence by 4 to 30 nucleotides or by 7 to 30 nucleotides.

Clause 191. The method of clause 129, wherein said first enhancer binding sequence and/or second enhancer binding sequence are separated from said modulator binding sequence by 4 nucleotides, by 7 nucleotides, by 12 nucleotides, by 20 nucleotides, or by 30 nucleotides.

Clause 192. The method of clause 129, wherein said first enhancer binding sequence and/or second enhancer binding sequence are separated from said modulator binding sequence by less than 200 nucleotides, by less than 150 nucleotides, by less than 100 nucleotides, or by less than 50 nucleotides.

Clause 193. The method of clause 129, wherein said first enhancer binding sequence and/or said second enhancer binding sequence are separated from said modulation site by 10 to 40 nucleotides.

Clause 194. The method of clause 129, wherein said first enhancer binding sequence and/or said second enhancer binding sequence are separated from said modulation site by 33 nucleotides.

Clause 195. The method of clause 139, wherein said first DNA-binding modulation-enhancing agent or said second DNA-binding modulation-enhancing agent enhance activity of said first modulating protein, said first modulating complex, said second modulating protein or said second modulating complex at said modulation site.

Clause 196. A method of modulating a target locus in a cell, said method comprising: (1) introducing into a cell comprising a nucleic acid encoding a target locus: (i) a first modulating protein or a first modulating complex capable of binding a modulator binding sequence of said target locus, wherein said modulator binding sequence comprises a modulation site; and (ii) a first DNA-binding modulation-enhancing agent capable of binding a first enhancer binding sequence of said target locus; and (2) allowing said first modulating protein or said first modulating complex to modulate said modulation site, thereby modulating said target locus in a cell.

Clause 197. The method of clause 196, further comprising introducing a second DNA-binding modulation-enhancing agent capable of binding a second enhancer binding sequence of said target locus.

Clause 198. The method of clause 196, wherein said introducing a first DNA-binding modulation-enhancing agent comprises introducing into a cell: (1) a vector encoding said first DNA-binding modulation-enhancing agent, (2) a mRNA encoding said first DNA-binding modulation-enhancing agent, or (3) the first DNA-binding modulation-enhancing.

Clause 199. The method of clause 197, wherein said introducing a second DNA-binding modulation-enhancing agent comprises introducing into a cell: (1) a vector encoding said first DNA-binding modulation-enhancing agent, (2) a mRNA encoding said first DNA-binding modulation-enhancing agent, or (3) the first DNA-binding modulation-enhancing.

Clause 200. The method of clause 199, wherein said introducing a second DNA-binding modulation-enhancing agent comprises introducing a mRNA encoding said second DNA-binding modulation-enhancing agent.

Clause 201. The method of clause 197, wherein said introducing a second DNA-binding modulation-enhancing agent comprises introducing a second DNA binding protein or a second DNA binding nucleic acid.

Clause 202. The method of clause 196, wherein said first modulating protein or said first modulating complex is not endogenous to said cell.

Clause 203. The method of clause 196, wherein the rate of homologous recombination at said target locus is increased relative to the absence of said first DNA-binding modulation-enhancing agent.

Clause 204. The method of clause 197, wherein said second enhancer binding sequence is linked to said first enhancer binding sequence by said modulator binding sequence.

Clause 205. The method of clause 196, further comprising introducing a second modulating protein or a second modulating complex capable of binding said modulator binding sequence.

Clause 206. The method of clause 196, wherein said introducing a first modulating protein comprises introducing a vector encoding said first modulating protein.

Clause 207. The method of clause 196, wherein said introducing a first modulating protein comprises introducing a mRNA encoding said first modulating protein.

Clause 208. The method of clause 196, wherein said introducing a first modulating protein comprises introducing a first modulating protein.

Clause 209. The method of clause 196, wherein said introducing a first modulating complex comprises introducing a vector encoding said first modulating complex.

Clause 210. The method of clause 196, wherein said introducing a first modulating complex comprises introducing a mRNA encoding said first modulating complex.

Clause 211. The method of clause 196, wherein said introducing a first modulating complex comprises introducing a first modulating complex.

Clause 212. The method of clause 205, wherein said introducing a second modulating protein comprises introducing a vector encoding said second modulating protein.

Clause 213. The method of clause 205, wherein said introducing a second modulating protein comprises introducing a mRNA encoding said second modulating protein.

Clause 214. The method of clause 205, wherein said introducing a second modulating protein comprises introducing a second modulating protein.

Clause 215. The method of clause 205, wherein said introducing a second modulating complex comprises introducing a vector encoding said second modulating complex.

Clause 216. The method of clause 205, wherein said introducing a second modulating complex comprises introducing a mRNA encoding said second modulating complex.

Clause 217. The method of clause 205, wherein said introducing a second modulating complex comprises introducing a second modulating complex.

Clause 218. The method of clause 205, wherein said first modulating protein or said second modulating protein comprises a DNA binding protein or a DNA modulating enzyme.

Clause 219. The method of clause 218, wherein said DNA binding protein is a transcriptional repressor or a transcriptional activator.

Clause 220. The method of clause 218, wherein said DNA modulating enzyme is a nuclease, a deaminase, a methylase or a demethylase.

Clause 221. The method of clause 205, wherein said first modulating protein or said second modulating protein comprises a histone modulating enzyme.

Clause 222. The method of clause 221, wherein said histone modulating enzyme is a deacetylase or an acetylase.

Clause 223. The method of clause 196, wherein said first modulating protein is a first DNA binding protein nuclease conjugate.

Clause 224. The method of clause 205, wherein said second modulating protein is a second DNA binding protein nuclease conjugate.

Clause 225. The method of clause 224, wherein said first DNA binding protein nuclease conjugate comprises a first nuclease and said second DNA binding protein nuclease conjugate comprises a second nuclease.

Clause 226. The method of clause 225, wherein said first nuclease and said second nuclease form a dimer.

Clause 227. The method of clause 225, wherein said first nuclease and said second nuclease are independently a transcription activator-like effector nuclease (TALEN).

Clause 228. The method of clause 225, wherein said first DNA binding protein nuclease conjugate comprises a first transcription activator-like (TAL) effector domain operably linked to a first nuclease (TALEN).

Clause 229. The method of clause 228, wherein said first DNA binding protein nuclease conjugate comprises a first TAL effector domain operably linked to a first FokI nuclease.

Clause 230. The method of clause 227, wherein said second DNA binding protein nuclease conjugate comprises a second TAL effector domain operably linked to a second nuclease (TALEN).

Clause 231. The method of clause 230, wherein said second DNA binding protein nuclease conjugate comprises a second TAL effector domain operably linked to a second FokI nuclease.

Clause 232. The method of clause 196, wherein said first DNA binding protein nuclease conjugate comprises a first Zinc finger nuclease.

Clause 233. The method of clause 205, wherein said second DNA binding protein nuclease conjugate comprises a first Zinc finger nuclease.

Clause 234. The method of clause 196, wherein said first modulating complex is a first ribonucleoprotein complex.

Clause 235. The method of clause 197, wherein said second modulating complex is a second ribonucleoprotein complex.

Clause 236. The method of clause 234, wherein said first ribonucleoprotein complex comprises a CRISPR associated protein 9 (Cas9) domain bound to a gRNA or an Argonaute protein domain bound to a guide DNA (gDNA).

Clause 237. The method of clause 235, wherein said second ribonucleoprotein complex comprises a CRISPR associated protein 9 (Cas9) domain bound to a gRNA or an Argonaute protein domain bound to a guide DNA (gDNA).

Clause 238. The method of clause 205, wherein said first modulating protein, said first modulating complex, said second modulating protein or said second modulating complex is not endogenous to said cell.

Clause 239. The method of clause 205, wherein said first modulating protein and said second modulating protein are not endogenous to said cell.

Clause 240. The method of clause 205, wherein said first modulating complex and said second modulating complex are not endogenous to said cell.

Clause 241. The method of clause 197, wherein said first DNA-binding modulation-enhancing agent or said second DNA-binding modulation-enhancing agent is not endogenous to said cell.

Clause 242. The method of clause 197, wherein said first DNA-binding modulation-enhancing agent and said second DNA-binding modulation-enhancing agent are not endogenous to said cell.

Clause 243. The method of clause 196, wherein said first DNA-binding modulation-enhancing agent is a first DNA binding protein or a first DNA binding nucleic acid.

Clause 244. The method of clause 196, wherein said first DNA-binding modulation-enhancing agent is a first transcription activator-like (TAL) effector protein or a first truncated guide RNA (gRNA).

Clause 245. The method of clause 197, wherein said second DNA-binding modulation-enhancing agent is a second DNA binding protein or a second DNA binding nucleic acid.

Clause 246. The method of clause 197, wherein said second DNA-binding modulation-enhancing agent is a TAL effector protein or a truncated gRNA.

Clause 247. The method of clause 197, wherein said first DNA-binding modulation-enhancing agent is a first TAL effector protein and said second DNA-binding modulation-enhancing agent is a second TAL effector protein.

Clause 248. The method of clause 197, wherein said first DNA-binding modulation-enhancing agent is a TAL effector protein and said second DNA-binding modulation-enhancing agent is a truncated gRNA.

Clause 249. The method of clause 197, wherein said first DNA-binding modulation-enhancing agent is a first truncated gRNA and said second DNA-binding modulation-enhancing agent is a second truncated gRNA.

Clause 250. The method of clause 197, wherein said first DNA-binding modulation-enhancing agent is a truncated gRNA and said second DNA-binding modulation-enhancing agent is a TAL effector protein.

Clause 251. The method of clause 205, wherein said first modulating protein is a first DNA binding protein nuclease conjugate and said second modulating protein is a second DNA binding protein nuclease conjugate.

Clause 252. The method of clause 205, wherein said first modulating protein is a DNA binding nuclease conjugate and said second modulating complex is a ribonucleoprotein complex.

Clause 253. The method of clause 252, wherein said first modulating complex is a first ribonucleoprotein complex and said second modulating complex is a second ribonucleoprotein complex.

Clause 254. The method of clause 205, wherein said first modulating complex is a ribonucleoprotein complex and said second modulating protein is a DNA binding protein nuclease conjugate.

Clause 255. The method of clause 196, wherein said first enhancer binding sequence is separated from said modulator binding sequence by less than 200 nucleotides, by less than 150, by less than 100 nucleotides, or by less than 50 nucleotides.

Clause 256. The method of clause 196, wherein said first enhancer binding sequence is separated from said modulator binding sequence by 4 to 30 nucleotides or by 7 to 30 nucleotides.

Clause 257. The method of clause 196, wherein said first enhancer binding sequence is separated from said modulator binding sequence by 4 nucleotides, by 7 nucleotides, by 12 nucleotides, by 20 nucleotides, or by 30 nucleotides.

Clause 258. The method of clause 197, wherein said second enhancer binding sequence is separated from said modulator binding sequence by less than 200 nucleotides, by less than 150 nucleotides, by less than 100 nucleotides, or by less than 50 nucleotides.

Clause 259. The method of clause 197, wherein said second enhancer binding sequence is separated from said modulator binding sequence by 4 to 30 nucleotides or by 7 to 30 nucleotides.

Clause 260. The method of clause 197, wherein said second enhancer binding sequence is separated from said modulator binding sequence by 4 nucleotides, by 7 nucleotides, by 12 nucleotides, by 20 nucleotides, by 30 nucleotides.

Clause 261. The method of clause 197, wherein said first enhancer binding sequence or said second enhancer binding sequence is separated from said modulation site by 10 to 40 nucleotides.

Clause 262. The method of clause 197, wherein said first enhancer binding sequence or said second enhancer binding sequence is separated from said modulation site by 33 nucleotides.

Clause 263. The method of clause 197, wherein said first DNA-binding modulation-enhancing agent or said second DNA-binding modulation-enhancing agent enhance activity of said first modulating protein, said first modulating complex, said second modulating protein or said second modulating complex at said modulation site.

Clause 264. A cell comprising a nucleic acid encoding a target locus modulating complex, said complex comprising: (i) a target locus comprising a first enhancer binding sequence and a modulator binding sequence comprising a modulation site; (ii) a first modulating protein or a first modulating complex bound to said modulator binding sequence; and (iii) a first DNA-binding modulation-enhancing agent bound to said first enhancer binding sequence.

Clause 265. The cell of clause 264, wherein said target locus further comprises a second enhancer binding sequence linked to said first enhancer binding sequence by said modulator binding sequence.

Clause 266. The cell of clause 264, comprising a second DNA-binding modulation-enhancing agent bound to said second enhancer binding sequence.

Clause 267. A cell comprising a nucleic acid encoding a target locus complex, said complex comprising: (i) a target locus comprising a first enhancer binding sequence; and (ii) a first DNA-binding modulation-enhancing agent bound to said first enhancer binding sequence, wherein said first DNA-binding modulation-enhancing agent is not endogenous to said cell and wherein said first DNA-binding modulation-enhancing agent is capable of increasing accessibility of said target locus relative to the absence of said first DNA-binding modulation-enhancing agent.

Clause 268. A cell comprising a nucleic acid encoding a target locus complex, said complex comprising: (1) a target locus comprising: (i) a first enhancer binding sequence; and (ii) a second enhancer binding sequence; (2) a first DNA-binding modulation-enhancing agent bound to said first enhancer binding sequence of said target locus, wherein said first DNA-binding modulation-enhancing agent is not endogenous to said cell; and (3) a second DNA-binding modulation-enhancing agent bound to said second enhancer binding sequence of said target locus, wherein said second DNA-binding modulation-enhancing agent is not endogenous to said cell, wherein said first DNA-binding modulation-enhancing agent and said second DNA-binding modulation-enhancing agent are capable of increasing accessibility of said target locus relative to the absence of said first DNA-binding modulation-enhancing agent and said second DNA-binding modulation-enhancing agent.

Clause 269. A kit comprising: (i) a first modulating protein or a first modulating complex; and (ii) a first DNA-binding modulation-enhancing agent.

Clause 270. A method for altering an endogenous nucleic acid molecule present within a cell, the method comprising introducing a donor DNA molecule into the cell, wherein the donor DNA molecule is operably linked to one or more intracellular targeting moiety capable of localizing the donor DNA molecule to a location in the cell where the endogenous nucleic acid molecule is located.

Clause 271. The method of clause 270, wherein the location in the cell where the endogenous nucleic acid molecule is located is in the nucleus, mitochondria, or chloroplasts.

Clause 272. The method of clause 270, wherein the one or more intracellular target moiety is a nuclear localization signal.

Clause 273. The method of clause 270, wherein the donor DNA molecule is from about 25 to about 8,000 nucleotides in length.

Clause 274. The method of clause 270, wherein the donor DNA molecule is single-stranded, double-stranded, or partially double-stranded.

Clause 275. The method of clause 270, wherein the donor DNA molecule has one or more nuclease resistant groups within 50 nucleotides of at least one terminus.

Clause 276. The method of clause 275, wherein the nuclease resistant groups are phosphorothioate groups, amine groups, 2'-O-methyl nucleotides, 2'-deoxy-2'-fluoro nucleotides, 2'-deoxy nucleotides, 5-C-methyl nucleotides, or a combination thereof.

Clause 277. The method of clause 276, wherein there are two phosphorothioate groups are located within 50 nucleotides of at least one terminus.

Clause 278. The method of clause 270, wherein the donor DNA molecule contains a positive selectable marker and a negative selectable marker.

Clause 279. The method of clause 278, wherein the negative selectable marker is Herpes simplex virus thymidine kinase.

Clause 280. The method of clause 270, wherein the donor DNA molecule has two regions of sequence complementarity with a target locus present in the cell.

Clause 281. The method of clause 278, wherein the positive selectable marker is located between the two regions of sequence complementarity of the donor DNA molecule.

Clause 282. The method of clause 278, wherein the negative selectable marker is not located between the two regions of sequence complementarity of the donor DNA molecule.

Clause 283. The method of clause 270, wherein the cell is contacted with one or more of the following: (1) one or more nucleic acid cutting entity, (2) one or more nucleic acid molecule encoding at least one component of a nucleic acid cutting entity, (3) one or more DNA-binding modulation-enhancing agent, (4) one or more nucleic acid molecule encoding at least one component of a DNA-binding modulation-enhancing agent, or (5) one or more non-homologous end joining (NHEJ) inhibitor.

Clause 284. The method of clause 283, wherein the one or more non-homologous end joining (NHEJ) inhibitor is a DNA-dependent protein kinase inhibitor.

Clause 285. The method of clause 284, wherein at least one of the one or more non-homologous end joining (NHEJ) inhibitors is selected from the groups consisting of: (1) Nu7206, (2) Nu7441, (3) Ku-0060648, (4) DMNB, (5) ETP 45658, (6) LTURM 34, and (7) Pl 103 hydrochloride.

Clause 286. The method of clause 283, wherein at least one of the one or more nucleic acid cutting entities is selected from the group consisting of: (1) a zinc finger nuclease, (2) a TAL effector nuclease, and (3) a CRISPR complex.

Clause 287. The method of clause 283, wherein at least one of the one or more DNA-binding modulation-enhancing agent is selected from the group consisting of: (1) a zinc finger protein (e.g., a zinc finger protein with no heterologous nuclease domain), (2) a TAL effector protein (e.g., a TALE protein with no heterologous nuclease domain), and (3) a CRISPR complex (e.g., a CRISPR complex comprising a dCas9 protein).

Clause 288. The method of clause 287, wherein at least one of the one or more DNA-binding modulation-enhancing agents is designed to bind within 50 nucleotides of the target locus.

Clause 289. A methods for performing homologous recombination in a eukaryotic cell, the method comprising contacting the cell with: (1) a donor DNA molecule and (2) (i) a nucleic acid cutting entity, (ii) nucleic acid encoding a nucleic acid cutting entity, or (iii) at least one component of a nucleic acid cutting entity and nucleic acid encoding at least one components of a nucleic acid cutting entity, wherein the donor DNA molecule is bound to an intracellular targeting moiety capable of localizing the donor DNA molecule to a location in the cell where the endogenous nucleic acid molecule is located.

Clause 290. The method of clause 289, further contacting the cell with one or more of the following: (1) one or more non-homologous end joining (NHEJ) inhibitor, (2) one or more DNA-binding modulation-enhancing agent, (3) one or more nucleic acid encoding a DNA-binding modulation-enhancing agent, and (4) at least one component of one or more a DNA-binding modulation-enhancing agent and nucleic acid encoding at least one components of one or more a DNA-binding modulation-enhancing agent.

Clause 291. A composition comprising a DNA molecule, wherein the DNA molecule is covalently linked to one or more intracellular targeting moiety and wherein the DNA molecule is from about 25 nucleotides to about 8,000 nucleotides in length.

Clause 292. The composition of clause 291, where the DNA molecule is a donor DNA molecule.

Clause 293. The composition of clause 291, wherein the one or more intracellular targeting moiety is a nuclear localization signal.

Clause 294. The composition of clause 291, wherein two or more intracellular targeting moieties are covalently linked to the DNA molecule.

Clause 295. The composition of clause 291, wherein the one or more intracellular targeting moiety is selected from the group consisting of: (1) a nuclear localization signal, (2) a chloroplast targeting signal, and (3) a mitochondrial targeting signal.

Clause 296. A Cas9 protein comprising two or more bipartite nuclear localization signals.

Clause 297. The Cas9 protein of clause 296, wherein the two or more bipartite nuclear localization signals are located within twenty amino acids of at least one terminus.

Clause 298. The Cas9 protein of clause 296, wherein the two or more bipartite nuclear localization signals are individually located within twenty amino acids of the N-terminus and the C-terminus of the protein.

Clause 299. The Cas9 protein of clause 296, wherein the two or more bipartite nuclear localization signals comprise different amino acid sequences.

Clause 300. The Cas9 protein of clause 296 further comprising at least one monopartite nuclear localization signal.

Clause 301. The Cas9 protein of clause 296 further comprising an affinity tag.

Clause 302. The Cas9 protein of clause 296, wherein at least one of the nuclear localization signals has an amino acid sequence selected from the group consisting of: (A) KRTAD GSEFE SPKKK RKVE (SEQ ID NO: 48), (B) KRTAD GSEFE SPKKA RKVE (SEQ ID NO: 49), (C) KRTAD GSEFE SPKKK AKVE (SEQ ID NO: 50), (D) KRPAA TKKAG QAKKK K (SEQ ID NO: 51), and (E) KRTAD GSEFEP AAKRV KLDE (SEQ ID NO: 52)

Clause 303. The Cas9 protein of clause 296, wherein at least one of the nuclear localization signals has an amino acid sequence selected from the group consisting of: (A) $KRX_{(5\ 15)}KKN_1N_2KV$ (SEQ ID NO: 53), (B) $KRX_{(5-15)}K(K/R)(K/R)_{1-2}$ (SEQ ID NO: 54), (C) $KRX_{(5-15)}K(K/R)X(K/R)_{1\ 2}$ (SEQ ID NO: 55) wherein X is an amino acid sequence from 5 to 15 amino acids in length and wherein $N_1$ is L or A, and wherein $N_2$ is L, A, or R.

Clause 304. The Cas9 protein of clause 296, comprising the amino acid sequence shown in FIG. 42.

Clause 305. A TALE protein comprising amino acids amino acids 811-830 of FIG. 46, wherein the amino acids at positions 815-816 and 824-825 may be Gly-Ser or Gly-Gly.

Clause 306. The TALE protein of clause 305 comprising amino acids amino acids 810-1029 of FIG. 46, wherein the amino acids at positions 1022-1023 may be Gly-Ser or Gly-Gly.

Clause 307. The TALE protein of clause 305 comprising amino acids amino acids 752-1021 of FIG. 46.

Clause 308. A TALE protein comprising amino acids amino acids 20-165 of FIG. 47, wherein the amino acids at positions 28-29 may be Gly-Ser or Gly-Gly and wherein the amino acids at positions 108-110 and 823-824 may be Arg-Gly-Ala or Gln-Trp-Ser.

Clause 309. A TALE protein comprising amino acids amino acids 821-840 of FIG. 47, wherein the amino acids at positions 827-828 may be Gly-Ser or Gly-Gly.

Clause 310. The TALE protein of clause 308, comprising amino acids corresponding to FIG. 46.

Clause 311. The TALE protein of clause 308, comprising a repeat region comprising from 4 to 25 repeat units.

Clause 312. A method for engineering intracellular nucleic acid in a cell, the method comprising introducing into the cell the TALE protein of clause 306 or nucleic acid encoding the TALE protein of clause 2, wherein the TALE protein is designed to bind to a target locus within the cell.

Clause 313. The method of clause 312, further comprising introducing a donor nucleic acid molecule into the cell, wherein the donor nucleic acid molecule has one or more region of sequence homology to nucleic acid within 50 nucleotides of the target locus.

Clause 314. A method for homologous recombination of an intracellular nucleic acid molecule at a cleavage site within a population of cells, the method comprising: (a) generating a double-stranded break in the intracellular nucleic acid molecule at the cleavage site to produce a cleaved nucleic acid molecule, and (b) contacting the cleaved nucleic acid molecule with a donor nucleic acid molecule, wherein the donor nucleic acid molecule has at least ten nucleotides or base pairs of homology to nucleic acid located within 100 base pairs of each side of the cleavage site, wherein at least 95% of the cells within the population of cells undergo homology directed repair with the donor nucleic acid molecule at the cleavage site.

Clause 315. The method of clause 314, wherein the donor nucleic acid molecule contains a selection marker or a reporter gene that is operably linked to a promoter present in the intracellular nucleic acid molecule after homology directed repair.

Clause 316. The method of clause 314, wherein the donor nucleic acid molecule is linked to one or more nuclear localization signal that allow for the donor nucleic acid molecule the donor nucleic acid molecule to localize to the nucleus of cells of the population of cells.

Clause 317. The method of clause 314, the population of cell is contacted with one or more of the following: (1) one or more nucleic acid cutting entity, (2) one or more nucleic acid molecule encoding at least one component of a nucleic acid cutting entity, (3) one or more DNA-binding modulation-enhancing agent, (4) one or more nucleic acid molecule encoding at least one component of a DNA-binding modulation-enhancing agent, or (5) one or more non-homologous end joining (NHEJ) inhibitor.

Clause 318. The method of clause 314, wherein the donor nucleic acid molecule is single-stranded, double-stranded, or partially double-stranded.

Clause 319. The method of clause 314, wherein the population of cells is contacted with one or more nucleic acid cutting entity or one of more nucleic acid molecule encoding one or more nucleic acid cutting entity and then the population of cells is contacted with one or more donor nucleic acid molecule.

Clause 320. The method of clause 319, wherein the population of cells is contacted with one or more donor nucleic acid molecule from 5 to 60 minutes after the population of cells is contacted with the one or more nucleic acid cutting entity or one of more nucleic acid molecule encoding one or more nucleic acid cutting entity.

Clause 321. A method of enhancing activity of a modulating protein or a modulating complex at a target locus in a cell, the method comprising: (1) introducing into a cell comprising a nucleic acid encoding the target locus: (i) a first modulating protein or a first modulating complex capable of binding a first modulator binding sequence of the target locus, wherein the first modulator binding sequence comprises a modulation site; and (ii) a first DNA-binding modulation-enhancing agent capable of binding a first enhancer binding sequence of the target locus; and (2) allowing the first DNA-binding modulation-enhancing agent to bind the first enhancer binding sequence, thereby enhancing activity of the first modulating protein or the first modulating complex at a target locus in a cell.

Clause 322. The method of clause 321, wherein the introducing a first DNA-binding modulation-enhancing agent comprises introducing a vector encoding the first DNA-binding modulation-enhancing agent.

Clause 323. The method of clause 321, wherein the introducing a first DNA-binding modulation-enhancing agent comprises introducing a mRNA encoding the first DNA-binding modulation-enhancing agent.

Clause 324. The method of clause 321, wherein the first DNA-binding modulation-enhancing agent is a first transcription activator-like (TAL) effector.

Clause 325. The method of clause 321, further comprising. (1) introducing into the cell a second DNA-binding modulation-enhancing agent; and (2) allowing the second DNA-binding modulation-enhancing agent to bind a second enhancer binding sequence of the target locus.

Clause 326. The method of clause 324, wherein the first enhancer binding sequence and the second enhancer binding sequence are located within 180 base pairs of each other.

Clause 327. The method of clause 324, wherein the first enhancer binding sequence and the second enhancer binding sequence are located on opposite sides of the modulator binding sequence.

Clause 328. The method of clause 321, wherein the first modulation protein is a DNA binding-nuclease fusion protein.

Clause 329. The method of clause 328, wherein the DNA binding-nuclease fusion protein is a TALE-FokI fusion protein.

Clause 330. The method of clause 321, wherein the first modulation complex is a CRISPR/gRNA complex with nuclease activity.

Clause 331. The method of clause 330, wherein the first modulation complex is a Cas9/gRNA complex with nuclease activity.

Clause 332. The method of clause 321, further comprising introducing into the cell a second modulating protein or a second modulating complex capable of binding a second modulator binding sequence of the target locus, wherein the second modulator binding sequence comprises the modulation site.

Clause 333. The method of clause 332, wherein the first modulation protein is a DNA binding-nuclease fusion protein.

Clause 334. The method of clause 333, wherein the DNA binding-nuclease fusion protein is a TALE-FokI fusion protein.

Clause 335. The method of clause 334, wherein the second modulation complex is a CRISPR/gRNA complex with nuclease activity.

Clause 336. The method of clause 335, wherein the second modulation complex is a Cas9/gRNA complex with nuclease activity.

---

What is claimed is:

1. A method of enhancing activity of a modulating protein or a modulating complex at a target locus in a cell, the method comprising:
   (1) introducing into a cell comprising a nucleic acid encoding the target locus:
      (i) a first modulating protein or a first modulating complex capable of binding a first modulator binding sequence of the target locus, wherein the first modulator binding sequence comprises a modulation site; wherein the activity of the first modulating protein or the first modulating complex is a nuclease or other enzymatic activity, and
      (ii) a first DNA-binding modulation-enhancing agent without nuclease or other enzymatic activity comprising a nuclear localization signal and a DNA-binding domain that is capable of binding a first enhancer binding sequence of the target locus; and
   (2) allowing the first DNA-binding modulation-enhancing agent to bind the first enhancer binding sequence, thereby enhancing activity of the first modulating protein or the first modulating complex at the target locus in the cell,
   wherein the DNA-binding modulation-enhancing agent is not fused with, covalently linked with, or linked by dimerization with the first modulating protein or first modulating complex of (i), a modulating protein, modulating complex, or other DNA-binding agent.

2. The method of claim 1, wherein the introducing of the first DNA-binding modulation-enhancing agent comprises introducing a vector encoding the first DNA-binding modulation-enhancing agent.

3. The method of claim 1, wherein the introducing of the first DNA-binding modulation-enhancing agent comprises introducing an mRNA encoding the first DNA-binding modulation-enhancing agent.

4. The method of claim 1, wherein the DNA-binding domain of the first DNA-binding modulation-enhancing agent is a first transcription activator-like (TAL) effector.

5. The method of claim 1, further comprising:
   (1) introducing into the cell a second DNA-binding modulation-enhancing agent; and
   (2) allowing the second DNA-binding modulation-enhancing agent to bind a second enhancer binding sequence of the target locus.

6. The method of claim 1, wherein the first modulation protein is a DNA binding-nuclease fusion protein.

7. The method of claim 1, further comprising introducing into the cell a second modulating protein or a second modulating complex capable of binding a second modulator binding sequence of the target locus, wherein the second modulator binding sequence comprises the modulation site.

8. The method of claim 7, wherein the first modulation protein is a DNA binding-nuclease fusion protein.

9. The method of claim 8, wherein the DNA binding-nuclease fusion protein is a TALE-FokI fusion protein.

10. The method of claim 9, wherein the second modulation complex is a CRISPR/gRNA complex with nuclease activity.

11. The method of claim 10, wherein the second modulation complex is a Cas9/gRNA complex with nuclease activity.

12. A method of displacing chromatin of a target locus in a cell, said method comprising:
   (1) introducing into a cell comprising a nucleic acid encoding a target locus:
      (i) a first DNA-binding modulation-enhancing agent, wherein said first DNA-binding modulation-enhancing agent is not endogenous to said cell; and
      (ii) a second DNA-binding modulation-enhancing agent, wherein said second DNA-binding modulation-enhancing agent is not endogenous to said cell;
   (2) allowing said first DNA-binding modulation-enhancing agent to bind a first enhancer binding sequence of said target locus; and
   (3) allowing said second DNA-binding modulation-enhancing agent to bind a second enhancer binding sequence of said target locus, thereby displacing chromatin of said target locus, wherein the DNA-binding modulation-enhancing agents of (i) and (ii) comprise a nuclear localization signal and a DNA-binding domain without nuclease or other enzymatic activity, and wherein the DNA-binding domain of the DNA-binding modulation-enhancing agents of (i) and (ii) are not fused with, covalently linked with, or linked by dimerization to each other, to a modulating protein, to a modulating complex, or to other DNA-binding agents.

* * * * *

SEQUENCE LISTING

```
Sequence total quantity: 143
SEQ ID NO: 1          moltype = DNA   length = 1442
FEATURE               Location/Qualifiers
misc_feature          1..1442
                      note = Description of Unknown: FAK sequence
source                1..1442
                      mol_type = other DNA
                      organism = unidentified
SEQUENCE: 1
ctcgatgtca ttgaccaagc aagactgaaa atggtgagca agggcgagga gctgttcacc   60
ggggtggtgc ccatcctggt cgagctggac ggcgacgtaa acggccacaa gttcagcgtg   120
tccggcgagg gcgagggcga tgccacctac ggcaagctga ccctgaagtt catctgcacc   180
accggcaagc tgcccgtgcc ctggcccacc ctcgtgacca ccttcaccta cggcgtgcag   240
tgcttcgccc gctaccccga ccacatgaag cagcacgact tcttcaagtc cgccatgccc   300
gaaggctacg tccaggagcg caccatcttc ttcaaggacg acggcaacta caagacccgc   360
gccgaggtga agttcgaggg cgacaccctg gtgaaccgca tcgagctgaa gggcatcgac   420
ttcaaggagg acggcaacat cctggggcac aagctggagt acaactacaa cagccacaag   480
gtctatatca ccgccgacaa gcagaagaac ggcatcaagg tgaacttcaa gacccgccac   540
aacatcgagg acggcagcgt gcagctcgcc gaccactacc agcagaacac ccccatcggc   600
gacggccccg tgctgctgcc cgacaaccac tacctgagca cccagtccgc cctgagcaaa   660
gaccccaacg agaagcgcga tcacatggtc ctgctggagt tcgtgaccgg cgccgggatc   720
actctcggca tggacgagct gtacaaggga agcggagcta ctaacttcag cctgctgaag   780
caggctggag acgtggagga gaaccctgga cctatgaccg agtacaagcc cacagtgcgg   840
ctggccacca gggacgatgt gcctagagct gtgcggacac tggccgctgc cttcgccgat   900
taccctgcca ccagacacac cgtggacccc gacagacaca tcgagagagt gaccgagctg   960
caggaactgt ttctgaccag agtgggcctg gacatcggca aagtgtgggt ggccgatgat   1020
ggcgccgctg tggctgtgtg gacaacccct gagtctgtgg aagccggcgc tgtgttcgcc   1080
gagatcggac ctagaatggc cgagctgagc ggctctagac tggctgccca gcagcagatg   1140
gaaggcctgc tggccccca cagacctaaa gagcctgcct ggtttctggc caccgtgggc   1200
gtgtcacctg accaccaggg caagggactg ggatctgctg tggtgctgcc tggcgtggaa   1260
gctgctgaaa gggctggcgt gcccgccttc ctggaaacaa gcgcccccag aaacctgccc   1320
ttctacgaga gactgggctt caccgtgacc gccgacgtgg aagtgcctga gggccctaga   1380
acctggtgca tgaccagaaa gcctggcgcc cttgggcaga cgagaccaca ctgagcctcc   1440
cc                                                                  1442

SEQ ID NO: 2          moltype = DNA   length = 1449
FEATURE               Location/Qualifiers
misc_feature          1..1449
                      note = Description of Unknown: EGFR sequence
source                1..1449
                      mol_type = other DNA
                      organism = unidentified
SEQUENCE: 2
ggtcgcgcca caaagcagtg aatttattgg agcatgggtg agcaagggcg aggagctgtt   60
caccggggtg gtgcccatcc tggtcgagct ggacggcgac gtaaacggcc acaagttcag   120
cgtgtccggc gagggcgagg gcgatgccac ctacggcaag ctgaccctga agttcatctg   180
```

-continued

```
caccaccggc aagctgcccg tgccctggcc caccctcgtg accaccttca cctacggcgt    240
gcagtgcttc gcccgctacc ccgaccacat gaagcagcac gacttcttca agtccgccat    300
gcccgaaggc tacgtccagg agcgcaccat cttcttcaag gacgacggca actacaagac    360
ccgcgccgag gtgaagttcg agggcgacac cctggtgaac cgcatcgagc tgaagggcat    420
cgacttcaag gaggacggca acatcctggg gcacaagctg gagtacaact acaacagcca    480
caaggtctat atcaccgccg acaagcagaa gaacggcatc aaggtgaact tcaagacccg    540
ccacaacatc gaggacggca gcgtgcagct cgccgaccac taccagcaga acacccccat    600
cggcgacggc cccgtgctgc tgcccgacaa ccactacctg agcacccagt ccgccctgag    660
caaagacccc aacgagaagc gcgatcacat ggtcctgctg gagttcgtga ccgccgccgg    720
gatcactctc ggcatggacg agctgtacaa gggaagcgga gctactaact tcagcctgct    780
gaagcaggct ggagacgtgg aggagaaccc tggacctatg accgagtaca agcccacagt    840
gcggctggcc accagggacg atgtgcctag agctgtgcgg acactggccg ctgccttcgc    900
cgattaccct gccaccagac acaccgtgga ccccgacaga cacatcgaga gagtgaccga    960
gctgcaggaa ctgtttctga ccagagtggg cctggacatc gggtggctca ggggtggccga    1020
tgatggcgcc gctgtggctg tgtggacaac ccctgagtct gtggaagccg gcgctgtgtt    1080
cgccgagatc ggacctagaa tggccgagct gagcggctct agactggctg cccagcagca    1140
gatggaaggc ctgctggccc cccacagacc taaagagcct gcctggtttc tggccaccgt    1200
gggcgtgtca cctgaccacc agggcaaggg actgggatct gctgtggtgc tgcctggcgt    1260
ggaagctgct gaaagggctg gcgtgcccgc cttcctggaa acaagcgccc ccagaaacct    1320
gcccttctac gagagactgg gcttcaccgt gaccgccgac gtggaagtgc ctgagggccc    1380
tagaacctgg tgcatgacca gaaagcctgg cgcctaccac ggaggatagt atgagcccta    1440
aaaatccag                                                           1449
```

```
SEQ ID NO: 3              moltype = DNA  length = 1402
FEATURE                  Location/Qualifiers
misc_feature             1..1402
                         note = Description of Unknown: Beta Actin sequence
source                   1..1402
                         mol_type = other DNA
                         organism = unidentified
SEQUENCE: 3
cacagcgcgc ccggctattc tcgcagctca ccatgaccga gtacaagccc acagtgcggc    60
tggccaccag ggacgatgtg cctagagctg tgcggacact ggccgctgcc ttcgccgatt    120
accctgccac cagacacacc gtggaccccg acagacacac cgagagagtg accgagctgc    180
aggaactgtt tctgaccaga gtgggcctgg acatcggcaa agtgtgggtg gccgatgatg    240
gcgccgctgt ggctgtgtgg acaacccctg agtctgtgga agccggcgct gtgttcgccg    300
agatcggacc tagaatggcc gagctgagcg gctctagact ggctgcccag cagcagatgg    360
aaggcctgct ggcccccac agacctaaag agcctgcctg gtttctggcc accgtgggcg    420
tgtcacctga ccaccagggc aagggactgg gatctgctgt ggtgctgcct ggcgtggaag    480
ctgctgaaag ggctggcgtg cccgccttcc tggaaacaag cgcccccaga aacctgccct    540
tctacgagag actgggcttc accgtgaccg ccgacgtgga agtgcctgag ggccctagaa    600
cctggtgcat gaccagaaag cctggcgccg gaagcggagc tactaacttc agcctgctga    660
agcaggctgg agacgtggag gagaaccctg gacctaacct gagcaaaaac gtgagcgtga    720
gcgtgtatat gaaggggaac gtcaacaatc atgagtttga gtacgacggg gaaggtggtg    780
gtgatcctta tacaggtaaa tattccatga agatgacgct acgtggtcaa aattccctac    840
cctttttccta tgatatcatt accacggcat ttcagtatgg tttccgcgta tttacaaaat    900
accctgaggg aattgttgac tattttaagg attcgcttcc cagtggaaca    960
gacgaattgt gtttgaagat ggtggagtac taaacatgag cagtgatatc acatataaag    1020
ataatgttct gcatggtgac gtcaaggctg agggagtgaa cttcccgccg aatgggccag    1080
tgatgaagaa tgaaattgtg atggaggaac cgactgaaga aacatttact ccaaaaaacg    1140
gggttcttgt tggcttttgt cccaaagcgt acttacttaa agatggttcc tattactatg    1200
gaaatatgac aacattttac agatccaaga aatctggcca ggcacctcct gggtatcact    1260
ttgttaagca tcgtctcgtc aagaccaatg tgggacatgg atttaagacg gttgagcaga    1320
ctgaatatgc cactgctcat gtcagtgatc ttcccaaatt cgaagctgat gatgatatcg    1380
ccgcgctcgt cgtcgacaac gg                                             1402
```

```
SEQ ID NO: 4              moltype = DNA  length = 1440
FEATURE                  Location/Qualifiers
misc_feature             1..1440
                         note = Description of Unknown: LRRK2 sequence
source                   1..1440
                         mol_type = other DNA
                         organism = unidentified
SEQUENCE: 4
gagggcggcg ggttggaagc aggtgccacc atgaccgagt acaagcccac agtgcggctg    60
gccaccaggg acgatgtgcc tagagctgtg cggacactgg ccgctgcctt cgccgattac    120
cctgccacca gacacaccgt ggaccccgac agacacatcg agagagtgac cgagctgcag    180
gaactgtttc tgaccagagt gggcctggac atcggcaaag tgtgggtggc cgatgatggc    240
gccgctgtgg ctgtgtggac aacccctgag tctgtggaag ccggcgctgt gttcgccgag    300
atcggaccta gaatggccga gctgagcggc tctagactgg ctgcccagca gcagatggaa    360
ggcctgctgg ccccccacag acctaaagag cctgcctggt ttctggccac cgtgggcgtg    420
tcacctgacc accagggcaa gggactggga tctgctgtgg tgctgcctgg cgtggaagct    480
gctgaaaggg ctggcgtgcc cgccttcctg aaacaagcg ccccagaaa cctgcccttc    540
tacgagagac tgggcttcac cgtgaccgcc gacgtggaag tgcctgaggg ccctagaacc    600
tggtgcatga ccagaaagcc tggcgccgga agcggagcta ctaacttcag cctgctgaag    660
caggctggag acgtggagga gaaccctgga cctgtgagca agggcgagga gctgttcacc    720
ggggtggtgc ccatcctggt cgagctggac ggcgacgtaa acggccacaa gttcagcgtg    780
tccggcgagg gcgagggcga tgccacctac ggcaagctga ccctgaagtt catctgcacc    840
accggcaagc tgcccgtgcc ctggcccacc ctcgtgacca ccttcaccta cggcgtgcag    900
```

```
tgcttcgccc gctaccccga ccacatgaag cagcacgact tcttcaagtc cgccatgccc    960
gaaggctacg tccaggagcg caccatcttc ttcaaggacg acggcaacta caagaccccgc   1020
gccgaggtga agttcgaggg cgacaccctg gtgaaccgca tcgagctgaa gggcatcgac    1080
ttcaaggagg acggcaacat cctggggcac aagctggagt acaactacaa cagccacaag    1140
gtctatatca ccgccgacaa gcagaagaac ggcatcaagg tgaacttcaa gacccgccac    1200
aacatcgagg acggcagcgt gcagctcgcc gaccactacc agcagaacac ccccatcggc    1260
gacggccccg tgctgctgcc cgacaaccac tacctgagca cccagtccgc cctgagcaaa    1320
gaccccaacg agaagcgcga tcacatggtc ctgctggagt tcgtgaccgc cgccgggatc    1380
actctcggca tggacgagct gtacaaggct agtggcagct gtcaggggtg cgaagaggac    1440
```

SEQ ID NO: 5             moltype = DNA   length = 4202
FEATURE                  Location/Qualifiers
misc_feature             1..4202
                         note = Description of Artificial Sequence: Synthetic
                         polynucleotide
source                   1..4202
                         mol_type = other DNA
                         organism = synthetic construct
SEQUENCE: 5

```
cgaccctctt ttgtgccctg atatagttcg ccatgaccga gtacaagccc acagtgcggc     60
tggccaccag ggacgatgtg cctagagctg tgcggacact ggccgctgcc ttcgccgatt    120
accctgccac cagacacacc gtggacccccg acagacacat cgagagagtg accgagctgc    180
aggaactgtt tctgaccaga gtgggcctgg acatcggcaa agtgtgggtg gccgatgatg    240
gcgccgctgt ggctgtgtgg acaacccctg agtctgtgga agccggcgct gtgttcgccg    300
agatcggacc tagaatggcc gagctgagcg gctctagact ggctgcccag cagcagatgg    360
aaggcctgct ggcccccccac agacctaaag agcctgcctg gtttctggcc accgtgggcg    420
tgtcacctga ccaccagggc aagggactgg gatctgctgt ggtgctgcct ggcgtggaag    480
ctgctgaaag ggctggcgtg cccgccttcc tggaaacaag cgccccccaga aacctgccct    540
tctacgagag actgggcttc accgtgaccg ccgacgtgga agtgcctgag ggccctagaa    600
cctggtgcat gaccagaaag cctggcgcct gagttgacat tgattattga ctagttatta    660
atagtaatca attacgggggt cattagttca tagcccccatat atggagttcc gcgttacata    720
acttacggta aatggcccgc ctggctgacc gcccaacgac ccccgcccat tgacgtcaat    780
aatgacgtat gttcccatag taacgccaat agggactttc cattgacgtc aatgggtgga    840
gtatttacgg taaactgccc acttggcagt acatcaagtg tatcatatgc caagtacgcc    900
ccctattgac gtcaatgacg gtaaatggcc cgcctggcat tatgcccagt acatgacctt    960
atgggacttt cctacttggc agtacatcta cgtattagtc atcgctatta ccatggtgat   1020
gcggttttgg cagtacatca atgggcgtgg atagcggttt gactcacggg gatttccaag   1080
tctccacccc attgacgtca atgggagttt gttttggcac caaaatcaac gggactttcc   1140
aaaatgtcgt aacaactccg ccccattgac gcaaatgggc ggtaggcgtg tacggtggga   1200
ggtctatata agcagagctc gtttagtgaa ccgtcagatc gcctggagac gccatccacg   1260
ctgttttgac ctccatagaa gacaccggga ccgatccagc ctccggactc tagaggatcg   1320
aacccttgcc accatgggtt ggagcctcat cttgctcttc cttgtcgctg ttgctacgcg   1380
tgtcctgtcc caggtacaac tgcagcagcc tggggctgag ctggtgaagc ctggggcctc   1440
agtgaagatg tcctgcaagg cttctggcta cacatttacc agttacaata tgcactgggt   1500
aaaacagaca cctggtcggg gcctggaatg gattggagct atttatcccg gaaatggtga   1560
tacttcctac aatcagaagt tcaaaggcaa ggccacattg actgcagaca aatcctccag   1620
cacagctac atgcagctca gcagcctgac atctgaggac tctgcggtct attactgtgc   1680
aagatcgact tactacggcg gtgactggta cttcaatgtc tggggcgcag ggaccacggt   1740
caccgtctct gcagctagca ccaagggccc atcggtcttc cccctggcac cctcctccaa   1800
gagcacctct gggggcaccg cggccctggg ctgcctggtc aaggactact ccccgaacc   1860
ggtgacggtg tcgtggaact caggcgccct gaccagcggc gtgcacacct tcccggctgt   1920
cctacagtcc tcaggactct actccctcag cagcgtggtg accgtgcctc ccagcagctt   1980
gggcacccag acctacatct gcaacgtgaa tcacaagccc agcaacacca aggtggacaa   2040
gaaagcagag cccaaatctt gtgacaaaac tcacacatgc ccaccgtgcc cagcacctga   2100
actcctgggg ggaccgtcag tcttcctctt cccccccaaa cccaaggaca ccctcatgat   2160
ctcccggacc cctgaggtca catgcgtggt ggtggacgtg agccacgaag accctgaggt   2220
caagttcaac tggtacgtgg acggcgtgga ggtgcataat gccaagacaa agccacggga   2280
ggagcagtac aacagcacgt accgtgtggt cagcgtcctc accgtcctgc accaggactg   2340
gctgaatggc aaggagtaca agtgcaaggt ctccaacaaa gccctcccag cccccatcga   2400
gaaaaccatc tccaaagcca aagggcagcc ccgagaacca caggtgtaca ccctgccccc   2460
atcccgggat gagctgacca agaaccaggt cagcctgacc tgcctggtca aaggcttcta   2520
tcccagcgac atcgccgtgg agtgggagag caatgggcag ccggagaaca actacaagac   2580
cacgcctccc gtgctggact ccgacggctc cttcttcctc tacagcaagc tcaccgtgga   2640
caagagcagg tggcagcagg ggaacgtctt ctcatgctcc gtgatgcatg aggctctgca   2700
caaccactac acgcagaaga gcctctccct gtctccgggt aaacgtaaac gaagaggcag   2760
cggggctact aacttcagcc tgctgaagca ggctggagac gtggaggaga ccctggacc   2820
tatggatttt caggtgcaga ttatcagctt cctgctaatc agtgcttcag tcataatgtc   2880
cagaggacaa attgttctct cccagtctcc agcaatcctg tctgcatctc caggggagaa   2940
ggtcacaatg acttgcaggg ccagctcaag tgtaagttac atccactggt tccagcagaa   3000
gccaggatcc tccccccaaac cctggattta tgccacatcc aacctggctt ctggagtccc   3060
tgttcgcttc agtggcagtg ggtctgggac ttcttactct ctcacaatca gcagagtgga   3120
ggctgaagat gctgccactt attactgcca gcagtggact agtaacccac ccacgttcgg   3180
aggggggacc aagctggaaa tcaaacgtac ggtggctgca ccatctgtct tcatcttccc   3240
gccatctgat gagcagttga aatctggaac tgcctctgtt gtgtgcctgc tgaataactt   3300
ctatcccaga gaggccaaag tacagtggaa ggtggataac gccctccaat cgggtaactc   3360
ccaggagagt gtcacagagc aggacagcaa ggacagcacc tacagcctca gcagcaccct   3420
gacgctgagc aaagcagact acgagaaaca caaagtctac gcctgcgaag tcacccatca   3480
gggcctgagc tcgcccgtca caaagagctt caacagggga gagtgttgaa agggttcgat   3540
ccctaccggt tagtaatgag tttgatatct cgacaatcaa cctctggatt acaaaatttg   3600
```

-continued

```
tgaaagattg actggtattc ttaactatgt tgctcctttt acgctatgtg gatacgctgc  3660
tttaatgcct ttgtatcatg ctattgcttc ccgtatggct ttcattttct cctccttgta  3720
taaatcctgg ttgctgtctc tttatgagga gttgtggccc gttgtcaggc aacgtggcgt  3780
ggtgtgcact gtgtttgctg acgcaacccc cactggttgg ggcattgcca ccacctgtca  3840
gctcctttcc gggactttcg ctttcccct ccctattgcc acggcggaac tcatcgccgc  3900
ctgccttgcc cgctgctgga caggggctcg gctgttgggc actgacaatt ccgtggtgtt  3960
gtcggggaag ctgacgtcct ttccatggct gctcgcctgt gttgccacct ggattctgcg  4020
cgggacgtcc ttctgctacg tcccttcggc cctcaatcca gcggaccttc cttcccgcgg  4080
cctgctgccg gctctgcggc ctcttccgcg tcttcgcctt cgccctcaga cgagtcggat  4140
ctcccctttgg gccgcctccc cgcctgggat gacgatatcg ctgcgctcgt tgtcgacaac  4200
gg                                                                  4202
```

SEQ ID NO: 6                moltype = AA   length = 887
FEATURE                    Location/Qualifiers
source                     1..887
                           mol_type = protein
                           organism = Natronobacterium gregoryi
SEQUENCE: 6
```
MTVIDLDSTT TADELTSGHT YDISVTLTGV YDNTDEQHPR MSLAFEQDNG ERRYITLWKN   60
TTPKDVFTYD YATGSTYIFT NIDYEVKDGY ENLTATYQTT VENATAQEVG TTDEDETFAG  120
GEPLDHHLDD ALNETPDDAE TESDSGHVMT SFASRDQLPE WTLHTYTLTA TDGAKTDTEY  180
ARRTLAYTVR QELYTDHDAA PVATDGLMLL TPEPLGETPL DLDCGVRVEA DETRTLDYTT  240
AKDRLLAREL VEEGLKRSLW DDYLVRGIDE VLSKEPVLTC DEFDLHERYD LSVEVGHSGR  300
AYLHINFRHR FVPKLTLADI DDDNIYPGLR VKTTYRPRRG HIVWGLRDEC ATDSLNTLGN  360
QSVVAYHRNN QTPINTDLLD AIEAADRRVV ETRRQGHGDD AVSFPQELLA VEPNTHQIKQ  420
FASDGPHQQA RSKTRLSASR CSEKAQAFAE RLDPVRLNGS TVEFSSEFFT GNNEQQLRLL  480
YENGESVLTF RDGARGAHPD ETFSKGIVNP PESFEVAVVL PEQQADTCKA QWDTMADLLN  540
QAGAPPTRSE TVQYDAFSSP ESISLNVAGA IDPSEVDAAF VVLPPDQEGF ADLASPTETY  600
DELKKALANM GIYSQMAYFD RFRDAKIFYT RNVALGLLAA AGGVAFTTEH AMPGDADMFI  660
GIDVSRSYPE DGASGQINIA ATATAVYKDG TILGHSSTRP QLGEKLQSTD VRDIMKNAIL  720
GYQQVTGESP THIVIHRDGF MNEDLDPATE FLNEQGVEYD IVEIRKQPQT RLLAVSDVQY  780
DTPVKSIAAI NQNEPRATVA TFGAPEYLAT RDGGGLPRPI QIERVAGETD IETLTRQVYL  840
LSQSHIQVHN STARLPITTA YADQASTHAT KGYLVQTGAF ESNVGFL                 887
```

SEQ ID NO: 7                moltype = AA   length = 7
FEATURE                    Location/Qualifiers
source                     1..7
                           mol_type = protein
                           organism = Simian virus 40
SEQUENCE: 7
PKKKRKV                                                               7

SEQ ID NO: 8                moltype = AA   length = 20
FEATURE                    Location/Qualifiers
REGION                     1..20
                           note = Description of Unknown: NLS sequence
source                     1..20
                           mol_type = protein
                           organism = unidentified
SEQUENCE: 8
AVKRPAATKK AGQAKKKKLD                                                20

SEQ ID NO: 9                moltype = AA   length = 25
FEATURE                    Location/Qualifiers
REGION                     1..25
                           note = Description of Unknown: NLS sequence
source                     1..25
                           mol_type = protein
                           organism = unidentified
SEQUENCE: 9
MSRRRKANPT KLSENAKKLA KEVEN                                          25

SEQ ID NO: 10               moltype = AA   length = 9
FEATURE                    Location/Qualifiers
REGION                     1..9
                           note = Description of Unknown: Myc NLS sequence
source                     1..9
                           mol_type = protein
                           organism = unidentified
SEQUENCE: 10
PAAKRVKLD                                                            9

SEQ ID NO: 11               moltype = AA   length = 38
FEATURE                    Location/Qualifiers
REGION                     1..38
                           note = Description of Unknown: Chloroplast Targeting Signal
                            sequence
source                     1..38
                           mol_type = protein
```

-continued

```
                         organism = unidentified
SEQUENCE: 11
LIAHPQAFPG AIAAPISYAY AVKGRKPRFQ TAKGSVRI                        38

SEQ ID NO: 12          moltype = AA  length = 25
FEATURE                Location/Qualifiers
REGION                 1..25
                       note = Description of Unknown: Mitochondrial Targeting
                        Signal sequence
source                 1..25
                       mol_type = protein
                       organism = unidentified
SEQUENCE: 12
MLSLRQSIRF FKPATRTLCS SRYLL                                      25

SEQ ID NO: 13          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 13
KRTADGSEFE SPKKKRKVEG G                                          21

SEQ ID NO: 14          moltype = DNA  length = 97
FEATURE                Location/Qualifiers
misc_feature           1..97
                       note = Description of Artificial Sequence: Synthetic
                        oligonucleotide
source                 1..97
                       mol_type = other DNA
                       organism = synthetic construct
SEQUENCE: 14
cggggtagcg gctgaagcac tgcacgccgt aggtcagggt ggtcacgagg gtgggccagg  60
gcacgggcag cttgccggtg gtgcagatga acttcag                         97

SEQ ID NO: 15          moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 15
gcacgccgta ggtggtcacg agg                                        23

SEQ ID NO: 16          moltype = DNA  length = 80
FEATURE                Location/Qualifiers
misc_feature           1..80
                       note = Description of Artificial Sequence: Synthetic
                        oligonucleotide
source                 1..80
                       mol_type = other DNA
                       organism = synthetic construct
SEQUENCE: 16
gctgcccgtg ccctggccca ccctcgtgac caccctgacc tacggcgtgc agtgcttcag  60
ccgctacccc gaccacatga                                            80

SEQ ID NO: 17          moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 17
ctcgtgacca ccctgacccca cgg                                       23

SEQ ID NO: 18          moltype = DNA  length = 2682
FEATURE                Location/Qualifiers
misc_feature           1..2682
                       note = Description of Artificial Sequence: Synthetic
                        polynucleotide
source                 1..2682
                       mol_type = other DNA
                       organism = synthetic construct
```

```
SEQUENCE: 18
ctggctaact agagaaccca ctgcttactg gcttatcgaa attaatacga ctcactatag    60
ggagtcccaa gctggctagc gtttaaactt ctgcggccgc gccaccatgg gaaaacctat   120
tcctaatcct ctgctgggcc tggattctac cggaggcgtg gacctgagaa cactgggata   180
ttctcagcag cagcaggaga agatcaagcc caaggtgaga tctacagtgg ccagcacca   240
cgaagccctg gtgggacacg gatttacaca cgcccacatt gtggccctgt ctcagcaccc   300
tgccgccctg ggaacagtgg ccgtgaaata tcaggatatg attgccgccc tgcctgaggc   360
cacacacgaa gccattgtgg gagtgggaaa acgaggcgct ggagccagag ccctggaagc   420
cctgctgaca gtggccggag aactgagagg acctcctctg cagctggata caggacagct   480
gctgaagatt gccaaaaggg gcggagtgac cgcggtggaa gccgtgcacg cctggagaaa   540
tgccctgaca ggagccccctc tgaacctgac ccccgaacag gtggtggcca ttgccagcca   600
cgacggcggc aagcaggccc tggaaaccgt gcagagactg ctgcccgtgc tgtgccaggc   660
ccatggcctg acacctgaac aggtggtggc tatcgcctct aatatcggag gaaaacaggc   720
tctggaaaca gtgcagcggc tgctgcctgt gctgtgtcag gctcacggct tgactccagt   780
acaggtggtg gctattgctt ccaatattgg ggggaaacag gccctggaaa ctgtgcagcg   840
cctgctgcca gtgctgtgcc aggctcacgg actgaccccc gaacaggtgg tggccattgc   900
cagcaacatc ggcggcaagc aggccctgga aaccgtgcag agactgctgc ccgtgctgtg   960
ccaggcccat ggcctgacac tgaacaggt ggtggctatc gcctctaata tcggaggaaa   1020
acaggctctg gaaacagtgc agcggctgct gcctgtgctg tgtcaggctc acggcttgac   1080
tccagaacag gtggtggcta ttgcttccaa tattgggggg aaacaggccc tggaaactgt   1140
gcagcgcctg ctgccagtgc tgtgccaggc tcacgggctg acccccgaac aggtggtggc   1200
cattgccagc cacgacggcg gcaagcaggc cctggaaacc gtgcagagac tgctgcccgt   1260
gctgtgccag gcccatggcc tgacacctga acaggtggtg gctatcgcct ctcacgacgg   1320
aggaaaacag gctctggaaa cagtgcagcg gctgctgcct gtgctgtgtc aggctcacgg   1380
cttgactcca gaacaggtgg tggctattgc ttccaacggc gggggaaac aggccctgga   1440
aactgtgcag cgcctgctgc cagtgctgtg tcaggctcac ggcctcactc ccgaacaggt   1500
ggtggccatt gccagcaaca cggcggcaa gcaggccctg gaaaccgtg agagactgct   1560
gcccgtgctg tgccaggccc atggcctgac acctgaacag gtggtggcta tcgcctctaa   1620
cggcggagga aaacaggctc tggaaacagt gcagcggctg ctgcctgtgc tgtgtcaggc   1680
tcacggcttg actccagaac aggtggtggc tattgcttcc aatattgggg ggaaacaggc   1740
cctggaaact gtgcagcgcc tgctgccagt gctgtgccag gctcacggac tgaccccccga   1800
acaggtggtg gccattgcca gcaacatcgg cggcaagcag gccctggaaa ccgtgcagag   1860
actgctgccc gtgctgtgcc aggcccatgg cctgacacct gaacaggtgg tggctatcgc   1920
ctctaatatc ggaggaaaac aagcactcga gacagtgcag cggctgctgc ctgtgctgtg   1980
tcaggctcac ggcttgactc cagaacaggt ggtggctatt gcttccaaca acgggggaaac   2040
acaggccctg gaaactgtgc agcggctgct gccagtgctg tgccaggctc acggcctgac   2100
ccccgaacag gtggtggcca ttgccagcaa caacggcggc aagcaggccc tggaaaccgt   2160
gcagagactg ctgcccgtgc tgtgccaggc ccatggcctg acacctgaac aggtggtggc   2220
tatcgcctct aatatcggag gaaaacaggc tctggaaaca gtgcagcggc tgctgcctgt   2280
gctgtgtcag gctcacggct tgactccaca gcaggtcgtg gcaattgcta gcaatatcgg   2340
cggacggccc gccctggaga gcattgtggc ccagctgtct agacctgatc ctgccctggc   2400
cgccctgaca aatgatcacc tggtggccct ggcctgtctg ggaggcagac ctgccctgga   2460
tgccgtgaaa aaaggactgc ctcacgcccc tgccctgatc aagagaacaa atagaagaat   2520
ccccgagcgg acctctcaca gagtggccgg atcccctaag aaaaagcgga aggtgggatc   2580
ctgaaagctt ctcgagtcta gagggcccgt ttaaacccgc tgatcagcct cgactgtgcc   2640
ttctagttgc cagccatctg ttgtttgccc ctccccccgtg cc                      2682
```

```
SEQ ID NO: 19          moltype = DNA   length = 551
FEATURE                Location/Qualifiers
source                 1..551
                       mol_type = other DNA
                       organism = Homo sapiens
SEQUENCE: 19
aactcaagtg atctgcccgc ctcgacctcc caaagtgctg ggattacaga tgtgagccac    60
cgcgccccgc caaatttgat tatttttaat aagaacttag ctgtatggta ttttaacagt   120
acctgctttt aaaattatta tcatcttttt cctttacagg tttttgatga agttgtgcag   180
attttttgaca aggaaggcta attctaaacc tgaaggcatc cttgaaatca tgcttgaata   240
ttgctttgat agctgctatc atgacccctt tttaaggcaa ttctaatctt tcataactac   300
atctcaatta gtggctggaa agtacatggt aaaacaaagt aaatttttt atgttcttt   360
ttttggtcac aggagtagac agtgaattca ggtttaactt caccttagtt atggtgctca   420
ccaaacgaag ggtatcagct attttttttta aaattcaaaa agaatatccc ttttatagtt   480
tgtgccttct gtgagcaaaa ctttttagta cgcgtatata tccctctagt aatcacaaca   540
ttttaggatt t                                                         551
```

```
SEQ ID NO: 20          moltype = DNA   length = 102
FEATURE                Location/Qualifiers
source                 1..102
                       mol_type = other DNA
                       organism = Homo sapiens
SEQUENCE: 20
ttcctttaca ggttttttgat gaagttgtgc agatttttga caaggaaggc taattctaaa    60
cctgaaggca tccttgaaat catgcttgaa tattgctttg at                       102
```

```
SEQ ID NO: 21          moltype = DNA   length = 102
FEATURE                Location/Qualifiers
source                 1..102
                       mol_type = other DNA
                       organism = Homo sapiens
SEQUENCE: 21
```

```
atcaaagcaa tattcaagca tgatttcaag gatgccttca ggtttagaat tagccttcct  60
tgtcaaaaat ctgcacaact tcatcaaaaa cctgtaaagg aa                      102

SEQ ID NO: 22           moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 22
ctggctaact agagaaccca ctgcttactg                                    30

SEQ ID NO: 23           moltype = DNA   length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 23
ggcacggggg aggggcaaac aacagatggc                                    30

SEQ ID NO: 24           moltype = DNA   length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 24
tgtgcagatt tttgacaa                                                 18

SEQ ID NO: 25           moltype = DNA   length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 25
tcaaggatgc cttcaggt                                                 18

SEQ ID NO: 26           moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 26
caaaaacctg taaaggaa                                                 18

SEQ ID NO: 27           moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 27
cttgaatatt gctttgat                                                 18

SEQ ID NO: 28           moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 28
acttcatcaa aaacctgt                                                 18

SEQ ID NO: 29           moltype = DNA   length = 18
FEATURE                 Location/Qualifiers
misc_feature            1..18
```

```
                        note = Description of Artificial Sequence: Synthetic
                         oligonucleotide
source                  1..18
                        mol_type = other DNA
                        organism = synthetic construct
SEQUENCE: 29
aatcatgctt gaatattg                                                    18

SEQ ID NO: 30           moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 30
catcaaaaac ctgtaaag                                                    18

SEQ ID NO: 31           moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 31
atgcttgaat attgcttt                                                    18

SEQ ID NO: 32           moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 32
acctgtaaag gaaaaaga                                                    18

SEQ ID NO: 33           moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 33
atattgcttt gatagctg                                                    18

SEQ ID NO: 34           moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 34
aggaaaaaga tgataata                                                    18

SEQ ID NO: 35           moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 35
ttgatagctg ctatcatg                                                    18

SEQ ID NO: 36           moltype = DNA   length = 18
FEATURE                 Location/Qualifiers
misc_feature            1..18
                        note = Description of Artificial Sequence: Synthetic
                         oligonucleotide
```

-continued

```
source                    1..18
                          mol_type = other DNA
                          organism = synthetic construct
SEQUENCE: 36
tgataataat tttaaaag                                                   18

SEQ ID NO: 37             moltype = DNA   length = 18
FEATURE                   Location/Qualifiers
misc_feature              1..18
                          note = Description of Artificial Sequence: Synthetic
                           oligonucleotide
source                    1..18
                          mol_type = other DNA
                          organism = synthetic construct
SEQUENCE: 37
ctatcatgac cccttttt                                                   18

SEQ ID NO: 38             moltype = DNA   length = 18
FEATURE                   Location/Qualifiers
misc_feature              1..18
                          note = Description of Artificial Sequence: Synthetic
                           oligonucleotide
source                    1..18
                          mol_type = other DNA
                          organism = synthetic construct
SEQUENCE: 38
ggtactgtta aaatacca                                                   18

SEQ ID NO: 39             moltype = DNA   length = 18
FEATURE                   Location/Qualifiers
misc_feature              1..18
                          note = Description of Artificial Sequence: Synthetic
                           oligonucleotide
source                    1..18
                          mol_type = other DNA
                          organism = synthetic construct
SEQUENCE: 39
ggcaattcta atctttca                                                   18

SEQ ID NO: 40             moltype = DNA   length = 18
FEATURE                   Location/Qualifiers
misc_feature              1..18
                          note = Description of Artificial Sequence: Synthetic
                           oligonucleotide
source                    1..18
                          mol_type = other DNA
                          organism = synthetic construct
SEQUENCE: 40
ttggcggggc gcggtggc                                                   18

SEQ ID NO: 41             moltype = DNA   length = 18
FEATURE                   Location/Qualifiers
misc_feature              1..18
                          note = Description of Artificial Sequence: Synthetic
                           oligonucleotide
source                    1..18
                          mol_type = other DNA
                          organism = synthetic construct
SEQUENCE: 41
atggtaaaac aaagtaaa                                                   18

SEQ ID NO: 42             moltype = DNA   length = 109
FEATURE                   Location/Qualifiers
misc_feature              1..109
                          note = Description of Unknown: UFSP2 sequence
source                    1..109
                          mol_type = other DNA
                          organism = unidentified
SEQUENCE: 42
catatttggt cgctgaggaa gacataagtt atagtatgca tccttgttcc aaaaatctgg   60
gcccttccat ccgcaccagc cctggataga gaagacggga aaggaaagc               109

SEQ ID NO: 43             moltype = DNA   length = 109
FEATURE                   Location/Qualifiers
misc_feature              1..109
                          note = Description of Unknown: UFSP2 sequence
source                    1..109
                          mol_type = other DNA
                          organism = unidentified
```

-continued

```
SEQUENCE: 43
gctttccttt cccgtcttct ctatccaggg ctggtgcgga tggaagggcc cagatttttg   60
gaacaaggat gcatactata acttatgtct tcctcagcga ccaaatatg                109

SEQ ID NO: 44             moltype = DNA  length = 109
FEATURE                   Location/Qualifiers
misc_feature              1..109
                          note = Description of Unknown: UFSP2 sequence
source                    1..109
                          mol_type = other DNA
                          organism = unidentified
SEQUENCE: 44
catatttggt cgctgaggaa gacataagtt atagtatgca tccttgttcc aaaaatctgg   60
gcccttccat ccgcaccagc cctggataga gaagacggga aaggaaagc                109

SEQ ID NO: 45             moltype = DNA  length = 109
FEATURE                   Location/Qualifiers
misc_feature              1..109
                          note = Description of Unknown: UFSP2 sequence
source                    1..109
                          mol_type = other DNA
                          organism = unidentified
SEQUENCE: 45
gctttccttt cccgtcttct ctatccaggg ctggtgcgga tggaagggcc cagatttttg   60
gaacaaggat gcatactata acttatgtct tcctcagcga ccaaatatg                109

SEQ ID NO: 46             moltype = DNA  length = 133
FEATURE                   Location/Qualifiers
source                    1..133
                          mol_type = other DNA
                          organism = Homo sapiens
SEQUENCE: 46
ttattatcat ctttttcctt tacaggtttt tgatgaagtt gtgcagattt ttgacaagga   60
aggctaattc taaacctgaa ggcatccttg aaatcatgct tgaatattgc tttgatagct  120
gctatcatga ccc                                                     133

SEQ ID NO: 47             moltype = DNA  length = 133
FEATURE                   Location/Qualifiers
source                    1..133
                          mol_type = other DNA
                          organism = Homo sapiens
SEQUENCE: 47
gggtcatgat agcagctatc aaagcaatat tcaagcatga tttcaaggat gccttcaggt   60
ttagaattag ccttccttgt caaaaatctg cacaacttca tcaaaaacct gtaaaggaaa  120
aagatgataa taa                                                     133

SEQ ID NO: 48             moltype = AA  length = 19
FEATURE                   Location/Qualifiers
REGION                    1..19
                          note = Description of Unknown: NLS sequence
source                    1..19
                          mol_type = protein
                          organism = unidentified
SEQUENCE: 48
KRTADGSEFE SPKKKRKVE                                                 19

SEQ ID NO: 49             moltype = AA  length = 19
FEATURE                   Location/Qualifiers
REGION                    1..19
                          note = Description of Unknown: NLS sequence
source                    1..19
                          mol_type = protein
                          organism = unidentified
SEQUENCE: 49
KRTADGSEFE SPKKARKVE                                                 19

SEQ ID NO: 50             moltype = AA  length = 19
FEATURE                   Location/Qualifiers
REGION                    1..19
                          note = Description of Unknown: NLS sequence
source                    1..19
                          mol_type = protein
                          organism = unidentified
SEQUENCE: 50
KRTADGSEFE SPKKKAKVE                                                 19

SEQ ID NO: 51             moltype = AA  length = 16
FEATURE                   Location/Qualifiers
REGION                    1..16
```

-continued

```
                    note = Description of Unknown: NLS sequence
source              1..16
                    mol_type = protein
                    organism = unidentified
SEQUENCE: 51
KRPAATKKAG QAKKKK                                                        16

SEQ ID NO: 52       moltype = AA  length = 20
FEATURE             Location/Qualifiers
REGION              1..20
                    note = Description of Unknown: NLS sequence
source              1..20
                    mol_type = protein
                    organism = unidentified
SEQUENCE: 52
KRTADGSEFE PAAKRVKLDE                                                    20

SEQ ID NO: 53       moltype = AA  length = 23
FEATURE             Location/Qualifiers
VARIANT             3..17
                    note = Any Amino Acid
                    note = X may vary between 5 to 15
VARIANT             20
                    note = Leu or Ala
VARIANT             21
                    note = Leu, Ala or Arg
source              1..23
                    mol_type = protein
                    note = Description of Artificial Sequence: Synthetic peptide
                    organism = synthetic construct
SEQUENCE: 53
KRXXXXXXXX XXXXXXXKKX XKV                                                23

SEQ ID NO: 54       moltype = AA  length = 21
FEATURE             Location/Qualifiers
source              1..21
                    mol_type = protein
                    note = Description of Artificial Sequence: Synthetic peptide
                    organism = synthetic construct
VARIANT             3..17
                    note = Any amino acid
                    note = X may vary between 5 to 15
VARIANT             19
                    note = N can be K or R
VARIANT             20..21
                    note = N can be K or R
                    note = N can vary between 1 to 2
SEQUENCE: 54
KRXXXXXXXX XXXXXXXKNN N                                                  21

SEQ ID NO: 55       moltype = AA  length = 22
FEATURE             Location/Qualifiers
source              1..22
                    mol_type = protein
                    note = Description of Artificial Intelligence: Synthetic
                     Peptide
                    organism = synthetic construct
VARIANT             3..17
                    note = X is any Amino Acid
                    note = X may vary between 5 to 15
VARIANT             19
                    note = N can be K or R
VARIANT             20
                    note = X can be any Amino Acid
VARIANT             21..22
                    note = N can be K or R
SEQUENCE: 55
KRXXXXXXXX XXXXXXXKNN NN                                                 22

SEQ ID NO: 56       moltype = DNA  length = 64
FEATURE             Location/Qualifiers
misc_feature        1..64
                    note = Description of Artificial Sequence: Synthetic
                     oligonucleotide
source              1..64
                    mol_type = other DNA
                    organism = synthetic construct
SEQUENCE: 56
caaaaactta ctcgatgtca ttgaccaagc aagactgaaa atggtgagca agggcgagga  60
```

-continued

```
gctg                                                         64

SEQ ID NO: 57          moltype = DNA   length = 42
FEATURE                Location/Qualifiers
misc_feature           1..42
                       note = Description of Artificial Sequence: Synthetic
                       oligonucleotide
source                 1..42
                       mol_type = other DNA
                       organism = synthetic construct
SEQUENCE: 57
caaaaactta ctcgatgtca ttgaccaagc aagactgaaa at               42

SEQ ID NO: 58          moltype =    length =
SEQUENCE: 58
000

SEQ ID NO: 59          moltype = DNA   length = 43
FEATURE                Location/Qualifiers
misc_feature           1..43
                       note = Description of Artificial Sequence: Synthetic
                       oligonucleotide
source                 1..43
                       mol_type = other DNA
                       organism = synthetic construct
SEQUENCE: 59
caaaaactta ctcgatgtca ttgaccaagc aagactgaaa atg              43

SEQ ID NO: 60          moltype = DNA   length = 33
FEATURE                Location/Qualifiers
misc_feature           1..33
                       note = Description of Artificial Sequence: Synthetic
                       oligonucleotide
source                 1..33
                       mol_type = other DNA
                       organism = synthetic construct
SEQUENCE: 60
agactgaaaa tggtgagcaa gggcgaggag ctg                         33

SEQ ID NO: 61          moltype = DNA   length = 43
FEATURE                Location/Qualifiers
misc_feature           1..43
                       note = Description of Artificial Sequence: Synthetic
                       oligonucleotide
source                 1..43
                       mol_type = other DNA
                       organism = synthetic construct
SEQUENCE: 61
caaaaactta ctcgatgtca ttgaccaagc aagactgaaa atg              43

SEQ ID NO: 62          moltype = DNA   length = 54
FEATURE                Location/Qualifiers
misc_feature           1..54
                       note = Description of Artificial Sequence: Synthetic
                       oligonucleotide
source                 1..54
                       mol_type = other DNA
                       organism = synthetic construct
SEQUENCE: 62
ctcgatgtca ttgaccaagc aagactgaaa atggtgagca agggcgagga gctg  54

SEQ ID NO: 63          moltype = DNA   length = 58
FEATURE                Location/Qualifiers
misc_feature           1..58
                       note = Description of Artificial Sequence: Synthetic
                       oligonucleotide
source                 1..58
                       mol_type = other DNA
                       organism = synthetic construct
SEQUENCE: 63
gcctggcgcc cttgggcaga cgagaccaca ctgagcctcc cctaggagca cgtcttgc  58

SEQ ID NO: 64          moltype = DNA   length = 37
FEATURE                Location/Qualifiers
misc_feature           1..37
                       note = Description of Artificial Sequence: Synthetic
                       oligonucleotide
source                 1..37
                       mol_type = other DNA
```

```
                          organism = synthetic construct
SEQUENCE: 64
gcctggcgcc cttgggcaga cgagaccaca ctgagcc                                      37

SEQ ID NO: 65           moltype = DNA   length = 40
FEATURE                 Location/Qualifiers
misc_feature            1..40
                        note = Description of Artificial Sequence: Synthetic
                        oligonucleotide
source                  1..40
                        mol_type = other DNA
                        organism = synthetic construct
SEQUENCE: 65
gacgagacca cactgagcct cccctaggag cacgtcttgc                                    40

SEQ ID NO: 66           moltype = DNA   length = 42
FEATURE                 Location/Qualifiers
misc_feature            1..42
                        note = Description of Artificial Sequence: Synthetic
                        oligonucleotide
source                  1..42
                        mol_type = other DNA
                        organism = synthetic construct
SEQUENCE: 66
gcctggcgcc cttgggcaga cgagaccaca ctgagcctcc cc                                 42

SEQ ID NO: 67           moltype = DNA   length = 50
FEATURE                 Location/Qualifiers
misc_feature            1..50
                        note = Description of Artificial Sequence: Synthetic
                        oligonucleotide
source                  1..50
                        mol_type = other DNA
                        organism = synthetic construct
SEQUENCE: 67
ggcttgggca gacgagacca cactgagcct cccctaggag cacgtcttgc                         50

SEQ ID NO: 68           moltype = DNA   length = 42
FEATURE                 Location/Qualifiers
misc_feature            1..42
                        note = Description of Artificial Sequence: Synthetic
                        oligonucleotide
source                  1..42
                        mol_type = other DNA
                        organism = synthetic construct
SEQUENCE: 68
gcctggcgcc cttgggcaga cgagaccaca ctgagcctcc cc                                 42

SEQ ID NO: 69           moltype = DNA   length = 48
FEATURE                 Location/Qualifiers
misc_feature            1..48
                        note = Description of Artificial Sequence: Synthetic
                        oligonucleotide
source                  1..48
                        mol_type = other DNA
                        organism = synthetic construct
SEQUENCE: 69
cttgggcaga cgagaccaca ctgagcctcc cctaggagca cgtcttgc                           48

SEQ ID NO: 70           moltype = DNA   length = 59
FEATURE                 Location/Qualifiers
misc_feature            1..59
                        note = Description of Artificial Sequence: Synthetic
                        oligonucleotide
source                  1..59
                        mol_type = other DNA
                        organism = synthetic construct
SEQUENCE: 70
gaatacctaa gggtcgcgcc acaaagcagt gaatttattg gagcatgggt gagcaaggg             59

SEQ ID NO: 71           moltype = DNA   length = 58
FEATURE                 Location/Qualifiers
misc_feature            1..58
                        note = Description of Artificial Sequence: Synthetic
                        oligonucleotide
source                  1..58
                        mol_type = other DNA
                        organism = synthetic construct
SEQUENCE: 71
```

-continued

```
gaaagcctgg cgcctaccac ggaggatagt atgagcccta aaaatccaga ctctttcg       58

SEQ ID NO: 72          moltype = DNA   length = 73
FEATURE                Location/Qualifiers
misc_feature           1..73
                       note = Description of Artificial Sequence: Synthetic
                       oligonucleotide
source                 1..73
                       mol_type = other DNA
                       organism = synthetic construct
SEQUENCE: 72
ggcgggggcg acctcggctc acagcgcgcc cggctattct cgcagctcac catgaccgag       60
tacaagccca cag                                                          73

SEQ ID NO: 73          moltype = DNA   length = 60
FEATURE                Location/Qualifiers
misc_feature           1..60
                       note = Description of Artificial Sequence: Synthetic
                       oligonucleotide
source                 1..60
                       mol_type = other DNA
                       organism = synthetic construct
SEQUENCE: 73
ggcgggggcg acttcggctc acagcgcgcc cggctattct cgcagctcac catggctgtg       60

SEQ ID NO: 74          moltype = DNA   length = 54
FEATURE                Location/Qualifiers
misc_feature           1..54
                       note = Description of Artificial Sequence: Synthetic
                       oligonucleotide
source                 1..54
                       mol_type = other DNA
                       organism = synthetic construct
SEQUENCE: 74
cacagcgcgc ccggctattc tcgcagctca ccatgaccga gtacaagccc acag            54

SEQ ID NO: 75          moltype = DNA   length = 54
FEATURE                Location/Qualifiers
misc_feature           1..54
                       note = Description of Artificial Sequence: Synthetic
                       oligonucleotide
source                 1..54
                       mol_type = other DNA
                       organism = synthetic construct
SEQUENCE: 75
ggcgggggcg acctcggctc acagcgcgcc cggctattct cgcagctcac catg            54

SEQ ID NO: 76          moltype = DNA   length = 80
FEATURE                Location/Qualifiers
misc_feature           1..80
                       note = Description of Artificial Sequence: Synthetic
                       oligonucleotide
source                 1..80
                       mol_type = other DNA
                       organism = synthetic construct
SEQUENCE: 76
gcgatatcat catcagctgt gcggttgtat gatgatgatg atatcgtcgc agctcaccat       60
gaccgagtac aagcccacag                                                   80

SEQ ID NO: 77          moltype = DNA   length = 64
FEATURE                Location/Qualifiers
misc_feature           1..64
                       note = Description of Artificial Sequence: Synthetic
                       oligonucleotide
source                 1..64
                       mol_type = other DNA
                       organism = synthetic construct
SEQUENCE: 77
cctccccgcc tgggatgatg atatcgccgc gctcgtcgtc gacaacggct ccggcatgtg       60
caag                                                                    64

SEQ ID NO: 78          moltype = DNA   length = 64
FEATURE                Location/Qualifiers
misc_feature           1..64
                       note = Description of Artificial Sequence: Synthetic
                       oligonucleotide
source                 1..64
                       mol_type = other DNA
                       organism = synthetic construct
```

```
SEQUENCE: 78
cctccccgcc tgtgatgatg atatcgccgc gctcgtcgtc gacaacggct ccggcatgtg    60
caag                                                                 64

SEQ ID NO: 79          moltype = DNA   length = 64
FEATURE                Location/Qualifiers
misc_feature           1..64
                       note = Description of Artificial Sequence: Synthetic
                       oligonucleotide
source                 1..64
                       mol_type = other DNA
                       organism = synthetic construct
SEQUENCE: 79
cctccccgcc gctgatgatg atatcgccgc gctcgtcgtc gacaacggct ccggcatgtg    60
caag                                                                 64

SEQ ID NO: 80          moltype = DNA   length = 65
FEATURE                Location/Qualifiers
misc_feature           1..65
                       note = Description of Artificial Sequence: Synthetic
                       oligonucleotide
source                 1..65
                       mol_type = other DNA
                       organism = synthetic construct
SEQUENCE: 80
cctccccgcc tgggaatgat gatatcgccg cgctcgtcgt cgacaacggc tccggcatgt    60
gcaag                                                                65

SEQ ID NO: 81          moltype = DNA   length = 65
FEATURE                Location/Qualifiers
misc_feature           1..65
                       note = Description of Artificial Sequence: Synthetic
                       oligonucleotide
source                 1..65
                       mol_type = other DNA
                       organism = synthetic construct
SEQUENCE: 81
cctccccgcc tggggatgat gatatcgccg cgctcgtcgt cgacaacggc tccggcatgt    60
gcaag                                                                65

SEQ ID NO: 82          moltype = DNA   length = 67
FEATURE                Location/Qualifiers
misc_feature           1..67
                       note = Description of Artificial Sequence: Synthetic
                       oligonucleotide
source                 1..67
                       mol_type = other DNA
                       organism = synthetic construct
SEQUENCE: 82
cctccccgcc tgggctgatg atgatatcgc cgcgctcgtc gtcgacaacg gctccggcat    60
gtgcaag                                                              67

SEQ ID NO: 83          moltype = AA   length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 83
KRTADGSEFE SPKKKRKVEG G                                               21

SEQ ID NO: 84          moltype = AA   length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 84
KRTADGSEFE SPKKKRKVEG G                                               21

SEQ ID NO: 85          moltype = AA   length = 7
FEATURE                Location/Qualifiers
REGION                 1..7
                       note = Description of Unknown: EmGFP sequence
source                 1..7
                       mol_type = protein
                       organism = unidentified
```

-continued

```
SEQUENCE: 85
VTTFTYG                                                              7

SEQ ID NO: 86         moltype = DNA  length = 21
FEATURE               Location/Qualifiers
misc_feature          1..21
                      note = Description of Unknown: EmGFP sequence
source                1..21
                      mol_type = other DNA
                      organism = unidentified
CDS                   1..21
SEQUENCE: 86
gtgaccacct tcacctacgg c                                              21

SEQ ID NO: 87         moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 87
VTTYG                                                                5

SEQ ID NO: 88         moltype = DNA  length = 15
FEATURE               Location/Qualifiers
misc_feature          1..15
                      note = Description of Artificial Sequence: Synthetic
                       oligonucleotide
source                1..15
                      mol_type = other DNA
                      organism = synthetic construct
CDS                   1..15
SEQUENCE: 88
gtgaccacct acggc                                                     15

SEQ ID NO: 89         moltype = AA  length = 4
FEATURE               Location/Qualifiers
REGION                1..4
                      note = Description of Artificial Sequence: Synthetic peptide
source                1..4
                      mol_type = protein
                      organism = synthetic construct
SEQUENCE: 89
LTHG                                                                 4

SEQ ID NO: 90         moltype = DNA  length = 12
FEATURE               Location/Qualifiers
misc_feature          1..12
                      note = Description of Artificial Sequence: Synthetic
                       oligonucleotide
source                1..12
                      mol_type = other DNA
                      organism = synthetic construct
CDS                   1..12
SEQUENCE: 90
ctgacccacg gc                                                        12

SEQ ID NO: 91         moltype = AA  length = 4
FEATURE               Location/Qualifiers
REGION                1..4
                      note = Description of Artificial Sequence: Synthetic peptide
source                1..4
                      mol_type = protein
                      organism = synthetic construct
SEQUENCE: 91
LTYG                                                                 4

SEQ ID NO: 92         moltype = DNA  length = 12
FEATURE               Location/Qualifiers
misc_feature          1..12
                      note = Description of Artificial Sequence: Synthetic
                       oligonucleotide
source                1..12
                      mol_type = other DNA
                      organism = synthetic construct
CDS                   1..12
SEQUENCE: 92
ctgacctacg gc                                                        12
```

-continued

```
SEQ ID NO: 93          moltype = AA  length = 1413
FEATURE                Location/Qualifiers
REGION                 1..1413
                       note = Description of Artificial Sequence: Synthetic
                        polypeptide
source                 1..1413
                       mol_type = protein
                       organism = synthetic construct
SEQUENCE: 93
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDRS RADPKKKRKV  1380
DPKKKRKVDP KKKRKVGSTG SRGSGSAHHH HHH                                1413

SEQ ID NO: 94          moltype = AA  length = 1403
FEATURE                Location/Qualifiers
REGION                 1..1403
                       note = Description of Artificial Sequence: Synthetic
                        polypeptide
source                 1..1403
                       mol_type = protein
                       organism = synthetic construct
SEQUENCE: 94
MKRTADGSEF ESPKKKRKVE DKKYSIGLDI GTNSVGWAVI TDEYKVPSKK FKVLGNTDRH  60
SIKKNLIGAL LFDSGETAEA TRLKRTARRR YTRRKNRICY LQEIFSNEMA KVDDSFFHRL  120
EESFLVEEDK KHERHPIFGN IVDEVAYHEK YPTIYHLRKK LVDSTDKADL RLIYLALAHM  180
IKFRGHFLIE GDLNPDNSDV DKLFIQLVQT YNQLFEENPI NASGVDAKAI LSARLSKSRR  240
LENLIAQLPG EKKNGLFGNL IALSLGLTPN FKSNFDLAED AKLQLSKDTY DDDLDNLLAQ  300
IGDQYADLFL AAKNLSDAIL LSDILRVNTE ITKAPLSASM IKRYDEHHQD LTLLKALVRQ  360
QLPEKYKEIF FDQSKNGYAG YIDGGASQEE FYKFIKPMDG TEELLV KLNREDLLV     420
QRTFDNGSIP HQIHLGELHA ILRRQEDFYP FLKDNREKIE KILTFRIPYY VGPLARGNSR  480
FAWMTRKSEE TITPWNFEEV VDKGASAQSF IERMTNFDKN LPNEKVLPKH SLLYEYFTVY  540
NELTKVKYVT EGMRKPAFLS GEQKKAIVDL LFKTNRKVTV KQLKEDYFKK IECFDSVEIS  600
GVEDRFNASL GTYHDLLKII KDKDFLDNEN EDILEDIVLT LTLFEDREM IEERLKTYAH  660
LFDDKVMKQL KRRRYTGWGR LSRKLINGIR DKQSGKTILD FLKSDGFANR NFMQLIHDDS  720
LTFKEDIQKA QVSGQGDSLH EHIANLAGSP AIKKGILQTV KVVDELVKVM GRHKPENIVI  780
EMARENQTTQ KGQKNSRERM KRIEEGIKEL GSQILKEHPV ENTQLQNEKL YLYYLQNGRD  840
MYVDQELDIN RLSDYDVDHI VPQSFLKDDS IDNKVLTRSD KNRGKSDNVP SEEVVKKMKN  900
YWRQLLNAKL ITQRKFDNLT KAERGGLSEL DKAGFIKRQL VETRQITKHV AQILDSRMNT  960
KYDENDKLIR EVKVITLKSK LVSDFRKDFQ FYKVREINNY HHAHDAYLNA VVGTALIKKY  1020
PKLESEFVYG DYKVYDVRKM IAKSEQEIGK ATAKYFFYSN IMNFFKTEIT LANGEIRKRP  1080
LIETNGETGE IVWDKGRDFA TVRKVLSMPQ VNIVKKTEV TGGFSKESIL PKRNSDKLIA  1140
RKKDWDPKKY GGFDSPTVAY SVLVVAKVEK GKSKKLKSVK ELLGITIMER SSFEKNPIDF  1200
LEAKGYKEVK KDLIIKLPKY SLFELENGRK RMLASAGELQ KGNELALPSK YVNFLYLASH  1260
YEKLKGSPED NEQKQLFVEQ HKHYLDEIIE QISEFSKRVI LADANLDKVL SAYNKHRDKP  1320
IREQAENIIH LFTLTNLGAP AAFKYFDTTI DRKRYTSTKE VLDATLIHQS ITGLYETRID  1380
LSQLGGDKRP AATKKAGQAK KKK                                          1403

SEQ ID NO: 95          moltype = AA  length = 1030
FEATURE                Location/Qualifiers
REGION                 1..1030
                       note = Description of Artificial Sequence: Synthetic
                        polypeptide
source                 1..1030
                       mol_type = protein
                       organism = synthetic construct
SEQUENCE: 95
MGKPIPNPLL GLDSTGGVDL RTLGYSQQQQ EKIKPKVRST VAQHHEALVG HGFTHAHIVA  60
```

```
LSQHPAALGT VAVKYQDMIA ALPEATHEAI VGVGKRGAGA RALEALLTVA GELRGPPLQL    120
DTGQLLKIAK RGGVTAVEAV HAWRNALTGA PLNLTPEQVV AIASHDGGKQ ALETVQRLLP    180
VLCQAHGLTP EQVVAIASNI GGKQALETVQ RLLPVLCQAH GLTPEQVVAI ASNIGGKQAL    240
ETVQRLLPVL CQAHGLTPEQ VVAIASNIGG KQALETVQRL LPVLCQAHGL TPEQVVAIAS    300
NGGGKQALET VQRLLPVLCQ AHGLTPEQVV AIASNGGKQ ALETVQRLLP VLCQAHGLTP     360
EQVVAIASNG GGKQALETVQ RLLPVLCQAH GLTPEQVVAI ASNGGGKQAL ETVQRLLPVL    420
CQAHGLTPEQ VVAIASNNGG KQALETVQRL LPVLCQAHGL TPEQVVAIAS NNGGKQALET    480
VQRLLPVLCQ AHGLTPEQVV AIASHDGGKQ ALETVQRLLP VLCQAHGLTP EQVVAIASHD    540
GGKQALETVQ RLLPVLCQAH GLTPEQVVAI ASNIGGKQAL ETVQRLLPVL CQAHGLTPEQ    600
VVAIASNIGG KQALETVQRL LPVLCQAHGL TPEQVVAIAS NNGGKQALET VQRLLPVLCQ    660
AHGLTPEQVV AIASNNGGKQ ALETVQRLLP VLCQAHGLTP EQVVAIASNI GGKQALETVQ    720
RLLPVLCQAH GLTPQQVVAI ASNIGGRPAL ESIVAQLSRP DPALAALTND HLVALACLGG    780
RPALDAVKKG LPHAPALIKR TNRRIPERTS HRVAGSPKKK RKVGSQLVKS ELEEKKSELR    840
HKLKYVPHEY IELIEIARNS TQDRILEMKV MEFFMKVYGY RGKHLGGSRK PDGAIYTVGS    900
PIDYGVIVDT KAYSGGYNLP IGQADEMQRY VEENQTRNKH INPNEWWKVY PSSVTEFKFL    960
FVSGHFKGNY KAQLTRLNHI TNCNGAVLSV EELLIGGEMI KAGTLTLEEV RRKFNNGEIN   1020
FGSPKKKRKV                                                        1030

SEQ ID NO: 96            moltype = AA  length = 165
FEATURE                  Location/Qualifiers
REGION                   1..165
                         note = Description of Artificial Sequence: Synthetic
                          polypeptide
source                   1..165
                         mol_type = protein
                         organism = synthetic construct
SEQUENCE: 96
MGKPIPNPLL GLDSTGGMAP KKKRKVDGGV DLRTLGYSQQ QQEKIKPKVR STVAQHHEAL    60
VGHGFTHAHI VALSQHPAAL GTVAVKYQDM IAALPEATHE AIVGVGKRGA GARALEALLT    120
VAGELRGPPL QLDTGQLLKI AKRGGVTAVE AVHAWRNALT GAPLN                    165

SEQ ID NO: 97            moltype = AA  length = 299
FEATURE                  Location/Qualifiers
REGION                   1..299
                         note = Description of Artificial Sequence: Synthetic
                          polypeptide
source                   1..299
                         mol_type = protein
                         organism = synthetic construct
SEQUENCE: 97
LTPQQVVAIA SNIGGRPALE SIVAQLSRPD PALAALTNDH LVALACLGGR PALDAVKKGL    60
PHAPALIKRT NRRIPERTSH RVAGSPKKKR KVGSQLVKSE LEEKKSELRH KLKYVPHEYI    120
ELIEIARNST QDRILEMKVM EFFMKVYGYR GKHLGGSRKP DGAIYTVGSP IDYGVIVDTK    180
AYSGGYNLPI GQADEMQRYV EENQTRNKHI NPNEWWKVYP SSVTEFKFLF VSGHFKGNYK    240
AQLTRLNHIT NCNGAVLSVE ELLIGGEMIK AGTLTLEEVR RKFNNGEINF GSPKKKRKV     299

SEQ ID NO: 98            moltype = AA  length = 7
FEATURE                  Location/Qualifiers
REGION                   1..7
                         note = Description of Unknown: NLS sequence
source                   1..7
                         mol_type = protein
                         organism = unidentified
SEQUENCE: 98
PKKKRVD                                                               7

SEQ ID NO: 99            moltype = AA  length = 20
FEATURE                  Location/Qualifiers
REGION                   1..20
                         note = Description of Unknown: NLS sequence
source                   1..20
                         mol_type = protein
                         organism = unidentified
SEQUENCE: 99
AVKRPAATKK AGQAKKKKLD                                                 20

SEQ ID NO: 100           moltype = AA  length = 25
FEATURE                  Location/Qualifiers
REGION                   1..25
                         note = Description of Unknown: NLS sequence
source                   1..25
                         mol_type = protein
                         organism = unidentified
SEQUENCE: 100
MSRRRKANPT KLSENAKKLA KEVEN                                           25

SEQ ID NO: 101           moltype = AA  length = 9
FEATURE                  Location/Qualifiers
REGION                   1..9
```

-continued

```
                         note = Description of Unknown: Myc NLS sequence
source                   1..9
                         mol_type = protein
                         organism = unidentified
SEQUENCE: 101
PAAKRVKLD                                                                        9

SEQ ID NO: 102           moltype = AA  length = 17
FEATURE                  Location/Qualifiers
REGION                   1..17
                         note = Description of Unknown: Nucleoplasmin bipartite NLS
                          sequence
source                   1..17
                         mol_type = protein
                         organism = unidentified
SEQUENCE: 102
KRPAATKKAG QAKKKKL                                                               17

SEQ ID NO: 103           moltype = AA  length = 14
FEATURE                  Location/Qualifiers
REGION                   1..14
                         note = Description of Unknown: NLS sequence
source                   1..14
                         mol_type = protein
                         organism = unidentified
SEQUENCE: 103
ASPEYVNLPI NGNG                                                                  14

SEQ ID NO: 104           moltype = AA  length = 8
FEATURE                  Location/Qualifiers
REGION                   1..8
                         note = Description of Unknown: NLS sequence
source                   1..8
                         mol_type = protein
                         organism = unidentified
SEQUENCE: 104
LSPSLSPL                                                                         8

SEQ ID NO: 105           moltype = AA  length = 10
FEATURE                  Location/Qualifiers
REGION                   1..10
                         note = Description of Unknown: NLS sequence
source                   1..10
                         mol_type = protein
                         organism = unidentified
SEQUENCE: 105
MVQLRPRASR                                                                       10

SEQ ID NO: 106           moltype = AA  length = 8
FEATURE                  Location/Qualifiers
REGION                   1..8
                         note = Description of Unknown: NLS sequence
source                   1..8
                         mol_type = protein
                         organism = unidentified
SEQUENCE: 106
PPARRRRL                                                                         8

SEQ ID NO: 107           moltype = AA  length = 30
FEATURE                  Location/Qualifiers
REGION                   1..30
                         note = Description of Unknown: NLS sequence
source                   1..30
                         mol_type = protein
                         organism = unidentified
SEQUENCE: 107
TLSPASSPSS VSCPVIPAST DESPGSALNI                                                 30

SEQ ID NO: 108           moltype = AA  length = 20
FEATURE                  Location/Qualifiers
REGION                   1..20
                         note = Description of Artificial Sequence: Synthetic peptide
source                   1..20
                         mol_type = protein
                         organism = synthetic construct
SEQUENCE: 108
KRTADGSEFE PAAKRVKLDE                                                            20

SEQ ID NO: 109           moltype = AA  length = 22
```

```
FEATURE               Location/Qualifiers
REGION                1..22
                      note = Description of Unknown: Bipartite NLS1 sequence
source                1..22
                      mol_type = protein
                      organism = unidentified
SEQUENCE: 109
SAARKRNSAT VHLCPVPRKR SG                                              22

SEQ ID NO: 110        moltype = AA  length = 22
FEATURE               Location/Qualifiers
REGION                1..22
                      note = Description of Unknown: Bipartite NLS2 sequence
source                1..22
                      mol_type = protein
                      organism = unidentified
SEQUENCE: 110
AAAKRPADDD DNASPAAKRR SG                                              22

SEQ ID NO: 111        moltype = AA  length = 24
FEATURE               Location/Qualifiers
REGION                1..24
                      note = Description of Unknown: Bi-partite NLS3 sequence
source                1..24
                      mol_type = protein
                      organism = unidentified
SEQUENCE: 111
SAAKRPSATV HLCDVPTKKT KRSG                                            24

SEQ ID NO: 112        moltype = AA  length = 17
FEATURE               Location/Qualifiers
source                1..17
                      mol_type = protein
                      note = Description of Artificial Sequence: Synthetic peptide
                      organism = synthetic construct
VARIANT               17
                      note = N can be K or R
VARIANT               16
                      note = N can be K or R
VARIANT               3..14
                      note = X may vary between 10 to 12
                      note = X can be any Amino Acid
SEQUENCE: 112
KRXXXXXXXX XXXXKNN                                                    17

SEQ ID NO: 113        moltype = AA  length = 18
FEATURE               Location/Qualifiers
source                1..18
                      mol_type = protein
                      note = Description of Artificial Sequence: Synthetic peptide
                      organism = synthetic construct
VARIANT               3..14
                      note = Any amino acid
                      note = X may vary between 10 to 12
VARIANT               16
                      note = N can be K or R
VARIANT               18
                      note = N can be K or R
VARIANT               17
                      note = X can be any Amino Acid
SEQUENCE: 113
KRXXXXXXXX XXXXKNNN                                                   18

SEQ ID NO: 114        moltype = AA  length = 21
FEATURE               Location/Qualifiers
source                1..21
                      mol_type = protein
                      note = Description of Artificial Sequence: Synthetic peptide
                      organism = synthetic construct
VARIANT               19
                      note = N can be K or R
VARIANT               20..21
                      note = N can be K or R
                      note = N can vary between 1 or 2
VARIANT               3..17
                      note = Any amino acid
                      note = X may vary between 5 to 15
SEQUENCE: 114
KRXXXXXXXX XXXXXXXKNN N                                               21
```

-continued

```
SEQ ID NO: 115           moltype = AA  length = 22
FEATURE                  Location/Qualifiers
source                   1..22
                         mol_type = protein
                         note = Description of Artificial Sequence: Synthetic peptide
                         organism = synthetic construct
VARIANT                  3..17
                         note = X can be any Amino Acid
                         note = X may vary between 5 to 15
VARIANT                  19
                         note = N can be K or R
VARIANT                  20
                         note = N can be any Amino Acid
VARIANT                  21..22
                         note = N can be K or R
                         note = N can vary between 1 to 2
SEQUENCE: 115
KRXXXXXXXX XXXXXXXKNN NN                                           22

SEQ ID NO: 116           moltype = AA  length = 18
FEATURE                  Location/Qualifiers
REGION                   1..18
                         note = Description of Artificial Sequence: Synthetic peptide
VARIANT                  1..2
                         note = Any amino acid
source                   1..18
                         mol_type = protein
                         organism = synthetic construct
SEQUENCE: 116
XXKRPAATKK AGQAKKKK                                                18

SEQ ID NO: 117           moltype = AA  length = 34
FEATURE                  Location/Qualifiers
REGION                   1..34
                         note = Description of Artificial Sequence: Synthetic
                          polypeptide
VARIANT                  8..27
                         note = Any amino acid
source                   1..34
                         mol_type = protein
                         organism = synthetic construct
SEQUENCE: 117
PKKRVDXXX XXXXXXXXXX XXXXXXXPKK KRVD                               34

SEQ ID NO: 118           moltype = AA  length = 34
FEATURE                  Location/Qualifiers
REGION                   1..34
                         note = Description of Artificial Sequence: Synthetic
                          polypeptide
VARIANT                  12..13
                         note = Any amino acid
source                   1..34
                         mol_type = protein
                         organism = synthetic construct
SEQUENCE: 118
LTPDQVVAIA SXXGGKQALE TVQRLLPVLC QAHG                              34

SEQ ID NO: 119           moltype = DNA  length = 52
FEATURE                  Location/Qualifiers
misc_feature             1..52
                         note = Description of Unknown: HTR2A_3 target sequence
source                   1..52
                         mol_type = other DNA
                         organism = unidentified
SEQUENCE: 119
tgttttgctg acttcaaaaa ctgcatgcaa gagctgagcc agctcccgca ct         52

SEQ ID NO: 120           moltype = DNA  length = 52
FEATURE                  Location/Qualifiers
misc_feature             1..52
                         note = Description of Unknown: HTR2A_3 target sequence
source                   1..52
                         mol_type = other DNA
                         organism = unidentified
SEQUENCE: 120
agtgcgggag ctggctcagc tcttgcatgc agttttgaa gtcagcaaaa ca          52

SEQ ID NO: 121           moltype = DNA  length = 52
```

```
FEATURE                 Location/Qualifiers
misc_feature            1..52
                        note = Description of Unknown: EFEMP1_4 target sequence
source                  1..52
                        mol_type = other DNA
                        organism = unidentified
SEQUENCE: 121
agttaggaaa agggctttca acattgtgaa tctcaaagaa aatacaggac aa          52

SEQ ID NO: 122          moltype =   length =
SEQUENCE: 122
000

SEQ ID NO: 123          moltype = DNA  length = 52
FEATURE                 Location/Qualifiers
misc_feature            1..52
                        note = Description of Unknown: EFEMP1_4 target sequence
source                  1..52
                        mol_type = other DNA
                        organism = unidentified
SEQUENCE: 123
ttgtcctgta ttttctttga gattcacaat gttgaaagcc cttttcctaa ct          52

SEQ ID NO: 124          moltype = DNA  length = 52
FEATURE                 Location/Qualifiers
misc_feature            1..52
                        note = Description of Unknown: CLRN1_2 target sequence
source                  1..52
                        mol_type = other DNA
                        organism = unidentified
SEQUENCE: 124
gccctgaggc attgacgagc agagctcccg ttttgcagag gacagtggct tt          52

SEQ ID NO: 125          moltype = DNA  length = 52
FEATURE                 Location/Qualifiers
misc_feature            1..52
                        note = Description of Unknown: CLRN1_2 target sequence
source                  1..52
                        mol_type = other DNA
                        organism = unidentified
SEQUENCE: 125
aaagccactg tcctctgcaa aacgggagct ctgctcgtca atgcctcagg gc          52

SEQ ID NO: 126          moltype = AA  length = 6
FEATURE                 Location/Qualifiers
REGION                  1..6
                        note = Description of Unknown: NLS sequence
source                  1..6
                        mol_type = protein
                        organism = unidentified
SEQUENCE: 126
PKKKRV                                                             6

SEQ ID NO: 127          moltype = DNA  length = 80
FEATURE                 Location/Qualifiers
misc_feature            1..80
                        note = Description of Artificial Sequence: Synthetic
                        oligonucleotide
source                  1..80
                        mol_type = other DNA
                        organism = synthetic construct
SEQUENCE: 127
gctgcccgtg ccctggccca ccctcgtgac caccctgacc tacggcgtgc agtgcttcag  60
ccgctacccc gaccacatga                                              80

SEQ ID NO: 128          moltype = DNA  length = 97
FEATURE                 Location/Qualifiers
misc_feature            1..97
                        note = Description of Artificial Sequence: Synthetic
                        oligonucleotide
source                  1..97
                        mol_type = other DNA
                        organism = synthetic construct
SEQUENCE: 128
cggggtagcg ggcgaagcac tgcacgccgt aggtgaaggt ggtcacgagg gtgggccagg  60
gcacgggcag cttgccggtg gtgcagatga acttcag                           97

SEQ ID NO: 129          moltype = AA  length = 6
FEATURE                 Location/Qualifiers
```

-continued

```
REGION                  1..6
                        note = Description of Artificial Sequence: Synthetic 6xHis
                         tag
source                  1..6
                        mol_type = protein
                        organism = synthetic construct
SEQUENCE: 129
HHHHHH                                                                               6

SEQ ID NO: 130          moltype = DNA  length = 82
FEATURE                 Location/Qualifiers
misc_feature            1..82
                        note = Description of Artificial Sequence: Synthetic
                         oligonucleotide
source                  1..82
                        mol_type = other DNA
                        organism = synthetic construct
SEQUENCE: 130
ggcgggggcg acctcggctc acagcgcgcc cggctattct cgcagctcac catgaccgag  60
tacaagccca cagtgcggct gg                                           82

SEQ ID NO: 131          moltype = DNA  length = 82
FEATURE                 Location/Qualifiers
misc_feature            1..82
                        note = Description of Artificial Sequence: Synthetic
                         oligonucleotide
source                  1..82
                        mol_type = other DNA
                        organism = synthetic construct
SEQUENCE: 131
ggcgggggcg acctcggccc acagcgcgcc cggctattct cgcagctcac catgaccgag  60
tacaagccca cagtgcggct gg                                           82

SEQ ID NO: 132          moltype = DNA  length = 52
FEATURE                 Location/Qualifiers
misc_feature            1..52
                        note = Description of Artificial Sequence: Synthetic
                         oligonucleotide
source                  1..52
                        mol_type = other DNA
                        organism = synthetic construct
SEQUENCE: 132
cggctattct cgcagctcac catgaccgag tacaagccca cagtgcggct gg          52

SEQ ID NO: 133          moltype = DNA  length = 82
FEATURE                 Location/Qualifiers
misc_feature            1..82
                        note = Description of Artificial Sequence: Synthetic
                         oligonucleotide
source                  1..82
                        mol_type = other DNA
                        organism = synthetic construct
SEQUENCE: 133
ggcgggggcg acctcggctc acagcgcgcc cggctattct cgcagctcac catggattcg  60
ccgcgctcgt cgtcgacaac gg                                           82

SEQ ID NO: 134          moltype = DNA  length = 63
FEATURE                 Location/Qualifiers
misc_feature            1..63
                        note = Description of Artificial Sequence: Synthetic
                         oligonucleotide
source                  1..63
                        mol_type = other DNA
                        organism = synthetic construct
SEQUENCE: 134
cacagcgcgc cggctattc tcgcagctca ccatgaccga gtacaagccc acagtgcggc  60
tgg                                                                63

SEQ ID NO: 135          moltype = DNA  length = 64
FEATURE                 Location/Qualifiers
misc_feature            1..64
                        note = Description of Artificial Sequence: Synthetic
                         oligonucleotide
source                  1..64
                        mol_type = other DNA
                        organism = synthetic construct
SEQUENCE: 135
caaattcgaa gctgatgatg atatcgccgc gctcgtcgtc gacaacggct ccggcatgtg  60
caag                                                               64
```

-continued

```
SEQ ID NO: 136          moltype = DNA   length = 49
FEATURE                 Location/Qualifiers
misc_feature            1..49
                        note = Description of Artificial Sequence: Synthetic
                        oligonucleotide
source                  1..49
                        mol_type = other DNA
                        organism = synthetic construct
SEQUENCE: 136
caaattcgaa gctgatgatg atatcgccgc gctcgtcgtc gacaacggc              49

SEQ ID NO: 137          moltype = DNA   length = 50
FEATURE                 Location/Qualifiers
misc_feature            1..50
                        note = Description of Artificial Sequence: Synthetic
                        oligonucleotide
source                  1..50
                        mol_type = other DNA
                        organism = synthetic construct
SEQUENCE: 137
atgatgatat cgccgcgctc gtcgtcgaca acggctccgg catgtgcaag           50

SEQ ID NO: 138          moltype = DNA   length = 73
FEATURE                 Location/Qualifiers
misc_feature            1..73
                        note = Description of Artificial Sequence: Synthetic
                        oligonucleotide
source                  1..73
                        mol_type = other DNA
                        organism = synthetic construct
SEQUENCE: 138
caaattcgaa gctgatgatg atatcgccgc gctcgtcgtc gacatgatga tatcgccgcg  60
ctcgtcgtcg aca                                                     73

SEQ ID NO: 139          moltype = DNA   length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 139
acggctccgg catgtgcaag                                             20

SEQ ID NO: 140          moltype = DNA   length = 50
FEATURE                 Location/Qualifiers
misc_feature            1..50
                        note = Description of Artificial Sequence: Synthetic
                        oligonucleotide
source                  1..50
                        mol_type = other DNA
                        organism = synthetic construct
SEQUENCE: 140
catgctggga gggcggcggg ttggaagcag gtgccaccat gaccgagtac           50

SEQ ID NO: 141          moltype = DNA   length = 49
FEATURE                 Location/Qualifiers
misc_feature            1..49
                        note = Description of Artificial Sequence: Synthetic
                        oligonucleotide
source                  1..49
                        mol_type = other DNA
                        organism = synthetic construct
SEQUENCE: 141
tgtacaaggc tagtggcagc tgtcaggggt gcgaagagga cgaggaaac            49

SEQ ID NO: 142          moltype = AA   length = 23
FEATURE                 Location/Qualifiers
REGION                  1..23
                        note = Description of Artificial Sequence: Synthetic peptide
VARIANT                 3..17
                        note = Any amino acid
                        note = X may vary between 5 to 15
VARIANT                 20
                        note = Lys or Ala
VARIANT                 21
                        note = Lys, Ala or Arg
```

-continued

```
source                  1..23
                        mol_type = protein
                        organism = synthetic construct
SEQUENCE: 142
KRXXXXXXXX XXXXXXXKX XKV                                      23

SEQ ID NO: 143          moltype = AA  length = 825
FEATURE                 Location/Qualifiers
REGION                  1..825
                        note = Description of Artificial Sequence: Synthetic
                         polypeptide
source                  1..825
                        mol_type = protein
                        organism = synthetic construct
SEQUENCE: 143
MGKPIPNPLL GLDSTGGVDL RTLGYSQQQQ EKIKPKVRST VAQHHEALVG HGFTHAHIVA  60
LSQHPAALGT VAVKYQDMIA ALPEATHEAI VGVGKRGAGA RALEALLTVA GELRGPPLQL  120
DTGQLLKIAK RGGVTAVEAV HAWRNALTGA PLNLTPEQVV AIASHDGGKQ ALETVQRLLP  180
VLCQAHGLTP EQVVAIASNI GGKQALETVQ RLLPVLCQAH GLTPEQVVAI ASNIGGKQAL  240
ETVQRLLPVL CQAHGLTPEQ VVAIASNIGG KQALETVQRL LPVLCQAHGL TPEQVVAIAS  300
NIGGKQALET VQRLLPVLCQ AHGLTPEQVV AIASNIGGKQ ALETVQRLLP VLCQAHGLTP  360
EQVVAIASHD GGKQALETVQ RLLPVLCQAH GLTPEQVVAI ASHDGGKQAL ETVQRLLPVL  420
CQAHGLTPEQ VVAIASNGGG KQALETVQRL LPVLCQAHGL TPEQVVAIAS NNGGKQALET  480
VQRLLPVLCQ AHGLTPEQVV AIASNGGGKQ ALETVQRLLP VLCQAHGLTP EQVVAIASNI  540
GGKQALETVQ RLLPVLCQAH GLTPEQVVAI ASNIGGKQAL ETVQRLLPVL CQAHGLTPEQ  600
VVAIASNIGG KQALETVQRL LPVLCQAHGL TPEQVVAIAS NNGGKQALET VQRLLPVLCQ  660
AHGLTPEQVV AIASNNGGKQ ALETVQRLLP VLCQAHGLTP EQVVAIASNI GGKQALETVQ  720
RLLPVLCQAH GLTPQQVVAI ASNIGGRPAL ESIVAQLSRP DPALAALTND HLVALACLGG  780
RPALDAVKKG LPHAPALIKR TNRRIPERTS HRVAGSPKKK RKVGS               825
```